US009797005B2

(12) United States Patent
Campan et al.

(10) Patent No.: US 9,797,005 B2
(45) Date of Patent: Oct. 24, 2017

(54) HIGH THROUGHPUT METHOD OF DNA METHYLATION HAPLOTYPING

(75) Inventors: Mihaela Campan, Los Angeles, CA (US); Peter W. Laird, South Pasadena, CA (US); Allen S. Yang, Valencia, CA (US); Hui-Lee Wong, South Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 12/094,952

(22) PCT Filed: Nov. 22, 2006

(86) PCT No.: PCT/US2006/045392
§ 371 (c)(1),
(2), (4) Date: Aug. 5, 2008

(87) PCT Pub. No.: WO2007/062212
PCT Pub. Date: May 31, 2007

(65) Prior Publication Data

US 2008/0286787 A1 Nov. 20, 2008

Related U.S. Application Data

(60) Provisional application No. 60/739,260, filed on Nov. 23, 2005.

(51) Int. Cl.
*C12Q 1/68* (2006.01)

(52) U.S. Cl.
CPC .................................. *C12Q 1/6858* (2013.01)

(58) Field of Classification Search
None
See application file for complete search history.

(56) References Cited

U.S. PATENT DOCUMENTS

2004/0219559 A1* 11/2004 Feinberg .......................... 435/6

OTHER PUBLICATIONS

Sasamoto et al. Int. J. of Oncol. vol. 25:1273-1278. 2004.*
Dupont et al. Anal. Biochem. vol. 333:119-127. 2004.*
U.S. Appl. No. 60/739,260, filed Nov. 23, 2005, Campan.
Bell et al. "Methylation of a CTCF-dependent boundary controls imprinted expression of the Igf2 gene," Nature, 2000, pp. 482-485, vol. 405.
Cui et al., "Loss of Imprinting in Colorectal Cancer Linked to Hypomethylation of H19 and IGF2," Cancer Research, 2002, pp. 6442-6446, vol. 62.
Cui et al., "Loss of imprinting in normal tissue of colorectal cancer patients with microsatellite instability," Nature Medicine, 1998, pp. 1276-1280, vol. 4.
Dupont et al., "De novo quantitative bisulfite sequencing using the pyrosequencing technology," Analytical Biochemistry, 2004, pp. 119-127, vol. 333.
Eads et al., "CpG Island Hypermethylation in Human Colorectal Tumors Is Not Associated with DNA Methyltransferase Overexpression," Cancer Research, 1999, pp. 2302-2306, vol. 59.
Eads et al., "MethyLight: a high-throughput assay to measure DNA methylation," Nucleic Acids Research, 2000, pp. e32 (i-viii), vol. 28.
England et al., "Pyro Q-CpG™: quantitataive analysis of methylation in multiple CpG sites by Pyrosequencing®," Nature Methods, 2005, pp. i-ii.
Frommer et al., "A genomic sequencing protocol that yields a positive display of 5-methylcytosine residues in individual DNA strands," The Proceedings of the National Academy of Sciences, 1992, pp. 1827-1831, vol. 89.
Grunau et al., "Bisulfite genomic sequencing: systematic investigation of critical experimental parameters," Nucleic Acids Research, 2001, p. e65, vol. 29, (7 pages).
Holmgren et al., "CpG methylation regulates the Igf2/H19 insulator," Current Biology, 2001, pp. 1128-1130, vol. 11.
Hoogendoorn et al., "Functional analysis of human promoter polymorphisms," Human Molecular Genetics, 2003, pp. 2249-2254, vol. 12.
Lau et al., "RUNX3 Is Frequently Inactivated by Dual Mechanisms of Protein Mislocalization and promoter hypermethylation in Breast Cancer," Cancer Research, 2006, pp. 6512-6520, vol. 66.
Lo et al., "Allelic Variation in Gene Expression Is Common in the Human Genome," Genome Research, 2003, pp. 1855-1862, vol. 13.
Nakagawa et al., "Loss of imprinting of the insulin-like growth factor II gene occurs by biallelic methylation in a core region of H19-associated CTCF-binding sites in colorectal cancer," The Proceedings of the National Academy of Sciences, 2001, pp. 591-596, vol. 98.
Sandovici et al., "Interindividual variability and parent of origin DNA methylation differences at specific human Alu elements," Human Molecular Genetics, 2005, pp. 2135-2143, vol. 14.
Sasamoto et al., "Allele-specific methylation analysis on upstream promoter region of H19 by methylation-specific PCR with confronting two-pair primers," International Journal of Oncology, 2004, pp. 1273-1278, vol. 25.

(Continued)

*Primary Examiner* — Angela M Bertagna
(74) *Attorney, Agent, or Firm* — Barry L. Davison; Davis Wright Tremaine LLP

(57) ABSTRACT

Particular aspects provide novel, high-throughput methods to quantify DNA methylation (e.g., at a single-base resolution) in an allele-specific manner. The methods comprise use of an allele-specific sequence polymorphism (e.g., allele-specific single nucleotide polymorphism; SNP) in sufficient proximity to a CpG methylation site to provide for distinguishing the methylation levels between two alleles. In particular aspects, after bisulfite modification, the genomic DNA region is PCR-amplified, and the product subjected to allele-specific pyrosequencing, and the percentage of methylation determined based on the percentage of cytosine to thymidine conversion. In further embodiments, MethyLight™ is used after bisulfite treatment. The inventive methodology has, for example, substantial utility for affording quantitative analyses in the regulation of analyses of X-inactivation, the allele-specific expression of genes (e.g., in the immune system) and junk DNA, etc., and in classifying an individual as to whether they have loss of imprinting (LOI).

7 Claims, 7 Drawing Sheets

(56) References Cited

OTHER PUBLICATIONS

Takai et al., "Large scale mapping of methylcytosines in CTCF-binding sites in the human H19 promoter and aberrant hypomethylation in human bladder cancer," Human Molecular Genetics, 2001, pp. 2619-2626, vol. 10.
Trinh et al. "DNA Methylation Analysis by MethyLight Technology," Methods, 2001, pp. 456-462, vol. 25.
Webber et al., "Location of enhancers is essential for the imprinting of H19 and Igf2 genes," Nature, 1998, pp. 711-715, vol. 391.
Wong et al., "Rapid and quantitative method of allele-specific DNA methylation analysis," BioTechniques, 2006, pp. 734-739, vol. 41.
Yan et al. "Allelic Variation in Human Gene Expression," Science, 2002, p. 1143, vol. 297.

* cited by examiner

Exp. seq GGG- (C / T) ------------ GGG- (C / T) ------------
-- GGG ------T --------- G Normal (C allele)

Tumor (C allele)

Normal (A allele)

Tumor (A allele)

HIGH THROUGHPUT METHOD OF DNA METHYLATION HAPLOTYPING

CROSS-REFERENCE TO RELATED APPLICATIONS

This application claims the benefit of priority to U.S. Provisional Patent Application Ser. No. 60/739,260, filed 23 Nov. 2005, which is incorporated by reference herein in its entirety.

FIELD OF THE INVENTION

Particular aspects relate generally to genomic DNA methylation and to allele-specific DNA methylation and genomic imprinting, and more particularly to methods (e.g., high-throughput methods) for quantifying the degree or extent of such methylation, and imprinting.

BACKGROUND

Variation in allelic expression is common in humans (Lo, H. S. et al., Genome Res 13:1855-62, 2003, Hoogendoorn, B. et al., *Hum Mol Genet.* 12:2249-54, 2003) and, underlies normal human variability and predisposition to human diseases (Yan, H. et al., *Science* 297:1143, 2002). Genomic imprinting represents the extreme end of this expression spectrum where only one allele is expressed in a parent-dependent manner. Normal genomic imprinting is regulated, in part, by methyl groups on cytosines within cytosine-guanine (CpG) dinucleotides, i.e., cytosine-deoxyribose phosphates adjacent to a guanine-deoxyribose phosphate. In principle, DNA methylation within regions differentially methylated between parental alleles (differentially methylated regions, DMRs) can predict normal imprinting or loss of imprinting.

As a proxy for parent-specific expression, current methodologies based on DNA methylation are either 1) labor-intensive (bisulfite genomic sequencing) (Frommer, M. et al., *Proc Natl Acad Sci USA* 89:1827-31, 1992) or; 2) do not assess parent-specific methylation levels but instead, average methylation levels (Dupont, J. M. et al., *Anal Biochem* 333 :119-27 (2004). Bisulfite genomic sequencing is a method that quantities methylation at a similar resolution and represents the gold standard in the field. However, bisulfite genomic sequencing requires the labor-intensive of subcloning PCR-amplified products into vectors prior to direct sequencing of multiple individual clones that each represent one parental strand from a single cell. Artifacts may result from strong assumptions that do not correlate with normal biological heterogeneity. For example, an average 50 percent methylation of a population of cells may represent either the assumed normal imprinting in the entire cellular population (zero methylation on one allele; 100 percent, the other) or variations of loss of imprinting (e.g. an allele with 75 percent methylation and another allele harboring 25 percent methylation).

Therefore, there is a pronounced need in the art for novel methods having substantial utility for assessing the degree of allele-specific methylation present in cells and tissues.

SUMMARY

Particular aspects provide novel, high-throughput methods to quantify DNA methylation at a single-base resolution in an allele-specific manner. The methods comprise use of an allele-specific single nucleotide polymorphism (SNP) in proximity to a CpG methylation site to distinguish the methylation levels between two alleles. Allele-specific methylation of CpG dinucleotides within an imprinting regulatory region (H19 imprinting center) was quantified, and this methodology was applied to the analysis of loss of imprinting. In particular aspects, after bisulfite modification, the genomic DNA region is PCR-amplified, and the product subjected to allele-specific pyrosequencing, and the percentage of methylation determined based on the percentage of cytosine to thymidine conversion. In further embodiments, MethyLight™ was used after bisulfite treatment. The inventive methodology also has substantial utility for affording quantitative analyses in the regulation of analyses of X-inactivation and the allele-specific expression of genes (e.g., in the immune system) and junk DNA, etc.

Particular aspects provide a high-throughput method for quantifying allele-specific genomic DNA methylation, comprising: obtaining a sample having genomic DNA, the genomic DNA comprising at least one allelic locus that is heterozygous for at least one allele-specific sequence polymorphism; contacting the genomic DNA with reagent or reagents suitable to deaminate cytosine, but not 5-methylcytosine, to uracil to provide converted DNA; amplifying the converted DNA, or a portion thereof, by polymerase-mediated amplification; and quantifying the level of allele-specific methylation using a methylation assay comprising at least one allele-specific reagent that distinguishes the alleles based on the allele-specific sequence polymorphism. In particular embodiments, quantifying the level of allele-specific methylation comprises use of primers specific to the allele-specific sequence polymorphism. In certain aspects, pyrosequencing with an allele-specific primer is used to quantifying the level of allele-specific methylation. Preferably, quantifying is achieved in real-time during the amplifying. Preferably, quantifying is by use of a MethyLight methylation assay comprising at least one set of primers, and at least one probe, wherein at least one of the primers, or the probe is specific to the allele-specific sequence polymorphism.

Specific embodiments provide a high-throughput method for quantifying allele-specific genomic DNA methylation, comprising: obtaining a sample having genomic DNA, the genomic DNA comprising at least one allelic locus comprising at least one homozygous CpG dinucleotide sequence, the allelic locus being heterozygous for at least one allele-specific sequence polymorphism; contacting the genomic DNA with reagent or reagents suitable to convert cytosine, but not 5-methylcytosine, to uracil or another base dissimilar to cytosine in terms of hybridization behavior to provide converted DNA; amplifying the converted DNA, or a portion thereof, by polymerase-mediated amplification; and quantifying the methylation level of the at least one allele-specific CpG dinucleotide sequence using a methylation assay comprising the use of at least one allele-specific reagent that distinguishes the alleles based on the at least one allele-specific sequence polymorphism. In particular aspects, the at least one allele-specific sequence polymorphism is an allele-specific sequence polymorphism distinct from but sufficiently proximate to the at least one CpG dinucleotide sequence to provide for distinguishing the methylation levels between the two alleles. In certain embodiments, the at least one allele-specific sequence polymorphism is an allele-specific single nucleotide polymorphism (SNP) sufficiently proximate to the at least one CpG dinucleotide sequence to distinguish the methylation levels between the two alleles. In particular embodiments, the at least one allele-specific reagent is a primer of a nucleic acid primer oligomer pair or is a probe oligomer, wherein the primer or probe is specific to the at least one allele-specific sequence polymorphism on one DNA strand or on the complementary DNA strand. In certain aspects, quantifying the level of allele-specific methylation comprises use of primers specific to the at least one allele-specific sequence polymorphism. In particular embodiments, measuring the relative methylation of each parental allele comprises comparing the experimental samples with an in vitro methylated DNA sample that is also heterozygous for the at least one allele-specific sequence polymorphism. Particular aspects comprise the use of pyrosequencing. In certain embodiments, quantifying comprises quantifying achieved in real-time during the amplifying. In certain aspects, quantifying comprises use of a methylation assay comprising at least one set of primers, and at least one probe, wherein one of the primers, or the probe is specific to the allele-specific sequence polymorphism. Preferably, the methylation assay is that of MethyLight. In certain aspects, where the at least one primer or probe that is specific to the allele-specific sequence polymorphism comprises a genomic cytosine residue position, the at least one primer or probe is specific to the sequence on the treated DNA strand that is complementary to that of the genomic cytosine residue position. In particular embodiments, the at least one allelic discriminatory sequence polymorphism and the at least one allele-specific CpG dinucleotide sequence are distributed differently between the three oligomers of a primer/probe oligomer set. In certain aspects, the at least one allele-specific CpG dinucleotide sequence is targeted by any one of the oligonucleotides of a primer/probe set, and the allele-specific sequence polymorphism is targeted by any of the remaining oligonucleotides. In certain embodiments, the at least one allele-specific sequence polymorphism and the at least one allele-specific CpG dinucleotide sequence are included together on a primer, or on the fluorescent probe. In certain aspects, the at least one allele-specific CpG dinucleotide sequences are distributed among the two primers and the probe, with the allele-specific sequence polymorphism located on any of the primers or probe.

DETAILED DESCRIPTION

Figure 1:
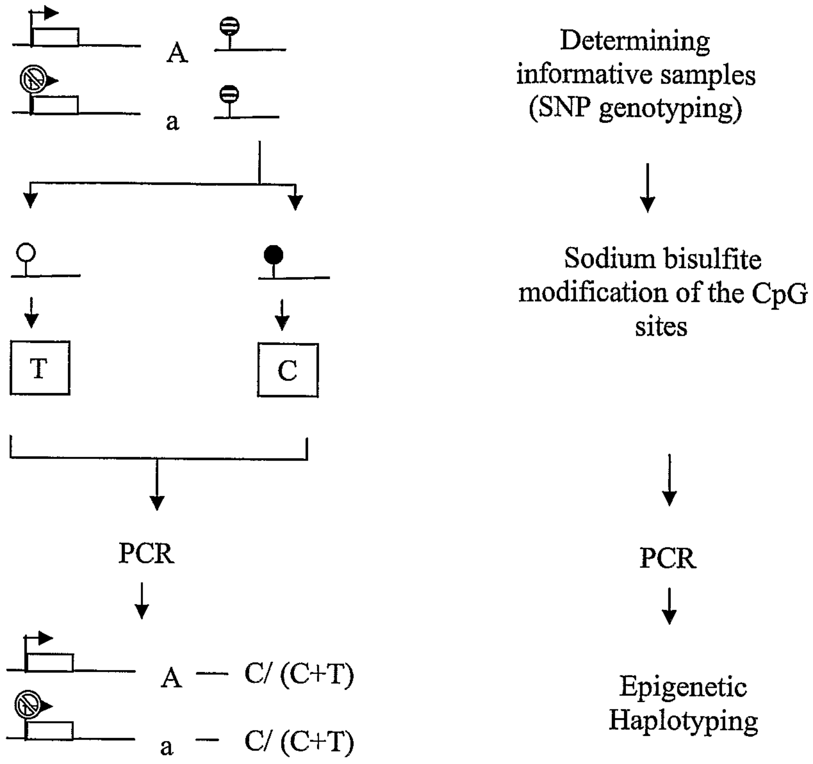
FIG. 1 shows a general schema of the epigenetic haplotyping assay in accordance with an embodiment of the present invention. Samples that were heterozygous for a single nucleotide polymorphism (denoted as Aa) in the differentially methylated regions were utilized in this assay.

The invention disclosed herein relates to methods useful for determining (e.g., quantifying) the amount of CpG methylation present on a specific allele. The methods disclosed herein utilize an allele-specific single nucleotide polymorphism (SNP) in proximity to (e.g., upstream of) a CpG methylation site to distinguish the methylation levels between the two alleles. For DNA samples that are heterozygous for the SNP, methylation of each allele may be quantitated at single base resolution.

It is widely accepted that DNA methylation is an important mechanism for regulating the expression of imprinted genes. Genomic imprinting is an epigenetic modification that results in the silencing of a specific allele depending on its parental origin. Unlike the great majority of genes that are characterized by a biallelic pattern of expression, only one allele of the imprinted genes is expressed (either maternal or paternal) while the other allele is silenced. The imprinting mark that distinguishes between the two parental alleles may be represented by the methylation of a limited number of CpG sites located in DNA regions called differentially methylated regions (DMRs). CpG sites are regions of DNA where a cytosine nucleotide occurs next to a guanine nucleotide. The term "CpG" refers to cytosine (C) and guanine (G) separated by a phosphate. DNA methylation may occur at the 5-carbon position of cytosine in a CpG to produce methylcytosine. Allele-specific methylation events generally occur on the parental allele that is silenced.

Loss of imprinting (LOI) is a type of epigenetic dysregulation that is associated with several human diseases including cancer. Several imprinted genes, including IGF2, have been shown to lose their imprinted status in many types of malignancies. Moreover, LOI of IGF2 has been detected in the normal adjacent colonic mucosa of colorectal (CRC) cancer patients, as well as in the blood of healthy individuals with family or personal history of CRC (Cui H. et al., *Nat Med* 11:1276-80, 1998). Therefore, development of novel effective LOI detection assays would provide valuable tools for early detection of cancer.

Until the present inventive aspects, there were not only few DNA-based methods available to detect LOI in the art, but such methods are not amenable to high throughput analysis of large patient sample numbers.

Aspects of the present invention provide novel, effective high throughput LOI detection assays that provide valuable tools (e.g., for early detection of cancer). Several strategies have been developed to detect allele specific methylation as a measure of normal genomic imprinting, as well as loss of allele-specific methylation (a measure of LOI), on bisulfite-converted DNA. A direct health application of this epigenetic haplotyping methodology is to classify persons as to whether they have loss of imprinting (LOI) in prospective epidemiologic studies.

In particular embodiments, the degree of methylation is measured by first treating DNA samples with sodium bisulfite, a reagent that selectively deaminates cytosine, but not methylcytosine, to uracil. Methylcytosine is the product of methylation at a CpG site. Subsequent PCR amplification of the sodium bisulfite-treated DNA converts the uracil to a thymine, while the methylated cytosine remains a cytosine, resulting in a primary sequence change in DNA samples having unmethylated cytosines. The site of methylation is then correlated with a specific allele by using a SNP (e.g., proximate SNP) as a marker, and PCR reaction conditions are optimized to achieve effective allelic discrimination.

A number of methods may be used to measure the degree of methylation, which is determined as the percentage of cytosine in sodium bisulfite-treated DNA. Some embodiments involve measuring the relative methylation of each parental allele by comparing the experimental samples with an in vitro methylated DNA sample that is also heterozygous for the specific SNP. One such method may utilize allele-specific sequencing primers in a real-time sequencing platform based on luminescence-detection of pyrophosphate released during step-wise nucleotide incorporation (Pyrosequencing, Biotage, Uppsala Sweden) (England, R. P., *Nature Methods Application Note for Nature Methods,* 2004). As shown below in the working Examples, this methodology correctly identified the percentage of allele-specific methylation within 3 percent at low percentages of methylation (<50 percent).

An alternative method for measuring the degree of methylation present in on an allele is MethyLight™. MethyLight™ is a sensitive, fluorescence-based real-time PCR technique that is capable of quantitating DNA methylation at a particular locus by using DNA oligonucleotides that anneal differentially to bisulfite-converted DNA according to the methylation status in the original genomic DNA. The use of three oligonucleotides (forward and reverse primers, and interpositioned probe) in MethyLight™, any one or more of which can be used for methylation discrimination, allows for specificity, sensitivity, and flexibility in methylation detection.

The term "sufficiently proximate," as used herein in particular aspects, is an operational term relating to the fact that the physical distance (e.g., in nucleotides) between the CpG dinucleotide sequence and the allele-specific sequence polymorphism must be within a sufficient distance that, in the context of the methylation assay, allows for association or correlation of the methylation measurement (e.g., quantification of the methylation of a particular allelic CpG sequence) with the particular allele-specific sequence polymorphism to provide for distinguishing the CpG methylation levels between the two alleles. For example, for primer sequencing-based (e.g., polymerase-based), or amplification-based methylation assays, where a primer and/or probe is specific for a particular allele-specific sequence polymorphism, the subject polymorphism must be sufficiently proximate (sufficiently close to along the nucleic acid polymer) to the allele-specific CpG sequence being analyzed, such that the extension or amplification products of the methylation assay encompass or include, or otherwise enable measurement of the methylation status of the nucleotide position corresponding to the cytosine residue of the genomic CpG sequence being measured. This distance may vary, depending upon the capabilities of the methylation reaction (e.g., size of amplicons, or primer extension products obtainable), and may, for example, be from 0 to several thousand base pairs (e.g., from 0 to about 3,000 or about 5,000 bp), or from 0 to about 2,000 bp, or from 0 to about 1,000 bp, or from 0 to about 500 bp, or from 0 to about 100 bp. The critical aspect being that a sufficiently proximate distance is a distance that allows for associating or correlating the measured CpG methylation with the particular allele by means of the allele-specific sequence polymorphism.

EXAMPLE 1

Methylation Levels Between Two Parental Alleles in the Same Cellular Population were Measured Overview In this example, the methylation levels between two parental alleles in the same cellular population were measured, and the methylation levels of each parental allele was measured by exploiting a single nucleotide polymorphism (SNP) upstream to the CpG dinucleotides of interest (rs2071094; dbSNP build 124) (e.g., as depicted schematically in FIG. 1). An analytical validation of a DNA-based LOI assay is presented using a system that is a paradigm for genomic imprinting: the H19 imprinting center. The H19 imprinting center regulates the paternally imprinted non-coding RNA H19 (Bell, A. C. and Felsenfeld, G. *Nature* 405:482-5, 2000, Webber, A. L. et al., *Nature* 391:711-5, 1998, Holmgren, C. et al., *Curr Biol* 11:1128-302001).

For DNA samples that are heterozygous for a SNP, the degree of methylation on each allele was quantitated at a single base resolution. To retain the methylation information on the CpG sites of interest, genomic DNA was treated with sodium bisulfite to selectively deaminate cytosine, but not 5-methylcytosine, to uracil. Subsequent PCR amplification converts the uracil to a thymine, while the methylated cytosine remains as a cytosine. This leads to a primary sequence change reflecting whether or not the parent DNA was methylated (Frommer, M. et al., *Proc Natl Acad Sci USA* 89:1827-31, 1992).

Methylation is determined as the percentage of cytosine on a real-time sequencing platform using a system that detects luminescence produced when pyrophosphate is released during step-wise nucleotide incorporation (Pyrosequencing, Biotage, Uppsala Sweden). In particular aspects, as shown herein, the inventive methodology correctly identifies the percentage of allele-specific methylation within 3 percent at low percentages of methylation (<50 percent).

Materials and Methods

Cell lines and human tissue samples. The Colo205 colorectal carcinoma cell line was cultured in Dulbecco's modified essential medium at 37° C. in a humidified atmosphere with 5 percent $CO_2$. Informed written consent was obtained and the Institutional Review Board at the University of Southern California approved all research protocols.

Preparation of samples for the allele-specific methylation. The Samples for the allele-specific methylation assay were samples heterozygous for a SNP in the H19 imprinting center. The H19 imprinting center is disclosed as NCBI dbSNP Accession No. rs2071094 (SEQ ID NO:1), and the human H19 gene is disclosed as NCBI Accession No. AF125183 (SEQ ID NO:2) with a C to A polymorphism at nucleotide 8008. Genomic DNA was extracted from cell lines and tissue samples using a standard phenol-chloroform method.

Sodium bisulfite modification of genomic DNA. Sodium bisulfite modification of genomic DNA was performed as described by Frommer et al. (Frommer, M. et al., *Proc Natl Acad Sci USA* 89:1827-31, 1992) with some modifications. DNA (~2 μg) was denatured in 0.2 M NaOH at 37° C. for 10 min. The sample was then adjusted to a concentration of 0.5 mM hydroquinone and 2.6 M sodium bisulfite (pH 5.0) with freshly prepared stock solutions and incubated at 50° C. for 16 h. The modified DNA was desalted with Wizard Plus kits (Promega, Madison Ill.) according to manufacturer's instructions. The DNA preparation was adjusted to 0.3 M NaOH for 5 min at room temperature. Glycogen (1 μg) was added, and the DNA was precipitated with 0.6 volumes of 10 M sodium acetate and three volumes of ethanol and washed with 70 percent ethanol before resuspension in 20 µl of water.

Amplification of bisulfite-converted DNA. Bisulfite-modified DNA (2 µL) was amplified in a primary PCR reaction and followed by a nested PCR reaction amplifying one µL of the primary PCR product. PCR reaction was performed in 25 µL volume using 10 pmol of each primer and the Eppendorf HotMaster Taq DNA kit (Eppendorf, Westbury, N.Y.) at reagent concentrations per manufacturer's instructions. The following primers in the primary PCR reaction were used to amplify a DNA fragment from bisulfite-treated SEQ ID NO:2 DNA: 5' GGA GTT GTG TTT TGG GAT AGA TGT 3' (SEQ ID NO:3) and 5' AAA CAA TAA AAT ATC CCA ATT CCA 3' (SEQ ID NO:4).

The primers for the nested PCR that amplified the 223 bp fragment (nucleotide positions 7876-8102 (SEQ ID NO: 5) of NCBI accession AF125183) were: 5' GTT TTT ATG AGT GTT TTA TTT TTA GAT G 3' (SEQ ID NO:6) (nucleotide positions 8102-8075; NCBI accession AF125183, reverse-complement bisulfite-modified strand); and 5' CCT CCT CAA AAA TCT TTA TAA ATA CAC 3' (SEQ ID NO:7) coupled with biotin (positions 7903-7876; NCBI accession AF125183, reverse-complement bisulfite-modified strand). PCR conditions included one cycle of 94° C. for 3 min, 30 cycles of 94° C., 30 sec; 53° C. (primary PCR) or 62° C. (nested PCR), 30 sec; 72° C., 30 sec, and followed by one cycle of 72° C. for 5 min.

Bisulfite genomic sequencing. The 223 base pair PCR fragments were cloned using the TA cloning kit (Invitrogen, Carlsbad Calif.). Plasmid DNA was purified from 40 clones using Promega, Madison Ill.). The nucleotide sequences of each clone representing a single cell was verified by cycle sequencing at the Laragen Sequencing Facility (Los Angeles, Calif.) using the M13 F (5' GTA AAA CGA CGG CCA GT 3'; SEQ ID NO:8) or R (5' CAG GAA ACA GCT ATG AC 3'; SEQ ID NO:9) primers.

Quantification of allele-specific methylation. Allele-specific methylation was quantitated using pyrosequencing with allele-specific sequencing primers and the PyroGold™ Reagent kit (Biotage, Uppsala Sweden) on a Pyrosequencing HS per manufacturer's protocol. In brief, 10 µL of PCR product for each sequencing reaction was immobilized onto streptavidin-coated beads (Streptavidin Sepharose HP, Amersham Biosciences Ltd) in binding buffer (10 mM Tris-HCl, pH 7.6, 2 M NaCl, 1 mM EDTA, 0.1% Tween 20) for 10 min. The biotinylated template was purified with the Pyrosequencing vacuum prep tool (Biotage, Uppsala Sweden) and incubated with 10 pmol/reaction sequencing primer in annealing buffer (20 mM Tris-acetate, pH 7.6 and 2 mM $MgAc_2$). The biotinylated single DNA strand represents the reverse-complement bisulfite-modified strand (SEQ ID NO:10, NCBI accession AF125183; nt: 7903-7876). The DNA strands were denatured at 80° C. for 2 min and re-annealed at room temperature for 10 min. Sequencing was performed using allele-specific primers with the Pyrogold™ reagent kit (Biotage, Uppsala Sweden) according to manufacturer's instructions. The allele-specific sequencing primers were 1) G allele: 5' GAATTTTAGTTG 3' (SEQ ID NO:11), and 2) T allele: 5' GAATTTTAGTTT 3' (SEQ ID NO:12). The allele frequency (% cytosine or % thymidine) was calculated from the peak height analyzed with the allele quantification module in the PSQ 96 HS software (Biotage). Percentage of methylation was determined by the percentage of cytosine-to-thymidine conversion, i.e., (% cytosine/(% cytosine+% thymidine)).

Statistical Methods. To assess the extent that the allele-specific methylation assay measures methylation, the concordance between the detected methylation and the expected methylation were examined by a goodness of fit test on the predicted linear regression. The intra-class correlation coefficient (ICC) was the correlation measure for determining reproducibility of replicate measures from the same DNA template ("subject"), where the multiple measurements (replicates) are ideally measuring the same percentage of methylation (Fleiss, 1999). After Fleiss 1999, excellent reproducibility is measured by an ICC>0.75, an ICC<0.4 indicates poor reproducibility, and levels between 0.4 and 0.75 represent good reproducibility. It was assumed that the proportion of variance due to is due to Pyrosequencing and ignored and intra-technician reliability. Unreliability (1-reliability) is assumed to be synonymous with within-subject variability and is the sum of imprecision (error due to measurement) and undependability (error due to short-term within-individual random fluctuations). Validity (Accuracy) is defined as lack of error due to the instrument and refers to the comparison of the method with a standard.

Results

The allele-specific methylation assay was generally found to be sensitive, specific, and reproducible. The cellular populations of normally imprinted genes comprise subpopulations parental alleles that may be methylated or unmethylated at CpG sites. These two subpopulations can be distinguished from genomic DNA heterozygous for a single nucleotide polymorphism near the CpG sites of interest. Plasmid DNA was used to simulate the methylated cellular allele sub-populations.

In a biological setting, heterogeneity may be observed at the level of tumor tissue (heterogeneous cells observed as some alleles are methylated, others are not) or at the level of the cells (all alleles are methylated at a very low level, i.e., leaky expression). Plasmid DNA representing the four possible allele-specific methylation patterns determined by SNP (G or A) and methylation status (G-methylated, G-unmethylated, T-methylated, T-unmethylated) were mixed prior to PCR amplification. The average methylation at each CpG site at each parental allele was determined on the scale of 0 to 100 percent (FIG. 2).

Figure 2A:
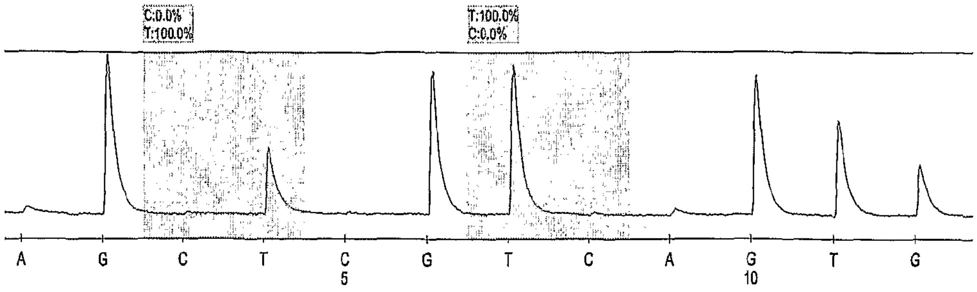
FIG. 2A shows a graphical representation of the light profile of CpG sites generated by sequential nucleotide dispensation (Pyrogram™) in accordance with an embodiment of the present invention. The template is a mock single-stranded DNA mimicking 0% methylation derived from mixtures of plasmids containing the PCR fragments of H19 imprinting region within the colorectal cancer cell line Colo205. Shaded areas highlight the two CpG sites of interest. The sequence of the nucleotide dispensation ("AGCTCGTCAGTG"; not itself a nucleotide sequence) for the pyrosequencing reaction is shown at the bottom of the panel, and where the region being sequenced is 16 nucleotides downstream from the sequencing primer (i.e., nucleotides 117-132 of SEQ ID NO:5, which correspond to nucleotides 7992-8007 of SEQ ID NO:2 (NCBI accession AF125183).
Figure 2B:
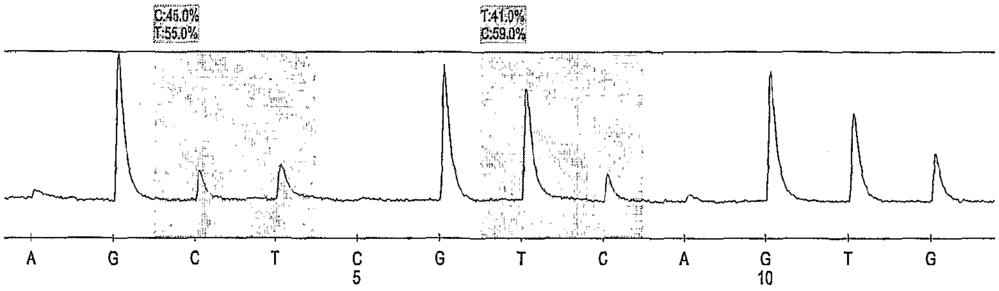
FIG. 2B shows a graphical representation of the light profile of CpG sites generated by sequential nucleotide dispensation (Pyrogram™) in accordance with an embodiment of the present invention. The template is a mock single-stranded DNA mimicking 50% methylation derived from mixtures of plasmids containing the PCR fragments of H19 imprinting region within the colorectal cancer cell line Colo205. Shaded areas highlight the two CpG sites of interest. The sequence of the nucleotide dispensation ("AGCTCGTCAGTG"; not itself a nucleotide sequence) for the pyrosequencing reaction is shown at the bottom of the panel, and where the region being sequenced is 16 nucleotides downstream from the sequencing primer (i.e., nucleotides 117-132 of SEQ ID NO:5, which correspond to nucleotides 7992-8007 of SEQ ID NO:2 (NCBI accession AF125183).
Figure 2C:
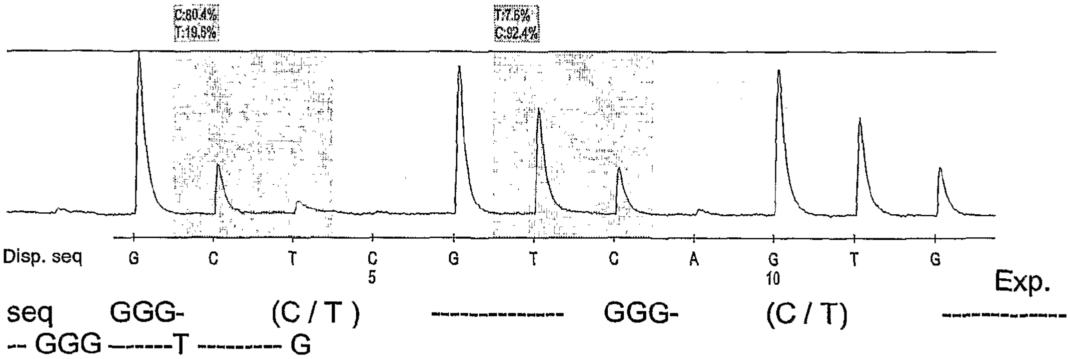
FIG. 2C shows a graphical representation of the light profile of CpG sites generated by sequential nucleotide dispensation (Pyrogram™) in accordance with an embodiment of the present invention. The template is a mock single-stranded DNA mimicking 100% methylation derived from mixtures of plasmids containing the PCR fragments of H19 imprinting region within the colorectal cancer cell line Colo205. Shaded areas highlight the two CpG sites of interest. The sequence of the nucleotide dispensation ("AGCTCGTCAGTG"; not itself a nucleotide sequence) for the pyrosequencing reaction is shown at the bottom of the panel, and where the region being sequenced is 16 nucleotides downstream from the sequencing primer (i.e., nucleotides 117-132 of SEQ ID NO:5, which correspond to nucleotides 7992-8007 of SEQ ID NO:2 (NCBI accession AF125183). "Disp. seq" refers to dispensed sequenced, and "Exp. seq" refers to expected sequences of the H19 imprinting center (IC) surrounding the two CpG sites of interest within nucleotides 117-132 of SEQ ID NO:5.

FIG. 2, shows a graphical representation of the light profile of CpG sites generated by sequential nucleotide dispensation (Pyrogram™). The emitted light pulse is in direct proportion to the molar quantities of the nucleotides present in the sample. The interogated templates are mock single-stranded DNA mimicking 0% methylation (FIG. 2A), 50% methylation (FIG. 2B) and 100% methylation (FIG. 2C) derived from mixtures of plasmids containing the PCR fragments of H19 imprinting region within the colorectal cancer cell line, Colo205. Shaded areas highlight the two CpG sites of interest. The percentage of cytosine correlates with the percentage of methylation on PCR-amplified bisulfite modified DNA. "Disp. seq" refers to dispensed sequenced, and "Exp. seq" refers to expected sequences of the H19 imprinting center (IC) surrounding the two CpG sites of interest. Inclusion of a cytosine (fourth nucleotide) and an adenosine (eighth nucleotide) in the dispensation order function as internal controls for accurate quantification of nucleotides in the template.

Figure 3A:
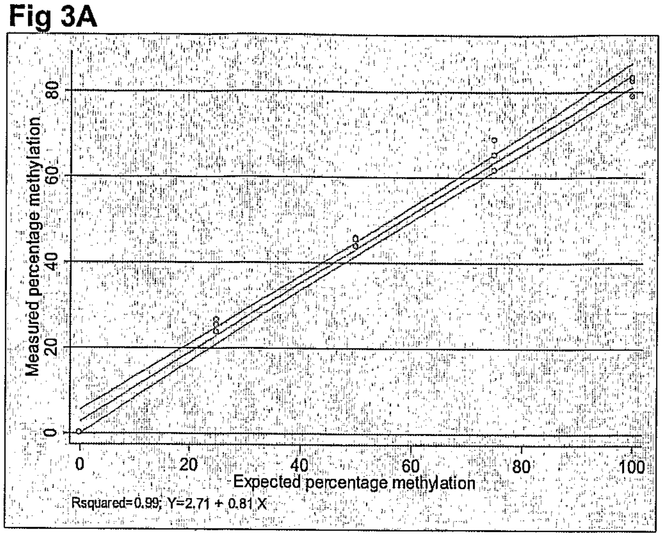
FIG. 3A shows an allele-specific methylation assay of cloned PCR products with known percentage of methylation (0, 25, 50, 75, 100) of C alleles probed with sequencing primers specific for the G allele, in accordance with an embodiment of the present invention. The concordance of the measured percentage of methylation and the expected percentage of methylation is represented as the solid line and the confidence belt, corresponding to 2 standard errors, as gray lines. Three separate measurements were performed.
Figure 3B:
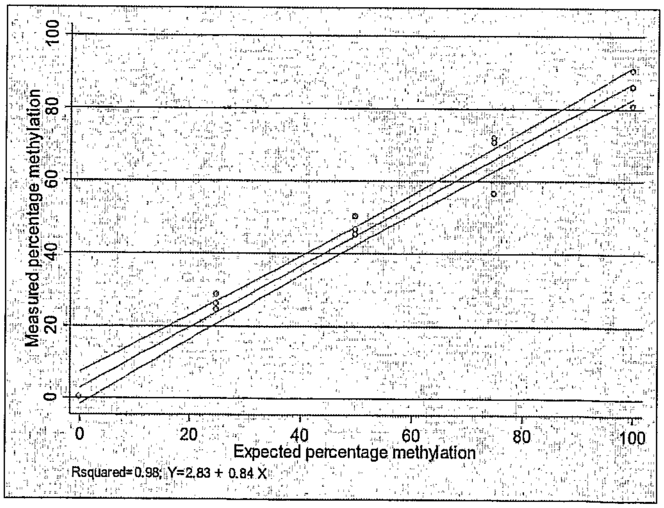
FIG. 3B shows an allele-specific methylation assay of cloned PCR products with known percentage of methylation (0, 25, 50, 75, 100) of A alleles, in accordance with an embodiment of the present invention. The concordance of the measured percentage of methylation and the expected percentage of methylation is represented as the solid line and the confidence belt, corresponding to 2 standard errors, as gray lines. Three separate measurements were performed.

To determine the analytical sensitivity of the new allele-specific methylation assay, the degree of methylation density on single-stranded DNA fragments that were cloned into plasmids, i.e. mock DNA of ascending CpG methylation density (0, 25, 50, 75, 100 percent methylation), was measured. The assay may accurately detect percentages of methylation as low as zero percent (FIG. 3). At low percentages of methylation (<50 percent), this methodology correctly identifies the percentage of allele-specific methylation within 3 percent (refer also to "reproducibility," below).

To assess the specificity of the new assay in measuring methylation in an allele-specific manner, the allele-specific sequencing primers were tested on the corresponding allele of the SNP, i.e., the sequencing primer specific for the G allele was tested on the DNA fragment with the T allele and vice versa. CpG methylation was only detected by the sequencing primers specific for the allele; no mis-priming of the allele-specific primers was observed.

To examine the reproducibility of the inventive assay embodiment in determining allele-specific methylation, the variability among the replicates of three, for each CpG site, were estimated. Reliability is defined as the extent to which the methylation measurement on a given DNA strand with known percentage of methylation is reproducible over independent measurements as compared to the known ("true") methylation status. The allele-specific methylation assay is highly reproducible on a linear scale (FIG. 4).

Methylation of the CpG dinucleotides in the present assay embodiment reflects methylation in the region that regulates H19 genomic imprinting. An established but labor-intensive methodology (genomic bisulfite sequencing) was used to quantitate the methylation levels at CpG dinucleotides within the H19 imprinting center.

Figure 4:
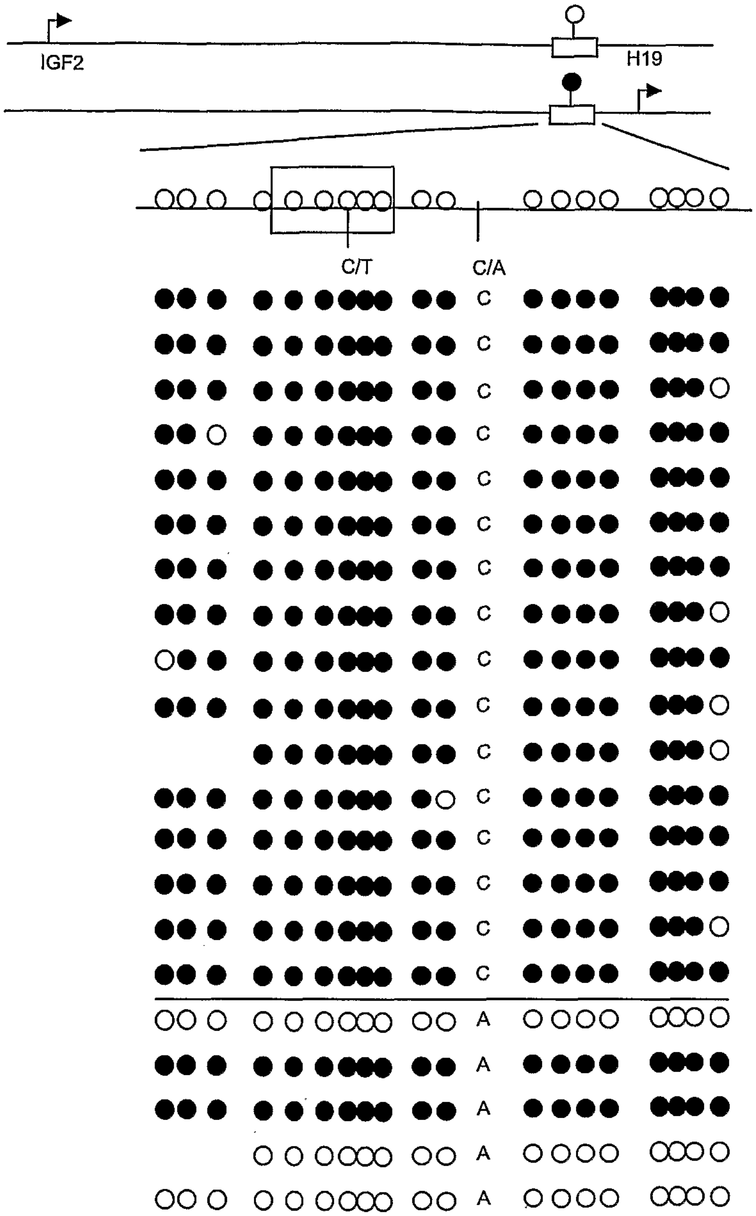
FIG. 4 shows the methylation levels in the colorectal cancer cell line, Colo205, that is heterozygous for a SNP in the near the H19 imprinting center (rs2071094, dbSNP build 124) in accordance with an embodiment of the present invention.
Figure 5A:
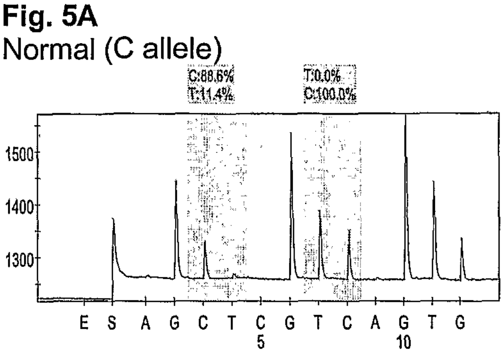
FIG. 5A shows the degree of methylation in bladder tissue with normal margins that show normally-imprinted IGF2 expression (mono-allelic expression; data not shown) in accordance with an embodiment of the present invention. Methylation on the parental allele is marked by the C allele of a C/A SNP within the H19 IC. The sequence of the nucleotide dispensation ("AGCTCGTCAGTG"; not itself a nucleotide sequence) for the pyrosequencing reaction is shown at the bottom of the panel, and where the region being sequenced is 16 nucleotides downstream from the sequencing primer (i.e., nucleotides 117-132 of SEQ ID NO:5, which correspond to nucleotides 7992-8007 of SEQ ID NO:2 (NCBI accession AF125183).
Figure 5B:
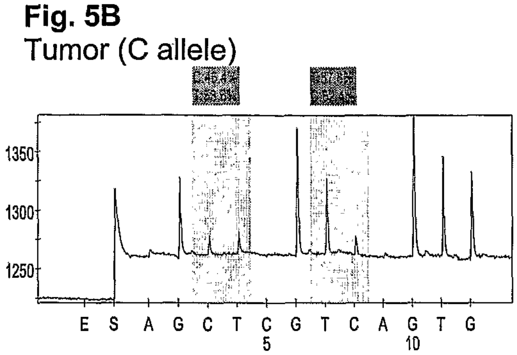
FIG. 5B shows the degree of methylation in bladder tumor tissue that shows loss of imprinting in accordance with an embodiment of the present invention (biallelic expression, data not shown). Methylation on the parental allele is marked by the C allele of a C/A SNP within the H19 IC. The sequence of the nucleotide dispensation ("AGCTCGTCA-GTG"; not itself a nucleotide sequence) for the pyrosequencing reaction is shown at the bottom of the panel, and where the region being sequenced is 16 nucleotides downstream from the sequencing primer (i.e., nucleotides 117-132 of SEQ ID NO:5, which correspond to nucleotides 7992-8007 of SEQ ID NO:2 (NCBI accession AF125183).
Figure 5C:
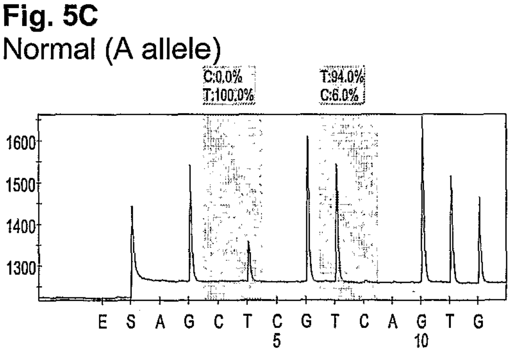
FIG. 5C shows the degree of methylation in bladder tissue with normal margins that show normally-imprinted IGF2 expression in accordance with an embodiment of the present invention (mono-allelic expression; data not shown). Methylation on the parental allele marked by the A allele. The sequence of the nucleotide dispensation ("AGCTCGTCA-GTG"; not itself a nucleotide sequence) for the pyrosequencing reaction is shown at the bottom of the panel, and where the region being sequenced is 16 nucleotides downstream from the sequencing primer (i.e., nucleotides 117-132 of SEQ ID NO:5, which correspond to nucleotides 7992-8007 of SEQ ID NO:2 (NCBI accession AF125183).
Figure 5D:
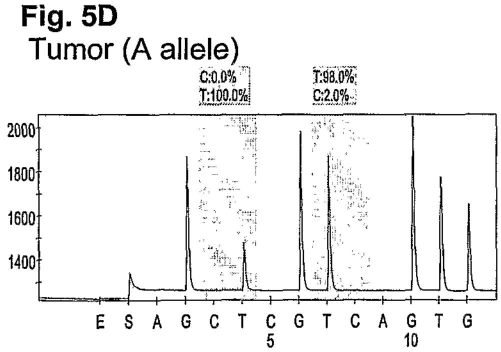
FIG. 5D shows the degree of methylation in bladder tumor tissue that shows loss of imprinting in accordance with an embodiment of the present invention (biallelic expression, data not shown). Methylation on the parental allele is marked by the A allele. The sequence of the nucleotide dispensation ("AGCTCGTCAGTG"; not itself a nucleotide sequence) for the pyrosequencing reaction is shown at the bottom of the panel, and where the region being sequenced is 16 nucleotides downstream from the sequencing primer (i.e., nucleotides 117-132 of SEQ ID NO:5, which correspond to nucleotides 7992-8007 of SEQ ID NO:2 (NCBI accession AF125183).

FIG. 4 summarizes the methylation levels in the colorectal cancer cell line, Colo205, that is heterozygous for a SNP near the H19 imprinting center (rs2071094, dbSNP build 124). The H19 IC is normally methylated on the paternal allele and unmethylated on the maternal allele at binding sites for the protein CCTCF binding factor (CTCF) that functions as a chromatin insulator and binds to the H19 IC in a methylation-dependent manner. The methylation of CpG dinucleotides surrounding the sixth of the seven binding elements in the human H19 IC was measured. These regions were shown to be differentially methylated in humans (Takai, D. et al., *Hum Mol Genet* 10:2619-26, 2001). The data show that the CpG dinucleotides adjacent to the SNP in the present assay predict methylation at the five CpG sites within the H19 IC.

While genomic bisulfite sequencing provides information on the methylation status of all CpG dinucleotides across the chromosomal region of interest, this methodology may be susceptible to cloning and selection bias (Grunau, C. et al., *Nucleic Acids Res* 29:E65-5, 2001). Preferential amplification or cloning of one of the parental alleles may result from either the presence of a SNP in the region or the methylation pattern converted to a three-nucleotide chromosomal fragment. Hence, the cloning and/or selection bias is reflected as an artifactual change in the ratio of the maternal versus paternal alleles, i.e., artifactual allele-specific methylation status and thus, artifactual imprinting status.

Allele-specific methylation in the H19 imprinting center may predict a loss of IGF2 imprinting. Allele-specific methylation in the H19 imprinting center regulates the parent-specific expression of the imprinted gene, Insulin-like Growth Factor −2. In an example of a paired normal tissue and bladder tumor tissue, the allele-specific methylation in the H19 IC, as measured by the present methodology, correlates with IGF2 imprinting status (FIG. 5). The IGF2 gene is normally imprinted in the normal tissue as demonstrated by mono-allelic expression. The allele-specific methylation in the H19 IC is retained where the allele marked by the C allele is methylated; the allele marked by the A allele is unmethylated. The IGF2 gene was expressed biallelically in the paired bladder tumor. This loss of imprinting corresponds to the loss of allele-specific methylation where the methylation on the initially methylated allele is reduced to nearly half.

The present Example, therefore, demonstrates application of a representative embodiment of a strategy having substantial utility for measuring loss of imprinting based on DNA methylation and the use of a genetic marker. The methylation status of the CpG sites in the assay predicts methylation in the H19 IC and the imprinting status of the gene of interest. This methodology is als applicable, for example, to assess differential gene expression due to regulation by allele-specific methylation including parent-specific Alu methylation (Sandovici, I. et al., *Hum Mol Genet* 14:2135-43, 2005), X chromosome inactivation, differential promoter and insulator activity, or non-coding RNA.

EXAMPLE 2

A Loss of Imprinting (LOI) Assay was Developed Using MethyLight™ Technology

Overview

MethyLight™ is a quantitative and sensitive technique that was developed to measure DNA methylation (Eads et al., (1999) *Cancer Res.* 59, 2302; Eads et al (2000), *Nucleic Acids Res* 28, e32). MethyLight™ analysis typically comprises prior bisulfite modification of DNA followed by subsequent fluorescent-based real-time PCR amplification of methylated DNA using Taqman® technology. As previously stated, DNA methylation that occurs at the 5-carbon position of cytosine (C) in a CpG context protects these cytosines from bisulfite-induced deamination. The unmethylated cytosines, however, undergo deamination that converts them to uracil. Following PCR amplification of the bisulfite modified DNA, methylated cytosines will remain cytosines while the uracil residues derived from the unmethylated cytosines will be replaced by thymines (T). Three oligonucleotides (forward and reverse primers, and a interpositioned non-extendable fluorescent probe) are used in the subsequent PCR amplification. All three may be specific towards methylated DNA; e.g., where they contain several CpG sites in their sequence.

Methylated DNA templates amplified by methylation-specific primers are detected in a quantitative fashion due to the release of the fluorophore from the methylation-specific probe following its specific hybridization to the PCR amplicon. The rate of release of the fluorescence signal is proportional to the initial concentration of the DNA template. The MethyLight™ assay platform may be used to generate detailed methylation profiles of many types of normal and cancerous tissues.

In this Example, MethyLight™ technology is used in the present inventive context as a tool to detect allelic-specific methylation, a phenomenon that is frequently associated with genomic imprinting. Similarly, loss of allele-specific methylation accompanied by loss of imprinting (LOI) can also be identified by this technology.

MethyLight™-based LOI Assays for the IGF2 Gene

The well characterized IGF2 locus was used as a model for the LOI assay. The IGF2 gene is expressed exclusively from the paternal allele, while the maternal allele is silenced by DNA methylation. The imprinted marks for this locus are linked to several differentially methylated regions (DMRs), three of which are located in the body of the IGF2 gene itself, and one is located upstream of the neighboring H19 gene.

LOI of the IGF2 locus in colorectal cancer (CRC) have been shown to be associated with changes in DNA methylation of one of the IGF2 DMRs (Cui et al., *Cancer Res* 62:6442, 2002), as well as the H19 DMR (Nakagawa et al., *Proc Natl Acad Sci USA* 98:591, 2001). The IGF2 DMR comprises three CpG sites located in the second intron of the IGF2 gene. The methylation status of these three CpG dinucleotides was determined in an allele-specific fashion in the MethyLight™ assay system. Five reactions specific for the methylated IGF2 DMR (M3, M4, M5, M6, and M7) and one reaction (U1) that targets an unmethylated IGF2 DMR locus were designed. The methylation- and bisulfite-specificities for all 5 reactions, and optimization of the PCR conditions against cross-hybridization for the IGF2-M3 and M4 reactions were then tested.

Development and Optimization of the IGF2 LOI Assay

Figure 6A:
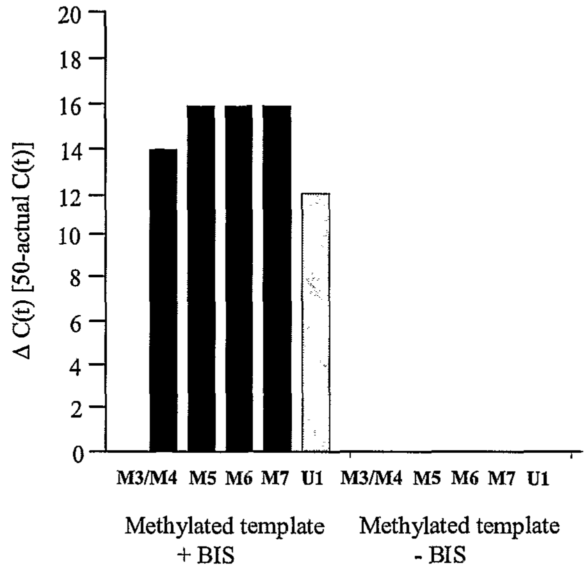
FIG. 6A shows an analysis of a bisulfite conversion and methylation in accordance with an embodiment of the present invention. All of the methylation reactions M3, M4, M5, M5, and M7 (in black) as well as the unmethylated reaction U1 (in gray) were tested against fully-methylated template (M. SssI-treated DNA) that has been bisulfite converted (-BIS). Conversion specificities are presented using ΔC(t) values. Because the MethyLight™ reactions are based on a 50 cycle PCR program, a sample that does not amplify has a C9g) value of 50. These reactions were specific towards bisulfite-converted DNA as there was no signal of each reaction on unconverted DNA (-BIS).
Figure 6:
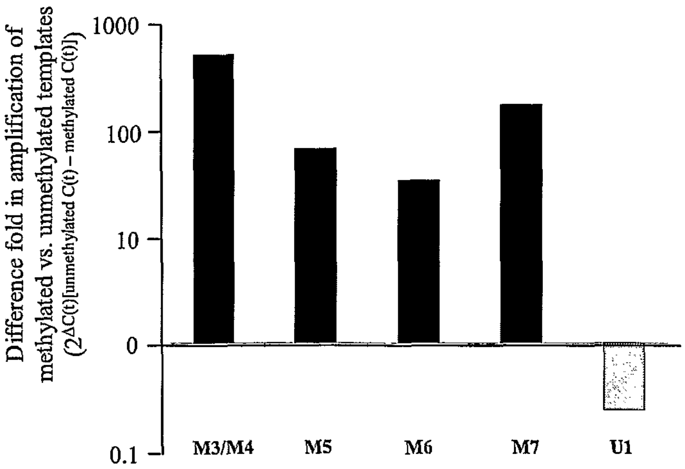
FIG. 6B shows an analysis of the bisulfite conversion and specificity. The same reactions as in FIG. 6A were tested against fully-methylated template DNA (M. SssI-treated DNA) and fully-unmethylated DNA (Phi29 amplified DNA) for methylation specificity in accordance with an embodiment of the present invention. The data are presented as $2^{\Delta C(t)[unmethylated\ C(t)-methylated\ C(t)]}$.

Bisulfite specificity of the IGF2 MethyLight™ reactions. As mentioned above, MethyLight™ reactions are not only specific for detecting methylated DNA, but are also specific for bisulfite-converted DNA, as cytosines in a non-CpG context will be converted to uracil and thymine after bisulfite-conversion and MethyLight™, respectively. The presence of a Cs in a CpG context, distributed across both primers and the probe may confer a high degree of specificity for bisulfite converted DNA in the MethyLight™ reaction, and thus non-specific amplification of un-converted DNA is unlikely. Between 15 and 16 such cytosines were covered by the IGF2 DMR LOI primers/probe sets (underlined nucleotides in TABLE 1B). No PCR products were detected when these reactions were tested on unconverted DNA samples (FIG. 6A), indicating that the reactions are specific for bisulfite-converted DNA.

Methylation specificity of the MethyLight™ reactions. The methylation specificity of each MethyLight™ assay is reflected by the number of CpGs covered by the primer/probe set. For the IGF2 LOI assay, there are only three CpGs that comprise the IGF2 DMR. Since these CpGs are closely clustered, they were included in the forward primer of each methylated primer/probe set (TABLE 1B). The reverse primer of each methylated reaction also contains a single CpG that is not known to be part of the DMR. However, since the DMR is not located in a CpG island (regions of the DNA with high CpG density that usually are not methylated), the CpG may also be methylated. A MethyLight™ reaction specific for the unmethylated IGF2 allele (IGF2-U1, HB-347), in which the three CpGs of the DMR have been converted to TpGs (TABLE 1B) was designed.

The methylation specificities of these primers were evaluated against two DNA samples. First, a genomic DNA treated in vitro with the M.Sssl CpG methylase was used as a positive control for IGF2 methylation. Second, a template DNA in which CpG methylation was nearly completely removed was used. To generate unmethylated DNA, the REPLI-g kit (Qiagen) that utilizes the Phi29 DNA polymerase for whole genome amplification was used. As Phi29 DNA polymerase amplifies genomic DNA, the methylation information cannot be retained, and therefore unmethylated DNA is generated during the reaction. Both methylated and unmethylated DNAs were subsequently bisulfite modified and tested with the methylation-specific IGF2 MethyLight™ primers.

The fully methylated DNA template was readily amplified by the methylation specific reactions (M3, M4, M5, M6 and M7), and less efficiently amplified by the unmethylated reaction (U1) (FIG. 6B). When using the methylation specific primers, a limited amplification of Phi29-treated DNA was detected, whereas the unmethylated primer/probe set produced a very robust PCR product. In comparison, the difference in amplification for the methylated and unmethylated substrates was of 1-2 orders of magnitude for the methylation specific reactions, suggesting that these are specifically targeting methylated DNA. For the unmethylated reaction there was only a 5-fold difference between the amplification of unmethylated vs. methylated templates. (FIG. 6B), however, there was still preference of the IGF2-U1 reaction for unmethylated DNA.

Allelic discrimination for the IGF2 DMR LOI reaction. To distinguish between the two parental alleles, a single nucleotide polymorphism (SNP) in the IGF2 DMR was identified. For this, 60 DNA specimens from normal individuals of Chinese origin were sequenced. A SNP (C/T) located at nucleotide 99318 (GenBank Accession Number AC132217, SEQ ID NO:13) was identified that had a 50% frequency in the analyzed population. The existence of this SNP in other populations was later confirmed by searching the dBSNS database (SNP Accession Number rs3741210, SEQ ID NO:14). Next, this SNP was used to discriminate between heterozygous parental alleles (C allele vs. T allele). This SNP, which involves a cytosine in a non-CpG is potentially problematic when using bisulfite-converted DNA because the SNP defining cytosine will be converted to thymine after bisulfite conversion and PCR, thus eliminating the ability to discriminate individual alleles. However, it was reasoned that if the strand was assayed on the complimentary DNA strand, the SNP is either G/A, and not susceptible to the effects of bisulfite. Therefore the IGF2 MethyLight™ reactions were designed based on the complimentary DNA strand and generated reactions specific for each polymorphism.

Due to specific DNA sequence characteristics, such as the relative large distance between the SNP and the DMR, as well as specific criteria required for the design of MethyLight™ reactions, the SNP was included in the probe (TABLE 1B) sequence with the three CpGs of the IGF2 DMR located in the forward primer in the MethyLight™ reactions. However, depending of the DNA sequence interrogated, LOI assays can also be designed such that the allelic discriminatory SNP and the methylation specific CpGs are distributed differently between the three oligomers (MethyLight™ primers and probe). For example, all the CpGs of the DMR can be targeted by any one of the oligonucleotides of the primer/probe set, and the SNP is contained by any of the remaining oligonucleotidess—there are 6 possible combinations of primers/probe sets that can be derived this way. Moreover, the allelic discriminatory SNP and the methylation specific CpGs can also be included together on any of the forward or reverse primers, or the fluorescent probe. In this situation, the other two oligomers would only be bisulfite specific. In this way three different primer/probe sets can be designed. The methylation-specific CpGs can also be distributed among the two primers and the probe, with the SNP located on any of the primers or probe. In these scenarios, another 18 possible combinations of primers/probes sets can be considered.

Two probes were designed, one specific for the C allele, and one for the T allele, both with a 5' FAM fluorophore and a 3' minor groove binding non-fluorescent quencher (MGB-NFQ) to satisfy the PCR melting temperatures. Because the allelic discrimination of these probes relies on a single nucleotide difference, the SNP-defining nucleotides were placed in the center of the probe sequence to maximize allelic specificity and minimize allelic-cross hybridization.

Additionally, non-fluorescent probes (cold probes) were used to prevent cross-hybridization between the MethyLight™ probe and the non-targeted alleles in the assay. These competitor probes have the same sequence with the 3' MGBNFQ, but do not contain the 5' FAM fluorophore. For example, cold probe containing the C SNP is added together with a fluorescent probe targeting the T SNP in order to reduce the cross-hybridization of the T-specific fluorescent probe with the C-specific allele.

Figure 7A:
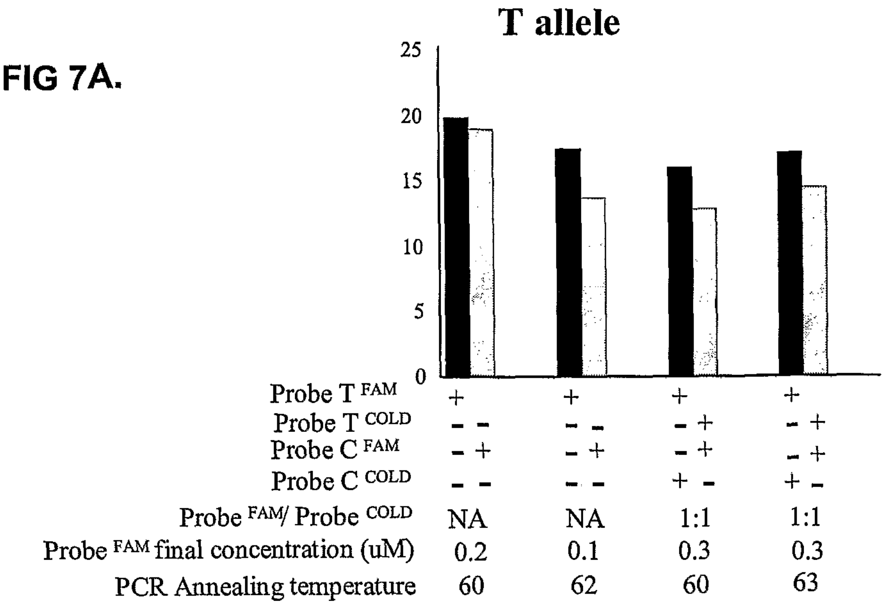
FIG. 7A shows optimization results for the IGF2 LOI assay in accordance with an embodiment of the present invention. The probe specific for the T allele was tested for non-specific hybridization against templates homozygous for the two different alleles (C and T alleles) using the IGF2-M3 and IGF2-M4 reactions (HB-322 and HB-333, respectively).
Figure 7B:
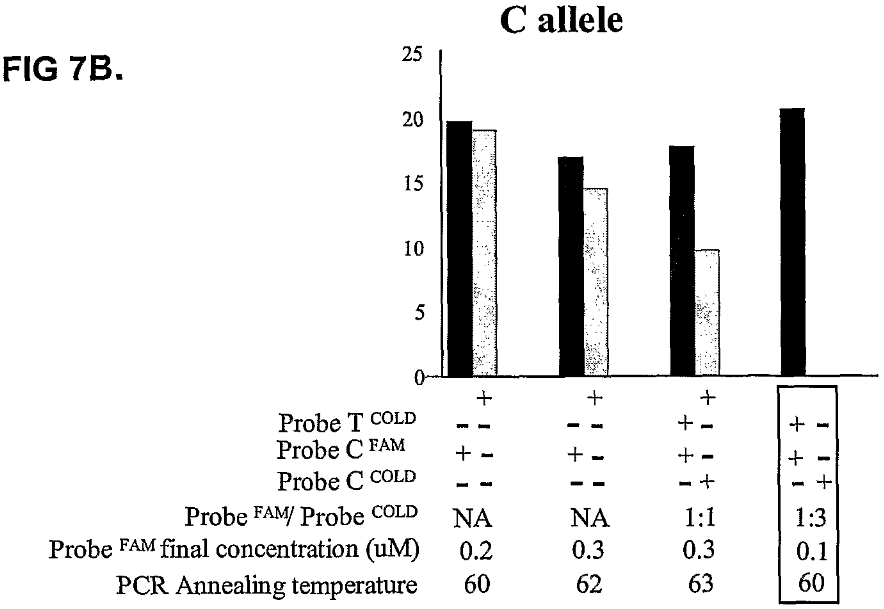
FIG. 7B shows optimization results for the IGF2 LOI assay in accordance with an embodiment of the present invention. The probe specific for the C allele was tested for non-specific hybridization against templates homozygous for the two different alleles (C and T alleles) using the IGF2-M3 and IGF2-M4 reactions (HB-322 and HB-333, respectively). The best results of the optimization experiments are presented together with the various combinations of parameters that have been varied are boxed.

Each MethyLight™ reaction specific for IGF2 methylation was evaluated on both combinations of fluorescent and cold probes (fluorescent T-probe with cold C-probe, and fluorescent C-probe with cold T-probe) Using DNA templates homozygous for each SNP (C/C or T/T) (FIG. 7A). The non-specific cross hybridization of a T probe to a C allele was completely eliminated when a fluorescent probe and a non-fluorescent probe were used in a 1:3 ratio (0.1 μM vs. 0.3 μM final concentration in the PCR amplification) and a 60° C. annealing temperature (FIG. 7B; boxed conditions). However, the non-specific cross hybridization of a C probe to an T allele was diminished but not completely eliminated when using a 1:1 ratio (0.3 μM vs. 0.3 μM final concentration) of the fluorescent probe and a non-fluorescent probe and 63° C. annealing temperature (FIG. 7A). It will be obvious to those of ordinary skill in the relevant art that, once given the context of the present inventive aspects, optimization of probe ratios and concentrations to enhance the discriminatory qualities of the C probe can be accomplished without undue experimentation. Such optimization may, for example, include testing PCR primers that are more stable at higher temperatures (TABLE 1B), or designing probes with two mismatches adjacent to the SNP.

While the description above refers to particular embodiments of the presently claimed invention, it will be understood that many modifications may be made without departing from the spirit thereof. The presently disclosed embodiments are therefore to be considered in all respects as illustrative and not restrictive.

TABLE 1A

| Reaction Number | HUGO Gene Nomenclature | UniGene Number | Reaction ID | Chromosomal Location | GenBank Accession Number | Amplicon Location (GenBank Numbering) | Amplicon Location (UCSC Numbering)[a] | UCSC Strand (+/−) | Reaction Type |
|---|---|---|---|---|---|---|---|---|---|
| HB-332 | IGF2 | Hs.523414 | IGF2-M3B | 11p15.5 | AC132217 | 99277-99359 | 2126075-2126157 | — | Methylated |
| HB-333 | IGF2 | Hs.523414 | IGF2-M4B | 11p15.5 | AC132217 | 99277-99359 | 2126075-2126157 | — | Methylated |
| HB-351 | IGF2 | Hs.523414 | IGF2-M5B | 11p15.5 | AC132217 | 99273-99361 | 2126073-2126161 | — | Methylated |
| HB-345 | IGF2 | Hs.523414 | IGF2-M6B | 11p15.5 | AC132217 | 99271-99362 | 2126072-2126163 | — | Methylated |
| HB-346 | IGF2 | Hs.523414 | IGF2-M7B | 11p15.5 | AC132217 | 99270-99364 | 2126070-2126164 | — | Methylated |
| HB-347 | IGF2 | Hs.523414 | IGF2-U1B | 11p15.5 | AC132217 | 99277-99359 | 2126075-2126157 | — | Unmethylated |

TABLE 1B

| Reaction No. | Forward Primer Sequence[c] | Reverse Primer Sequence[c] | Probe Oligo Sequence[c] |
|---|---|---|---|
| HB-332 | **CG**AGGTTAGTGAGGGA**CG**GC (SEQ ID NO:15) | CCT**CG**ATCCACCCAAAATAATATCTATAA (SEQ ID NO:16) | 6FAM-AAAAATTCATTTCCCCAAAAA-NFQMGB (SEQ ID NO:17) |
| HB-333 | **CG**AGGTTAGTGAGGGA**CG**GC (SEQ ID NO:18) | CCT**CG**ATCCACCCAAAATAATATCTATAA (SEQ ID NO:19) NFQMGB | 6FAM-AAAAATTCACTTCCCCAAAAA- (SEQ ID NO:20) |
| HB-351 | GA**CG**AGGTTAGTGAGGGA**CG**GC (SEQ ID NO:21) | AACTCCT**CG**ATCCACCCAAAATAATATCTATAA (SEQ ID NO:22) | 6FAM-AAAAATTCAYTTCCCCAAAAA-NFQMGB[b] (SEQ ID NO:23) |
| HB-345 | TGA**CG**AGGTTAGTGAGGGA**CG**GC (SEQ ID NO:24) | CAAACTCCT**CG**ATCCACCCAAAATAATATCTATAA (SEQ ID NO:25) | 6FAM-AAAAATTCAYTTCCCCAAAAA-NFQMGB[b] (SEQ ID NO:26) |
| HB-346 | CTTGA**CG**AGGTTAGTGAGGGA**CG**GC (SEQ ID NO:27) | CCAAACTCCT**CG**ATCCACCCAAAATAATATCTATAA (SEQ ID NO:28) | 6FAM-AAAAATTCAYTTCCCCAAAAA-NFQMGB[b] (SEQ ID NO:29) |
| HB-347 | **TG**AGGTTAGTGAGGGA**TGGTG**TG (SEQ ID NO:30) | CCT**TG**ATCCACCCAAAATAATATCTATAA (SEQ ID NO:31) | 6FAM-AAAAATTCAYTTCCCCAAAAA-NFQMGB[b] (SEQ ID NO:32) |

[a]UCSC Assembly date: May 2004

[b]Y was used for simplification to represent either a T or a C in the allelic discriminatory nucleotides of the SNP. Each set of primers should be used with only a C-containing probe or a T-containing probe.

[c]The underlined nucleotides represent the unmethylated cytosines that have been converted to uracils and thymines after bisulfite conversion and PCR, respectively. The CpG nucleotides interrogated by the Methyl ight primers are in bold.

The invention claimed is:

1. A high-throughput method for quantifying allele-specific genomic DNA methylation, comprising:

obtaining a sample having genomic DNA, the genomic DNA comprising at least one allelic locus comprising at least one homozygous CpG dinucleotide sequence, the allelic locus also being heterozygous for at least one allele-specific sequence polymorphism, such that one member of the at least one homozygous CpG dinucleotide sequence is an allele-specific CpG dinucleotide sequence;

contacting the genomic DNA with a reagent or reagents suitable to convert cytosine, but not 5-methylcytosine, to uracil or another base dissimilar to cytosine in terms of hybridization behavior to provide converted DNA;

amplifying the converted DNA by polymerase-mediated amplification; and quantifying the methylation level of the at least one allele-specific CpG dinucleotide sequence using a real-time methylation assay comprising the use of at least one allele-specific reagent that distinguishes the alleles based on the at least one allele-specific sequence polymorphism, wherein the at least one allele-specific sequence polymorphism is an allele-specific sequence polymorphism distinct from but sufficiently proximate to the at least one allele-specific CpG dinucleotide sequence to provide for distinguishing the methylation levels between the two alleles, and wherein the methylation assay comprises the use of at least one set of primers and at least one probe, wherein one of the primers is specific to the allele-specific sequence polymorphism on one DNA strand or on the complementary DNA strand, and wherein the at least one allele-specific CpG dinucleotide sequence is included in the at least one probe but not the primers.

2. The method of claim 1, wherein the at least one allele-specific sequence polymorphism is an allele-specific single nucleotide polymorphism (SNP) sufficiently proximate to the at least one allele-specific CpG dinucleotide sequence to distinguish the methylation levels between the two alleles.

3. The method of claim 1, comprising measuring the relative methylation of each parental allele by comparing the sample with an in vitro methylated DNA sample that is also heterozygous for the at least one allele-specific sequence polymorphism.

4. The method of claim 1, wherein the methylation assay comprises a real-time, quantitative methylation analysis comprising the use of a plurality of primer pairs and a plurality of probes.

5. The method of claim 1, wherein, where the primer specific to the allele-specific sequence polymorphism comprises a genomic cytosine residue position, the at least one primer is specific to the sequence on the converted DNA strand that is complementary to that of the genomic cytosine residue position.

6. The method of claim 1, wherein a plurality of allele-specific CpG dinucleotide sequences are present on the at least one probe.

7. The method of claim 1, further comprising, based on the quantifying, classifying an individual as to whether they have loss of imprinting (LOI).

* * * * *

SEQUENCE LISTING

<160> NUMBER OF SEQ ID NOS: 32

<210> SEQ ID NO 1
<211> LENGTH: 51
<212> TYPE: DNA
<213> ORGANISM: Homo sapiens
<220> FEATURE:
<221> NAME/KEY: allele
<222> LOCATION: 26
<223> OTHER INFORMATION: M is A or C

<400> SEQUENCE: 1
cacacatcac agcccgagcc cgcccmaact ggggttcgcc cgtggaaacg t 51

<210> SEQ ID NO 2
<211> LENGTH: 25738
<212> TYPE: DNA
<213> ORGANISM: Homo sapiens

<400> SEQUENCE: 2
gatccctgag atgaagtggc tctgtcagga ttcaatcaga gaagcaccac ctcctcacgg 60
tcaaagggca ggggctttgt tggaagggat cggaccttct gccaagatgg agctccaggc 120
tgtctgtgag acgctactgc ccggctctgg ggctgggcct gaagccagca ggacaggtgg 180
tcaggaaaga agatgggcaa gaagtgggaa ggggcaaggg ccacctggac ttcacgaggc 240
cacacgtgaa cccacgtgga cagtccagtg ccctacatct gtctcttacc actttatgct 300
gcactgaata atgttccctg gaaattcatg tccacccagg acctgtgagt gtccccggaa 360
attcatgtcc acccaggacc tgtgagtgtc cccggaaatt catgtccacc caggacctgt 420
gagtggggtc ttctgtggac aagggctttt gtgggtgcaa ccaaataaag acaaagtcac 480
actgaattga ggcgggggga agcatccatt caatgagtgt cgtccttgta acaagaggga 540
aatttgcaca cagagacaga cacacagtgg aggaggccgt gtgaagacag aggcagagac 600
tggagcaacg cagccacaca ccacaggaca cctggagccc ccagaagcca gaaggggcaa 660
ggaggggcca cgctagggcc ttgcgaaaga gggcggccct gccctcccct gggtggtgaa 720
cctctgggct ccagagctgt gagagagtcc attcctatgg ctaaagccac ccagtctgtg 780
atcactgtca cagcagcccc aggaatcaaa cccctccaat cccaaaacac aggggacatc 840
cggaggagca agcacccctc accagggggc cacagacacc catggcccag gacccagagg 900
agctgcaggc ttagggccca gggccagcag gctgagccag ggacggtgac accaggcatg 960
cgcagcagca gcacccaggc agcaccccag cagatgccaa tgtggtggcc gcttccaccc 1020
actggtcacg ttgcagccgg gtgagtctgc cagggctgcc gcaacaaacc gccatggacc 1080
gggaggctta aatgagggaa atatatcctc tcccagtcct ggaggctgga gtccaagatc 1140
agggctgctg cagagctggg tcctccaagg cctctctcct tggcttatag atcctgcctt 1200
ctccacatgt cctcacgggg tcatccctcc gtgtgtgtct gtgtcctcct ctcctcttcc 1260
tataaggaca cagtcctatg agactgtgct cacccctgct cacatcagga gaacggtcct 1320
gtgtctcctc tcgggacctc atcttcatgc ctccccccttg gttaccccac ggtcaggact 1380
cagccaccag cgtgagccca cacaccggct ctggagtggt gggcacaggt gagagggagg 1440
tacagctgcc acagccagga aaccccagga cgatcctgaa tgggcccaga gctggctttt 1500
ctctgtcacg gagagagaca tgagagggtc atgagtgtga agatcgccag ctcccagggt 1560
cagggcccag cctccttcca tctcactgct ctggactcct cagttcctca tggagtctgt 1620
ttagtgcctc tccagaaaag acaagttgaa gccctgacca ccagcatctc agagcacgaa 1680

-continued

```
ctcatttgga aatagggtca ttatagacgc aatcgatcag gtcagactgc agtagggcag   1740
gccctgaatc aaacatcatg gtgtcctcac aggtagagga gaggcacgag agagcaacgc   1800
tgcgtgaagg cgcaggatga gagcatcctg gaagatgggc acggctgggg tgacaggtct   1860
gggagcctgg gaacactggg aaagtcggcc agcactggag cctcccttag agctcgaaga   1920
aggagccagc cctgaccacc ccgactctga ccttctagca tcgaaacagg gagagacgca   1980
ttccacgtgg ttgttccaat cagcccagtt tctggggctt ccttatggca gcctcaggga   2040
actggcaaag cccaagtggg ctatcccatt acttatatct gggtaggtcc cagccacagg   2100
ggagagagaa gagaaagccc ctctatctaa tgacacgctg tactcatgtc ccacccgcat   2160
gatgtgccgt acccgtgtcc ctatccaggt gacgtgccgt acccgtgtcc cacccgggtg   2220
acgtgccgta cccgtgtccc acccgggtga cgtgccgtac ccgtgtccca cccgggtgac   2280
gtgccgtacc cgtgtcccac ccgggtgacg tgccgtaccc gtgtcccacc cgggtgacgt   2340
gccgtacccg tgtcccaccc gggtgacgtg ccgtacccgt gtcccacccg ggtgacgtgc   2400
cgtacccgtg tccctatcca ggtgacgtgc cgtacccgtg tcccacccag gtgatgtgct   2460
atgcccatgt cccacccagg tgacacgcta tacctgtgtc cctatccagg tgacacgctg   2520
tgccatgtcc ctatccgggt gacactgtgc catatcccta tccaggtgac acacagtgct   2580
catgtgtcta tctagatgac agcaccgtgc ccacatcttt atcccggtga cagcactgtg   2640
cccacgtcct gtcttggtga catcactgtg gttatatacc tgtccatgtg acatcactgt   2700
gcccacatct gcctccaggt gacagcgctg tgcccacatc cccacccaag tgctctgggc   2760
accttggctg gggctctggc cactttcatg ttggtgccac cctgtgtgtg gatcatagca   2820
cccaggcact caccattacc gtggccagca cagaccagac ccgaccccag tagtcctcaa   2880
aactaggtcc cctgctgggt gcggtggctc acgcctgtaa tcccagcact ttgggaggct   2940
gaggcgggcg gatcacaaga tgaggagatc gagaccaacc tggctaacac ggtgaaaccc   3000
catctctact aaaaatacaa aaaattagcc gggtgaggtg gtgggcgcct gtagtcccac   3060
ctacttggga ggctgaggca ggagaatggt gtgaacccgg gaggcggagc ctgcagtgag   3120
ccgagatcat gccactgcac tccagcctag ggacagagc gagactcaaa aaacaaaaaa    3180
acaaacaaaa aaaaactagg tcccctgtgc tgtgctgctg taccccagca gtcgcttcac   3240
tggcaagact actcttagca ggtgcgcctg gaagcagaaa ctgggcagct cccggtctgt   3300
cctatacaca tgcaaatgcc ccattagaaa gcaaatagcc cgaggtgttt gcctgctccc   3360
aggcaaaatc tcccaaatct tcctccggga atcagtgaac agaagagatg tccatcaccc   3420
ccaggagagt agtgtctgaa cccgtctaac cgcccaacag gttctccctg ccgccggtct   3480
ggacagagct gctttatcac aacaggtgac ttgcaataaa gtttaattca cacagagtcg   3540
gccgtgcagg agaccagagt tttattatta ctcaaatcag tctcccagga aatttgggga   3600
tcaaagtttt taaggatcat ttggtgggta gggggcgagt caatagggag tgctgattgg   3660
ttgggtcaga gatgaaatca tggagagtca aagccatctt tttctgctga gtcagttcct   3720
gggtgggggc cacaagacta gatgagccag tttatcaatc tggggggtgc cagctgatcc   3780
acccagtaca gggtctgcga aatatctcaa ccactgatct taggttctgc aacagtgatg   3840
taatcctagg agcaatttga ggaggttaaa aatctttcag cctccagatg tgtgactcca   3900
tgactcctaa accataattt ctaatctgtg gctaatttgt tagtcctgaa agtctagtcc   3960
ccaggcagga agagggtctg tcctgggaaa gggctgttat tgtctttgtt tcaaagataa   4020
```

-continued

```
actataaact aagttcttcc caaagttagt ccagcctgca cccagaaatg aataagaagg   4080
caagacagag ttggttacgt cagatctctt tcattgtcat aattttctgt tatatatttt   4140
tttttttttg agacagagtt tcgctcttat catccaggct ggagtccaat ggctcgatct   4200
tggctcactg caacctccac ctccggagtt ccagtgattc tcctgcctca gcctcccaag   4260
tagctgggat tacaggcgcc caccaccatg cccagctaat ttttgtattt ttagtagaga   4320
tgggatttcg tcaggttggc caggttggtc ttgaactcct gacctcaggt gatccaccca   4380
cctcggcctc ccaaactgct gggattacag gcatgagcca ccaccgccgg ccgattttct   4440
gtaataattt ttgcagaggc ggtttcacca ggagaaccaa gcattaatgc gctgtggctg   4500
atgtgtagta gagcggcatt tcccaatggg agaaccctgg ggctgtctag gagcccatgc   4560
atggctggga gcctaatccc agggacacca ccgatgacag ctcccatagc acgtaggaca   4620
gtggatactt ggaggcaaag agaaatctct gttctgcagt ggtcatgact tggaccccaa   4680
agaacttgag cccaaggtcc agagggagac cctcccaaca gggcctccag caggaacagg   4740
gatcgtggga gcctgccaag cacagcgcac aggtatttct ggaggcttcc cattcagtct   4800
tggatgccag cctcaccgag ggcggcccat cttgctgacc tcaccaaggg aggcccgtct   4860
cactgccctg atggcgcaga atcggctgta cgtgtggaat cagaagtggc cgcgcggcgg   4920
cagtgcaggc tcacacatca cagcccgagc acgcctggct ggggttcacc cacagaaacg   4980
tcccaggtct cccaggccag gtgccgcatt ggttcccgag ggttgtcaga gatagacact   5040
catgcgacta acatcgggct atgtgtttga ttcaccccag ggtgcattgt tgaaggttgg   5100
ggagattgga ggagatgctt gggggacaat gaggtgtccc agttccttgg atgataggga   5160
tctcggccta agcgtgagac ccctcctaca gggtctctgg caggcacaga gcctgggggc   5220
tcttgcatag cacatgtgta tttctggagg cttccccttc ggtctcaccg ccccgatggt   5280
gcagaatcgg ttgtagttgt ggaatcggaa gtggccgcgc ggcggcagtg caggctccca   5340
catcacagct caagcccgcc ccagctgagg ttcacccgcg gaaacgtccc gggtcacgca   5400
agctaggtgc cgcaaggttc acgggggtag tgagggatag aacactcatg ggagccacat   5460
tgggctacgt gtctgattca ccccagggtg cactattgag ggttggggag atgagatact   5520
ttggtgacaa tgaggtgtcc ccattctttg gatgatgggg atctcggcct cagcgtgagg   5580
cccctcccac agggtctctg gcaggcacag aaactggggg ctcttgcgta gcacatgggt   5640
atttgtggac gcttcccctt ctgtctcacc acccggatgg cacagaatcg gttgtaagtg   5700
tggactcaaa agtggccgcg cggcggcagt gcaggctcac acatcacagc ccaagccctc   5760
cctggatggg gttcgcccgc ggaaacgtcc tgggtcaccc aagccaggtg ccgcagggtt   5820
ctcggaggtc ttctgggaat aggacgctca tgggagccac accacgtctt cgtatcgggc   5880
catatccacg gccgcgtggc cccaggtcac actctgaggg cttcagtgtc atggcctggg   5940
actcaagtca cgcctacccg cgtgatgagc acagcaaatt ccgccaaaag cttatacttt   6000
ccacatccat cccagagcac agatccgact aaggacagcc cccaaatccc gagccttttt   6060
ctgaactgac aattgcctcc ccagtgaaca ctctgagctt gtcaatctta agtggccaga   6120
cattaacatt cccattcagt gcaggtttga gatgctaatt taggagcttg agatgctaaa   6180
gagctgggag tgccactgct gctttattct ggggtctagg atccttgtgt tggctgagat   6240
aatctgctaa tgtgggtgca gcagacatcc cgcggtttgt ggaatcgata aaggatgggg   6300
atcaatggtg tttgtgcact gtgcggtctg tgcccaattg cctgccttgt gctgtggaat   6360
ctgtacatct ggccaacatg tgcttgtgtg agcctgacag tgcattttcc agagcctcac   6420
```

-continued ctcggctctg ccctggaggc tctgtgctgc tggaatcaga ctcaaggacc tcatcagagg 6480
accatggccc cgtatcacct gggtcaggca ctgaagctgg gacaggagag cagagacttc 6540
caaaatgagg gatccctgtg ttctgaggtg atcatgactg ggacccaagg actcaagcgc 6600
atgctccaga gggaatcgtt tcccacaagg cctttggcag gaacagggat cctgggagcc 6660
tgccaagcag agcgcacagt gttcctggag tctcgctgcc cagatgccac ggaatcagtt 6720
gaaggtatgg aaacacaggt ggccacgtgg tagcagggca ggctcaggcg tcatagcccg 6780
agcccggcta cctgtggttt gcctgcagaa acatcccggg tcaacaggcc aggcaccgca 6840
ttggttcgcg agggtcatcg gggtaggac ccttgtacga gccacatcgg gctacgtgcc 6900
tgattcaccc cagggtgcac tgttgaaggt tggggagatg agaggagata cttgggggac 6960
agtgaagtgt ccccattctt tggatgatgg ggatctcggc ctcagcgtga gacccctccc 7020
acagggtctc tggcaggctc aagagcccag gggctcttgc atagcacatg aatatttctg 7080
gaggcttccc cttcagtctc accacccgga tggtgcagaa ttggttgtag ctgtggaatc 7140
ggaagtggcc gcgtggcggc agtgcaggct cacacatcac agcccgagcc cgccccagct 7200
ggggttcgcc cgcggaaacg tcccgggtcc cgcaagccag gcgccgcagg gttcacgggg 7260
gtcatcaggg ataggacatt catgggagcc acatcgggct atgtgtctga ttcaccccag 7320
ggtgcactat tgagggttgg ggagatgaga ggagatactt gggggacaat gaagtgtccc 7380
cattctttgg atgatgggga tcttggcctc agggtgagat ccttcttgca gggtctctgg 7440
caggcacaga gcccgggggc tcttgcatag cacatgtgta tttctggagg cttccccttc 7500
agtctcaccg cccggatggc acagaattgg ttgtagttgt ggaatcggag gtggctgcgc 7560
ggcggcagtg caggctcaca catcacagcc tgagcccgcc ccagctgggg ttcgcccgtg 7620
gaaacatccc aggtcatcca agccgggcgc cacagggttc acaggggtcg tgaggtatag 7680
gacactcatg ggagccatat cgggctacgt gtctgattca ccccagggtg cactgttgaa 7740
ggttggggag atgggaggag atactagggg aacaatgagg tgtcccagtt ccatggatga 7800
tggggatctc ggccctagtg tgaaaccctt ctcgcagggt ctctggcagg cacagagccc 7860
gggggctctt gcatagcaca tgggtatttc tggaggcttc tccttcggtc tcaccgcctg 7920
gatggcacgg aattggttgt agttgtggaa tcggaagtgg ccgcgcggcg gcagtgcagg 7980
ctcacacatc acagcccgag cccgccccaa ctggggttcg cccgtggaaa cgtcccgggt 8040
cacccaagcc acgcgtcgca gggttcacgg gggtcatctg ggaataggac actcatggga 8100
gccgcaccag atcttcaggt cggcattat ccacagcccc gtggccccgg gtcacactcc 8160
gagggcttca gtgtcatggc ctgggactca agtcacgcct acttatgtga tgatcacagt 8220
gtgttccacc aaaatcttac attttccaca tctatcccag agcacagctc cgactccgtc 8280
taaggacagc ccccaaatcc ccagcctttt actgaactga caattgcctc cccagtgaac 8340
actctgatct cctcagccct aagtggccag acattaacat tctcattcaa tgcaggtttg 8400
aggtgctaat tcaggagctt aagatgctaa agagctggga gcgccactgc tgctttattc 8460
tctggtccag gatccttgtg ttgctggaga taatccatta tcgtgggtgc agcagacacc 8520
ctgcggcttg tggactcggt acggggtggg gatcctgatg ggttaggat gttcgatggc 8580
tcgggtgtgc tccacgctca gggatcatca cgtccggccg gcggtagttg gcacgtggag 8640
aggtgaattt gcccacaggt gttccccgtg cctgcgcatt gctggcagca cgaccggatc 8700
ctgtgctagc cctcccaca atgcctggag caggagcgag gggcctgggg agccgccttg 8760

-continued

```
cctggagcat ttgtatttcc ggagtatttc ctgagtctcc ccttgggtct tgggtgctgt   8820
ccccagtgag cccatctccc agcgatggca cagaatcggt tgtggctgtg gagacggaaa   8880
tggccgagag gcggcagtgg tgactcacat cacagtctga aggtgaccca aggctggact   8940
ccacttttag caaaatgtgg gggtctgcct tggtctccta acttgggggt ccactcatgg   9000
aaaagcctga gaattttcat gccatggaaa ttcccccatg tcgtggggtt cacgcacgac   9060
aaagcccggc ggtcagtgct cagcaggcaa gcactcagcc ctttccggtg gggccatggg   9120
aacagagggt ttgccgaagg cgcggccagc ccttccacat cccagagggc ctgctgggtg   9180
attggacccg tgaactctgg gtcccttggc cctggtgctc cccttcacgg ctttgacact   9240
cgagacttga ggtgaacccc agggactgca gggccccaac aaccctcacc aaaggccaag   9300
gtggtgaccg acggacccac agcggggtgg ctgggggagt cgaaactcgc cagtctccac   9360
tccactccca accgtggtgc cccacgcggg cctgggagag tctgtgaggc cgcccaccgc   9420
ttgtcagtag agtgcgcccg cgagccgtaa gcacagcccg gcaacatgcg gtcttcagac   9480
aggaaagtgg ccgcgaatgg gaccggggtg cccagcggct gtggggactc tgtcctgcgg   9540
aaaccgcggt gacgagcaca agctcggtca actggatggg aatcggcctg gggggctggc   9600
accgcgccca ccaggggtt tgcggcactt ccctctgccc ctcagcaccc caccccctact   9660
ctccaggaac gtgaggtctg agccgtgatg gtggcaggaa ggggccctct gtgccatccg   9720
agtccccagg gacccgcagc tggcccccag ccatgtgcaa agtatgtgca gggcgctggc   9780
aggcagggag cagcaggcat ggtgtcccct gaggggagac agtggtctgg gagggagagg   9840
tcctggaccc tgagggaggt gatggggcaa tgctcagccc tgtctccgga tgccaaagga   9900
ggggtgcggg gaggccgtct ttggagaatt ccaggatggg tgctgggtga gagagacgtg   9960
tgctggaact gtccagggcg gaggtgggcc ctgcgggggc cctcgggagg gccctgctct  10020
gattggccgg cagggcaggg gcgggaattc tgggcggggc caccccagtt agaaaaagcc  10080
cgggctagga ccgaggagca gggtgaggga gggggtggga tgggtggggg gtaacggggg  10140
aaactgggga agtggggaac cgaggggcaa ccaggggaag atggggtgct ggaggagagc  10200
ttgtgggagc caaggagcac cttggacatc tggagtctgg caggagtgat gacgggtgga  10260
ggggctagct cgaggcaggg ctggtggggc ctgaggccag tgaggagtgt ggagtaggcg  10320
cccaggcatc gtgcagacag ggcgacatca gctggggacg atgggcctga gctagggctg  10380
gaaagaaggg ggagccaggc attcatcccg gtcacttttg gttacaggac gtggcagctg  10440
gttggacgag gggagctggt gggcagggtt tgatcccagg gcctgggcaa cggaggtgta  10500
gctggcagca gcgggcaggt gaggacccca tctgccgggc aggtgagtcc cttccctccc  10560
caggcctcgc ttccccagcc ttctgaaaga aggaggttta ggggatcgag ggctggcggg  10620
gagaagcaga caccctccca gcagaggggc aggatggggg caggagagtt agcaaaggtg  10680
acatcttctc ggggggagcc gagactgcgc aaggctgggg ggttatgggc ccgttccagg  10740
cagaaagagc aagagggcag ggagggagca caggggtggc cagcgtaggg tccagcacgt  10800
ggggtggtac cccaggcctg ggtcagacag ggacatggca ggggacacag gacagagggg  10860
tccccagctg ccacctcacc caccgcaatt catttagtag caggcacagg ggcagctccg  10920
gcacggcttt ctcaggccta tgccggagcc tcgagggctg gagagcggga agacaggcag  10980
tgctcgggga gttgcagcag gacgtcacca ggagggcgaa gcggccacgg gagggggccc  11040
ccgggacatt gcgcagcaag gaggctgcag gggctcggcc tgcgggcgcc ggtcccacga  11100
ggcactgcgg cccagggtct ggtgcggaga gggcccacag tggacttggt gacgctgtat  11160
```

-continued gccctcaccg ctcagcccct ggggctggct tggcagacag tacagcatcc aggggagtca 11220
agggcatggg gcgagaccag actaggcgag gcgggcgggg cggagtgaat gagctctcag 11280
gagggaggat ggtgcaggca ggggtgagga gcgcagcggg cggcgagcgg gaggcactgg 11340
cctccagagc ccgtggccaa ggcgggcctc gcgggcggcg acggagccgg gatcggtgcc 11400
tcagcgttcg ggctggagac gagggtgagt ttttccccct ctgccaccct cagcccccac 11460
ccgcccctcc ccacacaacc aacacgttct ccccacacga ctctctcgtt ctccccacag 11520
ccaggtctcc agctggggtg gacgtgccca ccagctgccg aaggccaaga cgccaggtcc 11580
ggtggacgtg acaagcagga catgacatgg tccggtgtga cggcgaggac agaggaggcg 11640
cgtccggcct tcctggtgag cgtgtctgcc ctccctgcgt caggacgcgg ccctgcccag 11700
accgccccgg cgcgccacca tctcactgcc ccgacctctg tcttctacag aacaccttag 11760
gctggtgggg ctgcggcaag aagcgggtct gtttctttac ttcctccacg gagtcggcac 11820
actatggctg ccctctgggc tcccagaacc cacaacatga aaggtgaggg gcttcctgcc 11880
acacttgggg tggggggcac gcgagaggag ctgagtggga cctcaactcc ttccccatcc 11940
acagaaatgg tgctacccag ctcaagcctg ggcctttgaa tccggacaca aaaccctcta 12000
gcttggaaat gaatatgctg cactttacaa ccactgcact acctgactca ggaatcggct 12060
ctggaaggtg agcaccagcg ctccttccgg aagcctccag gcccccgagc accctgcccc 12120
catcccaccc acgtgtcgct atctctaggt gaagctagag gaaccagacc tcatcagccc 12180
aacatcaaag acaccatcgg aacagcagcg cccgcagcac ccaccccgca ccggcgactc 12240
catcttcatg gccacccccct gcggcggacg gttgaccacc agccaccaca tcatcccaga 12300
gctgagctcc tccagcggga tgacgccgtc cccaccacct ccctcttctt ctttttcatc 12360
cttctgtctc tttgtttctg agctttcctg tctttccttt tttctgagag attcaaagcc 12420
tccacgactc tgtttccccc gtcccttctg aatttaattt gcactaagtc atttgcactg 12480
gttggagttg tggagacggc cttgagtctc agtacgagtg tgcgtgagtg tgagccacct 12540
tggcaagtgc ctgtgcaggg cccggccgcc ctccatctgg gccgggtgac tgggcgccgg 12600
ctgtgtgccc gaggcctcac cctgccctcg cctagtctgg aagctccgac cgacatcacg 12660
gagcagcctt caagcattcc attacgcccc atctcgctct gtgcccctcc ccaccagggc 12720
ttcagcagga gccctggact catcatcaat aaacactgtt acagcaattt gtctcgagga 12780
ctctggaatc cgggctgtgg gcatgatgtg ggggaggcca gccttgggca gagggggggct 12840 ggggggcatg gggaggagta catgaaaagg gggatggggg ttccagggtg ggggattctg 12900
ggatgggtgc agcgcagcac acaccagggg tggggtgagc acagggtgtg tggacctcag 12960
gggtgcaggg caggcggtca gcatgcagtg atggcagtgg aggggctgtg ggaccagggg 13020
cttcacagac tgggcggggg ctgggcttgc ggagggggcc tgcgctctga ggcaggggtc 13080
ggggaccacc aaaccatccc cgagcgagtg cctcctgtcg ccccaaagtc ccatcagaat 13140
gacgccttgg tgctggcccc agacccctga agcccgggct aggtgactgg ggtagagctg 13200
gccatggccg ctctgggagg cccacaaggt gctctgggcg accccacccc gacaggggca 13260
cgaaccccgc gccagtcccg ttcctgctcc ccttttgctg tgggtgggag ccggggccac 13320
gccggaggga cggccccgca caaggagcca gggggttggg ggggagccgg tgggcttctc 13380
agtgggcagg tggccttggg gcagaggtcc taaggaggcc aggggaccag gaggagggag 13440
gaaggagttg agggtggcca cagggaggag gtgaggagga gcgggagggc ccagggtgag 13500

-continued gggctcccgg gctccctccc cggggtcttg ctgctggagc tccaagaacc ccggtatgca 13560
ggggttcgct ccccaggtgc caaggcagcc cactcatggg ttcggggtca gcttccccgc 13620
agaggccagt ggccggcagc tccctcagcc aggcctccca gctcctggcc cctcgctgtg 13680
caggcgctgg gaacacaagg ggcagcccct ggaaataagg gtggggtccc ggcctcccca 13740
ttccttcccc cctccccct gccttccacc cccattccca gtgcacagag ctgtcaggaa 13800
aattcctccc cgactgacaa agaacagaca ggaaggcggt tagggacgcc cctcccctac 13860
cggcccagcc gcccttgggg tcttggtgtc cagggcggaa gagcagggtg gttccccacg 13920
ccccttgggt ctggcctccc ctctgcaccc tctcttgccc cctccccatc cagctgtggg 13980
ccctggggac tgtcagagac cgaggggttt ccagggacac acttgtgtgc taaaacctgg 14040
gcgggtggtc accccccagg atgcatgtag acatccggtg agggagtctc ttgaagtctc 14100
tgggatggtg cccctgggac tggctgccat ctcatggagg aggtcagagg tcgctggggc 14160
cagcccaggg tgaggccgca ttcatcttcc tgaccctaca ggccaatttg acttacccaa 14220
gtgggttttg gccggcagga tgaagtaacc catccattac atgtcaagag ttaggtctat 14280
aaacggcctt tattataaac atccaactct gcaggaggtt tacaaagcag ggctcaggag 14340
ataaaagccg gcttccccag gtggcggctg cagggtgcgg caggcagccc caggggtgcc 14400
cagggtggcg gggcagggga accgtaggga gggggagagg ggcacccaga aaacctctcc 14460
tggggaacat ggaagactct gcccacttca aatccctgcc tggggaagga cacatgggaa 14520
tggggccggg ggaaaaggcg ggccacctcg ggccttcgtc acctgtgtca gctcctaggg 14580
attgtctcct cctggtcact tggagagaac aggcgtgctg gacacgtcca catctctggg 14640
cccaggggtg tatgaatgac acgcttgctc tggagtttcc acctgggagc tgtatgggga 14700
cagggctgtt cctcctcaca cccgctgggg aagggacaca ggcctcttgg tggcccccac 14760
catctcccag cactgcccat ggctgtgccc acgctggctg ccccctgaga gcaggacgtg 14820
tactcagggg cagcgcctac ctctgggcag cccaggtttc tctgctccct gcagcggaac 14880
gggcttccta gggcagttcc tggggtggtg tccctagggc agcccctgag tgctggaggg 14940
ggtctgcgcc acaggccctg aaacagggag gtggtggggg cagcgttcag ggggctgaac 15000
ctcagggtga ggcgggcagg cggggagcca caggcccggg ggccccgcag caggtgctca 15060
gcctcggagc ctcctgccgc accccggggc gggggctggg agcccgcccg agcccctagc 15120
tctgagcgac ctgccaggtt ggaatgtgtg tttatctttg gcccaacccg atttcctgct 15180
ttttagaaaa ggggcttaga gagggttgtt agacaggctc caggcacccc aacacccaaa 15240
ggcactttga aaacgcccct gcactgactt cagtgcggag aagcaaacgg gctggaattt 15300
cactcccaaa ccccaacatg gggtggcgg ggccggggtg agggttgtgg ctgcctgcaa 15360
aggtgccagg aaatctgggg agggaggaac ttccaccgtt cagggagacc ctgagggtgc 15420
cctggcttct ggccacgtcc cagaccctgt taggcaccga ggtcttcaca cccagaccct 15480
ccacccaccc aagtttctgc ggcacgttta ggttgagtga agaccaagtc atccagttag 15540
agaagaggac ttgaggcgcg tgctgctgct gtggccacgc tggacctcgg tgcacgcatc 15600
tcctggcgag tcccctgaga tggcctgtgc agccatacac acccggggca cgcgacctca 15660
gctacctcgt caccgaggac gtgcatccac agctgtgcgt ctgtgcctgg gagcggggtc 15720
tccacttggt gggtctctgc atgctgacca gttaacccgc ctttccgggc tgtggagggc 15780
gtgggtcctg tccggcccgg agatgctccg cggggtgtgt gtgtgatcgt ggccctgtag 15840
cggggtggtg ttccctggag ggtggacccc tgagcctggc tgtgtgtggc tcgtgtctca 15900

-continued

```
gcatgaattc cgtgacccag gagcacgttt tcaggcaggg attaggggca gctgggtgtg  15960
ggaggcaggc acttggtata ccaccgaatg gagacagaaa atcccaactc tacgaaggaa  16020
gtgaagtccc ttcaacaggg acaaagcgat gttttgggtc tgactacaat gcaccctggg  16080
aagtctcaaa gaaaacagtc gggtactcaa ggagggcagc cccctctccc cgaccccgag  16140
ctcccaggaa gataaatgat ttcctcctct ctagagatgg gggtgggatc tgagcactca  16200
gagccaaggg cgcagtgggt ccgggcgggg gccctcctcg gccctcccaa catgggggcc  16260
aggaggtcag cccctcaacc tggaccccgg ctgggtctca gggaatggtc tcccccagtg  16320
gcccagcttg cttgttttca gatgggtgtg cacgggtgtg tgtgtgtgtg tgtgtgtgtg  16380
tgtgtgtgtg tgtgtgtgat gcctgacaag ccccagagag ccaaagacct gagtggagat  16440
cttgtgactt ctcaaaaggg ggattggaag gttcgagaag gagctgtggt cagccttgct  16500
ctcccttaag gctgtggtaa ccacactagg catagcatag gcctgcgccc cgtccctcct  16560
tccctcctcc gcgcctctcc tttctctttc tccccccctct accccgctcc ctggcctgct  16620
cctggtgaca ccgttggccc ccttccaggg ctgagggaag ccagcggggg cccccttcctg  16680
gaagcccacc tgcaggccgg cttgctggga aggggctgct ctcgcagagg ctcccgcccg  16740
ccctgcagcc gtttcctgga agcagtcgct gtgggtattc tgttccttgt cagcactgtg  16800
cttgcaaaga aagcagacac tgtgctcctt gtccttaggg agccccgctc catcacccaa  16860
cacctggctg gacacaggcg ggaggccggg tccgcgggga gcggcgcggg gctggggccg  16920
gaccagtaaa cacacacggg cgccaggcac tgcaggctcc tcctcctcct cctgcccagc  16980
gcctctgctc acaggcacgt gccaagcccc taggccagga ggcccagcag tgggtgcaga  17040
gcaagctcct gggaaggggg tgcagggcgg acccccgggg agaagggctg gcagggctgt  17100
gggggacgct gaccgtgggc cccacgttgc agaaaactgg ctgcctggct ggaagatggg  17160
ggagatgcca agcctctgag gcagcacgag cagggtgcat ggaggccggg gcgcggggag  17220
gctgcactgc agcatgcacc ccaaagccca gagggagtgg agaccaggcc ctggaatcga  17280
gaagtagaaa ggcggcttgg aggcctcgga accggctgac ctccaacaga gtggggccgg  17340
ccctggaggc aaagaggtgc ccggggtccg gccctgcctg ggggagctat gtgtcatggg  17400
cagccacagg atatgtagcc agctctgagc atatggaccc agggcagggc tgcaaggcag  17460
ggcaggggaa acagacgggg gagcaaggag cagagagggg gcctcaggct ctcccaggag  17520
gaacattctc ccgacaggag gaagagacgg cccaggggtg actgtgggga gccatggtgg  17580
cagctggggt cgtggcagat gggagagagg ctggcgaggt gaaggtgcag gggtcagggc  17640
tctggggccc acatgcctgt gggagcgggc aggcccaggg ctctccgcca ctccccactc  17700
ccgcttggct cataggctgg gcccaagggt ggggtgggat gagcaggaga tggggcccag  17760
ggggcaagca gggccccaaa gacatttaga aaaaccggtt tatgcaggca gcattcagag  17820
caggcggcgt gcgtggcggg ggccctggga gcacagagag gcacacgtag ggcccccgag  17880
gggctcccca ttggccggca gtgacatcac ccctgtgtca acagtgatgt ctgcagctcc  17940
ggccagccag ggtttatgga gcgagaccca gcccggcctg ggccctcact ccccaggccc  18000
acacactagc ccactgttca gggtccgggg tggcggcatg gcctgggggt cctggcaccg  18060
ctgctcctct gcccacccta acttcccggc atggcggctg ccccctctga gcgtccccaa  18120
ccagtaagtg tggggccagc aggcctgccg tcctcctcct cttccctcta gagagaaacg  18180
tggaggtcct ggggctgggg gcgctcatag ccctgtgaca caggtgcatg gggtcagggg  18240
```

-continued

```
tcccagaatg gcccctggga aggacctcag ctgggccggc ggctctaggc ttcaggggtc  18300
tgtctgcaca ggggctagcc cctcccagac ctctgtgaag ccagtacggg cctcccctcc  18360
ctgccccgtg ctctgtccgg tgcttcctgg actgcactgc gggccactgg tgagagggtg  18420
gacagggaag ggccgccgtg gtgcctgttc ctgcccacct ggctgtgtgg tcccctccaa  18480
gtagggacaa cccttctgag ggcttggggg caccctgggg ttgccagggc ctcccagagc  18540
cctgtgagcc cctggggggt ctggcctgat gccccccctcc acgtccaggg ccggctgtgg  18600
cccagaaccc cagcttccca gcaggccggt gtgcggtggt gacccaggag aggcctcgcc  18660
tccactgagg ggccaccgac ctctgccagg ccacagagac cccccaaggag tctgaaggct  18720
ggagacccgg ggctgggacc aggtgggact ttcccacgga gccgtcccca ggcccagctg  18780
gggacacgtc cccccttctct ccagacacac cctgcctgcc accacgacac accggcctgt  18840
tgggggtctc ttttaagtgc ctgccactct gaggtgactg tccctttcca aagaggtttc  18900
tggggcccag gtgggatgcg tcggcctgag caggaggatc tgggccgcca ggggctgggg  18960
actgtctcct ggggaaggaa gcgcctggga gcgtgtgtgc tgacccagga ccatccaggg  19020
aggcccgtct gtgcggcaag cgggaaggga gcggctggag aggcttggcc gcccccgccc  19080
tgcctcccat tccttagctc cctgcctgtc aacctctgtc acccagtgag tgatgtccag  19140
gggccctgga aaggtcacag catgtttgag cggggtgaga gagaggggaa aggcgggggc  19200
ggggaaaagt acgtggagga agctctaggc ccaaggaagg agaaagggtt ctgggaggga  19260
gggagccact ggggccgccg ggagggtccc tgcctgctgc tgccacccag aaccctcgcc  19320
tcttagctag cccccgcagc cccagcctttt ctggcctgtg cccctctccc ccatccccag  19380
ctgtcctgtg caaccaggcc ttggacccaa accctcctgc cccctcctct ccctcctcac  19440
cctcccaatg cagtggtctc cagcctggct ctgccctgcc gcaggtcccc tcccctcatt  19500
ccaggcctag agcctccagt cccggtggcc cccagcccga gggtgaacgg cctcaccctg  19560
ggtcgtggga cagagggcac gttcatcaag agtggctccc aagggacacg tggctgtttg  19620
cagttcacag gaagcattcg agataaggag cttgttttcc cagtgggcac ggagccagca  19680
ggggggctgt ggggcagccc agggtcaagg ccaggctgtg gggctgcagc tgccttgggc  19740
cccactccca ggcctttgcg ggaggtggga ggcgggaggc ggcagctgca cagtggcccc  19800
aggcgaggct ctcagcccca gtcgctctcc gggtgggcag cccaagaggg tctggctgag  19860
cctcccacat ctgggactcc atcacccaac aacttaatta aggctgaatt tcacgtgtcc  19920
tgtgacttgg gtagacaaag cccctgtcca aaggggcagc cagcctaagg cagtggggac  19980
ggcgtgggtg gcgggcgacg ggggagatgg acaacaggac cgagggtgtg cgggcgatgg  20040
gggagatgga caacaggacc gagggtgtgc gggcgatggg ggagatggac aacaggaccg  20100
agggtgtgcg ggacacgcat gtcactcatg cacgccaatg gggggcgtgg gaggctgggg  20160
agcagacaga ctgggctggg ctgggcggga aggacgggca gatgggatcc caaggacatg  20220
gaatttcgga ccttctgtcc ccgccctctc tgctgagcct aggaacctct gagcagcagg  20280
aaggccttgg gtctagagcc tagaaatgga cccccacgtc cacctgccca gcctagaccc  20340
ccagcattga agggtggtca gacttcctgt gagaggaagc cactaagcgg gatggacacc  20400
atcgcccact ccacccggcc ctgcccagcc ctgcccagtc cagcccagtc cagcccagcc  20460
ctgcccttcc cagccctgcc cagcccagct catccctgcc ctacccagcc cagccctgtc  20520
ctgccctgcc cagcccagcc cagcccagcc ctgccctgcc ctgccctgcc cttcccagcc  20580
ctgaccttcc cagccctgcc cagcccagct catccctgcc ctacccagct cagccctgcc  20640
```

```
ctgccctgcc cagccctgcc cagcccagcc ctgccctgcc ctgcccagct cagccctgcc  20700
caccccagcc cagcccagcc cagcatgcct tctctggctg gagagcacag gcttgacctt  20760
agaaagaggc tggcaacgag ggctgaggcc accaggccac tggtgctca cgggtcagac  20820
aagcccagag cctgctcccc tgccacgggt cggggctgtc accgccagca tgctgtggat  20880
gtgcatggcc tcagggctgc tggctccagg ctgcccccgc cctggctccc gaggccaccc  20940
ctcttatgcc atgaaccctg tgccacaccc acctctgagc tgtccccgct cctgccgcct  21000
gcaccccctg agcagccccc tgtgtgtttc atgggagtct tagcaaggaa ggggagctct  21060
tcaatcttgc cagtcagggt gctgtctgct gagtaagtgt ccccgtgctg tgccccaatg  21120
tccccatcct ttggcaaaca gccatcagcc tgtggatcct gcactcccat gcggtgggag  21180
agggagacct gggctcacct gagcctcccc acaagccagg gagaggggct gcccaatggc  21240
gggaggcccc catggatccc aaacggcagt tgcccgcact cctacccagg aactttgtct  21300
gtgatgaaca gtaaggaata aggaagcggg tgagaaagaa ggaaggaaag gcggtggggg  21360
gcatggcggg gggcggggag ggtgtttgga aagttccaga aaagagtcac ttcaccagaa  21420
aggccacaag ctccccgtgc ccccagcccc tgctcggctc cgaggtgaag gacttggagc  21480
gtcgacgctg gcgtggggac cagctgttct ccttgagttt gtttccttca gttccttccg  21540
ggcctcaccc tcctcttcct gccacacaca cactttttc ctttttaaat tgttttattt  21600
ggggccaggt gtggtggctc acacctgtaa tctcagtatt ttagaaggcc aaggtgggca  21660
gattgcttga gtccaggagt tggagaccag cctgggcaac atagtgagac cccatctcta  21720
ccaaatatca gccaggtgcg gcggcgcgca cctgtattcc cagctatgtg ggagactgag  21780
gtgagaggat cacgtgagcc caggaggttg aggctgcagc aagccatgat catacccactg  21840
cactccagcc tgggcaagag agtgacaccc tgtctcaaaa aaaaaaaaaa gtagaaaaat  21900
ttattttaaa aaattgtttt aacatttgag tgctgcaact gtccaaggag gagcagacgg  21960
cccgtgtcag acagcctgaa gcctgactgt ctgcgatcaa cggccccgtg gccagctgtg  22020
tgcagcagtt tggcctggcc tgatgcctct gtccttggca ccagctcaca gcccgtgccc  22080
ataacagacc tggggcaccg aaggaagggc agatccagcc cccacctgcc ctgggtctga  22140
agatctccca ggaggctcca tggggtgcct tgagtgggag gggctggccg atagccttga  22200
ggaattggca cggacatgca gagaggggca tgtcccaaac tcggggcgct gtggcctcca  22260
gctgccagga ggtagatgtg ttctgacttc tgggttccca ccaccagaac tgcaggggat  22320
atgaagcaag ctggacttgg ggagacatct ctgctcgagt gcacgttggc ctgatgacga  22380
ctgctcttgg gttcacgggt tccaggctct gcccgggagc ctcatgcaaa ctggtcccgt  22440
tctacagatg aggaaactga ggcacagagt gattacggct gtccctgagc tcctgcagcc  22500
agtaaggtga tacaccagga tgtgttccca ggttgtccgc tgggctcagt aacacagtct  22560
caactgccct gtgacactgc gtgtctgtgc ttgtggggaa ggtgaccaga ggccccccttt  22620
cctccacgcg gtgagcctac cagcaaggag acagtcctca ggtgtgagga tgagcctcgt  22680
agtaggcaca gagaaacagg aggaaccttc tggaaggtga agcctcccac ggctgggact  22740
cttggagaag ggcggatctc tgtccactcc tgcccactcc ccagcacaga cagagcaagc  22800
aggacagagg gcccaacgtc ccaggatact gcagagctca aaggagggca gagagcatcg  22860
ccccacatgg gcgccgggag aaaggtgggc ggggtgctca ggggcccctg gccgtcctga  22920
agtttgcctc agagaggtgt gggcttctcc tccctcccat acacagtgtc tctgaggatg  22980
```

-continued

```
aactgccatg tgcccggcgg ggatgccgtc cctggccctt gctgagtgcc tctgggacga  23040
ggtcagctga gcctgccatc ctaactcaga caccatctca ctctccaagt cccttctcgg  23100
tgagacgggg ggccttgcac ccacctccca gcccccacac acctgagggg gtccccgttc  23160
ccctaccccg tggctccacc acgccccacg catcctacct gagggacaga ggggactgtg  23220
agatgccccc cacaggctgg ttttcctctt tcacccataa caggcccagc aaattctcac  23280
ctccagaggc caggtctgcc ccgcaggtct taggaaatac agccctactt ccatccagca  23340
caccaaccca aggaagtgcc tcggagccct ggggcccgag gggggcctgg ccttggtctc  23400
acggcggcag ctccacctgg agaggagtga actcaagcca ggacgccccg tctccacagc  23460
ggaaaccgtg ttgccggctg ctccctcctg gggactctgg gcctgaggtt cctgtgggag  23520
ttggggggat agctgagtcc tatggaggtg cccctctcct ccccgcccag tggagcttgg  23580
ggtggggaca ggcgaagaca gggtgagaag cacggggcat tccccctcca cacagcgctg  23640
agaaagtaag ggagcatcca gaaaacggtg cccacttccg cgtcaggcgg atatcacggg  23700
caccagctcc aggtgaccct agcccagcca gagaacaagg accaggttgt gccgcaaagc  23760
ccgtgtccgc tccctcccgc ctgggaccac tgtggcgagg ggaagggagc gtggtggccc  23820
tctcctgact cctgaggcct gaagtccaag ctcccggccc tcaggcaggc cagggtctag  23880
acaccgctgc cccaaacaca ccccccagtc cccgcccgca ggcttcctgc aggatccccc  23940
agtgcacctg gggggctgagg agagtgagca gggcgcaaag aagcttcgtc gggagggcgg  24000
tccccacccg ccttggaccc ccggggatag tgtcctgggg cctgggctca gatggaccct  24060
gggaggaacg gtgcgggggc tgtttttttgc tccaagagga cattgcctca gcagagggct  24120
gccgagctgg gaggacccac agtgcaaggc cgcacaaacc cctaggaagc ctcagagcct  24180
tcaggttccg ggctgaggct gtgggcgtgg acccttgtgc aaaccccact ggaagaaaaa  24240
ccttacagct caggaggagg ggccccaccc gctcccagag cccgtaaacg aggggtggtg  24300
cccacatgag gcctggggaa gggctggggc tgggacaccc cctcaccacc cccagatacc  24360
ccaggcagcc cctccctcca cagagagacc cactgggcct gaccctgccc tgggcacagg  24420
gtcgagccag ggacggcccg tgggagaaag acggcttcat gggccgctgg ccgggccagg  24480
tgcgtccttc cccagttcta ggtggcaaat ggggtggggc cagagccttc tggctaggga  24540
agacactggc ctggttggtg tggcaggggc agcgaaggag ggtcaaaggc cactctggcc  24600
tggaagagtc cccagccacc tggacggggg tagccaggcc tggtccctgc ccccactctc  24660
caaggggtcg gggcagccgg gcagagccag taagtgtttg ttttcagatg acatttgtaa  24720
agaaaaacag cctcccacac tgcttgaccc tgtgtctgga atgtggggag gcaaacagct  24780
gtgcccttcc cagaccctgc acagcccctg gtgggggcag ggccctggtg ggagcagggc  24840
ccagaggtac agcctgggga ggcaccggcc attgtggttg gagcgcggca gccaggctct  24900
gggctctgtt ccgggcctca ctgtgtcccc agtggggtgc cgccaccacc cccccagcct  24960
gggccccgcc ggtcagacac ccgcagggac agcttgtctt ggctagctgg ctacagcacc  25020
tcgctggagt ccagcagaca cgcgctcccg tgcgcacgct gcgccccagg ccagccctaa  25080
cgccgctgct cgggtcaggc cccccgcctg ccgtgggctg ctggctgcct tggcccgccc  25140
cagctctctc cgcgcccctg cctccaggga gccctcctcg aggactccag ccacccaagc  25200
tcagcagggc cagcccgagc ccctgcccca cccagcctgt gtggagggtc ctcagccccc  25260
tgatccccca gaccctcccg gcagaagctg ggtccctggg gcttggggaa agccggctcc  25320
atggcccctg gcctggatga tttcccagag gccggtcccc tgccaagtgc ctggtgaccc  25380
```

-continued ttgttcctac ctggctgccc atggtccttt gtgcgacccc cgcccacagc ccaggagctg 25440
ggcaggagac tctgattggg tggcagcaga gccatcctag gggtgcccct gaccctggcc 25500
ctgaccctgc cctggagcct cgtttccaaa tcttgcctca tgctttcgcc agacccctgt 25560
ggccccttcc cgaccctgga gtgcccctgg ggcttcctgg aaagggcctc tcctttgctc 25620
acagttgggt gccgaacttc accagcattg accacccgaa ggcgcaggga cacccccgca 25680
gtccctctcc tgggggtccc atcaccaact ccccatgggc gggatatcag aagaattc 25738

<210> SEQ ID NO 3
<211> LENGTH: 24
<212> TYPE: DNA
<213> ORGANISM: Artificial Sequence
<220> FEATURE:
<223> OTHER INFORMATION: PCR primer

<400> SEQUENCE: 3
ggagttgtgt tttgggatag atgt 24

<210> SEQ ID NO 4
<211> LENGTH: 24
<212> TYPE: DNA
<213> ORGANISM: Artificial Sequence
<220> FEATURE:
<223> OTHER INFORMATION: PCR primer

<400> SEQUENCE: 4
aaacaataaa atatcccaat tcca 24

<210> SEQ ID NO 5
<211> LENGTH: 227
<212> TYPE: DNA
<213> ORGANISM: Homo sapiens

<400> SEQUENCE: 5
gcacatgggt atttctggag gcttctcctt cggtctcacc gcctggatgg cacggaattg 60
gttgtagttg tggaatcgga agtggccgcg cggcggcagt gcaggctcac acatcacagc 120
ccgagcccgc cccaactggg gttcgcccgt ggaaacgtcc cgggtcaccc aagccacgcg 180
tcgcagggtt cacgggggtc atctgggaat aggacactca tgggagc 227

<210> SEQ ID NO 6
<211> LENGTH: 28
<212> TYPE: DNA
<213> ORGANISM: Artificial Sequence
<220> FEATURE:
<223> OTHER INFORMATION: PCR primer

<400> SEQUENCE: 6
gtttttatga gtgttttatt tttagatg 28

<210> SEQ ID NO 7
<211> LENGTH: 27
<212> TYPE: DNA
<213> ORGANISM: Artificial Sequence
<220> FEATURE:
<223> OTHER INFORMATION: PCR primer

<400> SEQUENCE: 7
cctcctcaaa aatctttata aatacac 27

<210> SEQ ID NO 8

<211> LENGTH: 17
<212> TYPE: DNA
<213> ORGANISM: Artificial Sequence
<220> FEATURE:
<223> OTHER INFORMATION: M13 forward primer

<400> SEQUENCE: 8
gtaaaacgac ggccagt 17

<210> SEQ ID NO 9
<211> LENGTH: 17
<212> TYPE: DNA
<213> ORGANISM: Artificial Sequence
<220> FEATURE:
<223> OTHER INFORMATION: M13 reverse primer

<400> SEQUENCE: 9
caggaaacag ctatgac 17

<210> SEQ ID NO 10
<211> LENGTH: 28
<212> TYPE: DNA
<213> ORGANISM: Homo sapiens

<400> SEQUENCE: 10
gcacatgggt atttctggag gcttctcc 28

<210> SEQ ID NO 11
<211> LENGTH: 12
<212> TYPE: DNA
<213> ORGANISM: Artificial Sequence
<220> FEATURE:
<223> OTHER INFORMATION: Allele specific sequencing primer

<400> SEQUENCE: 11
gaattttagt tg 12

<210> SEQ ID NO 12
<211> LENGTH: 12
<212> TYPE: DNA
<213> ORGANISM: Artificial Sequence
<220> FEATURE:
<223> OTHER INFORMATION: Allele specific sequencing primer

<400> SEQUENCE: 12
gaattttagt tt 12

<210> SEQ ID NO 13
<211> LENGTH: 170027
<212> TYPE: DNA
<213> ORGANISM: Homo sapiens

<400> SEQUENCE: 13
gaattcattc acagaatccg tagctactga taccgggtac caggggcagt gttaatttaa 60
tcttagatta aatgaatcta atttaatcta agattaaacg aagataccac atctggcctg 120
gcagcccatt tggtgttgct acttggttga gtttgaggtc tgcaatcatc tattctgatt 180
cagccagtct gcagagaggc cagagagggg aaatcacgag agagatgggt gggggttact 240
acctaggcct tctttaactc tttgaaggtg gcatcaatct cagccatttc ccctgggaag 300
ttataggttt attgggggct aactgacata caataaacta cacatattta aaatatagag 360
gttttttttt ttttttttt tttagggagg tctctctctg ttgcccaggc tagagtgcag 420
tggtgcaatc tcggctcaat gcaacctctg catctagggt tcaagcaatt atcctgcctc 480

```
agcctcctga gtagctggga ctataggtgc gtgccaccac gcccggctaa gtttttttgta    540
tttttaatag agatgaggtt tcaccacgtt ggccaggcag gtctggaacc cctgacctca    600
ggtgatccac ctgcctcagc ctcccaaagt gctgggatta caggcgtgag ctaccacact    660
gggccaaaat gcagagtttt atgaattttg acatatgtgt acaacagtga gaccatcatc    720
accgtcaaca atttcttgta agttttaaat tcgtaattaa attacaactg tgtaatccct    780
tcctcccacc cctcctcccc agccttaggt aaccactgat ccgccttcta tcaggtattc    840
tttgcgttct acggtgttat gtcaatggac acatacagga tgtattcttt tgtctggctt    900
atctcatgcc atatacttat tttgagattc attgatattg ttgcaggtat caatcgttca    960
tttattttta ttgataaata acatgaatgg gtatatttgc ttataccttc acttgttagg   1020
cgtcacttgg attgtttctg gtttgggcta tctatgatcc aatgctataa acattcatga   1080
acaagtcttt gtggagacaa atgctttcat ttttcttgaa taaataccta ggagtggaat   1140
ggatggatca tatggccggc cggtgtgtgt ttcacctttt aagaatctac caaatcattt   1200
tttaaagggg ttgtaccatt aatcttccca ctcacagtgc atgagaatta cagtttctcc   1260
tacctttgcc aaaagttggt atgatcagtt ttaaagcaag aaaatttaac cattctaata   1320
ggtgtgtagc gatatctcat tacgattttt aattttcatt ttcctaatga ttaatgatgt   1380
tgagcatgtt ttcatgacct tatttattat ccatatatct tctttggtca agtgtgtagg   1440
agatatctgt atatcttttt tgctcatttt tatagggttg ttttcttact attcattttt   1500
gaaaatacac agagaatatg caatgaatat tctggatata agtccttcat cgtaatatga   1560
tttgtgaata tttcctatca gctgatggct tgctttcttt attctcttat gactgccttt   1620
caaaagagtg gaatttttaa attttgatga cattccattt agccaccttt cttttatgaa   1680
ttgtgccttt gccgtcatat cctttctgtg actaatctaa ggtcacaaag atttttccacc   1740
atgttttcat ctaacagttt cacagtttta catttatatt aggttactaa ttcattttac   1800
attaatgaat ttgaatacag cttgaggaat tggtcaaagt tattttgtct ttttgcaggt   1860
ggatatccaa ttgttccagc atcattggtt gaaaagatac aatttctcta ttaaactgac   1920
tttgcacctt tgtcaaacta gctgtcctca tgtgtgagtc tatttcttgg ctatctgatc   1980
tgttccactg atttacttct ctatcattat gccagtagaa cactgtctta attattataa   2040
ttttataacc ttgaaatcag atacagtaag tcctctaagt atgttgttct gtttcaaaga   2100
tgttttggtt actgtaggtc ctttggattt ccataggaat tttaaaatca gtttgtcagt   2160
ttctacagaa agcttgctgg ggtgctgatt gagattacgt tgaatctata gatgaatttg   2220
tcagaaactg acatcctgat aataattctg agtctttcaa tctaggactc agtatatttc   2280
tttatttatt tgggtattac ttgttttttc tcaggaatgt tttatagttt tcagtacacc   2340
agacttgtac atattttttt agatttctct cgcagtattt tgcattttta tgctagtaaa   2400
atttcaatgt ctgattgttc tttgtgtgtt tcatgtagat tctgtttgac catctacata   2460
ggcaatcatt tcttgtataa attaagacag tttttcttct tccattccaa tctgggtgta   2520
tttgtttctt tttattttct tattacactg ggtagagcag atatcttcac cttgtttccc   2580
atctcaggaa gaaagctttc aatcgtttac cattaaatat gttagctgta agtttttcat   2640
agatactcct tatcaggttg aagaaattcc cttttattcc taatttgctg agagttttta   2700
tcaggaaagg atattgtata ttgtttgtta gatacttttt cttagcattg cggtggttga   2760
ttttatgtat caaattggtt ggactactgt gcctagatgt ctggtcaaat attattctag   2820
```

-continued

```
atgcttcagc taaggtaact tttggatgag attaatgtta aattggtgaa ctccgagtag   2880
ggcagattaa cctccacaat gtgcagggtc cttgtcttag ttcattttgt gttgctataa   2940
agaaatacct gagactggag atctatacag aaaaaagatt tatttggctc atgattctta   3000
tggccgaaaa tttcaagatt gggcatctgc atcatggtga gagagaaagc aagagcgagc   3060
aaagaagggg agatgccagg ctcttttaat aaacagcaac cagtaaagaa ctgactcatc   3120
cttgagggag gatctattca ggagggatct ggcctcatca ccaaaacacc tcccattagg   3180
cctcacctct aacatcgggg atcaagcttc agtatgaagt ttggagggga caaacatcta   3240
aaccaggggt gtccaatctt ttggctttcc tgggccacac tgggaaaaga agaattgtct   3300
tgggctacac ataaaatata ctaacacgaa tgatagctga tgagctaaaa aaaattttgc   3360
aaaaaagtct catgttttaa gaaagtttac taatttgtgt tgggctgcat tgaaagcagt   3420
gcctggctgc atgtggccca tgggccacag gttggacaag cttgaaccat agtcctcatc   3480
taagcagttg acgaaggcct taacaaaaca aagattgact ttctctaagc cagaaggaat   3540
tctgccagca gactgctttt ggatttgggc tgcagctttt tcctggggct ccagtctgcc   3600
acttaccctg ccgattttgg attttctctc tctttttctc tctctctgtg tgtctctctc   3660
tctccacaca cacacacaca cacacacaca cacacgcaca cacccctgtt ggttctgttt   3720
ctctggagaa ccctaaccag tgcacatatg tatattgata ataatatgct tttccttttc   3780
tagtttcatt aatatgaaaa tttatattga ttgatttttg agtgttaaac caaccttgta   3840
ttctgaaacc acacttgatc atgagatatt atccttttta catattttca ggcttgattt   3900
gataaaattt tgtttagaat tcttgcatct atttttatga caggttttag ccttagtttt   3960
ctcttcttgt aatgtctttg cctacttttg gtatcagggt aataatcctg gtctcataga   4020
aatggtgaag gagtattccc tcttctttaa tttttagaaa gagtgtttct agaattggta   4080
tcctttttct ttaaatgttt ggtaaaattt accagtgatg ctgtgatgtt ttctttgtga   4140
atagaatttt tactagaaat ttaatttgtg tttgtgagtg tatttaggtt atctattttt   4200
tcttgtatga gttttggtaa tttcagtctt tcattgaatt tgttcatttt gtttaagatg   4260
tcaatttatc agaataaagt tatttgtaat agcccgtatt atcctttgga tatctgtaga   4320
atctgtaaat gatgtcatct ctcttacttc ctaatactgg cagtttctgt cttttttttc   4380
ctgattaatc ttggtagaag ttcagcaatt tgattgattt tctcaaaaag aatccatttt   4440
tggtttattg atttttttct catttttccc tgtgctttgt ttccttgatt tacttctcga   4500
tttttattgt ttccttcttt ctgttaactt tgaatttaat tttgaattgt aattcaattt   4560
ctttttggtc agagagcata ctttgtgttg cttgaatcct tttgaaatta ctgagacttg   4620
ttttatggcc catagtaaga tctgtctcag taaatgctcc ttgtgcactt gagaagatta   4680
tgtattgtgt tgttatcagg tggagcgtcc tattagtgtc agctaaatca agttgattgt   4740
tttgttcaag tctcttatat ccttaccaat tctctgtcta cttgttctat tattgaaaga   4800
ggaatattga atttcctgtt ataatgtgaa tttgtctatt tctcctagta atttggtcag   4860
ttttctgctt tatttgtttt aaggctctgt tactgggtgt ataaacattt tgattactaa   4920
atcctcttga tggactgact cttatatcat tatgaaatga cctttttgt cccagtaata    4980
ttctttgctt ttaaatctgc ttcccttata ttaccatagc tattctggct ttgattggtg   5040
ctagttttgc ttatgctttt taaaattctt ttacttctaa cctacttatg tctttataat   5100
taaagtgtat ttttggtagg cagcatatat atatttatgg gtcttgcttt ttctatgcaa   5160
cccaacaatc tatgtatatt aatgaaggtg tttagatcat ttatatttaa tgtaattgtt   5220
```

-continued

```
gatataattg gaattaagtc cattattttg taatttgttt tatatttgct tcatctgttt   5280
ttttcttcag attgagtatt tttcatgata tcattttctt tcctttgttg gcttatgatc   5340
tatagccatt tgtttcatta ttttagtggt tgctttagga tttctaatgc atatatttat   5400
cttatcagtc tttcttcaag tgatatttga ccacatcata catagcataa aaactttaca   5460
atagtatatt tccatttctt ccctcctcac ttttatgcta ttattgtcct gcattttact   5520
tgcatattat aaacctcaca ctatattgtt tctcattatt aagttaatat ttaaataaat   5580
tttttatttt agaatagttt tagcttttca gaaaatgtgt aaagttagta cagagagttc   5640
ccagtctatg ccacattcag tttactctat tgttaacatc ttgaattatt ttggtattgt   5700
tacaactata attatctttt aaagatatgt aaatagcaag ataaaaagta catatttacc   5760
catgtagtta tcatttctgt gctctttatt gctttgagat ccatatattt atttgatatc   5820
acttttcttc tgcgtgaaga agttccttta acatttctta cagtgcaagt cagttgacaa   5880
ttaattcttg tagcttttgt atatctgaaa aagtcgattt cactttcatt ttggaagata   5940
ttttcactga atagggaatt ccagttggca atttatttgc tttccctatt ttaaagatgc   6000
tgctcaccct tttattcttt gatttatttc tggtaagaaa tgtcactctt atctttcttt   6060
ctttctttgt atgtaatgtg tctttttccc cctctggctg cttttaagat ttatttttaa   6120
tactgatttt gagaaatttg attattatct tccctagtgt aattttctta gtgatagtga   6180
ttcttatgct gggactcatt aaaattttta gatttgtgtg tttataggtt ttctcaaatt   6240
tggatttttt tgcctattat gacagtttca ataaagtttt acattttaga acagttttag   6300
atttacagaa ttgttgcaaa gatagtacag ggaattccca taaaccccac acccagtttg   6360
tcctattatc accatcttac attggtatgg aacattatca tggttaatga accaatatgt   6420
atacattatt attaagtaaa gtctatagtt tttttcagat tccttcagtt ttcccctaat   6480
gttgcaggat tcccatccgg gataccatgt tacatttagc agtcatgttt ccatagcttc   6540
ctcctgctgg tgacgttttc tcagactttg ctttcttttg atgaccttga cagtttttga   6600
gaaatactag tcaggtgttt tgtagcattt tcctcaattg ggatttgtct gatttctcag   6660
gattaatttg ggattatggg tttgagtaag atgacagagg taatgccatt cgcatcatat   6720
taaggctcta tattatcaac atggcttatt gctcttgatg ttgactttta tcacctggcc   6780
caggtgctgt gatatggttt gcatctacat cctcacccaa atcttatgtt gaaacataat   6840
ccccagtgtt ggaggtgggg tctgttggga gttgattggc tcctgcgggt gtatttctca   6900
tgaatggttt agcaccgtcc tcttggtgct atccttgtgc tagtgagtga attcttgcaa   6960
ggtctggttg tttaaaaaag accctccctg tctctcttgc tcctgctttt accatatcat   7020
gtacccactc ccccttcacc ttccgccatg attggattgt aagcttcctg aggactcccc   7080
agaagctgag cagatgtcag caccatttcc tgtaaaactt gccaaaccat gagccaatta   7140
aacctctttt ctttataaat tactcaccct caggtatttc attatagcaa tgcaataacg   7200
gcctaacaca tgctgtttgt caggtttctc caccattaag tgactctttt ctccccttt    7260
aatactgtcc tctttggaag gatgtcacta gcacagccca catttaagga gtggggagtt   7320
atgctccacc ttgttaaggg tgaagtagct acataaattg tttgaaattc ttctgcatgg   7380
tagatttgtc tgttgtcttc catatattta tttattcaat cattgatttg tatcagattg   7440
cactccagaa tatttatttt ataatttggg ttataatcca ttactacttc atttattttg   7500
ttttattcaa attgttccag ctttggccac tggaagctct ttcagttggc tcctgtatcc   7560
```

-continued

```
ctttggcata tccccataat tgtaggtatt gtctgcagtg ctttcttact ttttggtact   7620
acaagatgct ctaacgtggt ctttttcttt tcttttaact tttattttaa gttcaggggt   7680
acatgtgcag gatgtgcagg tttgttacat aggtaaacat gtgttatggg ggcttgttgt   7740
acagattatt tcatcagcca ggtaattaag cctagtatcc accagttatt tttcctgatc   7800
ctctccctcc tccccgcctc cacccccctag taggcccagt gtgtgtttcc cccccaacca   7860
tgtgtcaacg tgttctcatc attcagctcc catttttgag taagaacatg cagtatttgg   7920
ttttctgttc ctgcattagt ttgctaagga taatggcctc ctccatccac atctctgcag   7980
aggacaggat ctcattcttt tttgtggctg tgtcgtactc catggtatgt gtatctatat   8040
ataccacatc ttctttttct ttttttcttt ttttttttg agatggagtt tcattctgtc   8100
acccaggctg gagtgcagtg aagcgatctt ggctcactgc aacctccgcc ttctgggttc   8160
aagcgattct cctgcctcag cctcccgact agctaggact acaggcgtgt gccaccacgc   8220
ccagctaatt ttttgtattt tcactagaga cggggtttca ccgtgttagc caggctggtc   8280
catgttttct ttatccagtt tatcactgat gggcgtttag gctaattcca tgtctttgct   8340
attgtgaata gtgctgcact gaacttacgt gtacatgtgt cattatggta gaacgattta   8400
tattcctttg ggtatatacc tagtaatggg attgctgagt caaatggtat ttctgtctct   8460
aggtctttga ggaatcacca cactgtcttc cacaattgtt gaaataattt acattcctac   8520
caacagtgta aaagcatcta gggccatcgt atatatttcc tgtgctattc ctagaatcag   8580
ctattttttc caagatttct tttactggag agtggtattt gataccaaga tctggtgctc   8640
attgctactg ggatttcttt gcttttaggc cctctcagcg gacagagaaa ggaaatatat   8700
gtgtatacat tagcatgtgt atatgcacac atcatagtat ttctaaatgt aaccatctgt   8760
gtctatatta cgctaaccat cggttgatac tgatgtctct aactgtactc ctgccccaca   8820
tggatttttc tagtctctcc ttgctcatct gtaaccttct actgcaacca taagacactc   8880
ggttcccacc attttacttc cacttactta actgtccaat tccagaatac gtattctgga   8940
atgatatctg atatcaggat gatatcagaa ttgttaaccc atacaagcat aagcaacaac   9000
cttaccaact agggtacagt gtttatgtat agttattttt gcattgagtc ttacagactc   9060
cactcatttc caaagttact taggccagca ctttattccc agctccctca gtgaggttgt   9120
ttcatacgta gatagcacag taagatgact gcatcgcatt ctgctttcca tcctgggatc   9180
tcctgacctg gtaaattatt attttttaaa atttgcatgc attaaggttt actctttgtg   9240
ctgtaaagtt ttatagcttt tgagacatgc ttatgccttg tagccaccac tacagtacct   9300
tttaaggtag taagaatagt tctactgccc taaaaaaaaa acctcctgtg cttcacctac   9360
ctctctcctc taccagcccc ctggcaatga ctgatgcgtc tactgtctct ctcgttttgc   9420
cttttccagt gtagcaggag tggggaccac gggcatttgg gccacttctt catgtaactt   9480
acttgtgtct tcaggatgtg ctcaggccgg atcatgtata tacctctctg ttggatgacg   9540
gagcactgct gtgcatgccc aactttatgg ctacgtgggt cagataattc cccagttcat   9600
ggtgggcagc tcagatcaca gggtaacttg gtggcccatg gtcaaacatt cagtttctac   9660
taaggcacgg cagcaggcca agccctgtct ctccaaagga gagtggttat ctgtggatgg   9720
tggcagggcc tcgccgcaaa gtcctaaagg cccgtgctgt gatccacctc cggcacccct   9780
atctaacacc acacgccagt cactattcac ctccggcacc cctatctaac accaaccagt   9840
cgccattcac ctacggcacc ccatctaaca ccaaccagtc accattcacc tacggcaccc   9900
catctaacac cacatcccag acgccactgc atctgctggg tcacatggcc cacagggcag   9960
```

-continued

```
agcagcttgc acggcagcct ggatctgcca tagagccttc tcctgctctg gtttctactc  10020
aaaactggca gcttttcagg gcacttgggc cagattaact acatgagaaa tgtgttgctc  10080
taaattcaaa gagggccggc gtggcggctc acgcctggaa tcccagcact gtgggaggct  10140
gaggcaggtg gatcacctga ggtcaggagt tcgagaccag cctggccaac acggtgaaat  10200
cccgtctcta ctaaaaatac aaaaattagc tgggcatggt ggcgtgcacc tgtaatccca  10260
gctactcggg aggctgaggc aggagaatcg cttgaacctt ggggggtggc agaggttgca  10320
gtgagctgag attgcaccac tgtacaccag cctgggtgac agagtgagac tttgtctcaa  10380
aaaaaaaaaa aaaaattcga agaggcccca ttcagcattg tctcttagtt atgactaaga  10440
aggggcagat gcaactgctt atccttcccc ttagaacggg taactccaca ggccacacgc  10500
cattggaccc ctagacgttt ccctgaggta gaaggctctg aattccagtt gggtttattc  10560
cccaccctcc gacaccaaca agtctaggat ggaggctact tcttgtgcct tacgtcccgt  10620
cagcatgatg tcaccagtgt aatgggccag tgtgacatcc tggggaaggg agcggtgatc  10680
gagactcctg agaattacct ctgacacggg ctggagaggc gagaggcccc tgaggtgggg  10740
cggcgagggg gcattgctgg cctggcttct gctgggccct gtggacaggg gtggaggaga  10800
acgcatttgc cggatcaaga gcttcgcacc agggagcagg agatgtgcta atttgctcaa  10860
gcgatggaac ctcgtctggc ccagcagctg cagctggagt caaacttagg acagtcccct  10920
gtcattctcc aggacccgcc tgtctctcct acgggccaaa taggcgggtg gaatcggctg  10980
tggtggggat caccgcccct gcacctctca agtccttggt ggtggcactg atgtctgcag  11040
tcccttcagg gatgtgggat ggcttttgac tgacggttct aggtagaggc ctttctaatg  11100
gcttccactt gtcctttccc cccatagcag acaccacacc ccaggtcagg ggacgcatgt  11160
ggggactctg ctggctgctg agtgtgtctg ttccacttac acatctggag ctgggaagat  11220
gaccacagga tgggctgggt acccactgga cccacagagt cagatctgag ctaaaactcc  11280
attgatcacc tggatcccta agcccctccc taactggagg gccacagtgt ccttccagcg  11340
tctcctagaa tcaatgtcag gacagagcca gtgtccaatc gtcccgaaat gttgcagtat  11400
tttcttttct ccaatacaca gtctctttca ggaagactgc ggaaaagatt atcaggataa  11460
attctgggga ctatacaggc ccgtgctgct gggggcgggg aggctgcttc cactggggca  11520
gggacgctgc tgcctctggg gctgggaatg acacttatgc tggttgtggg gagacttttt  11580
ctcaagggta cccgcctttc ttgcattcga gggttctggg tccgtagact gtctcaagtc  11640
tgtgaatgac caaggccatg attctctgtg tttttatgac tgaacttaga cttttgtcca  11700
cttggcctgg aagtttactg cttgtatcca gtaggaattg agcagatttc ctgtttattt  11760
cactgctagg aacatgataa gcagccagtg ccataggtct gcatgggtca gaccagtgac  11820
ccaggtctga ttgctgcttc gcttctgctg tccatcatgg taaccacacc cactttttct  11880
ttggccccctg ctaccccagg atccgattat tccccgttgc atgtaaagtt tcgcagttga  11940
ttgactgcaa ttcccactgt gagtctggcc tacagagaag aacaattgca gagctcttca  12000
aggagactgg gctccctcac agatctatgt ctcagtgttg tgagaggcct gcatcctggg  12060
ccctcccagg gtgggtgagg aggttttcat tgtcacattc ccatctccct gagcctttga  12120
acccctttcct ctatgttaag ccaagggagc ttgggtacct ccagctcgct cactgcgggc  12180
atcctttgat ccatgtttca accgaccagc cagttagagc ttttccaagt ccccctagctg  12240
cagcctggag tgcggcctct gcttggtgga cacgtctgca cacccggccc ctccacctcc  12300
```

gtgttcctcc cccagtgccc acacccagtg tctgctccca ctgatgcccc tgggtgtctg 12360
tctgtgtaaa tcagagaggt caagtggctc ttctggggtg tggctcgcct cctcctgtgt 12420
cacactgtgg gcctcacctt caggggcctc ctgggctgcg agtcttgtta taggtccaga 12480
agcaaaggga ggtggtgggg gaaggaccgg aggagaatca gcactgactt gcctggcaac 12540
cgccttaggg gaagtcctta ccctttcctc aggcaacgca ggttaatgcc ccagaggagg 12600
tggaaaggcc agagctgctg ggggcgggga ggctgcttcc actgggccag ggacgctgct 12660
gcctgtgggg ctgggaatgt cacttatgct ggttgtggag agactttttc cgtggtaaaa 12720
gaaggctcag tatttcaggg tgcaatgtcc ccagcttcat caaggccccc ctcccaggtc 12780
cccattccaa catatcaatt ctttctcaac caatgccttc cctttttttt ttaaatatca 12840
atttaattgg ttttattcat ttcaggcaac taattttaca acagaagtaa agcttttaaa 12900
tacaatttct gatatatatc aagtatgaga aatttggcta accaaacttt aatgctttat 12960
aaacatgtaa gcaaaaccaa atgtgagatc aatcccatta ggatgtaaat ttatcaacat 13020
ttctagacaa aattccacag ttaagaatca ccgtctttcc agtaaatgcc atttacacac 13080
aatgtgaatt tttagctgaa tattctaaaa tttctagatt cttattttgt atttctgtgc 13140
acaatacagg ataatcagag tttcttttat ttctctgtgc tttctttttt tttttttttt 13200
aatagaggag ttgtttaaaa cacaacatca gcaacataaa caacaaaaac ctttcctggg 13260
gctgtgataa aaacgttgca tttatctgag cctaccacag acacccagca aggccgagaa 13320
ctgcgtgatg agggcttgca tttgacttgc agcaattccg accctgtggc tataggacct 13380
aggttctccc tagggacaca cctagccgct gttaggtcat ttatgcggtg cttgagctga 13440
gaatccaaat acctgatctc attcttttcc ttcatcactt tgtcctggaa cattaggagt 13500
aaccaacagt tcattcattc cttcgttttc cacaaatgct ccaaagtatc atatacagag 13560
cctctaagtt ccttgcctct taaaagtggc tgctcacttt gggaggccga ggtgggagga 13620
tcgcttgagc tcaggagttc gagaccagcc ttggcaagat agtgagacct catctctaca 13680
aaaaataaaa taaaataaaa taaaataata aaataaaata aaataaaata taaaataaaa 13740
taaaatataa aataaaataa aataaaataa aataaaataa aataaaataa aataaaataa 13800
gaaaggatca cttgagccca ggaggttgag gctacagtga gctgtgattg tgccactgta 13860
ctcccacctg ggtgacagag agagcccctg ccacaataaa aaataaataa ataaggaaaa 13920
aaaattaaaa agtggttgct taggagtact taatgcatgt attttgcgta tctttataaa 13980
caatttatgg aatgactatc ggtactcttg gtactattgg aagtagagtc cttagcattt 14040
ttaagtctaa tcagactaaa gacccaattc cagaaactct aaaaccaatt tagggaactc 14100
actcttaaaa ttctgtcccc actagaacca ttcctggtac gtagtatgag ttacccagag 14160
agacaaaacc agtaggatgc agatagatac agatatagat gtagatatca aaattgatag 14220
agctatatga gacaggattt attatgggaa ttggctcatg caattatgga ggctgagaag 14280
tcccacaatg tgtttcctgc aagacggaaa accagggaag ccaagagcat ggctcagtcc 14340
aagtgtgcag gactcaggac caggaaagct ggtggtgtaa ctcagtctgc agatgatggc 14400
ctgagaaccc gggggacact ggtgcaagtc ctggagtcca agggctgaag aaccaggggt 14460
tccaatgtcc aagggcagtg gaagatgggt gtctcagctc caggaaagat aggtaggtag 14520
ataaatagag agagactgag caagtagacc attgaccttt ctgctctatc tgggccctca 14580
gacaattaga tagtgcccac ccacatcagg tgaagataga tcttccttat tcagtccacg 14640
gattcaaacg ccaatctctt ctggaaatgc cctcacaggg acacccatag ataatgcttt 14700
accagttatc tgggtatccc ttcaagttga caaccaaaat taacctttac aaggtgttat 14760
atatattttg ttaaatttat tcttaagaat tatgtttttg ggggttctat tgtaaatggt 14820
atcttttttt ttttatcatt tcagacttca gttgctcatt gctagtatat aggaaagtga 14880
tagactttgg tgtattaatg tgtatcctgg gtccttgcca tagttgcttt ttagttccag 14940
gagtattttg ttgatttctt agagattctc tagatgtaaa atcatggcat ctgcaaatat 15000
aaacagtttt atttctctct ttccaatcta tataccttttt atttcactct cttgtcttat 15060
tgaaatagcc aggactttga gtcctggtga atcaggaagt gtgatgcctc cacttcggtc 15120
cacttgctca acattgcttt agctatttgg ggtctttcat ggttctgtaa aaattttagc 15180
attgcttttt ctgtttctgt gcaaaatgcc actgcaattt tgatagagtt cgcattgact 15240
tttagatcac tttgggtagt gtggaaattt tgacaacatt aattcctctg atctgtgaac 15300
acaggacatc cttccatttg tttgttttca tcaatttctt tcatccaagt tttagttttc 15360
agtgtacata tctttcactt ccttgattaa atttattcct cagtatttta tcctttttga 15420
tgctattgta agtaaattgt tttcttaatt tctttttgg atagttcatt gttagtacat 15480
caatatgcaa ccaattttg tatattgatt ttgtgtccta aaaatttact aaattgatta 15540
gttctaactt tttttcatgg agtcattagg gttttctatg tatgtaatca tgtcattggc 15600
aaacagagat aattttactt cttcttttct gatttggatg ctttcttttt tttgcttttt 15660
tttcttacct aatttctctg gctaggactt ccagtattat gtataacaga actggcaaaa 15720
gtggacatcc tttttgttgt tcctgatctt agggagaaag cttttcactt tttatttttg 15780
agtatgttgt tagaggtgag atgtcatata tgacctttat tgtgttgagg tacattcctt 15840
ctataccaaa tttattgata cttttttatc atgaaatggt attgaatttt gacaaatgat 15900
ttttctgtat ctattgagat aatcatataa tttttatgtt ttattctgtt aatgtgatgt 15960
atcacttttt tgagttgctt atgttgaact atctttgcgt ctgagggata aatcccattt 16020
gatcttggcg tgtcactctt ctaatatgct tttgaatttg gtttgctgct agtattctgt 16080
tgaggatttt tgcatttatg tttatcaggg atattggttt gtattctttt cttgtagtgt 16140
ccttgtcttt cacatcagag taatacttgt tttataatat gaatttggaa gtattccaaa 16200
aatttagttt tttggaagag tttgagaaca gttgttatta gttcttctca aaacgtttgg 16260
tagaatttac tagtgaagcc gtgaggtcct gggcttttct ttgatatgtg attttgatta 16320
gttattcaat ctccttactt ggtctgttca gatttttctat tttttatga tgcattctta 16380 gttaatttta tgcttatagg aatatatctg tttcttctag attatccagt ttgttaacat 16440
ataattgctc atagtggtct attatgatcc tttgtatttc tgtagtatca gttgaatgtc 16500
tcctttttca tttttattta ttttagctta tctctttttt tcttcatcta gctaaatgtt 16560
tatcaatttt ggttatcttt tcaaaaaaca actcttaatt tcattaatct tttccacctc 16620
tgcttgttgt tattttcttc cttctgctaa ctttcagctt agcttgctct tctttttcta 16680
gttctttgag gtataaagtt aagctgctta tttgagatct ttccttttttc ttcatgcagg 16740 cgtttatcac tataaagttc tctcttagaa ctgcttttgt ggtatcacat acattttggt 16800
atgttgtgtt tccattttca tttgtctgag atatttttgg tgtccctttt gatttcttct 16860
ttgacccatt ggttgttcag gtgtgtgttg tttaatttac atatatttgt ggattttttct 16920 gttttttttct gttattgatt tctagtttga taccaaacta gaaattggaa atggttggaa 16980
aagacgcttg atataatttc agtcatttta aatttggtaa aacttgtttt gtggcctaac 17040

-continued

```
atatgatcta tcctagagaa tattctgtga atacttgaga agaatgtata ttctgctgct  17100
gttgaatgga atgttctgtg tatgtctgtt aggtccattg gtctaaagtg tagttcaagt  17160
ccagtgcttg tttccatatt gatttttctg tctgggtgat ctatccattg ttgaaagtgg  17220
ggtgttgagg tcttctatta ttatcattgc attgctgtct atttctccct ttagttagtt  17280
atatatttag gtgcttcaat gttgggtgca tatatgttga atattgttat attctcttgg  17340
taaattgatc actttatcat tatgtaataa tctttttctc ttgttagttt ttgatataaa  17400
gtctattttg tctgatataa gtacagctac ccctgctctc ttttggtttc catttgtatg  17460
aactatcatt tttcttccca tcactttcag tctatgtgta tcctcaaagt tgaagtgaat  17520
ctcatgtagg cagcatatac ttgggtcatg ctttttaaat gcattcagcc attgtgtttt  17580
gtttttttaat ttaaaagatg agatctcact atgtttccca aactggactt gaactcttgg  17640
gctcagtaat cctcctgcct tagcctcctc agtagctggg actacaggag tgcaccacac  17700
tttggctatt ctgtgtcttt tgattgtaga atttgatcca tttacattta aagtaattat  17760
taataggtaa agacttacta ttgctgtttt gttcattgtt ttctggatat tttatacacc  17820
ctttgtcgct ttcttccttt cttattgtct ttcttcgtga tctgatgatt ttctgtaatt  17880
gtatgttttg attttgtgta cctactatag gtttttgatt tgtggttacc aggagaattg  17940
cattaaacat catataacag tctattttaa gctgataata gcttaagtcc catacaaaaa  18000
ctacttcact cctcttcctt ccccacatta tatgtttatg atgaagtctg cagataaatt  18060
agtagggtct atggcctttc tcaccttctc tcagtttctt gcaaccactt agctgtgccg  18120
accacctcag tgttctcagt ggggtgagaa acagtgggcc tcttgggcag tttgccatat  18180
ggctggggga gcctggtgct cactcacttt cctctgtgga aaggtcatgg acctaataga  18240
tttattttgg cattgagcta tgctgccttg aaaaaggggt gatgtggata aagtcaaacg  18300
gttcttttac cctcttcaat gcatttatta ttagattttt tgctataact gtgctagaac  18360
ttctccactg gactcctgga cttccacaaa gatactgtca tctataggta gttgaaacat  18420
caatgctttt gtggagggat gatggtggaa atctcctatt ctgccatctt actgacttca  18480
ctctttttaa ctccagctgt tggtcataag atactttgga caagatcact aaaatcttgt  18540
cacagaaact ggatatacct atggtggctg cagccacttc ttacatactt ggagagctaa  18600
tgtcttcccc cttcagaaaa gtggagtaga ggagaagagg agtagtagag gagtagtgga  18660
gaagaggaag acagggaagg ggaagaagag aaagagcaga aagaagccaa agagagaaaa  18720
atgttaaata aattttctgc ttcatttgat atggttatat attgttttct ttagtctgtt  18780
gatgtgtgga ttacagagat tgctttttga atgctgaacc catcttgcat atctagaata  18840
aatcccattt ggattgtact tcataattct ttttatttat tattcgattc actttgctaa  18900
ttttaagaag gtctttgcat ttatattcat gagagatatt ggtctatagt tttcctttcc  18960
cataatatct ttacctgagt tttgttatta cagtaatgct gtcgtcatag aatgagttag  19020
aaagtgtgtc tgtcaccttg attttttgga agagattttt tggtggagaa tttggtatga  19080
cttcttcctt aaatttttaa tagaattcac tgctaaaacc atttgggcct ggtaatttct  19140
ttttaggaag gctactatta ttaattcaat taattcaatt tctttaatag atacagggat  19200
atccaggtta tttatttcac cttgtgtaag ttttggtaat ttgtgtcttt ccagaaattg  19260
gtctatttca tccatgtgaa atgtgtgggt atagagttaa ttatagaatt tctttattat  19320
gctttcacag tccatgggat taacagtgat gatacttttt catttctgat attgattatt  19380
tgtgtctttt ctttttttct tgcctaacct agctagaggt ttatgaattt tattaatatt  19440
```

ttcaaagcac cagctgttat ttctgttgat ttttttctgt tttgaatttc attcatttat 19500
cctctaattt ttattaaatt tttcttctgc ttgttttagg cctaaggtgg gagcttaggt 19560
tactgattgc ctttctaatt atagtcagtt aatgctatat tcagcattgc ttttgctgag 19620
tcctacaaat tttgatatac tgtattttca ttttcattta gttaaaaata ttttttaaat 19680
ttctcttgag acttcttttc agcttggatt atttagaggt gtattgcttg atttctaaat 19740
atttgaggat tttcctgcca gctttttgtt ttttatttct agtttaattc cactatggtc 19800
tgggaacact ttatataatt tctattattt tcaattaaag tatgttttat tctagaatgt 19860
ggtctatcac gatgaatgtt ccacatgagc tagagattaa tgtgtattat tctgttgttg 19920
gatgaggtag tctaaaatgt gaattagatc aagttgggct ataactgctg ttcaggtcaa 19980
ctttatcctt gtctattttc tgtcttcttg acctatcagt tactggccgt agggtcttga 20040
agtctccagc tgtaacagta aatttgtcta tttctccttg caggtctatc agcttttgct 20100
gcatgtgtat tggtgctctg ttgttaggta catacacatt aaggattgtt gtatcttctt 20160
ggaagtctgg ttcctttatc attatatagt gactttttaa tataatttca attttatttt 20220
ggatttaggg gttgcctgtg caggtttgtt acatgggtat gttgcatgaa cctgaggttc 20280
aaatggtctc atcacctatg tagcgagcat aatatccaat aggtagtttt taaggccttg 20340
ccccccttcct tctctccttt cttgggtagt cctcagtgtc tgttgttccc atctttatgt 20400
ccatgtgtat ccaatgcgta gctcccactt ataagtgaga acatgcagta tttggttttc 20460
tgttaattca cttaggataa tggcctccag ctgcatccat gctgcaaagg acatgatttt 20520
gttctttttt atggctgtgt agtattccat agtgtatatg taccgcattt tctttatcta 20580
atctaccctt gatgggcact taggttgatt ccatgtcttt gctattgtga atcatgctac 20640
agtgaacata tgaatgcgtg tgactttttg gtagaatgat tagtttttct ttgggtatat 20700
aaccagtaat gggactgttg cctgggatgg tagttctgtt ttaagttatt taagaaatct 20760
tcaaactgct ttccacagtg gctgaactaa tttacatttt gatcaacagt atataagtgt 20820
tccttttctt tgcagccttg ccgttatctg ttatttttg actttttaat aatagccatt 20880
ctgactgatg tgagatggta tcttattatg gttttgattt acatttctct ggtaattagt 20940
gatggtgagc atttttcat gtttcttggc catttgtatg tcttcttttg agatgtattt 21000
gttattgaat tttgcccatt ttttttttt tttgagacgg agtcttactc tgttgcccag 21060
gctggactgc agtggtgcaa tctccgctca cggcaagctc cgcctcccgg gttcatgcca 21120
ttctcctgcc tcagcctcct gagtagctgg gactacaggc gcctgccacc atgcccggct 21180
aattttttgt atttttagta gagatggggt ttcaccgtgt tagccaggat ggtctcgatc 21240
tgctgacctc gtgatctgcc cacctcggcc tcccaaatcc tcatgctagg attacaggca 21300
tgagccaccg cgcccagcca attttgccca ttttttaatg gggttatttg tttttcactc 21360
atcaaattgt ttaagttcct tatagattct ggacattaga cttttgtcag atacatagtt 21420
tgagaatatc tcccccattc tgtaggtttt ctgtttattc tgttgataaa cagataaaca 21480
gtgattacct tagcatttac aatatacatt ttaaatttac ctaagtccat ctccaaataa 21540
caccatttca cttcattagt agcacagata agtcctgtgt tagtccattt ggcattgcta 21600
taaaggaatg cctgaaactg ggtaattgat aaagtaaaga ggtttaatag ttctgcaggc 21660
tgtataagaa gcatgatgtc atcatctgct tctggtgagg cctcaggaag gttttaccct 21720
tggcagaagg caaagaggga gcaggcatgt cacatggcaa gagaggaagc aagagaggtg 21780

-continued

```
ccagaccctt ttaaataaac agctttcaca taaacttact gctgcagaga gggcaccaag  21840
ccattgatga gggatccact cccatgacca aaacacctat cactgggccc aacttccaac  21900
attgaggatc acatttcaac atgaaatttg gagggaacaa ataccaaact atataaagtc  21960
ccgattcctc ctcccatccc ttataatgct tgtcatttat tttacttacc catatgctgt  22020
aataacccaa tgcattctta ctaatattat ttgaaacaaa tagttatcat tacattgatt  22080
tagaataaga aaagatctta cttttacctt catttattcc ttctctgatg ctccttttct  22140
ctttatgcag attcaagttt ctgacctata attttcctct gtctaaaaaa gaatcttaac  22200
atttcattcg ggtgtggtgg ctcacacctg taatcccagc atttcttgta gggcagatct  22260
ggtgataaat tccttccatt tttgtttgtc tgcaaaagtc tttactttct cttcacccag  22320
cctatcactg tatataggct gggtgcaatg gctaacaccc ataatcccag cactttggga  22380
ggcagaggca ggaggatcac ttcatcccca gagttcaaga ctagccaggg caacatagtg  22440
agacctcatc tctacagaaa taaaaaataa aaacattgtc aggtgtggtg cagcacatct  22500
atagtcctag ctacttggga ggctgaagca ggaggatttc aaagtccagg aggtcaaggc  22560
tgcagtgagc tatgatcaca ccactgcact ccagcctggg caacagagtg agactgatgc  22620
tgaaaaaaaa tttttttttaa tgatagccta agagctgtga gaattaatgt gaattgcagg  22680
acacatgtat catcaacact ttgaacatac ttgtggccct tgttcctctc agggctttaa  22740
aaatcatttt tatataattt aaaaattata tgtaaatata tatgcacaca tacacacaca  22800
tatacacatg tgtatatata catatatgtg catatacata catgtatgta tatacacaca  22860
cacacatata tataaaactg gatatagaat tctaggttgg tagtatatgt ctttcaacac  22920
tttaattatt tcatctgatt gtcttcttgc ttgcagtttt cggacaagag gtcattgtaa  22980
ttcttatcca tatttctctc taggtaatgc ggtatttttc cttttgtgtc tttcaagaat  23040
tcttgttgtc ttaggtcttc tcagattaaa tataatatgt ctatgtgtag ttgagggttt  23100
tttaatgttt aaaaaattct gcttggtgtt ctctgagctt cctggatctg tggtttgatg  23160
tctatcatta attttgccaa gttctaagcc attataactg caaacatctc ttctgctcca  23220
ttcctttttt cttctctttc tggtattcca actacaagta tgttacattt tttaaatttc  23280
cctcagtttt tggttgctct gttctggttt tgttttgttt ttttcaattc ctcttttttc  23340
ctttgcattt cagtttggaa agtgtctgtt gatctgtctt caagctcctc aattctttcc  23400
ttagacttgc ttagcctatt gataatccca ttgaaggcgg tccctgtttc tgctaaaatg  23460
tttttattt ctagcatttc cttttgattc tttcccagga ttatcatatc tccgctcgat  23520
tacccatctt ttcttagcat tttgtcgatt tttttcatta gagctcttag catgttaatc  23580
atagttatat taaattatct atgtgataat tctgacatct gtgtcatatc tcagtctggt  23640
tctgtcactt gttttgtctt ttgaagctgt gccttttctt atcctttggt gtgccttgta  23700
aattttttgt ttatcaggta atagaaactg aggtaaagag ccctctactg tgagggttta  23760
tgttattctg acagggagtc aggtatgagg gggagaatag tgttctatat tctcccaatt  23820
aaatgcctta cagtgagcct gtgcctcggg ctgaaacctt cacaagtatt tcccagtgtc  23880
atagcttttg caacttggga gtgacaggag agctagaagg ggctggagtt ggggaaatgc  23940
ccttcaccca ggtgggataa ggctctggaa acatctttcc ccagaagagt agtactttgt  24000
tatggaaatt gctccacaat tactcttcac ccctgccccc tacctgcctc ctaccaggct  24060
cttctgcgct cttcacagtg agaaactggt tcctggaggt aaagtccatg aaagcgtgga  24120
gcccccaaga ctgcacaccc ccaggatctc ttactctcag ggtagcctgt ctcagcagtt  24180
```

gatcagaact accatttaaa catctgtgtc tgtttgtgtc tcccgtggct tctactccag 24240
taagccagtc ttggccacaa ctctctggac ttccccattt ccctgatttc aggagagtga 24300
tttgctctac aatctcaagt ctctgatggg tctgagaaag ttagtgattt tcaggttgtt 24360
ctgctttttc cggtggaagg atgggagctc tttacatgtt gagggtgaaa ataaaaatcc 24420
attctttttt cagaatgttt ttgtccctcc ctattctttc cttcaggccc tctaattact 24480
tgtatactag gccacctgaa attgtcccat agctcaatga tactcttatc attttaaaac 24540
aattcttgtt ttttcatttc atttggaata ttttctattg gtatatcttt aagtaatctc 24600
atccagtgta ttttttatct cagacattgc tgtgttcata ctgacagctc aatttggttc 24660
attcttacat ttttcacatc tctccacatc tctgtttagc tctttgtaca tagggaatgc 24720
agttacaata actgttttaa tgtccttgcc tgccaattct aacattcatg tctgttctgg 24780
gtttgttaca atgggttgat ttttctcccc attatgggtg tattttcttg cttccttgca 24840
gatcccacaa tttttttattg gttgcagatg ttgtgaattt tgccgtgttg gatactggat 24900
acgtctgcat tcctatgaac acggctgagc tttgttctgg gatgcagtta agatactttg 24960
gaacaacttg ttcctttcat atcttgcttt tatggcttgt caggcaggcc tgggacatta 25020
ctccatccag ggctaattat tccccactgc tggggcaaga cccttttatt ggtacactac 25080
ccaatgccct gtgaatcatg acattttcca gtctggctgg tgggaactgg ttcttctccc 25140
agttctgcat aggtactggg tcttgcagcc ccgaaccctt tcagttggtc cttccaggct 25200
tgggtcattc cctcccaggc ctgtgatgaa tgtatcctgc tgaatatttt agggggaacc 25260
ttctggagat ctccagggtt cactctttgt accactctct tctctgccct gcaaactcta 25320
gccaccttgg tctccccaaa cccccaattc tgttacctca acttggattc attgggctct 25380
gcctcaattt tcctccctgt attgcagtcc aaaaactctc tcagggcagc aagacaaggc 25440
aattgtaggg ctcactttgt ttttcttctc ttggggatca ctgtccttct ttgcccaata 25500
tcctttcttg aaaaccagtg tttctttttt tttttcttct tcaatctttt tgcttattat 25560
ttcagctgag aggggaaacc cagttcctgt tacttcgtct ttgccagaag tgggtgaaaa 25620
gccttggaga gtgtcatcag ttttgactta ttttctggct ttggagtaaa ggcaggttca 25680
gggacttcta cttgttcttt cctgccataa taggtcttac cacaaaggtc aaggagctga 25740
tgaaggagtc tgcctgctta tgggtccatg ttgattattt gtgtaggaac tgggggcgta 25800
atcttcaaat gggttcatga acatagccca ccccatgaga tagacctggg ccagatttcc 25860
acttattatc taactcccct atgctgcttc tttaatgggg ggcccatgat ggcacttggg 25920
tcccctagta ccagtgttat gagtgttatg cagactccat atgcaacagc cctgcaaaga 25980
tagttgtgtc cctcagttat cagctgtgat gatctgattc agtggctgta ggtcccttgg 26040
ggaaaggact gaggacatac cacaggttgc atttggtatg ctgtttcagg gtcctgcctc 26100
atggggaccc agcttctctt tccattggtg agtctgggtc tgagaactgg ctgaggtctg 26160
gaaatggtca aggggtcagg attgcatttg agagaatgat ctcagcctca ggcatccagt 26220
cttgatccct tgtttctata ttaaagggtc acctggttgg ttgcccacct gtcccctcta 26280
ggagcatcat gctctattat ccttctcaaa gacccctgtg ggtaaggcca actggtgcca 26340
tttcctcttt gctgcccgaa ttcactttct gtggctgcca taactaagta ccatagactg 26400
ggggacttaa taaccagaag tttatcctcc tcagtcctga aggctggaat ccaagatcaa 26460
ggtgtcacag ggctggttcc tcctgaggct tctccccttg gctggcagat ggctgccttc 26520

-continued

```
tagctgtgtc ctcacagggt cctccccctg tgtgtgtctg ggttctaatc tcctcttctc  26580
acaagtatat cagtcaggtt ggattaaagc tgctagaatt tggatgtttg tccactccaa  26640
acctcatgtg gaaatttgat ccaatgttga aagtggaggc ctaatgggag gtgtttgggt  26700
catgggagta gatccctcat gaacaggtta atgccctccc tggtagagcg gggcaaatga  26760
ggtctcactt tattagttcc ctcaagagca ggttgttaaa aagaggctag cacctccctc  26820
ccatctctct ggcttgctct cttgccatac ggtctctgca cacactggct ccccctcacc  26880
tccaccatga gtggaagcag cctgaggccc tcaccagcag cagatgcagg ccccgtgctt  26940
cctgtacagc ctgcagaacc atgaaccaaa taaacctctt ttctttataa attacccagt  27000
ctcaggtgtg cttttatagt aacacaagtg gactgagaaa attggtactg agagtggggt  27060
gttgctataa agatacctga aaatgtggaa gtggctttgg aactgagtaa tgggcagagg  27120
ttgaatgagt ttggagggct cagaagaaga caagaagatg agggaaagtt ttaaacttct  27180
tggagactag ttaagtggtt gtgactaaaa tgctgataga catgcaggca atagaggcca  27240
tgctgatgag gtctctgata gaaatgagga acttactggg gactggagcg aagatcaccc  27300
ttgttaaccc ctagcaaagg ttgcaactgc attgtgtccg tgctttaagg ctttgtagaa  27360
ggctaacctt aagagtgatg acccagaatg tttagtggaa gaaatttcta agcagcagag  27420
tgttccagaa gtaccatggc tacttttaac aacttacaat cactacaaca gcaaaggaat  27480
gatctaaagg tagaatttct aataaaaagg gaagtagagc atacaaattt agacaatttt  27540
cagcctggcc tgtggtagag aagcaaagaa tgttttcagg agaggaattc aaggtccttt  27600
gtgacaccgg ttgctagagg ggttggcatg actgaaagag ggtataatgc taacagtcaa  27660
aacaatgggg aaagggccct gaaggtattt tgaaggactt tgaggccacc ctgcccatca  27720
caggcccaga ggcctagcag aacagagtgg cttggagggt caggtccagg gtgccactgc  27780
tgtggaccac cttgggatgc tgcttcccac atcccagcca ccccagatcc agccatggtc  27840
ccaatggcct cagataccgc ttggacagct gccctgcaga gcacgaggca tgggacttgc  27900
tggcttccat gtattgttaa gtctgcagga atccagaatg caaaagtgct ggaggtttgg  27960
ccacttccat ttagatttca aagggtgtat tggaaagcct gggtgcccag gcagaaccct  28020
gctgcaggga tagagccctt cggagatatt cttctactgg agctgtggga atggggctgc  28080
cagggggacc ccagaattac agagacacca gcagtgtgca atcgcagcct ggaaaagccc  28140
caggcattgg actccaacct gtgagagtag ccacgtgggc tgggctcagc aaagccatgg  28200
gggcagggct gtccagagtc ctgggagccc acccttcctt ccagcgtggg atgtgggaca  28260
tggagtcaaa agagatttgg gagctttaag atttaatgtc tgttctgctg ggtttcaagc  28320
ttgtgtggga cctgtcctgc ctttcttttg gtcaatttct tccttttgga atgggaatgt  28380
ttacccaatg tctgtcccac cattgtacct tggaagtaaa tgacttgatt ttgattttac  28440
aggctcatac ctgaaagaaa cttgccttga gtcttagatg agactttgca ctttggactt  28500
ttaaatggat gcaggaagaa gctaaaactt taggggactc ctgagatggg atgattgtat  28560
tttgcatgtg agaaggacat aaatttgggg ggactgggga ggaatgctat agtttggatg  28620
tttgtccccc aacctcatgt tgaaatttga tgcccagtgt tggaggtggg ggcctgatgt  28680
gagccgttgg ggtcatgagg atggattcct catgagtgga ttaatgccct ccctggagga  28740
gggtgagaac taagttctta ctttgagttc ccatgagcac tgattgttaa gaagagccca  28800
gcaccttccc tctctcttgg ttcctctctc accatgtggt ctctgcacac cggctctcac  28860
cctcccgcca tgagtggatg caggctgagg ccccccccag cagcagatgc aggtgccatg  28920
```

```
cttcctgtac agcctgcaga accatgagcc aaataaatct catttcttta tcaattaccc  28980
agtctcaggt attcctttat agcaacacaa acagagtaag acaaaagccc acacccatga  29040
cctcgttagg actctcacac tggatcttgg attgtgaatt tatagatctg aacttggggt  29100
tttcttcctt caggaccttc atggctctca gcaaaagctg cccgttccac agctctttgc  29160
ttaaggtttc cccatagttc tcaagtgctg gggacatggc accaggtggt ctgtgatccc  29220
acagtgttct gctctagcct gccaggggct ctatccactc ctcccctgct cacccccatg  29280
aggggctcct ccttgccctg gtcagtgaga gagctgatca cagagcccac acctgggctc  29340
agcttcccag tgccatgcct ggcaccaact gtctcaggcc tgttcccctg aagaagaatc  29400
tgcagtgggg tttctcatgc atgggatttg ttgggggagg ggtgccctcc caggaagaga  29460
agaggctgag aacacaggca agcaagaggg ggtctcggca gcagacagcc tcagggagct  29520
ctggggcata aattgtacta tagtaggctg ggctttgagg taaggggact gggtttcata  29580
ttcctgggtg gtcactccta gcgtgggctg cccctgggct ggggcatagc ctcctgtttg  29640
cctgagaacg agtcactgag gaggggcagc tgtgagtact tgcagccaac ctctgtggct  29700
gggaatggtt gcagagccag tgtaggagtc aggtggagcc gagggtgtaa gggccaggcg  29760
gagcagaggc tggtataggg acccagtggg cacagggcat gaggacccag tgaggcgctg  29820
gcagcatgct gcaggctgga cagctccagg cacctttctc attaccacgt gtcctcctcg  29880
caccgggcat tgtgaagctt ccaaggctgg gtccacaggg cgttggaaca gggggagccc  29940
acagagagcc tgccaggcat gggggctgtc ctgggaagct gctctggccc caagaggtgc  30000
cttgggaagg cttggcctgg ccacagtcct gcagcacccc ctgggcatgg gacgggggtg  30060
cccagctcag ccaggctcag aggtcctggc cccctacagc aggcagcggg cagcatccac  30120
acctgtaggt ctccttgtcc cagcaggtgg gactccaggc acactcgctg cagcagcggt  30180
gtctgtctga gcctgccggc ctgggtgggc accgctgagg acgtttttttg ggcgttggtg  30240
ccagggtgtc ggtgctgggc gttggtagtg gtgtccctgt gggcaggcag ctgtgctggg  30300
agggcgggtg ttgctgggtg cccatgggtg tggctgtggc tgtgggtacg tgtggctgtg  30360
agaggatggg cacgtctctg cgtgcctgtg tgtgcccctg ttttgtgtgt ctgtgtgtgc  30420
ccatacgtct ctgtgcacct gcatgtgtct gagcatacct gtgtgtgtcc gtgtgtggct  30480
gtgcgtccct gttgtttgtg catgatggtg tgtatttgtg tttatctgtg tgtggctctg  30540
tgtgtctgtg ttttgtctgt tcatgtctgt gtggctatgt gtactgtgtg tggctgtgtg  30600
tatttgtgtt tatctgggta tggctatgtg tgcccatgtg tggctgtgtg tgtctgtgtg  30660
tacctttgtg tgcccatgtg tggctgtgtg tgctgtgcat ggctgtgtat atttgtgttt  30720
atctgtgtgt ggctgtgcaa gtctctgtgt gtctgtgtgt ctgtgtgtgt ctgtgtggct  30780
gtgtgtctgt gcgtgtccgt gtgtgtcttt gtggctgtgt gtctgtgtgt gtctttgtgg  30840
ctgtgtggct gtgtgtgctg tgcatagctg tgtgtgtttg tgtttatctg tgtgtggctg  30900
tgcatgtctg tgcgtgtctg tgtgtgtgcc ttgcgtgttt gtgtgtgtac ctgtgtgtgc  30960
ctggtgccct ccaggagaaa gggggcaggg agcccattgc aaggatgggc ggtgtacgac  31020
ctgtctccct gaggatttct gagggtgtga gggtggggta gccacaagtg tgtctatgcc  31080
gggctccctg ctgtttagag ggtggggtga taggcagctg agaaaggaga agggaagaag  31140
cagctctgag ctccctcctg acctcaggag accctgcacc cattgctgac cgcccacggc  31200
accctgctct cccaggggcc tgggagcagc cctggggcct ggctgtgagc ggggcctgag  31260
```

-continued aggtggggcg cggccctcgg ggctgcccat ctggcccagg ttacacctgg ctggtgccta 31320
ctttcctcag gtgaggacct gcgcatccca ggctcagggt cctctctgtg aagggggcac 31380
gatggtgaga ccaccctgag catccggtgc gcccagtgca tcccgcaggg aggccccatc 31440
ctcagctcct ctgggggtct gtccggagtg cctcttggtc cagctgcatc catccagtct 31500
gctggcactg actgagcacc tactggacac actgggatat agtgggggga tctgggccgg 31560
gcagggaccc ccacagggct tgtgggtcag ggcaggagaa ggcccggggc agtgggggca 31620
agcagaagcc aggctccgcg gcctctgaca ctgagggccc caggtgggcc tcctgggtgg 31680
ctgctctcct gcaccctctg cagacagcta cctcaccctc acgtctcccc aagccctggt 31740
cacacacttg gcctgtccac ttgagggcct cgcgggcttc tgaaaactca cttgtctggg 31800
acttgctccc ggtcccccct cacctacccc acagtggccg tcctggtccc ccttccccta 31860
tcccccagcg cccgtcccgg tccccccctca cctaccccc cagcacccgt cccagtcccc 31920
ttcacctact ccccagcggc cttccgggtc ccctctcacc tacccccgca gcgcctgtcc 31980
cagtcctccc tcatgtaccc tccagcaccc gtcccggtcc cccgtcacct accccctcagc 32040
gcccgtcccg gtcctccctc acgtaccccc cagtggctgt ctcagtcacc ctcacctacc 32100
ccccagcacc cgtgctccct ctggctactc ctggcttcca ttccatggaa tttagcacct 32160
cgagcttctg tgtgctcagt gacacctctg atctctgctt cctttccccc agggtggatg 32220
ctttgcgggt tctaggactg ggtctgtttt gctcctggct gtgacccagt gcccagagtg 32280
gagcctggct tgtgtatgaa ggggacaaat gtgtacccct gaacgaggac tggggtgtgt 32340
ggcctggctg gggaggctgc ggagccttcc tcacaggaga gggtccagta gagttaattt 32400
gggcaaaatg caggtgtgca aaggccctgc ggctagtcag gcatggacct gcagaggctg 32460
gggtgggtgg gcaccaccca aagcctgggg aggcaggtgg gccggcctag tcctagcaca 32520
aaggctctgt gtgggttctg cctgtgactt taccaaaggc cgacggatag ccctgggggc 32580
ctctaagcac ggagacgtgc ccactgatgc ccatgtttgc agaggtcagg ctgactcccc 32640
agaggaggat gagcagaggc agagtggcag agcaggaggg taaagggaga ccacggagat 32700
gtcactgccc tcccgatggc gtgtctgaag gacagaatgt gggggcagga aggagcagct 32760
gccagcgggg caggtggcag ggcaggtggc agggcagtag tacccagcat caaggtccgg 32820
cctggcgagg aggcccaggc ggtgaggagc cccggggctc gggcctgggg cagctggacc 32880
cgtgctgccg tctgtcgtct gagagtgaca gagggcagct ggcttctggg ttggagcaca 32940
ggggagaggg aggcggccta gcgggagacg gactgtggcc tgcgtgtagc cggcaactgt 33000
ggcaggaaga tgagaggagg ccgtctggag cagctccgga cccagtggaa gaggccgtcc 33060
cgcaaggacc tggggaggag cagcagagcg gggaagaaac agatgagggg ctgggaaggc 33120
aggaggaggt ctccagggct ggaggccaaa gcactgggcc ccttggcagt gcgggagctg 33180
actgacctgg actgtggtta gaagagaggt ggcatgaggt gacagggaaa gggagtggac 33240
aggccttctc tctttccaga catttaatgt gaagtaaaga ggttggcacg agctgtgtgg 33300
cagtctgtgg actcaaggga tgagtattta agatgggaga gaactgagcc tgtctagaag 33360
cccgtggaag aaatgagtta caggccacaa aaagacaggg agaaaccgct aactcgacat 33420
gtggaagagg ccaggctgca aaggattgta ggatcctgta gggttctacc cttaggacat 33480
tctggaaaca gcaaaaccat gaagacaaac gtcagcggct gccaggggtt agggaggcag 33540
gaggaacaaa caggtggagc atggaggatt tcggggccgt ggaacccctc tatggggtgc 33600
tgtaacagtg gatacagggt agtattagtc caaacccata gaacttataa caccgagctc 33660

```
caagcctcat gtaaactatg gcctttgcat aataattaag tattgatgta tttcaaaaca  33720
acgtgtagtg caggataaat atatgcattg ttatttgtca attacataaa cagaaatgtt  33780
ttttaaaaag catcagcgtg gataagcaaa gtgcgatctt ctcatacggt gggggatccg  33840
gacccacgct gtcacggggt ggacctgagg caggggctca gcgggaaaag ccaaacacgg  33900
aaggacggac gctgtgtgct gccactcaca tgaggctcct acagtcatca aatccgcaga  33960
gacgggaagt agaacagtgg gtgtcagggg ctgggggagg ggtggggagt ttgctttgaa  34020
tggggacaga gtctcatctc gggaagatga aagggttccg gagatggatg gcagtgaggg  34080
ctgcacacca gtgtgagtgt ccctaatgcc cctgaactgt gcattgaaaa acagtgtaca  34140
tttaggacag tacattgatg tgatgtgttt tttgccccaa taaaaagtat gcgactttaa  34200
aaaatgtcca atgggttcct ggccacagcg atgcaagagg ccagtaacgg ggagactgca  34260
ggcatggggg agggctgggc agggggtaga gcatcaggga actttctgta ctttctgctc  34320
cattttctat aaaccttaaa gtgtgttctt taaaaaaaaa aaaaaaaaaa aaaaaaaggc  34380
taccagttac aaaacagaaa aagcccagag gccaatgagg gcacccggca tagcctgcag  34440
gccagttggc cggaggggct ggaggaggtt gggatggggc tggcccctgc tgcatgccct  34500
gcctgcaccc ctctccaggc tgcaggtggg ggtctcctgg ggtttgcctg ttgcccctgg  34560
ggctgtgtgc tccatgctag caggagccag ggcagcctgc ccactcctgc gttcccccag  34620
cagggccagc ttctgctgcc tagcaggtct tcaggacatt gtgagaaaga gtggatggac  34680
tggacaaacg tgctcggagg agtgtgtgtg tggccacagt ggctcccagg gagggccatg  34740
ctcaacagga gctgggatgg tgccacggga ggctcagggc cacaaacctg gagatcaagg  34800
cacagatcaa ggccgtggcc agccccaggc agagctggga gtgagccagg ccgccccgact  34860
ggggtctgtg gcctggcctc ggccccagcc cgtcttggtt tcccacactc agggacccac  34920
tgtttgtgtg tctgtctcag tgggctgtca tttttaaaag gaggtgaagt tcacataccc  34980
agaattagct attttcagtg cacaatccag cgtatccagc acgatctcag tgctgtgcga  35040
ccctcacctc ggtctagctc tggagcacgt gcatccccca ggcggaaacc ctgtcactga  35100
gcggtcactc cccgtctcca ccaccccccct ccctgggcgg ccacccatct atttttgtcc  35160
ctatggattt gcctattctg gacatttcat ataaagggag tccatcacca cgcggcgttg  35220
tgtgcccggc ctcttccacc gaatgtggcg ttggtgaggc ctgtccatgc tgcagcctgc  35280
atctgtccat cattcctcgc atggcccaat aatgttccat tgtacaggca gaccacagtg  35340
ggctcgtctt tttttttttt ttgagacgga gtgtcactct gtcgcccagg ctagagtgca  35400
gtggtgcgat ctctgctcac tgcaagctcc gcctcccggg ttcacgccat tctcctgcct  35460
cagcctcccc agtagctggg actacaggcg cctgccatcg cgcctggcta attttttgta  35520
tttttagtag agacggggtt tcaccgtgtt agccaggatg gtctcgatct cctgacctcg  35580
tgatccaccc gcctcggcct cccaaagtgc tgggattata ggcgtgagac accatgcccg  35640
gcctgggctc gtcgttttcg tggttggtgc atgccggggt cgtttccacc tgttgcctct  35700
ggtgagtgat gctgccggga acatgggtgt gcacgtgtct gcctgagtcc ctgctttcac  35760
ttctggggat agacctgggg tgggattgct ggtcacacgg tagtgctggg ggtaaccggc  35820
ctgcgtggac cggccagggc atttcccatg gcagctgtgc tgctgacgtc ccacagctgt  35880
gtgaggcttg ctcacggggc tctaactgca tgcccactcc tggcccgtgg gtctggagta  35940
cacagagagt ggccggctct caagcgtctg agcagctccc acagcctggg cgcctgcctg  36000
```

-continued

```
gtgtggaggg gtcggggcag gtgtcttgct ggggactcca gcagcttcct ctggacttgt  36060
ctcccggctc cagggttgct gggaggctag ttctaaaaca ggggagaagc cgtgtgctct  36120
ctctgcccac tgggagcccc agtgtaggac gactgtgccc ttgtggggtg gggggagctg  36180
gtgcccacac cacgccaggc agctccccca ccctggcctc aggcagagct gccatccttc  36240
tccccttggt ttaaccatta actggtcgcc tgcggtgcac ccggagacaa tggcgtgttt  36300
gttcagcgca gtccgcaggg gcctgtgcag ggtctggcac agtcatcaaa gctttgcgat  36360
taagactatt agggacggga tttgtgcaaa caaagggaca ggtgcagggg ccaggccagc  36420
tgctggggcc gggtgctctg ctgggaggcc ataaacctcc ctgggccatg ggcctccct  36480
tgcctgcagc ccgctcactg aggctttgct gtttgcccag gcacagaggc cgggctgcac  36540
agggcagtgt gtccccaggg catcctgctc cccccacccc ttggctcctg ggctgcctgg  36600
aacctggttg gctcaggagc tttttatcta cagctcctct gtctatgtcc ccttggcagg  36660
tcctttttaa catgagtcct cctccagtga aggaaagggt catgccaggg cctgcaccta  36720
gggcctccgt tctccagtgg gtgtctttgc atgaaacggc ctgggccctg gcacttgccc  36780
caccagcgct gcctgcaacc ttgtccctgt acctcgggcc tccaccacat ccctggacct  36840
gcacgaagga gccctgagca tggaagtcag gggaagggag gtctcgacat gagcccagcc  36900
atggccagag tactgagccc agggccagca gcctcggctg gcagtgcagg gtgatgggtc  36960
tgtgggccgg gctgcccagg gacctcggcc ctggggtctg aggggcacca atgccttttg  37020
caggccacca tttccctttc cactttccaa atgtgattgg acacaggtgg atgcacctgc  37080
ctgcccagca gacagcccgg ttctgacccg tgtggagctg cgtggactgg gctcacctgt  37140
gccttcttgc atcaaccagg tgtggaccct gacaaggtgc cagccactgt cctccaggag  37200
ctacctcagg gacacgcagg gagggactgg acagacagat ggagcgcagt ccttgctgcc  37260
cggccaagcc cttgtgggca gggcagactc cttcaagatc atcaaatgaa agcaggcaaa  37320
aaccacgtcc ttttgtgacc taagcttgga agcaatgttg tcacttctgc ctcatcctat  37380
tggttagaag tgagccagga ggtcctgtcc acatccaagg tgggagtccc cgcaggacgg  37440
ggcctgggag gtgggcccat gggctccaga ggggctggac cacagcaaga agaacgaggc  37500
caacctccat gggtagcgca gaccggctca ggccctgccc ttcccgccgg ggtcccctgt  37560
gacaggacgc aagggcacag ctgcggagca gggtgggctg ttagagctgg gcagaggcca  37620
cagtggccag agggctggtg agagtggctc tcctgctgcc ctagccactg gctgaagatc  37680
tgcctgggga ggagtgggtt tgggcggccg ggcctaggac cccttcatag ctaccactaa  37740
tactcattct ctgctcctga gaaacctcct ccaggggcct ctggggtctt ggagatgaga  37800
cagagggacc tcaggcagga cagacaagag accctggtct cgggtgtcca cagagcggga  37860
gccaggcagg ctgggcggaa gtcctaggct tggaccctgt tacgggactt tccctgtcag  37920
aatgggctca ggagggagtg agtgcgtggt cctcaggtgt gcaagtgcca aggctggagc  37980
ccaccccctg ggaagcaggg ccagggtggc tggggcggac ttgatccctg gagaggagcg  38040
tgggcagcca gggcagggag gagggcaggc aggagggagg tccaggcctg tgggccgaca  38100
gggggtgagg aggcagtctg gggacctgag agaaggccga gtggctgtgg ggtgggtgac  38160
ctggggccct gactctgcct taccccttggc catggggcca cattcatgct cggcccccgc  38220
ccagcctggg ctgggaaggc atcagcctgg ccatgaggca aggggccggc catgcctggg  38280
gccagagggg gtcccccagc ccttcgcctt ctctccatct cctgagtagg gcccctgccc  38340
tgctctgaca gggtggtcac cttgccccgc tccgtgccca gtcctgagct ggcagtgtct  38400
```

ccagcctttg cagcgtggcc ctgtctgcct ctgtgtgtgt ctgggctcct ctcatttggc 38460
cgccctgccc gtctacactg gtgccccccc acctgcactg tccaccgggc caggctctgt 38520
ctctgccacc tgttgggtgc ttgccagact ccgccatcct ctccgctccc agcttgcggc 38580
ttctgcctcc actggcctgg gcctgccctg ccgccgcctc cttgtgccct ggctgtctgc 38640
tgccccctct gctgcccatt ggccagccgc tgagctccct accaggaaga aaaagggcca 38700
ggccatgccg gaccaggact gggcacagcc tccagcactc caggtggaca ggctgagaag 38760
cgcggcgagc gaggcagcct gggacgggtg atttctggaa catggggcca gccagccttg 38820
gcgtgaggtg tggacagctg ccagcttctt ctcagggctg ctcacaggca gcgggggagt 38880
gaccccgttt tctgcttggc acctggcttg ccatcccgct ctaccccagg gcactcagac 38940
ctcaaactcc tcagctgcct ggaacaccag ggaagcccag gctatgtgag cctgtgccca 39000
gcaggccagg gggcaccagg acatccccct cttctctgat attccaaacc ttcctgcctt 39060
tgaggaatgc ctcccggtcc ttctggtttt ctaggccatg ggctcaccct ggtctgccag 39120
ctctggagct ctgagaatat tcctgcaaaa tgcacatccc aggcctggcc gcagactgtg 39180
agtcacaggt agggcctggg atcagcattt tcatggattc tgcaggcact gctgagagca 39240
gctgcccggg gtcaagccag ggcgtgggct gtcctcatca ggctccccct ctcagaggcc 39300
gcccttctgg cctggcctgc acctttcccc actcactgcc caccagctgc agacacactc 39360
actcctgcct cagggcctct gcacggtgca gacattcctc ccacagcttc ccagggaggc 39420
tgaagagcaa ggaacctgcc tctcctcacg gagccctctg ctcccgccac acggctggat 39480
ttttcttgga tgccagcgtt tgacatctct atgtgagatc tgcttcttcc ctgatcgtga 39540
cattccctcc accagcaggc agccgcatga ggaccagcgc ctgctcaccg ctgtgtccct 39600
cctacgtgcg gggcaggcac ccagcagcag gtgttcggtg cccactggga gcgtgcctgg 39660
gcccctgctc ctgctcctca gagggaacaa acaactgacc tgctgatgga ggctgtgaac 39720
ccacacgggt tgtctgcaga cgtaacgggg catctcctat gacgcttctg gagagggcaa 39780
ggctccacgg ctgagggctt tctttgggtg acaaccatgt gaaatgccat gaccttgtgc 39840
caccccgtgg cagatgactc tctcagaagg tggtgcgtac cctttcccca ttatggtgtg 39900
gacacgcaga tgtggggcct ctcccacctc ttacaactgg ggcaggctga caaccacagt 39960
agaagggaca ccctggaact cccagaccac atcataagag gccacgcagc ttcctcctgg 40020
agctctcggg cagctgccct tggagcctga ctgccatgct gtgaggaagc ccaggtgcca 40080
ccgaggcggc acatgcagat gtgcagccaa tggccctggc agaacctgac aaagtcagca 40140
ccagccacca gacctgccag caaggatgct ctgagccgac gtccactcca gctgtcgtct 40200
gactgcccac gagacaccct gagtgagcac tgcccagcta agacccgtca actccagaac 40260
tgtgagaggc gatggttcca cgacttcctg gctgtagtca ctgctgttgg gcagctgtgg 40320
gtgaccctga agggacactc tgataaggga catctgcctg catgtgtgac ctgagtccca 40380
gcctcagctt tctcatgtga aaaatcagga ccacggtaga ccctacctta taaggcagct 40440
gcaagagtga aatacaatgg aaaatgtaca caagataggg tggctgttcg acgccctctt 40500
ggttcttcaa atctaaggcc catgtcaagt tttaccatca ttttgccatc atgatgagaa 40560
aagaaatgag accagcctga ccaacatgga gaaaccccat ctctactaaa aatacaaaat 40620
tagctgggca tggtggcact cgcctgtaat cccagctact ggggaggctg aggcaggaga 40680
atcactcgaa ctcaggaggt ggaggttgca gtgagccgag atcgcaccat tgcactctgg 40740

-continued

```
cctgggcaac aagaatgaaa ctctgtctca caaaaaaaaa aaaaaaaaaa aaaaaagaaa  40800
tggaacttaa acaaggaaat agtgttttcc ttgttttgtt tcttgcttat tgaaagcacc  40860
ttgcctgatg ggttgaggga gggattttca taaatcactg ttgtatacac acgtagagag  40920
aaaataccag caagtaaggg ttactgtccc cacatttgag tccacttcct ccgggtcaat  40980
tttgtctaga gtcattgcac cgaggctgtc cctcatacac tcttcctttg ggccatgtac  41040
agggctgggg gacacccgtt ccccaagagg ggcctccacg attgacccgg gaacttttgc  41100
ttgctctgcc ggtatctaga tcttaccagc aggtgccagc aaatgatctc tggacggcgc  41160
cccagactca ctgtccttcc ctagatgggc ccttgaggct tgggatggaa gtgtagaggg  41220
gtcactgcca ggtgatacag tcaggttcat ccgtgttgag ctggggccac catgtcatga  41280
acctggctgt tggcagcatt cacatgaaac ctgctttcag agacaataag tgtaaacaaa  41340
tgtcttagga tcagtgcatt gtgtcccgga taagcccctt ctcccaatgt ccctccacaa  41400
cactcacacg aggaaaggag gctgggaggt ggggaggctg ggaggtgggg aggctgacag  41460
gctgggaggt ggggaggctg agaggtaggg aggtggggag gctggaaggt aggggcgtgg  41520
ggaggctggg aggtagggag gtgaggaggc tgggaggtag ggaggctggg aagtagggag  41580
atggggaggc tgggaggtag ggaggtaagg aggctgggag gcagggaggc tgggaagtag  41640
ggagatgggg aggctgggag gtagggaggt ggggaggctg aaaggtggca ggctgggaag  41700
tgaggatgct gggaggtggg gaggctgaga ggtagggagg tgaggaggct gggaggtagg  41760
gagactgaga ggtagggagg tggggaggct gggaggtaag gaggcaggga ggctgggaag  41820
tagggaggtg gggaggctgg gaggtgggga ggctgagagg tagggaggtg gggaggctgg  41880
gaggtgggga ggctgagagg tagggaggtg gggaggcttg gaggtagaaa ggtgggcagg  41940
ctgggaggtg gggaggctgg gagttgggga ggttggaagg cagaggggct aggaagtggg  42000
gaggctggaa gactgggctg ttgggaggta gggaggctgg aggctgggca gtagggaggt  42060
ggagaggctg ggaggtgggg aggctgagag gtggggaggt ggggaggctt ggaggtagaa  42120
ggtgggcagg ctgggaggtg gggagcctgg gaggtgggga ggctggaagg ctgggaagta  42180
gggaggttgg aaggcagagg ggctgggaag tggggaggct ggaaggctgg gctgctggga  42240
ggtagggagg ctggaggctg ggagggaggg aggtggggag gctggaggct gggagggagg  42300
gaggtgggga ggatggctgg ctgggatgtg aggaggtgtg gaggctgagc cttggcagaa  42360
tgtgggcttt tttcagcgaa tcactagccc ctgaagacag cccaggtcag gtgcagcacc  42420
gccccagagg ccaattagtg atttgtcacc ctctgccttg gggaacaagg ctgccaggag  42480
tcctgccccc agccacagca tccagctatg ctccctgccc tctggcagga ggtagggaaa  42540
cctctgcttt cacatctgtg gggaggcccc catacttggc ccctgccctt caggcccaac  42600
ccaccctgtc atggaatcct ctagagtcct tgaaggggca gagtcccacc cccaccagga  42660
attccatcgg tgatcctagg aacggagtcc cggaaggcct gctcctacgg ccctgggggc  42720
aggaattgaa gcaggcgctc cctttaggca gcgggacagg atggtgccgt acagacactc  42780
caagtccctc tccgtgtgac tggatgtcac caccttctga ccctcaggct ccggagggtc  42840
ctaggagagg atccccgccc agggttgtgg agaggagcga accggatcct ggggtcaggc  42900
tgcgtcctgg cacctggcac acagtagggc tgccatcagg catgtccacc catgctgtgg  42960
acctttgcta ctgccagggc agtggaaggg ggcacctagg ctgtagcagg ggagctctca  43020
agggcccccc ctctgtgcag ttcagccgag gccaggcctg tcccatcagg gtgaggcttc  43080
ccttggggtg aggggtcctc ctcacctcct gatcgtaaag gcccagggct gggctaggga  43140
```

```
ccccggtgtt aaaagggcca gaaaatgccg tccaggcaga tagtcccagg gagagggccc  43200
agagcacctg ccgccaggct agggacgcac gagggggcca tggtgtcacc cagcacccag  43260
caccccccag aagctcctgg atccccgtta aaactgggtg atcattaagt ggagtgcggt  43320
tgtgtcacag cccccagaag ccccacccac cactccccag ccacccctgg gagcaaggcc  43380
ctcacccaga gaggtggggt gtcaccggcc tggccagaac ctcagggtga ggcaggggcc  43440
tcgggtcact gcaggggggcc tccagtggac ccaggggtgg ggctgacccc agccgctccc  43500
tctggagata gagttctgga tgtttctacc cttgctccga ctgccagccg ccccttgggt  43560
ggggcccttt gatgtccccg aactcacagg tgggcggggc cccgaggcct ccccctggccc  43620
tttgaagctg ggaactcttg tggcccagtc ccagcagaca caggctaaca ccgcgttcac  43680
cctggagtcc accggctccc ccagcccagc cccaggatcc caggcctgct ctcctcaggg  43740
gtccctggag ggccagttcc cagcctgtgg tccaacatcc tcacctccct gaacctccat  43800
agcaatagct gctggtttgg cccctggctg agctgtctcc tggtctccct tgtctccatt  43860
agcaccctgt tctttaggta aggaaactga ggcacagggg cttgggaagg cagaagcccc  43920
acccacggga gtcatcaggc agagggaggg aggtgggatg ggagaaatag gaggccacgg  43980
gcttgcaggg gtctgtatcc cagagtcccc ctaacctgag ggtacctgcc ccccaggcct  44040
cccggtgacc tggcggaggg gccggcggcc aggtcccagg cttgctgtgc cggcacccca  44100
cagaggcaca ggggcaggga ccaggcctta tcagagcggc cgcccgccac ccgcctgcag  44160
ctgacagagg gatggggaga ccagccgtaa acccgtctgt tcccctaaag gagagaggga  44220
acaaaggcat aggctaataa aactcagatc aaagctgact tatctcttca ttttgctatt  44280
aaaatttaga atcaaaaggg aaggcggccc ctttatggtt caggattaca gagatttctg  44340
tgcctgtggg gccctgcagg gcccccgctg cccatcccag cttcagagcc ctagcctcgg  44400
gctgcaaggg ttcctggagt tgaccttccc aagggcactc ctgggacatg ggctccaggt  44460
ccctcctggg cctcgggggg ccacaaggag ggagtgaaca gctctaccta aggccccctt  44520
gagacaccaa gacaccccgt ggctgacctc ccccacaccga tggctctgca ggtgaagggg  44580
tttcctggcc tgcgccctgc gccctcttgt ctctgcagaa gacctccctc ggtccccagt  44640
tcctgaaact cctagacccc tctaggaggg agacagccag aggggcaggg cctctgccag  44700
ctgcacccaa gtcaagcctg gaggccacag ggctgggtgg gtgggttcct ctcctccatt  44760
tctcggctgt cccaggtctc tggggtgggg ggcaccactc agcaccggat ggagtggaac  44820
ccctggaatc ttgggcagcc aggcagtcac tccggcaggc cctgcgtccg cagcagaggc  44880
ccctgtgcac tgcgcaggtg acacgcgcgg acctgtctgc acctacccag gcttgctgtg  44940
acacacggtc cagtcccgtg tgtgagcacg tgcccaagct cccgtcggcc ggcgcccctc  45000
ccccatgccc agggggggccc cgcacgcttc ctgtgcacgc ttcacctctt ctctaaccaa  45060
cgcctgagct ccctgctccc tggtaggaag ctggcggccc ttcccttcca aacaggcctg  45120
acaggttatg acactgaaga ttacaaacct cccccagggt gggtggggga ggggcgagga  45180
gggaaggtag acttcggggc aggggctttg aatggccttc agcccctacc ccagatgtcc  45240
cggtgcccag aggctggacc ccgtaacctt catctccaca ctccaggggt gcaggacatt  45300
cctgggtgga gtgtaggccc agggccaggt gaaggagcct tccctaggtg gctcttgcag  45360
gcacgggcca gggcggggca ggcggggcag gcagggcagt cctgccatgc cccaggtgcc  45420
cagggctacc ctctccacca tgctctgagc cctggcatga gctgggtttg gagggagggg  45480
```

-continued

```
ttgccacgtg gatgcaggtt ccaggcatgg atgagggtgg ggtctggcct cagcctcctt  45540
gctgcccaga cattgcattt ttgggcaggg cctggcagac acctgggatg aaccaagcac  45600
tagaggacca tgtggtctag aactcatggg ggtcttaatg gcccccatgg gggagggaga  45660
ggaggaaggg ttgagggatc ccctctgttt cagaggagta gaggaccttt ctgctgggcc  45720
tagaagacaa gagtgactgg acagcacaca gctcctagca tcccctcagc ggggtcctga  45780
gattccccta cagggagaca ttgtacagat gtgtgcaccc atttatctac taaatcttaa  45840
tgtggtatac tgatgcttgg cagaggactt agaaggtacc cagttagcag tgggcagccc  45900
ccctaccatg gctaagcccc aggtgggcca gggtttcagg gttacgttaa ctagctacca  45960
agtctgacat tggtaaggat tggggtttca gagaactgga ggtctgttag gtctgtttac  46020
aagagggtca acccaggcaa atgtccaagc tggcagggac cagagttgag tctttagact  46080
aaggatatgg tgtttggaat acagcaaagg tctttcttct cagtttccat ccacccattt  46140
atccatcatc ccacttatcc atctatccat ctattcatcc atccatccat ccatccatcc  46200
atccatccat ccatccatcc acctcatcca tccatccatc catccatcca tccatccatc  46260
catccatcta tccatccatc catccacctc atccatccat ccatccatcc atccatccac  46320
ccatccactt atccatccat ccattttgcc atccattcat tcatcccttt acccatctct  46380
ccctctcttc ctcccgtcat cctttgatct gtctgtgcat ctatctttag gcacctatct  46440
acacatttat gtatctattc atccatctat ccattaactc tcaccacttt tatgagcaga  46500
tgggcatggg ttaaatcaca acttatctct tattagctta agagcttttg gggtccagag  46560
agtacatgtc tcagtgtgcc cataatcata tgggaggggt cccagaagtt ctttcatgaa  46620
taaatcttcc taaagcagtt ggactgtttt attaattcag ttgctttgaa aatatctctt  46680
tttcaccttc atagagaatt gacctttggt tgttggtcga ctctgagtcc aggtttgttc  46740
tgcagttggg tggtccccgt cctctcttgt gggggctgct cgagggtgaa aaaaggaact  46800
ggcagatgac aggacacccc cgggaaggtg gacagatgtg ggtgggcggc tgggaggaag  46860
ggctgttgga ataggctgtc tggggccagg aggcaggcaa caagcccaga cgccagggca  46920
gtccttcccc agctgatggc cttgcccatg cgtccacctc tgcagcctcc gtgtctcctt  46980
ggtgaagtct gggagtgtct gctttgtggg aagagggtga ggatccaaca ggaccgtggc  47040
ccatcgtggg ggttctgtaa agggcgtagg tgtggccttg gtggaggtag tcaaggctaa  47100
atgagggcac aagtgtgggc tctgacccca tacagtgagt atccttataa gaagagaccc  47160
cacagcactt gcttgctgtc catgtgagcc tggggaggcc ccgacgggga gccaagaagc  47220
gggttctcac cagcaaccgc atctgctggc cccttgatct gggccgccca gaccccagag  47280
ctatgggaaa tgaatgcgta gggtttaagc ccccagtctg tggccctttg ttctggctgc  47340
ctgagttgac tgagctctca ggatagcgag cgtctttagt cccggaggcc gcccaccagg  47400
gcaagattgt gcaggccact gctttctctg ccctggcctg tccagagccc tggtcgttct  47460
gtgcccgctc cctgtccagc ccctgcctct gtcttgccct cacctccaca ccctgtctgt  47520
cctgctcagc acaggggaca ttttctccag gtggaacggc catccagtgc tcaccggtgt  47580
gcccgggtag gtgccagggt ggaggatggg ctgggacacg ggtggggagg gggatctggc  47640
ctgccttagg atgcagactt aggcctctcg gaggagcccc ggtcctatcc agctcaggaa  47700
gggggctgct gggctgaaac aagcaactgg ggagtctggg gacccagaaa caccttgggg  47760
ctctgggctc acaccctgct agctgcaggg ctggccccgt gagccatcag aggagccaac  47820
agcgcacctg cgctgaacgc tgcaccatga gctgaccccg ggcccctgcc accctgccgg  47880
```

ccataccaca ttcagagtgg ggcagcatgc agtaggcgct tataaaggcc tcggccagag 47940
tggcccagca acaagtctgc agcagggcag tcatgggatg ggccccagct gtggcctggg 48000
ggttctgtcc agggcccact gcagcaacgg gctgctcctg gaggtggggc attctctgtg 48060
ctcagcctca gaggtccctg gtggatgcca ggtcacctga ctgtccaaaa gttccagcaa 48120
aagggcccct gtcttgggaa ggcccaggct gaggagggga ggatggcccg accttagggg 48180
acatagtcag agactatgct ttcaagcctc catggcctcc cttgcacggc agagaagtgg 48240
gtatagaaag tatggtcagg gagcccagtg gagacggagc tggccagcca ggaaggacct 48300
aggtattctg ggcaggaggg tgagaagggc tccctcctcc aggcctgccc aggccgcctc 48360
ctgctccagg ctccgctagc tgccccgggc tccgctagct gccctgttcc ccgcaccacc 48420
acgtcccctc acgcctgcgg cagggaaaca ggagatgctg tggttttgtg acgtctgccc 48480
tcatgtcccc agctggaggc cctctgcggg tcagcctgtc tgactctcac ccactcctgg 48540
ttgtccctgt ctgcaggtgc tggctgtgct ggacaaaggg ctgtgccttg gctggcagtc 48600
ctctaggcca ttggtctgtg gctgtctgtc tgtggtggtc aacctgccca gggcagacag 48660
tgagctatgc cagccaggcc ctggctccca ctgctcagct cagaaggtcc ggggctaggt 48720
atgtctgtga gggctgtgct gtgccgactt cggacaccca ggcgcgagac cctgcaggca 48780
caggtgactt ttggtgctgg aacagttgta ttcccagcca gtagccaggc ctagcgctag 48840
ttaaaggagg gatgctggcc ctgtggaggc gagaggccca gcaccaggtg gcctcgtctt 48900
gctgtccacc agaactggga cgacatgggg ctgggctggc ctgtgaatga ccacatggca 48960
ggcccagctc ctagttctgt ggagcagggg ccacgacccc ttccctgcca gtggctgtga 49020
ggacaggatc ctggaggggg aagggatgca cccgacatcc ctggggtggg ttttgaggag 49080
gagccctcct gatcccaggt gaagatactg gccaggcctg gtccctggac agcccctaga 49140
aaggtgccgc ctgccaggtc tctgggtcct tgaggtgggc tcaaggccac ctcagcagac 49200
gactcatgcc atgtccccac cccgacgtgc atgccaagtc cagtgactgt ggggactcca 49260
ggggccccca ctggccccct cctctgtccc ctgagctggg ctttgccctg ggagaaagga 49320
agcagcgagg tcctgagtgg gatggcacag ggcacgtggg gtgtgggtga tggaggacgt 49380
tgagctgggt ggggaggggt ggggcatgtg tgcggcctgg ccatgtggat cctcccaggg 49440
gagctgaagc ccaggggcca agatgccccg gcagttggtg cctggttagg gagctggggt 49500
tgcggaccgg cccccgtttg tcacttgctg gcctctcccc tgctaccctg caggctgggc 49560
tgtggtgcca cacggtggtc tctttctggg ctggggtgtg attctttcct ttctcctgtg 49620
gtgtaagagt gcacagctgt gcaggaggcc gccgagggcg tgtgtgtgac tgtgtgtgct 49680
gcgcgtaggg ccgtgtgtgc tggcatctgc gcacgcgtgt ttgcagggcc cgcaagtgtg 49740
tgtgtgcatg tgtggtgtgt ggcatgcgac gtgcctgtag agaaagtgtg tctgggggcc 49800
ccacgtcctc aggcctggcg cccattgacc cccgttaagc ccaagcccca tggctagatt 49860
gtaggcggga ctgagttgct tcggagacct ctgcactcga ctgtgggagt cttatggggg 49920
cctcctggga cgtgagcaac ccctgccctg cctggcagtg tcagcacctc gggcggccca 49980
cgcctggccc cgccaccctt cccctgcccc actcctgtgg cagtcacggt tgagccgcac 50040
ctcctgcggt cctgtccctc cctcggggtc ctggggacca gcctggttcc ctgagagcaa 50100
tctgatggag accccctgag tcccacccca gctccccttt cctgacccct tcccagcccc 50160
tctcctcctt gaggaaccag caccctcctc ctgcagcccg gccacctgga catgggacga 50220
gggccccacc gtgtggccac ctggacaccc tgcagggcgg ctcctcggcc tgacttctgc 50280
cttcagcacc cagggctcct cctcctctcc gactgtacat gtgagatggg agacagagac 50340
acggggacgg ggacacagag acagggagac agagatgcag agagatggag gcggggagac 50400
agagacgcag agagacagag acagagagac agggagacag agacacagag agacagagat 50460
gaggagacag aggcgcagag acagggacac agagatgggg agacagagat gcagagagac 50520
agaagagaga tggaggtggg gagacagaga tgcagagatg gagacagaga cagggagaca 50580
gagacacaga gagacaaaga cagggagaca gagacacaga gagacagaga gatggagaag 50640
gggagacaga gacatagaga tgaagacaga gatgaggaga cagagacaca gagacaagga 50700
cacagagatg gggagacaga gatgcagaga gacagaagag agatggaggc ggggagacag 50760
agacacagag atggagacag agagacagaa acagagagac agggagacag agacacagag 50820
agacagaggg atggagacgg ggagacagag acgcggagac gaagacagag atgaggagac 50880
agagacgcag ggagacagaa gagagatgga ggcggggaga cagagatgca gagatggaga 50940
cagagacggg gagacagaga cacagggaga caaagacaga gagacaggga gacagaggga 51000
aggagacggg gagacagagg cacagagatg aagacagaga caagcagacg gagatgcaga 51060
gacagggaca cagacacggg gagatagaca gacagaaaca gagagacggg ggaacagaga 51120
cgcagagaca gggagacaca gatggggaga cagagatgca gaaatggaga aagagatgga 51180
gatacaaaga cagaattaga gagagacaga gatgggaaga gaaacagaga cagagacaga 51240
agcagagaaa tagagacgca aagatagaga cagatgggga agagacagat agagatggag 51300
acagacagac agagacacag atagagatag acagagatgg ggagagaggc aggtagagac 51360
agaggcaaac agagaaacag agactgatga ggccacacac ccatccttct gttcacctca 51420
aaccctctac ccctctccct gctacagatg gagaccccca tgacctgtgt ggtccagaac 51480
ccaggtcttc acctcccccc agtgttcctg ggcccaccgg tttctcgagg ataatagtga 51540
gcatggcggt ggctggagcc cagagccagc tgggccacag cacagcccag ggacggccca 51600
ccctctacca ggccagattc agccccctga tgccaagacc ccagatccag cccaggccca 51660
agctgacccc tgccacatct gcccctgtga gtggtgccca cgagatctga tgccctgact 51720
cacaggcagg ggtgggcacc ggccccccat cttggcaggc caggacgccc tcctcccaag 51780
atgcctcttc ctcaaggagg tggaagcagc ctggctcccc tagtctgaag gcctgggccc 51840
cgctgccact cactgtccac aggcttccgt tttcccacct gtggaatggg ggtgatggaa 51900
atacagcccc agggcgtcgt ggtgctgcac aaatttgcga ggccaccagt gccctgcaaa 51960
gctggggggt gccccattgc gaatacctca gcgcaaccct ccccgggggc gggaagcggg 52020
gagcagcctt gctcagggct ggggtctgaa cttggagccg cgtggccccc cagaacaagc 52080
cagggcctga ctgcatgagt gctcactgca tggccggttt gctaagggtg ggctggccaa 52140
ttcagaaggg aggaaagagc ccttggtggg agtcagtgag gggcagaggt cctctcaggc 52200
ctccagagac ctttcgagaa gccccctgct cctacctggg tgtctgggag ctgtgtggaa 52260
gtgtccctag aaaattctac ccctgactga ccatgtcagg gacttgggga gcccagaggc 52320
atctgggaaa ttggggccca tgggcaccca ccttcagtgc acccgatgcc agctggcccg 52380 ggggccccctg aggtgcccac aaatgtcccc acagactgcc ctgtcaggtt tgcctgccag 52440
gcccctcccc gggcagggag ggggctttgt ggacccccag cctctttccg gcacaggcgg 52500
ccgggagcga ggttatgccg cagatggccg caagggggtg ccagcctcag ggaacaccag 52560
ggaaggggct gggcctcagt ctgcaaggac agagatggcc cagcatgcct gccacctgcc 52620
acccaccaag aagtgtgcac cccaggcagc aagagagagg atgacagctg cagagaagag 52680
gagcggtggc cagcggagct tagctggggc atgggcttga gtgtggctgc agccatcccc 52740
atccacggag ctagagggtg tggacaagtg ggagtggggc aggcgccgga gcccctggga 52800
gcaagcatgc tggagggtcc ctggggtgag ctcagggtgc aggggccagg gaagctgcag 52860
gacccaggac cccaccccat ccatatccca gatcaacatg atccagggag aaacatactt 52920
gcaacttctc agcccacaga tgcacgcagt cacatacaaa cgcacacaca ctcagcccat 52980
ctgcagcaaa ctcacgtcca tgccctgcag aagcacccgt gcacaccatg gagacccttg 53040
tgcccaggaa gggcgcacag cctgctcagg tttgtccctg tccctgcagg caggtcccag 53100
atccagctgg gcggcaggac caggacccaa cgcctcccca tctgctgtcc cctccctccc 53160
tgtccccgct tgcagccacc atcaccgctc tcagcaggct aagctggcct tcacaggtgg 53220
cctggtcttc cattgaccct cggcatgcac acacgggtgc acacagggcc aggttcacac 53280
actctgactc tcacatgtgt gcacacaggg ccgggctcac acactctgac tctcacatgt 53340
gtgcacacag ggccgggctc acacactctg actctcacat gtgtgcacac agggccgggc 53400
tcacacactc tgactctcac atgtgtgcac acagggccag gttcacacac tctgactctc 53460
acatgtgtgc acacagggcc gggctcacac actctgactc tcacatgtgt gtgcacacag 53520
ggccgggctc acacgctctg actctcccat gtgtgcgcac aaatcgcagc tgtttcaaca 53580
ccagcactac tctgataagt ccccgggcac aggccccagc tccccacccc ccgggtttgg 53640
agtctggggt cttgagggag aagaacgtgg ggccgagggt acagagggct aggcctcgag 53700
tatggggttt caggtggggt gtccctgtgg gtggattccc aggggcctgc cctccatggg 53760
gttcatagca gcccccagcg agggtggacc ggacagtaaa caggagcttc cctgcaggcc 53820
tgtagctgag gcccttccaa gaacaagggt ggggctgggc ccctgctggg cactgtgccg 53880
agctcccgcc ccgtgctcca ccctgtactc cctgctccag gccggcccga tggtgcctcc 53940
attcctgccc ctgcttttcc cctccctgtg tccacttggg cccctgctgc cctcatggac 54000
ggtctctcct taattgaccc ccagcccgca tcctgacaga gctgtgcctt cctcggtctc 54060
cccgctgctg aggacagcac acggcacacc ctgcccctgc ctggagcctc tgcctacctc 54120
ccagtggagc ggagcaatgg tgtcacctgt cacagtgaca cagaccaggg ccactgtgtc 54180
gcagagcaga gcagctcagc ggtgcccgca ggcaaggtca ggatgcacat cctgggagag 54240
aacatcttgt gccacagcca gcaggaccgt ctggggctgg tgcacccacc aggccctgtg 54300
acgccactgt atctgcctga gccatcattg caccctgtca ctccgctgat tcccaccgta 54360
gcccacgggg ttggtataag gacacatgcc acccaggtgg ggacactgag gcccaccgga 54420
gagtggccaa atgaggcctc gagcctgggc ctcctctttt ttttgaggag acggagtctc 54480
actctgtggc ccaggctgga gtgcggtggc acaatctcgg ctcactgcaa actctgactc 54540
cctggttcaa gctattctcc tgcctcagcc tcctgagtgg ccgggattac aggcatgcgc 54600
caccaagctg ggcctcgttt ttacacagca acctccccag ggccaaccct gttctggcct 54660
ctgagctgcc cccaggcagc ctctctcctg tttacctaga cactgtcaga ccctgcacca 54720
gtgcctgatg cccaggacaa cactggcccc tcagtgggca gggctgtagc cagccttacc 54780
cctggaaaca ggggagaaag ggagggaggg gggcccacat gcagtggtcg gccgctgtgc 54840 accccccctgc agagtcagct caagacaccg ggctctgcct tctggggttc ccaaggctgc 54900
tcccctgaag aagactgctc agtcccagct gccccagacc aggcccttgg tggggggtcc 54960

-continued ctgagcctcc actccctccg ggaatggctg atcctccttg gagccgagtt tttgtgctgt 55020
ggggagagca cccaaccatg gggggcaccc tggtagctca cgacatggac ccctgcccac 55080
gggcatgccc tcggccagcc tggagacagc tgctctattg actgccgggc caggagtgtc 55140
ccaggttaag ccaacaagcc cccgctttct gagagaaaaa tcacctcctt tgggtgtgga 55200
atatgggggg gcggggagct gggaggtcgg gagccctggc tggaccacag ggcctatggc 55260
tggggacctc tcgctgccga ggtcacagtg aactgagacc ccctcgggtc tcagcctgga 55320
gggggtgacc caggagggtg catttctgct tccccccctga gaagtcacac cacacctagc 55380
aggggcccct ccagggtgta ccccaggggt ctaggggatg ttaatgattg gccgtctcgg 55440
ttcacaaaga tagtcatcac cagcaccatg gagtggccac cgcccagctc tgtcaaacct 55500
ggacttagcc tcatgtgcac cttgatttaa agaacaagaa accagccctg cccacgcccc 55560
tggctcactg tgcttccctc cctccttccc tccttcccca gacatagcca ccactttgaa 55620
tctcgtgtcc catggggtgt ccacacaggg cacctgattt atccaggctc ggggaggagg 55680
ggtcacagat tgttccccag gggactttac ctagtccgtg tgtttgcttt aggagttctg 55740
aggccatttg gtttctttat gcatttctgt atcttttgca tttttctagt gagcgtgggg 55800
ttactctttt aatcgtaaat atatatatac ctattttttc agttaaaaaa ctgtggtttc 55860
aggccaggtg tggtggctca agcctgtaat cccaatgctt tgggtggtca aggcaggggc 55920
atcgcttaag cccaggagtt tgagactagc ctgggcaaca cagtgagacc ccgtctctac 55980
aaaaaattgt tttcaaattc gcagggcatg gtggcgtgta cctgtagtcc cagctactca 56040
ggaggctgag gtcggaggat tgattgaggc catggagatt gcagtgagcc atgatcctgc 56100
cactgcactc cagcctgggt gacagagaga gacctgtctc aaaacgaaaa caaaaatctg 56160
tgcttcctca ataacaaatt gaagccacca acaccctcgt ccaccgaaag gttagcatgt 56220
gcctggtgac aaagtcaaca gacaaagggg actggggaac agttctgttc ctcttcctca 56280
gagtcctagg ccccaggccc ctccctgaga cagcctcagg gcctcctcct tcccctccct 56340
catcctcctc cttccctctc tctccttcct cctttgcttt ctccctctgc aatctcagcc 56400
acctgcatcc gcttcctcca ccccgacctt cccgccaggc aggtgccctg ggcttgctca 56460
gcatgggcag cccccggctc tgccccctgc acactgggag gctgctccac tctcaggggt 56520
ctctggcttt ccgtgtccct gcaattagcc tccgcgtgcg tgcaagaagt caacacaatt 56580
tggctccacg tggccccggt gccgattgtg gacagataaa agacaaacta acgtcctgcc 56640
ctgaggatta agatgcagct gtttccctgg ataccggatc aggcgtaatt agacaaaggg 56700
agtgctttcc aaacctactc agccgaaggc ccaggggcag gcagccctca cccccaggca 56760
gctggcacgg gctcgggccc ttccttcctc cttgttaaaa gcggattgat acagacgcca 56820
tggaaaaggt ttctgacacg cagcgggatg atggcagcaa ggccacctgc ggtgacagcg 56880
aaacaagatg ctcagagccc cattagcagg gcggccacgt gtgcgttcgc cttcgcctct 56940
gcccctgttt tctccagttt tgttcacttt gctgtatcat ggacgataac acatcttagc 57000
aagaaatcaa taaacggtcc cgaggctttt aatggagaag aaataaatag caaccgcgct 57060
tggcagtctg gaggaaccag cgctttctgc ctggaccctg agcctcaggc ttcaccgcca 57120
acacggccat ccctgtgggg cgggagcagc ctggaacggg aagggtccac ccttctttcc 57180
cggcttcctg cagagggcgg ggagaggctc tgtcaccgtg cccctcggaa gccggcctgg 57240
gctgtgtaac tggggacttg tggacaacaa gccagagggg gtcctgccag gctctggatg 57300
cccactctgc ccatgaggag ggcacaggca gcgcagtgcc gtggcaggca ggctgccgac 57360

-continued

```
cttatgcccc aggggcggcc ttagtgctgt gtagacccag aggggacacg ccccagggct  57420
ccctgaggtg ctgcctcagt ggctgtgcac tcccagcacc cggggggtgt gcccaccagc  57480
tgcccggccc ctgagtgggc ctgtgtccag tgccccccctg gcctcccggg aggagctgct  57540
tgctctgccc cagggttgct gagagacagc cttgccactg acccggccgg tctctgcctc  57600
cagcccaggc ctctgtgcac gctgactgcg gtggaaactc caggcctggc aaagaaaaac  57660
acgtgaggca gcccgccatc cagcagaaga gttcgctctg gggtctcttt gtcaacatgc  57720
ttttctccct ttatttgtgt tatacttttt ccagtttttt gtggtcaaat acacataaca  57780
caaaacttct catctgaacc acttccagtg cacggttcgg cagcattaag cacattcacg  57840
ttgccgggca gccatcacca ccgtcatctc cagaactctg tcatcttccc aaaccgaact  57900
ctgtcccctg aaacactcac gccccatccc ctccgccagc cccccgcagc cccattctcc  57960
tctccatcct gacagatttg acgtctttag ggaccacgtg ggagtggact cgggcagcat  58020
ttgtcctgtt gtgactggct cctctccctg attgtaaggt tctcgaggtt catccacggt  58080
gtagcggatg taagaatgtc cttcctgggc cgggcgccgt ggctcatgcc tgtaatccca  58140
gcactttggg cggccgaggc gggtggatca caaggtcagg agatcgagac catcctggct  58200
aacacggtaa aaccccgtct ctactaaaaa tacaaaaaat tagccgggcc tggtggtggg  58260
tacctgtagt cccagctact cgggaggctg cggcaggaga atggcgtgaa cacgggaggc  58320
ggagcttgca gtgagccgag atcgccccac tgcactccag cctgggtgac agagcgagac  58380
tccgcctcaa aaaaaaaaaa aaaaaaaaag aatgtccttc ctttttgagg ctgaatctga  58440
atcgtgcccc gttgtatgcg tggaccacat tttgctctta gccggcggac actgggttgg  58500
ttccactttc cagcaatagt gaataacact gttgtgagca gtcacacaca cgttcctggg  58560
tggacatagg tttcatttct tctgggcatc cacgtaggaa caggattgcg gcagcctgta  58620
gtgcctcttt aacccgcggg ggagctgcca gggtgctgtc cgcagcggct gccctgcggc  58680
acgacccacc gcaggggctc tgatttctcc acattctcgt gagcacttgc tattttgtgt  58740
tctgcattgt ttgggtttgt tgacggtggc caccctaacg ggtgtggaat cctgtcgcgc  58800
cgtgattttg attggcattg ccctaatgat tcgtggcatt gagcaccttt ccctgcggct  58860
gctgtcctgg atacaccttc cctggagagg cgcccgtcta cgtccttcgc ccacttttga  58920
atctggtgtt tggcggttgt gttttagggg ttctctgtgg gttccgggta ctactccccg  58980
atcaggtgtg tgatttgcgg cattttctcc tgttctggga gttgcctttt tacggttgat  59040
gatgtcctct gatgcacaaa gttgtttgtt tgtttgtttg tttgttttaa ttttcaagcc  59100
caatttatct ctttgttgct tgcacctttg gtgtcacatc tgggaaatca ctgccaggtg  59160
tgaggccatg aagcttttgc cctgtgtgtt ctctctaccg tctcaggccc tacgtccagg  59220
ccgttgacct gtttggggggt aatttttgga tgggaaggga gggttccagc gtcacacttc  59280
tgcatgtggg catcccggtt tcccagcccc gtctgtggag gaggctgtcc tttccccact  59340
gaatggcctt ggcacctgtg ccaaagatca cgggactgca tttgccaggg ggattgccag  59400
tctctcctct acgtatttgt gaatagggat ctatacacat tccacgaaca cacaacaggg  59460
ccacgggaca gccctgtgcc aggttcctac ctccccgccc agaggctgtg tggatagagc  59520
acacgtgtgt gggtatggca tgtgtagtat gtggtgtgtt catgtgtgtg acatgtggag  59580
ttgtgtgggg tgagtgtgct gtgtgtatga tgtgtgtttg tgatgtgtgt ggtatatggt  59640
gtgtgtggta tgtgtggagt gtgtggggtg tgtgtggttg tgtgtgtggt gtgtagcgtg  59700
```

-continued

```
tggtgtgtat gtgtgtggtg tgtatgtagg taagtgtgtt gtgtgtgcgg tgtgtattgt  59760
gtgtagtgta tgtggtgtgt ggtgtgtgtg gtgtgtgtgt atgattggtg tagtttgtgt  59820
ggcatgtgtg tggcgtgtat gtaggtgtgt gtgttgtgtg gtgtgtgtgg tgtgtatgtg  59880
tggtgtgtgt gtagtgtctg gtgtgtgtgt ggtgtgtggt ttatgtgtgt tgcatgtggc  59940
atgtggtttg tgtctatgtg gtatgtatgt aggcgtgtgt ggtatgtgcg gtgtgtgtgg  60000
tttgtgtgtg ttgtgtgtgg cgtgtagctt gtgtgtatgt ggggcatggt atgtatgtag  60060
gtgtgtgtgg tgtttgtgtg tggtgtgtgt atggtgtgtg tggcatgtag cttgtgtgta  60120
tgtggtgtgt ggtgtgtgtg tgtggtgtgt atgtggcatg tggtgtttgt gtgtgtggtg  60180
tgcatgtgcg tatgtgtgcg tatgtggcgt gtggtgtttg tgtgtatggt gtgtatatgt  60240
gtggtttgtg tgtggtgtgt ttgtatgtga tgtggtgtgg tgtgtgtggt gtgcatgtgt  60300
gtggtgtgta tgtggtgtgt gtggtttgtg tgtgttgtat gtggcgtgtg gtgtgtgtat  60360
ggtgtggtgt gcatctgtgt gtgtgtgtgg tgtgtggtgt gtggtgtgta tgtggtgtgt  60420
ggtgtgtttg tgtgtgtgtg tgtctgtgtg tgtgcacgca cttagatatc ttgtgttcgc  60480
agcttgtcat ggagagcagt cagtccctgg ctgcctggcg ccgcttcctt ctcgggctgc  60540
catcctggga agggccccct tcgcccggcc gtgcctcctg ctcctgcctc tgctgccctt  60600
cgaatgcagc cgccctttc agcagcctct ccagggaggc ctgggtgggc cgccctcatc  60660
ttttgtctcc tcagcggggg ttgcagtggc ttcacctgga ggctccgagg gagcacacgt  60720
gcgtcctctg ggtgaaggct gcccaagtgc ttgcgtctgg gcgccatcct gtggtgccca  60780
cagggatatc aggctgagaa ggcctttgtg ctggggtcct ttataaaata agcttaccgg  60840
ggcatctacg gcaggtcaga gtcaatattc aaacgtgttg ttgtctaaaa atgcctggaa  60900
attttactcc taatgtcaaa ggaggcccct cccatgggct ctgagactgg agcgtggggg  60960
ttgtgagcag aaggacgcag aggaggggaa gtgctagaga gtggggggtc cggcccacca  61020
ggggccctgc gttggcaaga cctgaggtca tgccatcatt ttcaggcagt gggagccatt  61080
gaaagtgctt gagtaagaga gtggccaagg caacgtgcgt ttgatgaaat caatgaagca  61140
cctgtattgg gaggtgtttg ctggaaagag atagagtgag ggtggctggg aagaaccgtg  61200
aggcctgtgt acacatttca ggggtcctca ctaagcctgg gtgtctcatg gagctgtggc  61260
aggctgcatg gaccgtggga tttgtttgga ctcccagctc tccgtgggga tgtggagaag  61320
gtgagaggcc ctggggctga gggggcaata gcctggatcg gagaaggtgg caagcagagg  61380
tcagatgggg agggactgga acgccccaaa ccacagccat ttacacctgg gtgccaggtg  61440
ggagccagga agaggggcca ggatgttgga cgccagctcc accccgtgac tgctccctgc  61500
ccaggcggac agtggggagg gggcatacag cactctgagg atcataaggg tggggacccc  61560
aggagctgaa tctagaagga aagggctcct tccagaggag gtcatttgga gatcctgcca  61620
tccccacccc cttccaaaca gccaaacccg ctctggcacc accgccttcc ctatgccccc  61680
accccagctc cagctgaacg ccctcgccca gcttccttgg gagactgcca atctaggctg  61740
agttttgcag ctccttctct ggagcgcgag ccaggcgcag gctctgacac tgtcagggca  61800
gcggtaatga catcggcctc gagtccaggg ccagcccagg ccccctgtgc ccgtagacga  61860
accctcagag gatgcaagcc tgagggtccc cattctggtc cgaatgggaa gccactccag  61920
aggcgcgctg gcgcaggggg cggggatccc gaggtggcct ggacagagtc agcctcctca  61980
tgtcgcccag ccctggcgcc caggccctcc ccaaggaagg tggggtgcat ggcctgcctg  62040
ctccctccgc agggctccct gcggcatctc agtgcttgtg gagctgacag ctctctctgc  62100
```

```
cttcctaacc cttgatccct ttgataaaca tcaaaacctc agcatcagca ttgcctggag  62160
gccatgccct ccatgctgcc tcccctgcac aggcactcac agatacattc accccaattc  62220
agaagattct gcccagccca ccatctgtgg tttgtaaaag agaaacaata gaccatcggt  62280
tgctattgct tctaaatgca aaactgcgct atgacattac atgtgctttt ctgggaacac  62340
agtcccctac cccagtgtgc acgagaaagg tgctggtgct tcccttcttt gggggaacat  62400
tgctgttttt ggggtaggtt gttggacaag atccggatgg cagaaaccac aaaggagacg  62460
gttgacaagc gtggctcccc gaagccacat cattgccaag ccttcttgat gaccacagtc  62520
tccataaaca cggtaaaggg tggaccaggc tctgggagat gatacttcct gccgaaaagg  62580
attcatgtcg ggaatgcgta aagaattccc acatctcatc aggaaaagtg taagctccaa  62640
agggaagatg aggggaggaa gtgaagggat cgttcgagag agggagaagt agagatgctc  62700
gggaagcaag cggacctgag atgccgctga agtgtcattc aagctttgta atgtcgggcg  62760
tggatgatga cctggaagac agacgctgtt gggtcgcgct ggcggagtgt gacgggagag  62820
gtgctggggc attcctaaga acatgaatgt gggctcccag agctcataag ctcatgattt  62880
ccctcctccc caaaggggct caccctccag tatccaggct ggggggccag gagcacacgc  62940
accttttat atttgtgttt gtgcacgtgt gtatgtgtgt gttcaaagga gaatctgttg  63000
ctcatgtaac taaaattaaa aataatatag atgtagagaa attggaagtc ttgtgctctg  63060
ttggggggag tgtgtaatgg tccaacatgg cccaacaatg ccacctctag gtctagcccc  63120
aaaagaattg aaagaaggct gggtgcagtg actcatgcct ataattccaa cactttagga  63180
ggccaaggca ggaggatcac ccaggccagg agtccaacac cagcctgggc aacatatgga  63240
gatcccctat ctctacaaga aattaaaaca ttagctgggc gtggtggtgc gcacctgcat  63300
tcccagctcc ttgggaggct gaggtgggag gattgcttga gcccaggagt ttgaagctgc  63360
agtgagctat gatggtgcca ctgcactcct gggtgacaga gtgaggcccc atctcttaaa  63420
aaacgtatgt gtgtgtgtat gtgtatacag aaagggggt ctcagctggg cgcggtggct  63480
cactcctgta atcccagcac tttgggatgc cgaggcaggt gaatcatgag gtcaggagtt  63540
ccagaccagc ctggccaata tggtgaaacc ctgtctctac taaaaatata aaaattagcc  63600
aggcatggtg gcgcatgcct gtaattccag ctactcggga ggctgaggca ggagaatcgt  63660
ttgaacccgg gagacagagg ttgcagtgag tcgagatcac gccactgcac tccagcctgg  63720
acagagcgag acttcatctc aaaaaaaaaa aaaaaaaaaa aaaaaaaaaa agagggggag  63780
tctcaaggag atgcttgtat gctcacgttc ataggttcag aactcacaag agccaaaaag  63840
cggaagcaac ccaagtgtgt gttgacaggt gaatgaatgg acaaaagatg gcccatccta  63900
gagaggaaga aaattctgac actgctgcat agggatgacc ccgagggcat cgtgctgagt  63960
gaaataagcc tcagaagcac aggtactgca gcatcccact tagacacagt ccctaaggca  64020
gtcacaggcg tagagacaga gagccattgt cggtaccagg agctgaagaa cgagtgttta  64080
atggggaaca gagtttcagt tttagaagat gaaaagagtc ctggagatgg cagtggtgac  64140
ggttttgcaa ccatgtgaat gtacttaatg ccactgaact ggacaatgaa cagtggttaa  64200
aatggtaaaa tttagccagg cgcagtggct cacgcctgca agcctagcac tctaggaggc  64260
tgaggtgctg ggaggtgtga gggtcacttg agtgccaggg ttcaagacca gcatgggcaa  64320
cacagagaaa cctcatctct acaaaaaagc cggatgtggt ggcacctgct tatagtccca  64380
gctacttggg gggctgaggt ggggggattg cttgaaccca ggtgttcgag gctgcagtaa  64440
```

-continued

```
gccaaaattg tgccactgca ctgcagcctg ggggacagac tgaaaccctg cctcaaaaaa  64500
aaaaaatcaa aaacgaaaac aaacaaacaa acaaaaaaaa caggtaaatc ttatattatg  64560
tacatcttac cacagcaaaa caataatcat tttacaagcc cagtaataga aagcagtcag  64620
aacagaggag ggtggcgaca gcctcggagg tcctcggggc tccaagtgca ccccggcctg  64680
cggggagtgg gcagggacgg gggtggagaa gggagcgggc ttcggggaaa gggccggagg  64740
gaagcagccc ctgctccgag ccgcctgggc ccatgctgga gaacccaagt cccgggtcca  64800
ctggccgtgg cagggagagc tggcccatgg ctttgccatg tggcggctga tccaccctct  64860
cttctcatct ctgagccggg tgttcccaaa cttccctcct ggtctgttca tccaccaggc  64920
tctgagggcc agccctgcct ggcaaggggg gaaccaaggg gccaacttta gttttccaga  64980
agcctctgtc caggggagga gtcgacgtga acgaatcggt cacacacacg cagaaaggtg  65040
ccgctgctgg ggacctgtgg ggcgggggcg gggcagaagg aaggtcccct gtttggggga  65100
ccctttatta aaaacaggcg gcaagctgag gcgtccagct gagttcatcc caggccccaa  65160
agtaatcgca cggccaataa gccctgccta agatgaggac gggtgggtct ggaccgaggc  65220
cctggcggga gggagggtcc tgggcgtgcc accagctctc cggtcggaag cttctgcatg  65280
ggccgtgccc tgcgctggga gactcctgcc cgggcagcct tgctccaagg tcggctccac  65340
agagggtgcc cgccctctca gccctggcct gtggcacctg cccacagccc tttcttccct  65400
ggatgcagtt tttgcccccct ctgtgtcctc ggctgcacga gtaggggctt tcttgggttg  65460
gctgcccgcc tggcccggac tgacccggac tggctgaggc tgaggctgac agtgcaggga  65520
aggagccaga agccactatg gctgctgtgc agagaccaag gtgtctccct acacctgtgg  65580
cccccagggc cccagggaca cagggtccac accctgcccc acctgctcca tctccgggac  65640
gccctcgctc cccaatctga ttgcacaggg tggggggccc agcagccttg gtgacagttc  65700
ttcatcccaa gggcccgccc agtttctcct ggctcctggg gatgggagtg gcctgggttg  65760
tggccccacc agctctgtga cagggctctt gatgcttctc aggccctagt tttcctgaga  65820
cctgctggcc aggagctcag gcctcctggt ttctggttac ttttcctccc ctagaaagca  65880
gccttggcag acagaacaga ggcccagaag atcccgggag gctccccagg cccagaatct  65940
ggggaacttg caaggatttg gaatcctggc cgggtgtggt agccgagcct gtaatcccag  66000
aatttgggga ggctaaggtg ggaggattac ttgaggccag gagattgaga ccagcctggg  66060
caacacagtg agaccccctc tctacaaaaa aatttttaaa aatagccagg cgtgctggtg  66120
tgcccctgca gctccagcta cttgggaggc tgaaatggga ggatggcttg agcccgggag  66180
gtcaaggctt cagtgagcca tgatcaagcc actgcacttc agcctgggtg acaaagaccc  66240
tgtctctcaa aataaacatt taaaaaatag aagttaaatc ctcttttgga gactgtgggg  66300
tgaggggagt gtggccacac cacagccctt ccacctcccc attgtgtgcc ccgaactgtg  66360
ctgtgctggc cactggcctc accctccctg aagcatggca ggtcccccac ccccaaggcc  66420
atgctggggt ggggacaggg gccatgtgct tcccacttgg agggggctgt tccagacacc  66480
tccctggccg cccctggcag ggtctcggct gtactggatg tgaggaccgt gggcctccct  66540
tcccccagac tatgagagcc tccaaaattg ggaccgtgct gtttcccttt ccgtgctgtt  66600
tcccaaaggg cacccaggaa atgcttgctg cgtgaatcag tgaatgagtg agttcattca  66660
cctgggggct gggtggggac gatggagcct tccagcctcc tgggacctgc cctcagtgtg  66720
gaaagtgagg aggcatctgt cttcctgagg aaaacctggg cttagtcctc cctctggccc  66780
aggaggggac cggaccccac agctggaggg agccggctta gctgacagcg agtgtattaa  66840
```

aaacaagctt tggagcaaag cggacaagct caggtgttgg tagagttcat cccaggcccc 66900
aaagtaatca catggcaaac aagccctgtc taaatatcac ggcggctggg gcagcggcac 66960
gcagcggcct ggaaatgtca gccgggggtg ggggctcctc cgagccccgg gattagcaga 67020
ggtacctgaa gtgaatgcgc ccacctcctc cttcctgctc ctgctcagga cctgggctgg 67080
gccagcccgg ggcacctggg gaggggctca gagggtctca ctggggccag gggctcttct 67140
ttcagcccca gcccgggctg gttcccatgg ggtagcaggc tgaggagagt ggggagactg 67200
agcttggccg gagtggggcg gacgcacttc caggcccaaa ccagcagccc acgggtgggg 67260
gcagagaaag ctgccccccct gcaggcccag tgagtcctcg agagaggggg ccacccggcc 67320 atggggggggt ggtgatgttg gttcggggaa cctagggcat ctggaccagc ccctggacaa 67380
ggcggtcaca gcagccactg cctgagcagg ccacctgcgg gcttccctcc aggtctgccc 67440
atcggctcag ggcttccaga gcccaaggga gcaacacgtt tctcctgagc acgggtggag 67500
ggaaaataag gatgtttacg atcgagttgc ccatggaagc gttaccaagc cccctggaga 67560
ctcatctcac cgcagtggga cctttgcatt ctctcaggcg gtgggggtct ctgccgtgtt 67620
gtccgtaaag tgtcagcgtg gggccaactg gggacctcag cagccacgtc caaccctcat 67680
ctgaaacaag aactagaggc ctgggctgct cctcccttcc cgccctcagg agcacagggt 67740
ggcaggaggt gaactccatg ggcgaggggc tcttgctctt gcaggccccc aaagtcaggc 67800
aggtgcagaa gggaaggaca ggattcaggg acaggagaca cacagggggt cccctctgtt 67860
ccaggatgct cccaaatctg agcccagctg cccccagggt ggagggtgtg tggacagccg 67920
gccaagaggg gcggggccac agaaggccct ggcgaggccg tggggccaag cagaggagcc 67980
tacagtggct ggccagacgg gtcctaggtg atgcaagggg tcctccgcac ccctgttctg 68040
tttccccggc tctgacccag tgtgcggcct ctcctccatg tctgtatgtg gctgcctcca 68100
aggcccctct cctcaggccc tgtatgtcca agctgggcct ccttcctctg atcgcccttg 68160
ggagaggtgg cattgaggtc acctcctccc ctcccagagt ctgcatcttg tgggcaaatg 68220
ccccagtgcc tcccaccatc ctccatgcat gcagctgcct gcccaggtcc cctgtgaacg 68280
cagcccaggg ccgtgcaggc cacaggcggg gctcctctcc ccaggtgggg cctccaagtc 68340
tacacgtgtg gctgggaagg ggagtcacag cacagatgga atgaagcaca tgagccctgg 68400
gtgtggacct gcctcagctc agagcagcgg tgggaccaca tcttctccct gccacaggcc 68460
aggtgactag cacccaagcc cgtggcactg gcactgctgg ggggccaggg cgggctgtgg 68520
ccttgcaatg agatgtgatt tgctgtcaaa gcacagctgc cgcctcggtg agtgactaat 68580
gagaactgaa tgccgctctt attgcttttc actcgactaa tttgtcagag gctgtcaaga 68640
gccaggggga gggggcagag ggtggggacc ggaggtctga ttgagtcacc ggcatggggg 68700
cgaggctggg tgcccggagg ggtctgcaag aaaccaggag cacctggcag gaactcaggg 68760
ccggtgggga ccttggccat gatgtcgtgt gagagtccgg agggacacag gagctggggt 68820
caccctgttt gttccatatc aatggctggt cagctcttct aagcccctac tgtacacaca 68880
catgcacatg catacatagg acacacacac acacttacac aaacacacgc atgcatgcat 68940
gtggacataa aatcatacac tcacatgaat aattttagaa gcatgtacaa cacatgtaca 69000
cgcagagaag cactcccaca catgcttcct ggcacacaca cacacgcgca cacacacaca 69060
cccttgaatg cacactctgt ctcccacaca gacacagacc agcgaaaact ccaggccaag 69120
ctctggtgcg tgggttccca agcctggctg cacacacaac cagggtgctc tcggcaattc 69180

-continued

```
cagcatctcc ataccccctgg agcctcttgt cctggtgtgg gcttcctggt gatgtgggcc  69240
agccaggtat gggtggaacc gtcctactcc ccctccagcc ccaagcctga gccagcctga  69300
gtctggcatg gagctcctgg agccaggtga gcagtgaggg gcgctgggag ctggggagat  69360
gccctgtggg taggagatgc gcaccccgcc cacccggatg cccttccttc cagctgaatg  69420
cctggctgcc agggaccacg gtgacttctc ttgcttggct ctgtaacctg ccccccttcgt  69480
accctttccc tccctctgcc tccacctctg cccgactcgg tcccacagga ccctctggcc  69540
actggatccc cttccctgga agcacccctc actgctcacc tggctccagg agctccatgc  69600
cagactcagg ctggctcagg cttagggctg gagggggagt aggacggttc cacccatacc  69660
tggctggccc acatcaccag gaagcccaca ccaggacaag aggctccagg ggtatggaga  69720
tgctggaatt gccgagagca ccctggttgt gtgtgcagcc aggcttggga acccacgcac  69780
cagagcttgg cctggagttt tcgctggtct gtgtctgtgg gcctttgggg gtcccacaca  69840
cacaaggggc tcaaggctga cccctcctcc cacaagggcc tgcaactgct aatccctgat  69900
gccccccact gtgtggatgg caaaactgag tccagggccc aaggggctga gtcaggaccc  69960
tcttttcggc cccctacatg gtgggtctca acactgaggc agtccctaca ggcaacaagg  70020
atggaaggac agcactggct gtccaggctg gagggactca gagaggaggc cactggggga  70080
ctgcctggag gaggagggca gcccgggcct gagggcctgg caggatttgg tggggaaggg  70140
aaagtggagc cccaggtggg cagcagcagt agcagaaggg gggcagggag ccgtctgtgg  70200
gggacaggga gggtccggct gcctgtccag ggtgtggagg aggagaggca gcccacaggc  70260
tcagagcccg aaggaggcgt ggtgcctgct ctgccggcct cgctctgggc ctgacttcca  70320
aacacccaat tatccctaag tgcatccgat cgactggcag ggcggctgtt ccggggccca  70380
cctcgtccat gcgctccgcc cgccctgctg tggggctcca tctgatggcc tcattagggc  70440
taattgctct ggcatttggg tctgacaggg acggcggatt ctgtcctgtg ttggggcgtc  70500
ttggttcttc cagcttgggg gatggagggg agctgcttcc ttacacggca gagaaaggcc  70560
ctgcacccca ggcggggcaa gatggcgtga ggggaggacg caggactcac tgtcccctgc  70620
cttcttggga caatgggaac tgagggacag cccagggtgg catgacaccc caaatcctca  70680
ggaggtcccc cactgtctcc caaatgtgag tgggggtctg ggaggctgca ggccggtgtc  70740
cctgggagcc aggctctaga gggggcatct ctggggaccc tggggacccc gggctataaa  70800
gagaactgcg gagtagacat gggcgggggg gcagtgtgtg ctccagcatg tgtgtgtgtg  70860
tgtgcatgta cacgtgtgca cctgtatcgc ctgtgtgtgt gcatgtgatg tgtacacgtg  70920
tcatgcatgc acgcacatgt gtagtgtgtg ctcgtgtgtg gtgtgtgcct gtgtcatgta  70980
tgagcacact tgtatatgtt gtgtgtactg tgtcatatat gagtgtgttt gcctgtgtag  71040
tgcatgcaca tccgtgtgtg catctggtgt gtccgtgggt cattacgagt gcatcgtatg  71100
tgtatcgtgt acatgagtac acttgtatgt gtggtgtgta caggtgccat gtaagtgtgc  71160
ttgtacatat atgcatgcat gtgtcatatg catctgtgtg tgcatgtgtg tggtgcacac  71220
atgtgttatg tctgagtgtg cctgtatgtg tgctatgtac acgtcatgtg tgagtgtgct  71280
tgcatgtgca gtgtgtggat gctgcttgta cctgtggtgt gtacctgtgt catgggtgct  71340
cacacgtgca tggagtgttg tgtgtgtgct tgtgtgcccc atgtgtgcat gtgtgtgtgc  71400
ctcacacaga tgcctgcatt tgcctaggca cttgcaagag gacaccatgc tggctctcaa  71460
agatcacagg gccacctgag ccctgtgcac accacagcca ggccatggct agaccctgca  71520
gagccacagg gcgatgcctg tcagccaggg gacccagaac acctcctggg ctcctcccca  71580
```

-continued

```
gcacatggct gggctcctcc agcaggcctg gatttgggaa gggcccgtgg tgggcaaggc  71640
tggtgctggg gagcaggcct ggtggcctca gagactcgcc ctgtgggcgg agcagcctca  71700
cagccaggtc gaagtcagca ctctgaccct gccccacgcg gggagtgggc accagtccca  71760
gggcacagac gtgctgggtg attaatctgg gtgattaagc ctcgggctga gaggctgttg  71820
agagagaaca cgctccattg tggagctggc tcagcattcc ttacggccat ggtggcaggg  71880
gctgtaacca cagggacggc ggaagtggtg gagggtggtg gggtatggag ggaagcccag  71940
agggctccgt gcaggaaggt ggagcctggt gcaatggagg ggacagcaag ggctcctcag  72000
acctctgcgg ggcccccact cccctggtca cctgttttgt ctctgatctg gcctgggtcg  72060
gccctcactc ctggccccac ctcatagccc cccctggtgg ggctccgctc cagcccttct  72120
ccttcccagg ggccagtatg ctggccccag gggtctcttg gggcgtgacc tcggcctcca  72180
gagaaccctg tcccagctct gcccttccct ctggggtctc tgtagatggg acgctggtca  72240
cagcagcctg tctgatttgt tccctgtggc ctaggttcct gagccccaca gtgccagggg  72300
atggatgcca ccggatcttt gaaagaccag tgtcaggccg ggcgcagtgg ctcacgcctg  72360
taatcccagc actttgggag gccgaggtgg gcggatcacg aagtcaggag atcgagacca  72420
tcctggctaa cacagtgaaa ccccgtctcc actaaaaata caaaaagtta gctgggcgtg  72480
gtggtgggcg cctgtagtcc cagctacttg ggaggctgag gcaggagaat ggcgtgaacc  72540
ggggaggcgg agcttgcagt gagccgagat cgcgccattg cactccagcc tgggtgacag  72600
agcgagactc ggtctcaaaa aaaaagaaaa aaaggaaaga ccagtgtctt gggagttggg  72660
aaacctgggc tggagactca ctgcatgacc cctgagaagt tgcacctcag aacctcagtc  72720
ctcgcatctg cagaatgggt ctgtgaacac ctcagctgcc cgaacgtgga tgccgcaggc  72780
tgacccagca ctgagctcta ccaagaccag gggccagccg tgtgctccct ccaggcctgt  72840
gcccagcgtg gagaggcctc gtcccgtggg cgctggagtg gagccttcct ggtgtttgtg  72900
gacatctctg gagagggcca gaggcaggtg ggtgacacgg ggcatggctc aatcatgggt  72960
ggtccagact ggagaggtac cctcgggctg ggagcgggga ggctggccag ggtagacttt  73020
tggggcctcc atggataccc tcaccatctg gaatcggaga ggggcacggc acaaaggagg  73080
gcggggccag ggccaggact ggagtcgggg gcacctctgt gccaacaggg gccttggatc  73140
tggggtacag catggttccc cggccctgaa ggggctggcg tgtgggacag gcttcccagg  73200
aatggatagg cagggatgga tgctgcctga ttggggcggg aggctggagg cagggcaggt  73260
gcaggcacct gagggcagca ctcacctcca caggggtcca ggggcctccc cagcctcagc  73320
acctggcctg ggctcctgcc tccagagagc ctggccccaa ggaagagtct agtaagctta  73380
gttcccatcg ggcttccatg aaagcacaac tggcccggca ggaaaccgaa ttaaaaagca  73440
atatttgtat cagtggaaga catttgctga aaggttaaat ccacatccgg cagtgtgggc  73500
catgagcctc cggcgtggtg ttcatcaggc atgtctctcc tcctggcctg ggcacctgag  73560
cactggggcc gccctgggca gagctggggc ggggtgctgg ggggcctgga gctgcctcac  73620
cgagggatcc tcagcagccg accctggggg aggcaaatga gactctttct ggggaccttg  73680
aggggagctc gggggagcca tgcagagctt caccaggcct ggacactggg catggaggct  73740
gggccaccca agggccatca ccagggactc aggtgggtgg gcctcagccc tgggtgacag  73800
aagctcacgg gccgcagggc gaggccagag gctgagcctt caggctgagg tcttggaggc  73860
aaatccctcc aacgcccttc tgagcaggca cccagaccta ctgtgggcag gacccacagg  73920
```

-continued

```
aggtggaggc ctttggggaa cactgtggag gggcatagca tctccgagag aggacagggt  73980
ctgcactggg tgctgagaga cagcaggggc cgagcggtag gcttccctgc ccccagggat  74040
gttccagagg agcgcaaggg aggggcatta atatcgtggc aagaaagggc aggcattgca  74100
gagtgagcag cgacggaact gggttttgtg ggatgcatag gagttcaccc ggataagagg  74160
tgggtgagga atgacactgc aaaccgggga tcacggagcc ccaaatcctt ctgggccagg  74220
aagtgggaag ggttgggggg tcttcccttt gctttgactg agcactcagc ctgcctgcag  74280
agggcagcga ggagccacgg aggggtgtgg gacagggatg ccatggctga agcagtttta  74340
ggaaaggtcc caggggctat tgttgaagag agaacgggga gcggggagtc ccacagctga  74400
caggagcaga gtgggccctg agagatgcca gctctggctg ccacagtgac cagccggggt  74460
aggccttcga gaagtcaggg agcgtctagg gcttctggct cctgctgggc ccagggtgtc  74520
atcttgggct gccaacacca gaaagcccag cagatacagg aagccccaag ccctgtcgga  74580
aacggttctt ctccaggagg gacagcggtg gcagcgttca gccgcaggcc atgcactctg  74640
gggccacgtc cttccctctg tacagtccag cattgtcaag gcaggctctg gccatctctg  74700
ctgaccccag agggatgggg aggcctcccc ttccaccaga agggccagaa gccaccctgg  74760
gcaggggcat cactctccct gggtggggca gcggctggga gcaggaggtg ccagtgggcg  74820
tgggctggat gcgggtgcct gcggggcgga catggaactt gggggaggct ctaggctggg  74880
gttgtcctca agggagttct caggtcaccc cagggtcacc ctcaacccgg ggcctggtgg  74940
ggtagaggag aaactgcaaa ggtctctcca aggggaaggc atcagggccc tcagcactga  75000
gggacgtgcg tgctctttaa agaaggggcc acaggacccc gagggaagcc aggagctagc  75060
agtgggccat agaggggctg agtggggtgg gtggaagccg tccctggccc tggtcgccct  75120
ggcaaccctg gtggggactg tgatgcagga ggtggcagcc atttggaaac gcgtggcgtc  75180
tccttagaga tgtcttcttc agcctcccag ggtcctccac actggacagg tgggccctcc  75240
tgggacattc tggaccccac ggggcgagct tgggaagccg ctgcaagggc cacacctgca  75300
gggcccgggg gctgtgggca gatggcactc ctaggaacca cgtctatgag acacacggcc  75360
tggaatcttc tggagaagca aacaaattgc ctcctgacat ctgaggctgg aggctggatt  75420
ccccgtcttg gggctttctg ggtcggtctg ccacgaggtt ctggtgttca ttaaaagtgt  75480
gcccctgggc tgccagaaag cccctccctg tgtgctctct tgagggctgt ggggccaagg  75540
ggaccctggc tgtctcagcc ccccgcagag cacgagcccc tggtccccgc aagcccgcgg  75600
gctgaggatg attcagacag ggctggggag tgaaggcaat tagattccac ggacgagccc  75660
tttctcctgc gcctccctcc ttcctcaccc acccccgcct ccatcaggca cagcaggcag  75720
gggtggggga tgtaaggagg ggaaggtggg ggacccagag ggggctttga cgtcagctca  75780
gcttataaga ggctgctggg ccagggctgt ggagacggag cccggacctc cacactgagc  75840
catgcccacc cccgacgcca ccacgccaca ggccaagggc ttccgcaggg ccgtgtctga  75900
gctggacgcc aagcaggcag aggccatcat ggtaagaggg caggtaggtg cccggcggcc  75960
gcagtggacc ggagcccagg gctggtgcca gctgcctctg ctactcccca gcctggctgg  76020
cagccccagg ctcagggtcc atgcaaaccc ctgggacgcg gcgtggatgt ggaggcctgg  76080
gcacagcggc atcccctgtg cctggtgttt gagtccctgt tgggggaggg tgaggtgatg  76140
cctgtccctg tgtgtgcccc tcttaggccg acctctctcg ggggtcgtgt gggtctctgt  76200
gtcttgtttc atcttgaatc ttaacgatcg gaatgtggaa acaaatccat ccaaaaaatc  76260
caagatggcc agaggtcccc ggctgctgca cccagccccc accctactcc cacctgcccc  76320
```

tgcctccctc tgccccagct gccctagtca gcaccccaac cagcctgcct gcttggggag 76380
gcagccccaa ggcccttccc aggctctagc agcagctcat ggtggggggt cctgggcaaa 76440
tagggggcaa aattcaaagg gtatctgggc tctggggtga ttcccattgg cctgttcctc 76500
ccttatttcc ctcattcatt cattcattca ttcattcatt caccatggag tctgtgttcc 76560
ctgtgacctg cactcggaag ccctgtgtac aggggactgt gtgggccagg ctggataatc 76620
gggagctttt cagcccacag gaggggtctt cggtgcctcc ttgggcactc agaaccttgg 76680
gctccctggc acatttaaaa tggtttttta tttatggacc ttgattgaaa tgtggtgtga 76740
gttgtagcag tgtcatttcc aggtaccttc tcagggacac agggcgccct cccccgtcct 76800
cccccgccct cccctaccct cccccaccag gctccccatc aggcatcccc tccccagggc 76860
gccccggggc ccagcctcac aggctctccg tggcctggaa ctgcagcccc agctgcatcc 76920
tacaccccca ccccaagggt aagtaagagg ggactctggg aggggcttct gctgctcccc 76980
ttcatgttcc acaaccctgg aagctcagga tgaagctgat tcttctctta caaggggccc 77040
agagccttct tgggagttca gctccaaggg atgagcccca ggtgtctgcc aagtccccct 77100
ctgtccaggc ctgggacggc tctgggatcg aggggtcaga ggcgctgagc ccagggagag 77160
acacctgcgc ccagagctat gacaaagggt ggagggatga caaggcagcc aggagcgggc 77220
gcctgcgggg tggcacagag gggcagggcc cgaggacagg tgtcctgatg ggagtgtgag 77280
aaagggtccc ctgtgcggca gccaggaggg taggggggtt gttcactggg gccctgtggg 77340
ggcagctcct tcctgagctg ccgttccctc cccggcagcc gatgccactg tccatcaaga 77400
catcgccctc ttcccatcac taatccagtt agcgcctggc ctggggatga gtgacacagc 77460
gtctctgtct gtctgctcgc cacagagtgg ggagcaggcg agcaccttcc cagcccccac 77520
tcctccccca ccaccactgc ttctgactgg gctgccccca tcgggaaggg cgtgcaatgc 77580
ccgcaggcac ctcggctagc atctgcccca gcaggcacac agtaggcgct caaaaacgtg 77640
ctctcatccc ctgcctctgt gtgccatcag cgctgcccga ctgtgggacc agctgtgggt 77700
ggaggtcccc gggtctcagc aggtggagga ggcatgggtg ccccttgtcc ccacagtccc 77760
cgcggttcat tgggcgcagg cagagcctca tcgaggacgc ccgcaaggag cgggaggcgg 77820
cggtggcagc agcggccgct gcagtcccct cggagcccgg ggaccccctg gaggctgtgg 77880
cctttgagga gaaggagggg aaggccgtgc taaacctgct cttctccccg agggccacca 77940
agccctcggc gctgtcccga gctgtgaagg tgtttgaggt gagctggtgg ccttcgtgtc 78000
cctggggcaa gttcacctgt gggtggggct gtgtgggctg agttcctgac ccctctatag 78060
cagaggtgca gctgcccagg cccccgaggc cggcacagga tgcagcaggg gagtctcagg 78120
cctcagctca gcccccatgg catctagcca cacccccgtg tttttgaggg atcctgagcc 78180
cacccctagg gctgaggcta ccaagcccca ctgtgcctct tgccttgccc atcccctgga 78240
tccccctcac ccaccatttc ccacgtgggg ggctcccagc agggcagcac aagaggcagg 78300
ggcagggcag tgtgccctct cccacccacc cagcacagtg gctcaggtga ccactgattg 78360
cattagtcac tccggcccca ctgtgccccg ggaggcaggt gacccagctc ccggaagaag 78420
ctcccaaatg acattaaagc cagactcccc gccccccagc tcccagagcc agttttgtgg 78480
cccgagggcc actgcgaccc accgcccttg ttgctaggca acaggaggtg gggtggagc 78540
ggacccttct ggccagtgtc ctggacgctc aggggccagt gagactcagg gcccatccta 78600
caaacctgga tgaggccacc agggttgggg gcaccttctg accagtggct gaggagccgg 78660
actgtgtggc atggccttgg gacacacaca ccgagccgcc cagaaccagg ttaagcctca 78720
agcggtgaca actcctggtt aggcacgtaa cacaaaatcc aacttgccag tggcaaaccc 78780
tggcctggtg gccgacagct gacctgagcc tggaagaacg ggatctgtgt gctgctagca 78840
caaaagtcaa gggcagggcc tggccagcca gccagatgtg cctcctcccc gcccacccca 78900
ccctctctct ccatctctgt ctctttctcc ttctctctct cttcctgctt ttgctcccta 78960
agacgtttga agccaaaatc caccatctag agacccggcc cgcccagagg ccgcgagctg 79020
ggggccccca cctggagtac ttcgtgcgcc tcgaggtgcg ccgaggggac ctggccgccc 79080
tgctcagtgg tgtgcgccag gtgtcagagg acgtgcgcag ccccgcgggg cccaagggtg 79140
aggcggtttt ctgtccttga gggccaccaa atgaccttga gaggctgggg tgcaggggct 79200
cctgcagggg gaccctacag tgaccacgtg gtggtggcct ggttccctct ctgcgggctc 79260
cactccgcac cccgttttgc tacacatccg tgtccgggcc tggggccact ccaggatccc 79320
cccgcagctc tcacagcccc ggctgcctct gccccccgga agtcttgtag gggaggctgc 79380
ttcaaggtgg gtgacacagc cccacggctc cgagctcacc aagatctctt cctccatcac 79440
ccataaagtc ccctggttcc caagaaaagt gtcagagctg gacaagtgtc atcacctggt 79500
caccaagttc gaccctgacc tggacttgga ccacccggtg agtggtgcgc ccctcactca 79560
ggcctcctgc ccctgatcac atcccctacc cttagcccaa ccctggacag gagtctgtcg 79620
gctccaggag cctccgtggc ctgtgccccc accccagcac agcctcctga cccgtgcatc 79680
ccctctgccc tcagggcttc tcggaccagg tgtaccgcca gcgcaggaag ctgattgctg 79740
agatcgcctt ccagtacagg cagtgagggg cccctgcgct cgggacccag actccgtcct 79800
gcaggctgac gctggacctg gggggtggga gggaaggaca aaggggagga cccatcttgt 79860
caccagcatc agtgcctcct gccaggcagc tctgctccag ggctttccat gtccccaaat 79920
cccagtgggg aaactgaggc ccaggggggc tagagcaacc tgccgaggcc acatagccgg 79980
ctcacggcac agtcagctgg ggtgcaccct cctgtccatc ctccaaccca aaggcctcgc 80040
tgcactaggc gggtgtggac ctgtgcccag tgaagctccc tccctccctc ctgcccttct 80100
cactccccga ggggacctgc tgaccactgg ccccctcccc agcggcgacc cgattccccg 80160
tgtggagtac accgccgagg agattgccac ctggtgagac ctccgtgcag ctaggggctg 80220
gggaggagcc cgggggatgc ctcctggaat cctggcgtgt gagggccgcc tccagggacc 80280
ttggcacaac aggagagact aaggccggga agaagaggga cttgcagggc tcagaatgtt 80340
gggttgggag gaagaggcta cccatcctgt cgggccatcc ccagtgtgct gagggaccgc 80400
ccctcatggc cccctatccc ctgggattcc ctaaagccac cagcaaaagc ccctcccggg 80460
ggcctgggtc ttcaggggtc cccaagaggc ctgcgttggt aggggctcag gcaggcagag 80520
gcacccacag ttcaggaggg gggtttcggg cactggggtg gggcattaga gggccctgag 80580
cctggctgcc cgcaggaagg aggtctacac cacgctgaag ggcctctacg ccacgcacgc 80640
ctgcggggag cacctggagg cctttgcttt gctggagcgc ttcagcggct accgggaaga 80700
caatatcccc cagctggagg acgtctcccg cttcctgaag ggtgtgccca gacgggaggg 80760
gcgcagagcc ggggggccgg ggatggtcag ccaagcgccc caccccagcg cggctccagc 80820
ccgtcccggc tcggcagtga cccgcgtggc cccttgcaga gcgcacgggc ttccagctgc 80880
ggcctgtggc cggcctgctg tccgcccggg acttcctggc cagcctggcc ttccgcgtgt 80940
tccagtgcac ccagtatatc cgccacgcgt cctcgcccat gcactcccct gagccgtgag 81000
tgcgcgccct ggccgccagc ccgagggtgg ggggtgcgac gggcggcccc tcagcccccct 81060 tctccctcct acgcgcaggg actgctgcca cgagctgctg gggcacgtgc ccatgctggc 81120
cgaccgcacc ttcgcgcagt tctcgcaggt acgccgcggc ctcggaggga gccggggtca 81180
cccaggggct ggcttggcgc cgggggcggg cggggatcga tgtgcgggtg ggtgaagtgt 81240
gctgcctgct cccgggcccc gccaaggagg ctcggcgccc cgagggtcgc gcggcatagg 81300
gcggggctgg agcggagcct cccacggcct gtgctgccac ctgccggcta cctgggaacg 81360
gcgcccacgg gcttaggaat gtggtcaagg agggctgcct ggaggaggag gcccggtgga 81420
ggtgcggatc ctgggcggcc agggaaggtc tctgccgcca gggaagtgtc ccagagaccc 81480
ctggaggggc tgctgacacc cccggtgccc ccacctcgag catgacccag ggctgcctct 81540
ccccatcctt catcctccct gctccacagg acattggcct ggcgtccctg ggggcctcgg 81600
atgaggaaat tgagaagctg tccacggtgg gttgacccct ccctgcaggg cctggggtgt 81660
gggtttgggg gtctgaatcc aggcctcacc ctcttgccgt ccaggctgag gcctctcctt 81720
ccacccacga attgtgaccc tcaccctggc ctgcctgcat cctggcctgg cctccctggg 81780
ggtggtatcc tggtcacggg tgaccagggg ctgcccggtg ggcggcagct gtctctgggc 81840
tgatgctgcc cggcttcccc gcagctgtac tggttcacgg tggagttcgg gctgtgtaag 81900
cagaacgggg aggtgaaggc ctatggtgcc gggctgctgt cctcctacgg ggagctcctg 81960
gtgagagtct ctccttgctg cagcccccag cagaggggca gggctggggg acggtgcagg 82020
gaggggacag gctcccagtg ggaggaaact gaggcctgga cctccaggac tcaggctctg 82080
tttgggagaa ggcttgtctc tgcccagtcc tcaccccaca ttatcccagg cctccgaagg 82140
cccggcgggg gagatggggg tgactctacc caaggaaccc acccagcgtc aggccacggt 82200
gccccagttc cctcggggac ctgggtgcag tggagtcagt gatgccattg gcctcctgcc 82260
agcactgcct gtctgaggag cctgagattc gggccttcga ccctgaggct gcggccgtgc 82320
agccctacca agaccagacg taccagtcag tctacttcgt gtctgagagc ttcagtgacg 82380
ccaaggacaa gctcaggtgg gctaggctgc tagggcaagc cccccatggt gcccccaaac 82440
tgggccagcc aggccttcct tctggccttg agcagggctg gacctgtgag cccaggtcac 82500
agatgagaaa accgacccct ggttgcagca gcccccacac agcagggaca ccatccgtga 82560
gaaggacccc agcgtctggg gaggggcaga cctacaggac tgggggctgc tgggtggccg 82620
ggtcaaggcc agtcttggag gtgctgacag agcctgagct ttgtgaggac gtcctgtgga 82680
acctgtcccg gccccctgcc ctgggatggg gagaagtcag ggggatagac agagtcaagg 82740
tgggggacag ggcgggagtg gggtccccag ggctgggggc ctttggtgca gtgaccagag 82800
tgtcaggaga ggggagcaaa gccctctagc ctcatcctca taaaaggtct catcattttc 82860
cctccagcct cttatgcact ggggaaactg aggccagggg ctatgtgtcc agcggacagg 82920
ggtgctgaat tccacccaca ggcttaggga tatggtcaag gaaagcttcc tggaggaggc 82980
ccagtggagg ttcagggagg gatggggtgc ccggcagtct ctagtggaaa aggcgcctag 83040
cctatctccc ccatgaaccc cctcacccag ccctggaaga ggcctcagtg tcccgcctgt 83100
gaccagttgg ctcagaaaag ccctgggagc tctgagccac tgtgaaggtg gaaacgcggc 83160
ccctggcctc ccctctcctg gaggctgcag actctgcccg ccagttgacg agggctctgc 83220
cgctctcctc cccaggagct atgcctcacg catccagcgc cccttctccg tgaagttcga 83280
cccgtacacg ctggccatcg acgtgctgga cagcccccag gccgtgcggc gctccctgga 83340
gggtgtccag gatgagctgg acacccttgc ccatgcgctg agtgccattg gctaggtgca 83400

-continued

```
cggcgtccct gagggccctt cccaacctcc cctggtcctg cactgtcccg gagctcaggc  83460
cctggtgagg ggctgggtcc cgggtgcccc ccatgccctc cctgctgcca ggctcccact  83520
gcccctgcac ctgcttctca gcgcaacagc tgtgtgtgcc cgtggtgagg ttgtgctgcc  83580
tgtggtgagg tcctgtcctg gctcccaggg tcctgggggc tgctgcactg ccctccgccc  83640
ttccctgaca ctgtctgctg ccccaatcac cgtcacaata aaagaaactg tggtctctac  83700
acctgcctgg ccccacatct gtgccacaga gacagaccct gggatcctca gactcccaca  83760
cccccacccc agcctcactc agaggtttcg ccctggcctc cttcctcctc tgggagatgg  83820
ctggccgccc tggccaggca gctggcccct ccgggcctgg tttccccgct caccctgagg  83880
ccccgcccag ctctgagccc caagcagctc cagaggctcg ggcaccctgg ccgagctgcc  83940
ccatctccgt ggggtgccct cccaaggtgg ggagccacgt gacagtggga gggcctctct  84000
caggcctggc agggagcagg ggtcacaaac tgtgctggct gggggtggtc tcagaggtgg  84060
gcctgcaggc ctaaccctcc ctgctgacag ggctcccagc ccttgagaga aacagggatg  84120
gaggaacagc tgccctgatg ccctcaccca cccggagcag gccctgcgaa ccaaggggaa  84180
cctcagtgtg gcccccagca tgtgtgctga tggggagggt ctggctgagc tggtgcccag  84240
gcagatggtc tgggcctgtc tccccagcga ggcaggatgg gggctggatt tcagactctg  84300
taagatgccc ctggcttact cgaggggcct ggacattgcc ctccagagag agcacccaac  84360
accctccagg cttgaccggc cagggtgtcc ccttcctacc ttggagagag cagccccagg  84420
gcatcctgca gggggtgctg ggacaccagc tggccttcaa ggtctctgcc tccctccagc  84480
caccccacta cacgctgctg ggatcctgga tctcagctcc ccggccgaca acactggcaa  84540
actcctactc atccacgaag gccctcctgg gcatggtggt ccttcccagc ctggcagtct  84600
gttcctcaca caccttgtta gtgcccagcc cctgaggttg cagctggggg tgtctctgaa  84660
gggctgtgag cccccaggaa gccctgggga agtgcctgcc ttgcctcccc ccggccctgc  84720
cagcgcctgg ctctgccctc ctacctgggc tccccccatc cagcctccct ccctacacac  84780
tcctctcaag gaggcaccca tgtcctctcc agctgccggg cctcagagca ctgtggcgtc  84840
ctggggcagc caccgcatgt cctgctgtgg catggctcag ggtggaaagg gcggaaggga  84900
ggggtcctgc agatagctgg tgcccactac caaacccgct cggggcagga gagccaaagg  84960
ctgggtgtgt gcagagcggc cccgagaggt tccgaggctg aggccagggt gggacatagg  85020
gatgcgaggg gccggggcac aggatactcc aacctgcctg cccccatggt ctcatcctcc  85080
tgcttctggg acctcctgat cctgcccctg gtgctaagag gcaggtaggg gctgcaggca  85140
gcagggctcg gagcccatgc cccctcacca tgggtcaggc tggacctcca ggtgcctgtt  85200
ctggggagct gggagggccg gaggggtgta ccccaggggc tcagcccaga tgacactatg  85260
ggggtgatgg tgtcatggga cctggccagg agaggggaga tgggctccca gaagaggagt  85320
gggggctgag agggtgcctg gggggccagg acggagctgg gccagtgcac agcttcccac  85380
acctgcccac ccccagagtc ctgccgccac ccccagatca cacggaagat gaggtccgag  85440
tggcctgctg aggacttgct gcttgtcccc aggtccccag gtcatgccct ccttctgcca  85500
ccctggggag ctgagggcct cagctggggc tgctgtccta aggcagggtg ggaactaggc  85560
agccagcagg gaggggaccc ctccctcact cccactctcc cacccccacc accttggccc  85620
atccatggcg gcatcttggg ccatccggga ctggggacag gggtcctggg gacaggggtg  85680
tggggacagg ggtcctgggg acaggggtct ggggacaggg gtcctgggga caggggtgtg  85740
gggacagggg tgtggggaca ggggtgtggg gacaggggtc ctggggacag gggtctgggg  85800
```

-continued acaggggtct gaggacaggg gtgtggggac aggggtgtgg ggacaggggt gtggggacag 85860
gggtgtgggg acaggggtct ggggacaggg gtccggggga caggggtgtg gggacagggg 85920
tgtggggaca ggggtgtggg gacaggggtc tggggacagg ggtgtgggga caggggtcct 85980
ggggacaggg gtgtggggat aggggtgtgg ggacaggggt gtggggacag gggtgtgggg 86040
acaggggtct ggggacagca gcgcaaagag ccccgccctg cagcctccag ctctcctggt 86100
ctaatgtgga aagtggccca ggtgagggct ttgctctcct ggagacattt gcccccagct 86160
gtgagcaggg acaggtctgg ccaccgggcc cctggttaag actctaatga cccgctggtc 86220
ctgaggaaga ggtgctgacg accaaggaga tcttcccaca gacccagcac cagggaaatg 86280
gtccggaaat tgcagcctca gcccccagcc atctgccgac ccccccaccc caggccctaa 86340
tgggccaggc ggcaggggtt gagaggtagg ggagatgggc tctgagacta taaagccagc 86400
gggggcccag cagccctcag ccctccagga caggctgcat cagaagaggc catcaagcag 86460
gtctgttcca agggcctttg cgtcaggtgg gctcaggatt ccagggtggc tggaccccag 86520
gccccagctc tgcagcaggg aggacgtggc tgggctcgtg aagcatgtgg gggtgagccc 86580
aggggcccca aggcagggca cctggccttc agcctgcctc agccctgcct gtctcccaga 86640
tcactgtcct tctgccatgg ccctgtggat gcgcctcctg cccctgctgg cgctgctggc 86700
cctctgggga cctgacccag ccgcagcctt tgtgaaccaa cacctgtgcg gctcacacct 86760
ggtggaagct ctctacctag tgtgcgggga acgaggcttc ttctacacac ccaagacccg 86820
ccgggaggca gaggacctgc agggtgagcc aactgcccat tgctgcccct ggccgccccc 86880
agccaccccc tgctcctggc gctcccaccc agcatgggca gaagggggca ggaggctgcc 86940
acccagcagg gggtcaggtg cactttttta aaaagaagtt ctcttggtca cgtcctaaaa 87000
gtgaccagct ccctgtggcc cagtcagaat ctcagcctga ggacggtgtt ggcttcggca 87060
gccccgagat acatcagagg gtgggcacgc tcctccctcc actcgcccct caaacaaatg 87120
ccccgcagcc catttctcca ccctcatttg atgaccgcag attcaagtgt tttgttaagt 87180
aaagtcctgg gtgacctggg gtcacagggt gccccacgct gcctgcctct gggcgaacac 87240
cccatcacgc ccggaggagg gcgtggctgc ctgcctgagt gggccagacc cctgtcgcca 87300
ggcctcacgg cagctccata gtcaggagat ggggaagatg ctggggacag gccctgggga 87360
gaagtactgg gatcacctgt tcaggctccc actgtgacgc tgccccgggg cgggggaagg 87420
aggtgggaca tgtgggcgtt ggggcctgta ggtccacacc cagtgtgggt gaccctccct 87480
ctaacctggg tccagcccgg ctggagatgg gtgggagtgc gacctagggc tggcgggcag 87540
gcgggcactg tgtctccctg actgtgtcct cctgtgtccc tctgcctcgc cgctgttccg 87600
gaacctgctc tgcgcggcac gtcctggcag tggggcaggt ggagctgggc gggggccctg 87660
gtgcaggcag cctgcagccc ttggccctgg aggggtccct gcagaagcgt ggcattgtgg 87720
aacaatgctg taccagcatc tgctccctct accagctgga gaactactgc aactagacgc 87780
agcccgcagg cagccccaca cccgccgcct cctgcaccga gagagatgga ataaagccct 87840
tgaaccagcc ctgctgtgcc gtctgtgtgt cttgggggcc ctgggccaag ccccacttcc 87900
cggcactgtt gtgagcccct cccagctctc tccacgctct ctgggtgccc acaggtgcca 87960
acgccggcca ggcccagcat gcagtggctc tccccaaagc ggccatgcct gtcggctgcc 88020
tgctgccccc accctgtggc tcagggtcca gtatgggagc tgcgggggtc tctgaggggc 88080
caggggtggt ggggccactg agaagtgact tcttgttcag tagctctgga ctcttggagt 88140

-continued

```
ccccagagac cttgttcagg aaagggaatg agaacattcc agcaattttc cccccaccta  88200
gccctcccag gttctatttt tagagttatt tctgatggag tccctgtgga gggaggaggc  88260
tgggctgagg gagggggtcc tgcagggcgg ggggctggga aggtggggag aggctgccga  88320
gagccacccg ctatccccag ctctgggcag ccccgggaca gtcacacacc ctggcctcgc  88380
ggcccaagct ggcagccgtc tgcagccaca gcttatgcca gcccaggtcc agccagacac  88440
ctgagggacc cactggtgcc ttggaggaag caggagaggt cagatggcac catgagctgg  88500
ggcaggtgca gggaccgtgg cagcacctgg cagggcctca gaacccatgc cttgggcacc  88560
ccggccatga ggccctgagg attgcagccc aggagaagca gggaaccgcc agggccacag  88620
gggcagagac cagggccagg gtccccctgc agccccttag cccacccccct cccagtaagc  88680
agggctgctt ggctggcttc ctttgctaca gacctgctgc tcacccagaa gggcccacgg  88740
gccctggtga caaggtcgtt gtggctccag gtccttgggg gtcctgacac agagcctctt  88800
ctgcagcacc cctgaggaca gggtggctcc gctgggcacc cagcctagtg ggcagacgag  88860
aacctagggg ctgcctgggc ctactgtggc ctgggaggtc agcgggtgac cctagctacc  88920
ctgtggctgg gccagtctgc ctgccaccca ggccaaacca atctgcacct ttcctgagag  88980
ctccacccag ggctgggctg gggatggctg ggcctggggc tggcatgggc tgtggctgca  89040
gaccactgcc agcttgggcc tcgaggccag gagctcaccc tccagctggg gacctggcca  89100
ctggggcagc cctgttcctg aagctctgag ctcacccctt ccccatgacc acatcagccc  89160
ccctccaccc agagatgtca cagcccccag ctagccccgc ctccagagtg gggggccaagg  89220
ctgggcaggc gggtggacgg ccggacactg gccccggaag aggagggagg cggtggctgg  89280
gatcggcagc agccgtccat gggaacaccc agccggcccc actcgcacgg gtagagacag  89340
gggcgccctg ctggagctga ggtatgtgag ctcgcgcggg gctgggccaa agcggggccc  89400
ggtgggccgg ctgggaggct gcccaccagt cagccatcgg ccaagctgtt gccctggctg  89460
accctgatgg ccaacaaggc cgtagggagt gatgggcaga ggccccttct gggaggggag  89520
ggtcagtgct ctgtggggga ccgtgtgttg gagtggaggg cagcaggagg agccctttgg  89580
tgtccaggga ctcctggagc tgccccagcc ttccaggact tgcagggcag ctggcactgg  89640
ctggtgctgg gggctgagga gtgtcttttg aggggccaaa ttttctgtga cttctgtcct  89700
gggggacctc tgacctgagg cctcaggaga gggcaaggcc gcccacccaa aagagatgca  89760
gccatggttc gcggtgccct cggctgccct gggccagagc tggggctagc tttcaccttg  89820
ttgagaccca ggactctgtc ccccaagcct gtcttcgcca gcgccttgac cccacccctc  89880
atatactgtg tcctggaaaa cgtggacacg ggagaccgca gccagggcga ggtatcgccc  89940
ctccatcccc ccaggcccaa tgagaagcag ttggccaagg tgatccaggt ggcagaggca  90000
gcatcagacc cagtctcctg tcaggcacca ccttgggtgc cggtccccag atgccctggc  90060
ggggagtgtg catgctcccg gagcccccag gtcaccccat gtgagccagg cccacagagc  90120
ttggctctgc aatgcctgct gggctgctgc ccatgctcca cccc ttctgg gaagctaaaa  90180
gacagccctt cagtgtccag agacctgcct ggccttggag cctcggtttc acatgcccac  90240
cgggctggca ggggcactca gctgcctcca gccccggcgg tcaccctggc attgggtcca  90300
tctaactgct ccccagtcac aaggcagctg ctccccaagt ctccccaaac ctgctggccc  90360
ctctagaagc ctctgtccat tcctggagga ccgagggcag cctgcatgcc atcccgcaca  90420
cagccttctg tctgggcgtc ctgccttcac acatgctgca cagggaggaa actcttatac  90480
cacattcctt aagcagagac tgaagcctgg agccaggcac atggcacgtg ctcccaccca  90540
```

-continued cccaggacac actgcggtgt ggctgcctcc aggctggccc cctagattgc gtctgctcct 90600
ggcatggata actggcgcct ttgcctggcc gttggggcag tgtttgcctt cccctgtcgg 90660
cagcaaatat ttactgtcct ccgtctccag gactctccag gcctgagcag accccggggg 90720
gatgagtgtg gactcagcgg tgctgagggt agccccctgc ccttcgggtc ctggtgccca 90780
gcaggggtcc agcccaggga agagactgag gccaggacag gcagtgttta agcctgagtt 90840
tctgggaaag gtagccctgg gcagaacttg ggccgaacgt tggccagtgt ctctctccag 90900
ccaggctgtg aggtagctgt ttccaggatg ggcacctttc cacacccagc aatgtggcca 90960
ggagccgcca ttcacgggtg cgaccagcag atggcatcag agcctcactt ttgatgcact 91020
ccggccacca gccacgggtc caggttctgg ccaccaccca gggtctgagc agctgcatcc 91080
tgcccctgcc gggcactccc gggggctgtg gggcctgtgg gggccctgcc agacactctt 91140
gggggctgtg gggggccctg ccaggcactc ccagggacta tgggggctgt ggggggccct 91200
gctgggcact ctgaagggca tggggcttag gaatgagagg agctgtctga tgatgatggt 91260
gggggcattg cagaggcccc cggcctgctc aggtccagtc tcggccccta agtcaagcct 91320
caggccagcc tctcaccagc ctgggtttct cagagggccg ggacaaatgt tctgggtctc 91380
taatattcca agaaagcctc tggctggact ctgagcccca cctgcgagcc cctagaatca 91440
cagagagcta gggtgagaag accaggggga ctccgtccca ccctcgtcgt ggctgagccc 91500
actgtggccg gtggtggacc aggctgtggc ctttgctgag ggtccccagg gcccctgggg 91560
gctactgagg ctggaggcca gcggtggcca ggagggtccc tccctcagcc actcaagcca 91620
gaaggtcgag tcctggtttc tatgtgagga gggggcttca ggggctggga cctgggggca 91680
ccgaaggcct ggagctgggg tccaggcggc tgagggttag tgcgttccca cgctcccctc 91740
cgccagcgcc gtgaggagag ggaggtccac tctggaaaga atgtttgagg gcaggggtag 91800
acagggtctg ggaacgcgga gatgacacac tggggtgccg cctccgcacc ctccgccctt 91860
cctcccacta ttgtttctgg cctcggccgc aggaacagca aggcagattc cttcgaaagt 91920
ggggccggcc ggaggcggca ccccatcgtc cctctcgcgg cccagccgtg ctgtgctggc 91980
gccaagctcc ccgccggcct cccacgcgct cctccgcgtc ctcagctcac tcctctgctc 92040
ccaggtggcc ccagtcctca ccccacctcg cttggactcc ccacttcctg cccatctgcc 92100
gctgttggga gaccctctcc ctgaccccag ggactgctga ggcagcctcc aagcctccca 92160
gtgtccccga ggctgcccct agaagctggc ttggggctgt accaaaaggt caccccacag 92220
tccccactcc aaggcaggtt gatagcaggg atctcagggt gcccatggat caaggactaa 92280
gtcagagtcg gggtccctca ggccgagggt aacgtaggtg gtgcctgcca ggctctcctc 92340
gcccaggggg gctgagaatg tctaaacccg ggtggctgtg acccctaggc agagccagcc 92400
cagcccttgc cagggatgga gaccggcctc gaggaggcca agccctgggg gtccacaggc 92460
ctgtgggctt cggggaggct ctgctccctg tggccctgtg tggcccaggc tgctgagtca 92520
tcagaacctc gggggcgccg cgggccccac attccgccca ggcctctctc tgaccccctt 92580
cccagcccat ctgtgttttt ggaaaacaga gccagagccc cccgcggccc tgccagcttg 92640
cggctgctca cgctgggact caaatcgcac ccttctgtct tcaaagtcca ccttcacttc 92700
aaagctcggt cccaccccag cccggcctcc acagggccac cacctgccca catccaggcc 92760
cgctgctgcc cagtttcgga gggaccttgg gcatcccctg atcctctcta gagcgcgggg 92820
ttcctggcat gggcccgtta cacatgggtg gctcggtggg tggtgaggac ggggctggga 92880

-continued

```
gaagatcctg gggaccccat ggtggaggca atgaggcacc caaaccccaa ctccagcgat  92940
ggctgcttcc acggggccct ccgagccctg accttcaagg tgcaagaaaa gctttcaggg  93000
gcaggggtga gtggaaggtg ggcttcctcc cttgccacct ggggggcggg cccaggacag  93060
atgctccgtg agagcacttc ccaacctagg cccagctgtg gggaaggagg gagcaggcgg  93120
ctgggctcca ggcaggggga agagttgcct gagaactcag ggagagaggg agggctgggg  93180
caccccatgc cagctccagc tgcagcacca gagctcagag cagaggaggc aggagccagc  93240
aggctgggag gcttcctgga ggaggtgtcc caggcccctg ccagcactgc agccttgagc  93300
acgaggccac gctgggctcc tgcttccagg gccgcagacc cagcccagca ctgcccatgc  93360
tgcccttgcc agggaccctt acagagctag cacctgggtc cctccccctg gctgggcatg  93420
ggctggtctc gacaacaaag aaggggtagc tgtggcctca aggtctacaa caggttgtga  93480
tctgtgggtg ccaagaagtc atgggccctc agcatcctca gggccagtga gtgtccacct  93540
gggccagtgt ggggctgaag ggtgagagct gagaggcggg gctgacatcc tggctctgct  93600
gccagtggct gtgtggcctt gggaaagtca cttagcatct ctgggccttg gtttcctcat  93660
ccatcagaag ggaaccaaag aaggccctgc ctgcctcagc tgctggatgg tgtagctcag  93720
tgttgtctgt gagaggcagg cccttcggca gccgcgcctc tggcttcagt acacccgtga  93780
gctgctttct gtgcccaggc cttcaaatca cggggacagc cccgtgggtg tggttcaggt  93840
ctgggcacca caggcaaggg gaagctgaca tgtcctccgt gggaagtggc agtccccatg  93900
gctaccgggc atgcacaggg cgtgtggaag ggaccttgga gggaggagca gctcctcgag  93960
ggaggagccc ggggctgggg tacggaggcc tctgcacatc ttagagtaaa acaagcagga  94020
gaggctgggt gcggtggctc atgcctataa tcccagcact ttaggaggct gaggcgggca  94080
gatcacctga ggtcgggagt tcaagaccag cctgaccaac agggagaaac cccatcttta  94140
ctaaaactac aaaattagct gggtgtggtg gcacatgcct gtaatcccag atattcggga  94200
ggctgaggca ggagaatcgc ttgaacctgg gaagcagagg ttgcgctgag ccgagatggc  94260
accattgcac tccagcctgg gcaacgagag cgaaactccg tctcaaaaaa acaaaaacaa  94320
aaaaatcaaa acaatcaaaa aaacaagcag gaggggctct gaggtgcctg caacacccag  94380
gtacaatccg tggccctgag gcccatcaca gggaaggggt ctttgcagct ctttcaaccc  94440
ccagcccagc atccaaggaa gcccagggca gggagaaacc tcagctgcac catcagagct  94500
cagaacagag aaggcagaaa ttagcaggga gtggggctgg ggaggcttcc tggaagacgt  94560
gtctcccgcc ttgctggcac tgaggccttg aggatgggtc catactgggc ccccactgcc  94620
agggatgcag atccggccca ctgctgaaat ctgtgctcct ggagcctccc tcctgttcat  94680
gggccacagg ctgtgaaaac cccagagtcc tcccaggcag caagttttgt tttgtttttt  94740
gtttgtttgc ttgtttgttt tttgagagtc ttgctctgtc atccaggctg gagtccaatg  94800
gtgcgatctc agctcactgc aacccctgcc agccagcaag ttttgctgga gcaggtggag  94860
gagtctttgc agcgagctcc cgagctgcct aggcctgccg aagagttgct gagcacatga  94920
ccaccaaaaa aggtttcggc acctgtggac ctgtgggtag gggaggcagg ggcaaatgtc  94980
actttacgtc agggggagga taaaatcgaa cgtttattaa cattgatttt gtgccagagg  95040
tggctaccca gacccatcca ctgtagccgt gaggttggaa gggagagggg aggcatgaac  95100
tggtttgtcc aaggtcgttg gcagagcgcg gctgtgaact gggttagccc ccaggcccct  95160
cctgcccatc cgtcctccaa gcactgatgt gcgagtggca cagtggtccc cttggccctg  95220
ccagcccctc gggctgtggc cctatagcct ttgaaggacg gcctcacttc cccagcagag  95280
```

```
gcagcctggc cttccagtac ctcgatggtg tagggctctg gggccacagt ctggtgtttt  95340
caggactagg ttgtgggtta cttcctcctc ttctctcaat tcccaaggtt tgttaagcgg  95400
ccctgtagct acggtcatgg caatatggat ttactggcgg tgctttctga agctgtggat  95460
gcaattctca caagtggcca catggtgtca ggctcgggcc agattaggaa atctccgctt  95520
tacaggtgga gccgggtggg gctggggaag cgagttaaga acgaaattca gcccatctgg  95580
gctcatccta gggacgctgt ctctgaaagg gggtctcaac gttctgcccc gggcctctca  95640
gtaatagatc tcattttatg ttcatgctaa tgtggtggtt tcctctctta gaacaaaacg  95700
gatgcttcag aaaggtgttc cagacctatc ctgtggctta ggccctaagc tttaggatgc  95760
tcaccaggcc acagccccct cgggttagga gacacccgaa gggaggaatt ccctcagcgc  95820
cccctctcag tcctgtaatg ccgggacaga agcagataag agccccggtt ccaaacacaa  95880
aggtgcagga cccatggcac cctgacactg tagggaggcg tcctgacttt gcccccagag  95940
tccccctcca gagtgcccca aattgcggcg cccaagacct ttgggttatg ccactgtaat  96000
tctagaaatg gccgccaggt gtcagcataa ggccacttaa gaggctaaat ggcgaaagct  96060
tggtgtagca gatttctggg ggttcccaag actctcatgc atgaacaggg gtgggctgag  96120
cctctcccag gcctaagagg cagtggagca aggaggtttt tctatgtcgt gtccctcaat  96180
cctgcacccc agtttttgtc cattttgcgg tccctctcac ctgtctccat aaagcatgtg  96240
tcccccagac ccttgcgtgg aaaatctgtg gaatgtagtg ctgtggggcc acagccctca  96300
caccccaact cactgatccc caatgcctct agtcctgcct cggtggcacc atggcttagc  96360
tgctccccgg gggccctttc tatcctgacc gcttctccct gctctccttc tcctgtttac  96420
acaccctggg ttccaagatc ctgatgggat aaaatagcct tggagactag agtgagctcc  96480
tcctgggccc atccagagat ggaattccag tccagggcag agtttggatt caagacacca  96540
ttgtgggcct gggaggctcc aggtttccag gagtttgacc tgtgggctgc ttccctttca  96600
gccccatagc tgcccacctc ctcaacctgg ggactgttca tttggggggg catcccatgg  96660
aatcacttca tctggctggg tgtcagcccg tcactctctc taggtccatc tgcagcttgg  96720
aaagtcccag ccaagtgtct ccagagggct ctggcagtcg ctgtttgcaa catttgggca  96780
tcttgcagca gacactggga ccagcacatg ctacggggtc tctaagccat agagccccgg  96840
agcaagggct gcttcatgct gacctccttg tatctttgtt ttgtttcttt ccctgagtct  96900
ttgttttgtg ccttctcttc ctgcaggctt gaggaagagg tgtcaaattc ccagtaagac  96960
ttgatctaat ccaatgggtg attctatctg agccctccct gagctgctgc cagctctgag  97020
tctgtgcttt agctggaaag actgtgaacc cattcagtgc tctggacctg acagggccat  97080
taacatccct ccccacccaa aagccgagtg aaaaatccca ttttccctcc tcccatggga  97140
gggcatggct ctggggcatc tacgtcttat ttgagacatc cccaacacaa tgccagattt  97200
gaatcccctt caagtctaac tctcttccct gctgaaatcc ttgttgtccc cactagatgt  97260
cctattcctc cagctaatga agggatttaa gacgagggct tgaaagaaaa agggagaggg  97320
gacaattaaa tcccaacaca ggctagtaaa actaatcaca ctgaaggtgg ttggggtgcg  97380
tgggtgttgg aggggggac tggtggctct ctggaaagta cacgtctttg cctcttcctg  97440
agtctttgct agcttgggga agaggttaga aatttccagt gtgatttagt ccaatctggt  97500
ggatgcttct atatgaaccc tcacccagct gctgtcagct ttgagtctgt gctttaatta  97560
gaaaggctgc gaacctgtcc aatcgcccaa tccagaaatg cctgcaagtg ccccctgcag  97620
```

```
cagtgtcatt agagcttagt accacacagg gagtgtctga ggtcagatca gacgtgacca  97680
gtgaagtgaa aaacccccca gctgagtacc ttgctcatgg aagatggaag gacataactg  97740
cacagtacat aactgtaccg ggagcaccta aaatccaatt tttctgctga ttcttgaacc  97800
ctgctttgtc ccccttattc cccccccccc cgccatttta ccagtgccac gtccaccaac  97860
attccagggt gtcaagtaac tgccaagtgt cactctaagt aaagctacac ccactcccca  97920
ccacctccac atagccccca cctcctagct ggcagggagc ttctggctta tgcccacgcc  97980
cacaggcgcc tttctgccag gtcaggggtg ggccaaacct ccacccgcta atgtaccatg  98040
ccctggtgct ggaaagtgcc tgagccagct gccccagcgg cctcagcact accaagttgg  98100
cacaaagctc cccaaattcg gaggggctca gggaaacgag tggaggggat gaggaggtga  98160
ggggtaaacc catcatttca gttggcattt gagcaggtgc catgctcagc ggagatgagg  98220
ctctcccatc tgtaggggcc gtattaacat gcacactcta aaagtgccct tcgtttctcc  98280
agcctcagct ttgtccctct cctcctccac gtcaacctgg ccagagggtc tggacgccac  98340
agccagggca ccccctgctt tggtggtgac tgctaatatt ggccaggccg gcggatcatc  98400
gtccaggcag tttcggcaga gagccttggg caccagtgac tccccggtcc tctttatcca  98460
ctgtccagga gctgcgggga ctgcgcaggg actagagtac aggtaactgg gctcccatcc  98520
cttgagtgtg agagaaaagc tgcactttaa gtgttcaggc gtgggtgggc cgggagcttg  98580
gggcagctgc caggatcctg gtttctgaag gaggggaaga acttctgctg ctggagggtg  98640
cagggaagcc tcctgagagc agcctcaact tcagggatgg ggtgtgcagg aaaggccatt  98700
gtggagaggg ttctccttta gggctgcaca aagccactga ggcttttgca aggaaaatag  98760
gttttccttg actaattcac caagcaaaat gggaggggta ggggaggagg gctaggccgc  98820
tcttcccagc gggaacacac agctgtcttc acaagtgtga aaggaagagt ctttctgtgt  98880
gaaaagtttc ctcccgttgc atccccccatc ccattcccag agacaaacag gagactttgc  98940
agaggagcca ggggcccgag attctggcgc agagatttta tttatacata tatacaccat  99000
tttacaggta aagcttcctt ccctcctgcc tccctatgcc tcctgaccac cagcaagaaa  99060
ttggacagga gactgaggag aaatgccggg agaggcaaca accgccctcc atgtcccccc  99120
taggtttagc ttctctcctc ctgatggcgc acctggtccc ccttgctgct ctcccagcct  99180
ccctggcaca gagaggcgcc ctggggccaa ggcagtttcc ctgggaatgc tcattcatgc  99240
atgaagtttt tctctgttgc accctggacc cagactcctc gatccaccca gggtggtgtc  99300
tgtggggagg gggttcattt ccccaggaag cacagccacg ccgtccctca ctggcctcgt  99360
caagcagagc tgtgtgtcca gtggcttttg ctggggcccc ctccttatct ccttccaagg  99420
tgggggtgtt tggaggtgga ggaggctttc atattccgtg ccatgacccc tcaaggcggg  99480
ccattcgtgt gcaccctcca cccccagtgc caggcagaag cccatcctca cccaggaaca  99540
gggcagcctg tccaacagaa gggtctcggc ctctccatca gcaccgggaa gccctttcta  99600
ggcaaacttc tcaccacttc ttccctccct tatactttga aagagggagc tctaggcagg  99660
ggaggggcta gagggggaag ccgctgccca gatcctgaca aggtgacctg aaggaacccg  99720
gggaggggga tgggacaggg ctcaggcttg gggtgtatgg ggaggggggc tttgctttta  99780
aaagaggtca tctcagcaat atctttttgt ttttccccag gggccgaaga gtcaccaccg  99840
agcttgtgtg ggaggaggtg gattccagcc cccagcccca gggctctgaa tcgctgccag  99900
ctcagccccc tgcccagcct gccccacagc ctgagcccca gcaggccaga gagcccagtc  99960
ctgaggtgag ctgctgtggc ctgtggccca ggcgacccca gcgctcccag aactgaggct 100020
```

ggcagccagc cccagcctca gccccaactg cgaggcagag aggtgagtgt ctcaggcacc 100080
ctgaggcctg gcagagaggg ccacaggctc tgcgcgggag tcttcgaact gggatctccc 100140
ccttctgcaa gcagctttgg ctcagagagg ctggcgtgga ttcagtcaca cagctgggat 100200
ctggagttcc gtggttggct ccaggtgctt ccgtctaggg gccagagcag gtgtgggcag 100260
agcaggttcc ccgcagtctc cacggcaccg aggtcctggc aggggagctc ctgggagacg 100320
aaagagggca aagaagggga gaggggcagg gagagagcgg gcagccaaag gggagaagat 100380
ggggggcaga aagtgggtag agagggaaaa agggaaaata tcattgggga agaacctaaa 100440
aacccaagga aagctgggct ctgctggggg ctgtgagacc cccgggttct ccccgcccca 100500
ggctgctggc catggggtct tgcaccaatg gcctgacctt tctgtcggtc tgtatttatc 100560
aaagtgggtg acagtctcag gcctcctggc tgttcagaat tgaggtaata accagaggcc 100620
ttctgagcaa agggcctaag gggctccggc gtcaggatcc cattgtggtc aggagcctgc 100680
ggggcttccc gtgtgcaaga ggggtgaaag gtggctagaa aggcccagcc agtggcctct 100740
gcctcagcca gagggagctc tgtagtgggg gcagcaccca ttcactggtc aggcactggg 100800
gtgacagggg aggctccagg acttggggag cgttggagct ggaggcacat ggattggagt 100860
ccctgtacct gccccacgac agggcctgca gggagggatc cagcaggtga ctcttcaggc 100920
tgatttgccc atcccagata gaagccggga gtgttctttc aaaggtgtct ttaccttaga 100980
cactcaataa aatggtaaca cagtggcgcc gcctcagtcc tttggagtgt gcaccgtctg 101040
aacccctctc ccagggccct ctcccaagca ccccaacctg gacccatatc ccccacgtac 101100
ttttggcttt gggcagattg agcagccttg gggtggtctg tgctgtctgg tgtggagggt 101160
tgcagttcgg gtccttagtc ctacttccca ggccggccgg gctgacgcca gcgagtgtgt 101220
ccttccccag cgaggggagt gagcgcaagg tcagcgcctc gtctgcggcg ccctgcaggg 101280
ggtgacggag gggcgctctg aggacccttg gagaaaggag ctgggtttgt aaaatgctgg 101340
gcttggtccc acggacggcg gagcggtgag ctcagagcca gagctgggga ggaaatggga 101400
atgagaaagg cccacttcag ggctggtgag cgaggggatg gggagcagcc acaggccgag 101460
gctggggcat gggccaggct ccatggggtg agtctgagtc cttgagggga tgttcatcct 101520
ctgtggaatg tgggtttgcc agtggagagg agaccagcgt tgccctggtg aggtgctggt 101580
tcagggctgg ggggcggacg ctgcttgggg ctaaagttcc tgccggccaa gctctgggtg 101640
ggaggagacc ctggcccccct cccaacaccc ttggactgct ggcgggaccc ttcctacctc 101700
cgggggctgg aagtagtggg ggaggagcca gtcttgagga agaaccccga tgctggtctt 101760
gactagaggg gagccggtgt gcttttcgag cctcagggtg acccgcgtct gccccagcct 101820
ccagcctgcc ctggtcactt ctgactaaat aaggagagca ctcagcaggc agccccacga 101880
gggaggggga acatgtgtgc acccccactc ccccacctgc tcctccctcc ctacagggcc 101940
actacaccct gctgtgggca ccccaaggtg accctcagcc ttcttcctac cttaaaaagt 102000
ccaggcatgc attttcaagc atgagcggtg gccccctggg ggaaggcacc tcggcagggc 102060
agaacaaagg gaagggaccc ccaaacaggt cactggtgta attgtcccca gcaccccccaa 102120
agaggaggag aacccacaac tcggaactgg ggctcacccc cgatgcccaa cctgtcccca 102180
gcctgggaag caggcgtgga ggagaaggtg gggggagcct agagctggcc ctgggggccc 102240
tggttttgtc catgacggga gcctcggcaa cctagtccgc tctcccgggg accaggtttg 102300
cagacaggca cctttcaaat gctcctcacc cccaaattta caagtcaccc tgcagaggaa 102360

-continued aacatcaaca cagccagggg ttctctgctg gaggctcccc cttctatagg cacagccgga 102420
gaggccagag agctggggac acggggaggc tgcagaaggc tggtgggaag gggggcagtg 102480
atgggtgggg agagatgggc cagatgttct tggaatggga catgggggtg attgatgcag 102540
acagaaattt gaaggggaca ttcccacgtg tcttgttctg tgggtggaaa atgggctgtt 102600
tttcatggtg ggggcgggtt ctccctgtct tgccaagcta atgtgaaaga gatgcctcat 102660
cctgcccagc tccccacacc tgtccaaggc cattaacttc tgcctcccca gtgtcaggct 102720
ttgagatgcc ccccttctag ccggggtcct cctatggggt gacaatgggg acaagcaatg 102780
cccactgtag ttgccccagg atccccccacc attctgctgg tccccagcgg tgccccctct 102840
ctggcagtac ccccacccac cccacaggtc cccttagggc cactgcccca tcgcccgaca 102900
ttgcccaacg ccaaggggtg accttgttcc tgccgacagg gccgttgggc gcctgcatgc 102960
gggtttaata tttgcctata aggaactggg ctttccccag ccggagtgga cagactttcc 103020
ctgaaaattc gcttggagag aacgaaaaga gacccctggc accccagcgg cgtgcagccc 103080
tgcacccccc tcctcccggg ccccgtgttt ctcattttcc tccccacttc ctctgctctt 103140
cagtgttacc caaacaaaac tggtttcacc cttgtttggt gctggcgaag gcccgaacgg 103200
cgcgcgcaaa gctccggggc aggccggagg tggccaccgg gggtgctccg ggcccccaag 103260
ccaagccggg gactagcctg cccccggtgg cggctcggcc gcggcttcgc ctaggctcgc 103320
agcgcggagg cgagtggggc gcagtggcga gggggagcct gcggacctcc cacgcgggga 103380
ccgagcaggt atctgggagt cccgggagcg cccgggaagc agcgtcctgg tcgctccctc 103440
gcggcccttg ggtttcttcc ttacacccgg acgcccgcta agctcgggct gccgccacaa 103500
acgcgctctc cgtgtggaga aggcaaagaa aaaaaaaaat aaaagcaaaa ggaagaaaaa 103560
ccccaaagaa cgaaaagcag aatttcagcc ggccgtgcgc gccagggcgc tccgcgctac 103620
ctgcccgcgc cgcccgcgct cgggttcccg gggagggcgc cagtgctccg cgcgcgcccc 103680
agccaaggtg aatccccggc agcgccttcc ttccgctgcc cgggaagctt gagctcaaca 103740
attagccctt gatcctcggg ggattccaat ccacggaaca acttccctgc tttccccgaa 103800
ctcggacatt ttactttttc tgggatcctc taaatttaag cattgcttcc caagtcttct 103860
aaatatactc accatttcga cgggtcacaa taattttctt ggacgttaat ttccggggac 103920
gtcaaaacac atcagtcccg gcgggctttt ccagacttac actatgtggc ctggggcccc 103980
agatgtgctt tctcccaggc tctggacagt tttatacacc ccctccaggt cccacagatt 104040
tacaggccac taacccggct tccctaattt taaagacgaa gcccttggtc cgtggtggtc 104100
gcgctgacca atttgcctgg ctccccagga tgtggacagt gccttttcca catttaggca 104160
ttgtttccaa aacaagtgga actttcccgc ataattttga atattaactc cagggtctcc 104220
taagcttact gtttccggca cacgtccgcc ccattccgcg cccccccacc ccacccccgc 104280
gccccttccc gttcacctca gcatgggaca tttgctgttg ggtcccgcaa atctattcac 104340
actaacctgg gttccctaaa ctttacacgt tgaatcccaa gtccctcatg acactcagca 104400
gggctggaag gttggaaccc tcagagtatg aaaattgctt cccatacctt cccccaaatt 104460
cggtcattac acccagagca tgttgaatcc ttttctgaat cataaacgac ctgccctctg 104520
attgcctgag tttcataaaa tggagggatt tccccagtga ttccccaaag ctattgagaa 104580
tgttgtgggt gtgtgagtca caaagctttg gggcattaac gtctatggct ctatatgctg 104640
cctggccacg aatcaggtcc cttaagatgt agacagtgcc acccaggtcc ctggagcaca 104700
ctgagcagtt accaggaggt gctcaagtgt gacccaggat tctccaggtc cccccaaatc 104760
acacagggtc tcccgggtcc ctctgggcta caccaagcac aaaaggaccc cttgggcaga 104820
gcctactttt atttctgtta tgccaggtgt tgctaacggc cccagttccc aaacattccg 104880
agcactttct ctgcatcaca acatattgac tattaaacaa ttctctgggt cccaggagct 104940
tcataacaag aatcttgctt ttctaaaatt caggcattgg tctgaaaccc caacggccag 105000
gatcacactg gacccttttc ctggtccccc atacttggat gttctggacg ctgccctcca 105060
ggccctctag gaacattcag cattgccctc ggatcacagg acagcactga tttcttgggc 105120
tccaaacaac ccactgagtc atctcaaagt taagcaatat ttccttcaag cacactgcac 105180
actccctatc acaaaatctg aaaattccta agtcctaaga cctaggaatt ctgaatcccc 105240
tttctttaaa atgtacatat ggacccccaa gtcctccaag gactctgagc aacttcccta 105300
gatctttaga ttcaaaaacg attttcctgg agcccccaaa ttgcggtatt gtctcccagc 105360
cttccaaagc aaattgagat ttttttccct tcacaaaaca attgaggttt ttttttttt 105420
aatactgatt tatgagtctc ctgactttat ggtccctgcc ctgggtcccc ctacatttag 105480
aaaatgttcc atggaccccc aaagcacact aaaaaatgtc cctgggtccc aagaaatccc 105540
aggcatggaa aaacctgcga cctataagtt tcctagctac taactaggtt tccagaaatt 105600
tagatatcaa atctccattg ggtaatttcc atgtgtccca aaaacttgaa atgtgtttca 105660
ctggggctcc cccaaatgca gacgacatcc aggaaaatat atagtctttt tcttatttac 105720
caaaaataag ctaatggaaa tcatttaaaa attagcatag aaaaataata ctgatttttt 105780
attttttat tttttatttt gctttcccca aatgtactga tcacactcca ggctccccca 105840
aaatctagac agtgctttct tccatctctg aagggtgtta aaacctttcc ctgaagccac 105900
agtaattatg aaggttattt tttccccggc tgctgccagc gtccaggcca ctaacttata 105960
ttcttaagat gtgaaaatta atctcagctt cccccctaaca caccaagaat gtgtttggat 106020
ccccaaaatg tgttccttgc tttcatctgc caattttacg taatatggct ctacggcaaa 106080
attcccaatt tcatatggag aattttcttt aactacccct cctcacaaat tggtccccca 106140
agctagctgg cccctatttg agacctcttt ctctatgttc ccaattgcat ggagcaactt 106200
ctctcatccc ccaaacctgt aatctatttt tctggagtct cgagtttagt cattaatcac 106260
ggttcccaca ttaacggagt ccccggggtc ccctcctcca ggacacccat tcgctaagcc 106320
cgcaaggcag aaagaactct gccttgcgtt ccccaaaatt tgggcattgt tcccggctcg 106380
ccggccaccc actgcagctt ccccaacccc gcgcacagcg ggcactggtt tcgggcctct 106440
ctgtctccta cgaagtcccc agagcaactc ggatttggga aatttctctc tagcgttgcc 106500
caaacacact tgggtcggcc gcgcgccctc aggacgtgga cagggagggc ttccccgtgt 106560
ccaggaaagc gaccgggcat tgcccccagt ctcccccaaa tttgggcatt gtccccgggt 106620
cttccaacgg actgggcgtt gctcccggac actgaggact ggccccgggg tctcgctcac 106680
cttcagcagc gtccaccgcc tgccacagag cgttcgatcg ctcgctgcct gagctcctgg 106740
tgcgcccgcg gacgcagcct ccagcttcgc ggtgagctcc ccgccgcgcc gatcccctcc 106800
gcctctgcgc ccctgaccgg ctctcggccc gcatctgctg ctgtcccgcc ggtgctggcg 106860
ctcgtctccg gctgccgccg gggaggccgg cgtggggcgc gggacacggc tgcggacttg 106920
cggctggcgg ctgcgctcgc tcctgctggg cgcccccgaaa tccgcgccac tttcgtttgc 106980
tcattgcaaa gatctcattt gtggggaaag cggctggagg gtcccaaagt ggggcgggca 107040
gggggctggg gcgagggacg cggaggagag gcgctcccgc cgggcggtaa agtgcctcta 107100
gcccgcgggc ctaggactcc gccgggaggc gcgcgcggag cgcgggcgaa gtgattgatg 107160
gcggagcgag gggggcgagg ggggccaggg gggcgcgaga ttccgccggc ggccccttcc 107220
ccttggctag gcttaggcgg cggggggctg gcggggtgcg ggattttgtg cgtggttttt 107280
gacttggtaa aaatcacagt gctttcttac atcgttcaaa ctctccagga gatggtttcc 107340
ccagaccccc aaattatcgt ggtggccccc gagaccgaac tcgcgtctat gcaagtccaa 107400
cgcactgagg acggggtaac cattatccag atattttggg tgggccgcaa aggcgagcta 107460
cttagacgca ccccggtgag ctcggccatg caggtaggat ttgagctgtg tttcccgccc 107520
tgatcctctc tcctctggcg gccggagcct ccgtaggctc caagcctggc ccagattcgg 107580
cccggcgcag ccggccttcc gcgcgtcccg cacctggcgg gggctccggg gctccggcgc 107640
ggcaccgggg ggcgctcggg atctggctga ggctccaagc gccgcgtggc cggctcctcc 107700
tgctggggca ggtggcggct gcgcgccccg cccgagccca ggggcccccct cagccgcaac 107760
aaccagcaag gaccccccga ctcagcccca agccacctgc atctgcactc agacggggcg 107820
cacccgcagt gcagcctcct ggtggggcgc tgggagcccg cctgcccctg cctgcccgga 107880
gaccccagct cacgagcaca ggccgcccgg gcaccccaga aacccgggat ggggcccctg 107940
aattctctag aacgggcatt cagcatggcc ttggcgctct gcggctccct gccccccacc 108000
cagcctcgcc cccgcgcacc ccccagcccc tgcgaccgcc gccccccccc cggggcccca 108060
gggcccccag cccgcacccc ccgcccgct cttggctcgg gttgcggggg cgggccgggg 108120
gcggggcgag ggctccgcgg gcgcccattg gcgcgggcgc gaggccagcg aggcccgcgc 108180
gggccctggg ccgcgggctg gcgcgactat aagagccggg cgtgggcgcc cgcagttcgc 108240
ctgctctccg gcggagctgc gtgaggcccg gccggccccg gcccccccct tccggccgcc 108300
cccgcctcct ggcccacgcc tgcccgcgct ctgcccacca gcgcctccat cgggcaaggc 108360
ggccccgcgt cgacgccgcc cgctgcctcg ctgctgactc ccgtcccggg cgccgtccgc 108420
ggggtcgcgc tccgccgggc ctgcggattc cccgccgcct cctcttcatc tacctcaact 108480
ccccccatcc ccgcttcgcc cgaggaggcg gttccccccg caggcagtcc ggctcgcagg 108540
ccgccggcgt tgtcaccccc ccccgcgctc cccctccagc cctccccccg gcgcgcagcc 108600
tcgggccgct cccctttccg cgctgcgtcc cggagcggcc ccggtgccgc caccgcctgt 108660
ccccctcccg aggcccgggc tcgcgacggc agagggctcc gtcggcccaa accgagctgg 108720
gcgcccgcgg tccgggtgca gcctccactc cgccccccag tcaccgcctc ccccggcccc 108780
tcgacgtggc gcccttccct ccgcttctct gtgctccccg cgcccctctt ggcgtctggc 108840
cccggccccc gctctttctc ccgcaacctt cccttcgctc cctcccgtcc cccccagctc 108900
ctagcctccg actccctccc cccctcacgc ccgccctctc gccttcgccg aaccaaagtg 108960
gattaattac acgctttctg tttctctccg tgctgttctc tcccgctgtg cgcctgcccg 109020
cctctcgctg tcctctctcc ccctcgccct ctcttcggcc ccccccttc acgttcactc 109080
tgtctctccc actatctctg ccccccctcta tccttgatac aacagctgac ctcatttccc 109140
gataccttt ccccccccgaa aagtacaaca tctggcccgc cccagcccga agacagcccg 109200
tcctccctgg acaatcagac gaattctccc cccccccca aaaaaaagcc atccccccgc 109260
tctgccccgt cgcacattcg gccccccgcga ctcggccaga gcggcgctgg cagaggagtg 109320
tccggcagga gggccaacgc ccgctgttcg gtttgcgaca cgcagcaggg aggtgggcgg 109380
cagcgtcgcc ggcttccagg taagcggcgt gtgcgggccg ggccggggcc ggggctgggg 109440
cggcgcgggc ttgcgccgga cgcccggccc ttcctccgcc cgctcccggc ccggggcctg 109500
cggggctcgg cggggcggct gagcccgggg gggaggagga ggaggaggag gaggacggac 109560
ggctgcgggt cccgttccct gcgcggagcc ccgcgctcac cctggcggcg gagctggggg 109620
tggggtgggg gcgtcgggaa gggccgaggg aggtgtgagg tgtctgcagg ggcgacttcc 109680
cggtcggtct gtgggtgcag gggtgccgc ctcacatgtg tgattcgtgc cttgcgggcc 109740
ctggcctccg gggtgctggg taacgaggag gggcgcggag ccgcagaagc ccaccctggt 109800
atgttgacgc ggtgccagcg agaccgcgag aggaagacgg gggtgggcgg ggccaggatg 109860
gagaggggcc gagttggcag gagtcatggc agacgccaca ttcgcgacat ctcccccaca 109920
ccccctctgg ctctgtccgc aacatttcca aacaggagtc ccgggagagg gggagagggg 109980
ctgctggtct gaggctaaga agggcagagc cttcgacccg gagagaggcc gcggcccctg 110040
cccagtgggc agcgtggaag tttccataca aggaggtggg aaggagaccc cccccccctt 110100
cactgccctg tgcagagatg agccgggggt gcaggatggg agcccatggc acttcgctac 110160
gggatggtcc agggctcccg gttgggggtg caggagagaa gagactggct gggaggaggg 110220
agagggcggg agcaaaggcg cgggggagtg gtcagcaggg agaggggtgg ggggtagggt 110280
ggagcccggg ctgggaggag tcggctcaca cataaaagct gaggcactga ccagcctgca 110340
aactggacat tagcttctcc tgtgaaagag acttccagct tcctcctcct cctcttcctc 110400
ctcctcctcc tgccccagcg agccttctgc tgagctgtag gtaaccaggg ctgtggagtg 110460
aggacccccg ctgccatccc actccagcct gaggcagggc agcagggggc acggcccacg 110520
cctgggcctc gggccctgca gccgccagcc cgctgcctct cggacagcac ccccctcccc 110580
tcttttcctc tgcccctgcc cccacctggt ctctgctccc tcacctgctc cttccctttc 110640
tgttccttcc cttcggcccc ctccttgccc agctcaggac ttttcctggg ccctcacctg 110700
ctccgcaccg ctgcatgctt cctgtcctgc tttctgccgg tcccctgacc cggacctcca 110760
agttcagagt ggtggggctt gttgcggaag cgcggcgagg gctagagtgg ccagctggcg 110820
gagtgtgctc ttagaatttg gaagggggtg gcagaggggg cggtgagagg actggccagg 110880
gtccagtcaa ggagatgacc aaggaggctt tcagatcctc ggcgcagctg cccactagtc 110940
tttagagagg gcatgcaaag ttgtgcttct gtcccactgc ctgctcagtc gctcacataa 111000
tttattgcat caaaaactcc cctgggtctg cggagcgaag gctggggctg cccgcctgga 111060
gggttccacc ttctgcaggg gcagggccaa cttgctgtgg tggctcccgg cctcccaccc 111120
ccgagtgggt taacccggcc ctgtggccct gcagcctgtg gagggggtgt gtcctaagac 111180
tggcctcccc ttccagattg tagtctgggg aacctggtgt cggacttccc aggtggcctg 111240
agctggtctc tccagctccc acggggagag tttggtagcg caaataggga gatgttctgg 111300
aggcccctgg ccttactggt tcgatttgag gcctggaaag gaggctctgg gcgtgtgtgt 111360
gtgtgtttgg gggtacccaa ggcagactgg agttggagaa ctgggtgact gggaaaacaa 111420
ggtttctaga gcatgggtgg cgtggttgtg ttaaccattg gagtccttga cccaggcctg 111480
gctcagctgc agactggaaa ggtggaaaag ccagggggag gggcggggct ggcccagcag 111540
gactggcctg ctgctttgag ggcgatggtc ctcctggacc ccccctgctc agctgggggt 111600
tgtggggagg aagggactgg tcctcctgga tgcacatgct ctgtaggggt ggggctgtct 111660
gccatcttgg ctggcgctgg aggcctgaga agtggcgatg tgacgctggg ctggccctgc 111720
ccccatggtg tcataggacg gaggccaggt cgggtgtcca gcctgggccc ctgcagctgt 111780
ggatgccgct gagctcctgc aataatgacc gtggagatgg tcacccctcg tgtaaaatta 111840

-continued

```
ctagtgcttc ttgcaaatgg aaggaactgg gccttttctg tgtgcttctg gacgcttcat 111900
tctgcacatg gccctgcgcc ctcacctcgg cattatgacc tgtgtgttac ttttgtaata 111960
aaaataatgt ttataggaaa gccgtgcttt caattttcaa ctgaatttgt aggttggcaa 112020
atttggtttg ggaggggcac ctctggcctg gggcttggcc tggctgcccc gctcacgcca 112080
cttctctccc gcccccagac accaatggga atcccaatgg ggaagtcgat gctggtgctt 112140
ctcaccttct tggccttcgc ctcgtgctgc attgctgctt accgccccag tgagaccctg 112200
tgcggcgggg agctggtgga caccctccag ttcgtctgtg gggaccgcgg cttctacttc 112260
agtaagtagc tgggaggggc ttcctcagac ctggtcaggc ccctagagtg accggtgagg 112320
acgcccaacc tcaagccagg ggagcacact cctaggtcag cagcccagcc gcttgctctg 112380
agactttgac cttcccgccg cgtttctgag cacgtgcggt gtcccagggc atccacacca 112440
gctgcctttc ccatcacacg cctccttcga agggtgggcc agaggtgccc cctagacgtc 112500
aggggcactc acaggggtct ccctgggcat cagaatttct gttgggggcc gtgaggctcc 112560
tgctcctgag gcaccgcacg cctagtgcag ggcttcaggc tctggaggaa gagcctgcct 112620
ttcttcctgc accttttgga cattctgaca agggacgtgc gttcggtgaa tgatcagaat 112680
taaaatcaat aaagtgattt atataattaa aatcaataag acaagtgcag ttggtgggtg 112740
gcaggggtga gcggtgcatg cgcctccttg ggccccaagg ctgccgtggg gggtgcccac 112800
ctgctgacct caaggacgct tcagcctttc ctcatgtttc tctcttggtt ctccagcctg 112860
ggggctggca ggtgggtgca tggcccattg tccttgagac cccaccccca gatagggggg 112920
ctgggtggat gcagaggcag gcatggtgcc tgggcatgcc tgatggggca ggggaggggc 112980
cgctccttac tggcagaggc cgcacggctt attccacctg acactcacca cgtgacatct 113040
ttaccaccac tgcttactca cgctgtgaaa tgggctcaca ggatgcaaat gcacttcaaa 113100
gcttctctct gaaaagttcc tgctgcttga ctctggaagc cctgcccgc cctggcctct 113160
cctgtgccct ctctcttgcc tgccccattt gggggtagga agtggcactg cagggcctgg 113220
tgccagccag tccttgccca gggagaagct tccctgcacc aggctttcct gagaggaggg 113280
gagggccaag cccccacttg ggggaccccc gtgatggggc tcctgctccc tcctccggct 113340
gatggcacct gccctttggc accccaaggt ggagccccca gcgaccttcc ccttccagct 113400
gagcattgct gtgggggaga gggggaagac gggaggaaag aagggagtgg ttccatcacg 113460
cctcctcact cctctcctcc cgtcttctcc tctcctgccc ttgtctccct gtctcagcag 113520
ctccaggggt ggtgtgggcc cctccagcct cctaggtggt gccaggccag agtccaagct 113580
cagggacagc agtccctcct gtgggggccc ctgaactggg ctcacatccc acacattttc 113640
caaaccactc ccattgtgag cctttggtcc tggtggtgtc cctctggttg tgggaccaag 113700
agcttgtgcc catttttcat ctgaggaagg aggcagcaga ggccacgggc tggtctgggt 113760
cccactcacc tcccctctca cctctcttct tcctgggacg cctctgcctg ccagctctca 113820
cttccctccc ctgacccgca gggtggctgc gtccttccag ggcctggcct gagggcaggg 113880
gtggtttgct ccccccttcag cctccggggg ctggggtcag tgcggtgcta acacggctct 113940
ctctgtgctg tgggacttcc aggcaggccc gcaagccgtg tgagccgtcg cagccgtggc 114000
atcgttgagg agtgctgttt ccgcagctgt gacctggccc tcctggagac gtactgtgct 114060
acccccgcca agtccgagag ggacgtgtcg acccctccga ccgtgcttcc ggtgagggtc 114120
ctgggcccct ttcccactct ctagagacag agaaataggg cttcgggcgc ccagcgtttc 114180
ctgtggcctc tgggacctct tggccaggga caaggacccg tgacttcctt gcttgctgtg 114240
```

tggcccggga gcagctcaga cgctggctcc ttctgtccct ctgcccgtgg acattagctc 114300
aagtcactga tcagtcacag gggtggcctg tcaggtcagg cgggcggctc aggcggaaga 114360
gcgtggagag caggcacctg ctgaccagcc ccttcccctc ccaggacaac ttccccagat 114420
accccgtggg caagttcttc caatatgaca cctggaagca gtccacccag cgcctgcgca 114480
ggggcctgcc tgccctcctg cgtgcccgcc ggggtcacgt gctcgccaag gagctcgagg 114540
cgttcaggga ggccaaacgt caccgtcccc tgattgctct acccacccaa gaccccgccc 114600
acgggggcgc ccccccagag atggccagca atcggaagtg agcaaaactg ccgcaagtct 114660
gcagcccggc gccaccatcc tgcagcctcc tcctgaccac ggacgtttcc atcaggttcc 114720
atcccgaaaa tctctcggtt ccacgtcccc ctggggcttc tcctgaccca gtccccgtgc 114780
cccgcctccc cgaaacaggc tactctcctc ggccccctcc atcgggctga ggaagcacag 114840
cagcatcttc aaacatgtac aaaatcgatt ggctttaaac acccttcaca taccctcccc 114900
ccaaattatc cccaattatc cccacacata aaaaatcaaa acattaaact aacccccttc 114960
cccccccccc acaacaaccc tcttaaaact aattggcttt ttagaaacac cccacaaaag 115020
ctcagaaatt ggctttaaaa aaaacaacca ccaaaaaaaa tcaattggct aaaaaaaaaa 115080
agtattaaaa acgaattggc tgagaaacaa ttggcaaaat aaaggaattt ggcactcccc 115140
accccctct ttctcttctc ccttggactt tgagtcaaat tggcctggac ttgagtccct 115200
gaaccagcaa agagaaaaga aggaccccag aaatcacagg tgggcacgtc gctgctaccg 115260
ccatctccct tctcacggga attttcaggg taaactggcc atccgaaaat agcaacaacc 115320
cagactggct cctcactccc ttttccatca ctaaaaatca cagagcagtc agagggaccc 115380
agtaagacca aaggaggga ggacagagca tgaaaaccaa aatccatgca aatgaaatgt 115440
aattggcacg accctcaccc ccaaatctta catctcaatt cccatcctaa aaagcactca 115500
tactttatgc atccccgcag ctacacacac acaacacaca gcacacgcat gaacacagca 115560
cacacacgag cacagcacac acacaaacgc acagcacaca cagcacacag atgagcacac 115620
agcacacaca caaacgcaca gcacacacac gcacacacat gcacacacag cacacaaacg 115680
cacggcacac acacgcacac acatgcacac acagcacaca cacaaacgca cagcacacac 115740
aaacgcacag cacacacgca cacacagcac acacacgagc acacagcaca caaacgcaca 115800
gcacacgcac acacatgcac acacagcaca cacactagca cacagcacac acacaaagac 115860
acagcacaca catgcacaca cagcacacac acgcgaacac agcacacacg aacacagcac 115920
acacagcaca cacacaaaca cagcacacac atgcacacag cacacgcaca cacagcacac 115980
acatgaacac agcacacagc acacacatgc acacacagca cacacgcatg cacagcacac 116040
atgaacacag cacacacaca aacacacagc acacacatgc acacacagca cacacactca 116100
tgcgcagcac atacatgaac acagctcaca gcacacaaac acgcagcaca cacgttgcac 116160
acgcaagcac ccacctgcac acacacatgc gcacacacac gcacaccccc acaaaattgg 116220
atgaaaacaa taagcatatc taagcaacta cgatatctgt atggatcagg ccaaagtccc 116280
gctaagattc tccaatgttt tcatggtctg agccccgctc ctgttcccat ctccactgcc 116340
cctcggccct gtctgtgccc tgcctctcag aggagggggc tcagatggtg cggcctgagt 116400
gtgcggccgg cggcatttgg gatacacccg tagggtgggc ggggtgtgtc ccaggcctaa 116460
ttccatcttt ccaccatgac agagatgccc ttgtgaggct ggcctccttg gcgcctgtcc 116520
ccacggcccc cgcagcgtga gccacgatgc tccccatacc ccacccattc ccgatacacc 116580

-continued ttacttactg tgtgttggcc cagccagagt gaggaaggag tttggccaca ttggagatgg 116640
cggtagctga gcagacatgc ccccacgagt agcctgactc cctggtgtgc tcctggaagg 116700
aagatcttgg ggaccccccc accggagcac acctagggat catctttgcc cgtctcctgg 116760 ggaccccccca agaaatgtgg agtcctcggg ggccgtgcac tgatgcgggg agtgtgggaa 116820
gtctggcggt tggaggggtg ggtgggggc agtgggggct gggcgggggg agttctgggg 116880
taggaagtgg tcccgggaga ttttggatgg aaaagtcagg aggattgaca gcagacttgc 116940
agaattacat agagaaatta ggaaccccca aatttcatgt caattgatct attccccctc 117000
tttgtttctt ggggcatttt tccttttttt tttttttttg ttttttttt acccctcctt 117060 agctttatgc gctcagaaac caaattaaac cccccccca tgtaacaggg gggcagtgac 117120
aaaagcaaga acgcacgaag ccagcctgga gaccaccacg tcctgccccc cgccatttat 117180
cgccctgatt ggattttgtt tttcatctgt ccctgttgct tgggttgagt tgagggtgga 117240
gcctcctggg gggcactggc cactgagccc ccttggagaa gtcagagggg agtggagaag 117300
gccactgtcc ggcctggctt ctggggacag tggctggtcc ccagaagtcc tgagggcgga 117360
ggggggggtt gggcagggtc tcctcaggtg tcaggagggt gctcggaggc cacaggaggg 117420
ggctcctggc tggcctgagg ctggccggag gggaaggggc tagcaggtgt gtaaacagag 117480
ggttccatca ggctggggca gggtggccgc cttccgcaca cttgaggaac cctcccctct 117540
ccctcggtga catcttgccc gcccctcagc accctgcctt gtctccagga ggtccgaagc 117600
tctgtgggac ctcttggggg caaggtgggg tgaggccggg gagtagggag gtcaggcggg 117660
tctgagccca cagagcagga gagctgccag gtctgcccat cgaccaggtt gcttgggccc 117720
cggagcccac gggtctggtg atgccatagc agccaccacc gcggcgccta gggctgcggc 117780
agggactcgg cctctgggag gtttacctcg cccccacttg tgcccccagc tcagcccccc 117840
tgcacgcagc ccgactagca gtctagaggc ctgaggcttc tgggtcctgg tgacggggct 117900
ggcatgaccc cgggggtcgt ccatgccagt ccgcctcagt cgcagagggt ccctcggcaa 117960
gcgccctgtg agtgggccat tcggaacatt ggacagaagc ccaaagagcc aaattgtcac 118020
aattgtggaa cccacattgg cctgagatcc aaaacgcttc gaggcacccc aaattacctg 118080
cccattcgtc aggacaccca cccacccagt gttatattct gcctcgccgg agtgggtgtt 118140
cccgggggca cttgccgacc agccccttgc gtccccaggt ttgcagctct cccctgggcc 118200
actaaccatc ctggcccggg ctgcctgtct gacctccgtg cctagtcgtg gctctccatc 118260
ttgtctcctc cccgtgtccc caatgtcttc agtggggggc cccctcttgg gtcccctcct 118320
ctgccatcac ctgaagaccc ccacgccaaa cactgaatgt cacctgtgcc tgccgcctcg 118380
gtccaccttg cggcccgtgt ttgactcaac tcaactcctt taacgctaat atttccggca 118440
aaatcccatg cttgggtttt gtctttaacc ttgtaacgct tgcaatccca ataaagcatt 118500
aaaagtcatg atcttctgag tgttccactc tctgacttgg gtactggact gccagaggga 118560
gggaaggggc tgagcacctg gaagcaggca gagggggata gaagagggaa ggggaaggaa 118620
ggccttaggg gtgtggacac ctctctccgt cccctgatca catacatgga gaaatgagag 118680
agctggaagc cagactctca gactcactgt cgtgcacctg aagccagggg gtctgggaca 118740
gtgtcaggca ccaagttctc aaagatgggg gtgccacgaa gggtaggagc ctggggggct 118800
ttttcagaga aaaagcaaag taccatcagt accaactcca gggaatgcct cccccaccaa 118860
cagccttaga ggactggggc tgggcaacct ctaaaaggtt ctggaaaccg tatctgtggc 118920
tggagatggg ggctcagggc cactctcacc cagggactca gccccccttcc aaggttgagg 118980

-continued ctgcccagat gtcattagta ccactgcctc ctgccagggc tcagcctgta cccacctgtc 119040
ccaagggtgc tggcctctag ctttcaaggg tccctgagca tgggaggagg ggtaggctgg 119100
gctgctggga gcctggccca gcctcttctc tccatccccc tccaggaact ttccagcagc 119160
cttgggcagt ggatctgcct gtgccccgcc tgctgtgggg atggagggac aggggcgcca 119220
cagaaggagc ccagaagtgt gcccagggcc ctgcagcctt cagtgctggg caggcggtgg 119280
ggaggggcct gactgggttg ggggcgtgct tgcatcctgg cccccagggt ctgcccctgg 119340
tcaagccctg tcccttgatg gctgcctctg tccctagcat ttctcctgtg ccgggcactg 119400
gagggtgctg ggctgtcacc caagcctctg aggcctgggg acacgtctac acggacagtg 119460
tcactgccca caccatctga gaaccactcc aagggaaggg agagggtggg cggtggtttg 119520
gggagttgcc tggaggagga gggattagcc ttgaagatga ggagggctgg gggttggaga 119580
agagcagatt ggatatgggg ggcaccatgc ccttcctgag ctggtccctg gctctgcacc 119640
tcagtgctag gtctaagctg gagggtccag ggcccaggtg gcattgctga cccccagggg 119700
gtcggggctg ctctgaggcc cttctgtaga tgtagatgga agcctagtcc tgtccacctt 119760
cctgaggcca ggtggagttg ctttccctgc aagcccaggc agctctgccc tgtgcccctc 119820
ccccagccct gcagtccccc aggcccacgc agggccggcc tcatggtctc gcttcctctc 119880
tgggtctgct tcagggccca gcctccagcc ccatgagcct gggccctcct gctcctgtcc 119940
ccactggccc caggtcactt ccacactggc tctccccgca ccctgggcct gctcagccac 120000
tcttgcccac agccaggagc ttctgtgcag cttctttcct ttcacttgca gcctgcctgc 120060
cctctgcttc cccggacccc ttgtgacctt ccctgacctc tctgcagaac tgggcaaagc 120120
cactcaccct ggttcccccg ggtttagcct ggtctcttga cacccactca gggctgccca 120180
gccttcatcc tgcttcactg ggcccagcct cattccaggg cttctgagac tgcagggccc 120240
tctcttctcc cctctccctg ctttgcaaat tctcagttca tcctggcagc tccaactctc 120300
catccctcca cccatccatc cccccatccc tccacccatc catcccccca cccatccctc 120360
cacccatcca tccccccatc catccaccca tccctccacc catccctcca ctcatccatc 120420
cactcatccc tccacccatc cctccaccca tccatccacc catccatcca accatccctc 120480
cacccatccc tccactcatc catccactca tccctccacc catcccctac ccatccagcc 120540
acccatccat ccacccatcc ctccacccat ccatccaccc atccctccac ccatccatcc 120600
aaccatccaa ccacccatcc ctccacccat ccatccaccc atccctccac ccatccactt 120660
acccactcat tcaccaactc atccatccac tggtccatct gcccaccaaa ccatccactc 120720
accatccacc cattcaccta tttatccatc ccatccaccc acttaccact cactcaccca 120780
ctcatccatc catttactca cccctccatc cacccaccca ctcatccatc tattcttcca 120840
cccactcacc cactcactca cccacgcacc cattcaccca tctattcatc cacccaccca 120900
accatccact cacccaccca tccacctatt catccatccc atccacaaac accccaccta 120960
ctactcactc acccactcat tcatccattt acttacccct ccacccatcc acccattcat 121020
ccatctattc atccatccca tctacccact cacccactta cccagtctca cccactcatc 121080
catccaccca tctattcgtc cacccaacag tccacccacc cacccatcca ctcacccatc 121140
catccaccta ttcatccatc ccacccaccc actcacccac ttatccactc actcacgcac 121200
tcatccatcc atccactcac cctcccatct acccatccac tcatctatcc atctacccac 121260
tcgcccactc atcatccacc cactcaccca cttacccaca aactcaccca ctcatccatc 121320
catccactca ccctcccatc cacccaccca gtcatctatc catctaccca ttcacccact 121380
tacccactca ctcacccact catccatcca tccacgcacc ctccatccac ccacccactc 121440
atctatctac tcacctgtcc atccacccac ttaactctca ctcacccact catccatcca 121500
tccactcacc ctccatccac tcacccagtc atctatctat tcatctgtcc atccacccac 121560
tcacccactt acctctcact cgcccactca tccatccatc cactcaccct ccatccaccc 121620
acccactcat ctatctattc atctatccat ctacccactc acccacttac ccactcaccc 121680
actcatccat ccatccactc accctccatc cacccaccca gtcatctatc tattcatcta 121740
tccatctatc cactcaccca cttacctctc actcgcccac tcatccatcc aaccactcac 121800
cctccatcca cccacccagt catctatcca tctatccatc tacccattca cccacttacc 121860
cgctcaccca ctcatccatc catccactca ccctccatcc acccacccag tcatctatct 121920
attcatctat tcatctatcc atctacccac tcacccactc acccactcat ccatccatcc 121980
actcaccctc catccatcca cccactcatc tatctatcca tctatccatc tacccactca 122040
cccacttacc cgctcaccca ctcatccatc catccactcg ccctccatcc accccccagt 122100
catctgtcta ctcatctgtc catctaccca cttaactctc actcacccac tcatccatcc 122160
atccactcgc cctccatcca ccccccagtc atctgtctac tcatctgtcc atctacccac 122220
ttacctctca ctcgcccact catccatcca tccactcacc ctccatccac ccacccactc 122280
atctatctat tcatctatcc atctacccac tcacccactt acctctcact tgcccactca 122340
tccatccatc cactcaccct ccatccaccc acccagtcat ctatctattc atctatccat 122400
ctatccactc acccacttac ctctcactcg cccactcatc catccaacca ctcaccctcc 122460
atccacccac ccagtcatct atccatctat ccgtctaccc attcacccac ttacccactc 122520
acccactcat ccatccatcc actcaccctc catccaccca cccagtcatc tatctattca 122580
tctattcatc tatccatcta cccactcacc cactcatcca tctatccact cgccctccat 122640
ccacccccag tcatctgtct actcatctgt ccatctaccc acttgactct cactcaccca 122700
ctcatccatc catccactca ctcctccatc cacccaccca ctcatccacg tatacaaaca 122760
catggacagg cactacccac atgctggact ttcagccaag agataagctc agcgtcatgg 122820
agggaagaaa gcgaaaggtg ttcggtgctc ttttaagcaa gacaggcctc atggagaagt 122880
tggcgtgggg gcagagactg gacggagctg aggcctcatg gagaagttgg cgtgggggca 122940
gagactggaa ggagctgagg aaggagtatg aagcatccag aaagagcgtt cttcctcaca 123000
gggataaaac atgagtggtc tgggagtgtt tgagccacag caggaagtcg ggggtttggg 123060
ttggtgggag ctgcagcagg aagaggtgga gggcctgtgt agggggctga ggtcagagct 123120
gtaatggggg gcagatggcc tgggctgcat aggccatgcc gtttgttcaa cagacaccat 123180
gggaccctga ggccatgggg tgaattgtgg ccctcagaaa ggtctgtccc gtcatgtgca 123240
gtgactcgaa cctgtaatcc cagctaccca ggaggctgag ccaggaggat cacttgagcc 123300
caggagtcca aggttatagt gagctgcgat ggcacctgtg aacagacact gcactccagc 123360
ctaacctaac cctaacccta acccaacctc cacgcagcac ccacgtggcc tcgtggcaca 123420
gctcggttca tagtccagca gtggtacctt atttccttgg tgacaagcaa caccctcatg 123480
atgacccatg aggccacctg acccacacta cccatcacca ccaccgctat gacacctgcc 123540
cagccacagt ggtcccaggt tgggttgccc ctgcctagac cccttcccct gcagaccttt 123600
gcccaggtca tcttggcgtg gttgcaccct cggcatggag tctgccttgg aattcctctg 123660
cacaatggca gcccgtgtgg acctgtccca caaacgctct gagaatgaag aggacacact 123720
tccaatggca cctgctgtgg ccagcttcac tcctccagga tgtcctgcag acccctcacc 123780
cagcatgcgt ctgccggtcc accactgccc tccaccacac ctcacattga gttagttgag 123840
gagatccacg gactccacca ggccctggcc cctgctgctg tccagcctcc tgtagagcca 123900
gcccctctgg ccatgctcca tatgggacca gagcagtggg gccagagtct gcctctctcc 123960
acttagagcc ctccgtgaat cccgtgggcc actggcaaat ccaggccctg gccaggcttt 124020
ccagcacctg gccccatccc tggtcctccc acccacccct ccactcccag tcccaggctg 124080
cacctgctgc cctcttgccc aggccctctg gtatcaccct tgtcctggta actcacgcac 124140
gccctctgct gtactgtgcc atcctgaccc ccaggagtct ggcctccctg gtctcccttc 124200
ctgtttgttc tggcattgag ccccccacca tccgccagag acactgctaa ccatggtccc 124260
aagacgcctg ctggcaagtc ctctccagga tccctggggc tctgtctggg gctcccagac 124320
cagaggggtc agacagaagg ccctggaggg tgcctcgagg gactctggca ccccaccaat 124380
ggctaactcc ctgctccccg ggttagcttg tcccctgccc ctgtgttagc ttcccccttg 124440
ccccctaccc ctgggttagc ttgccccctg cccctgggtt agcttgtccc ctgccccccg 124500
ggttagcttg tcccctgccc cccgggttag attggcccct gcccctgggt tagcttggcc 124560
cctgcccccc gggttagctt ggcccctgcc cctgggttag cttggcccct gccccctgcc 124620
ccccaggtta gcttgccccc tgccccccgg gttagcttgc cggggagacc cagctgccag 124680
gcatccttgc tgaggttgcc caccggcccg ctcagcaggc ctcatcctgg aggaacctgt 124740
ccctctgggt ctggccccca gggtccccgc tcttcccagc tcccacacag gtgcggccag 124800
gccagggctg gcacccacag gctgacagcc ccacccctca agcctggtct ccaccttctc 124860
agctgggccc ctggccctgc ccactcccct ctggcccagg ccggggctgc agccccaggc 124920
tcagagtgta gtctccagcc tgtcccccgg ctcccagccc cagccagccc aggcctcagc 124980
cggcctgaaa ccaaagagaa aatgcctgtt tatgccagtc atgccgaaag caaaacagtt 125040
tgtggtttgt gacccaaatt ttttgccttt ttttttcaga acataacaaa gcccaagaca 125100
actccctccc cgctcccagc cctcccccca aggcagacag aaatgatctg tttacactgg 125160
ccgcggcaca ttccggccgc cagcccggcc ctctccccag tgccgtgccc tccgtgctgg 125220
gctcctcctc ggtggaaggg gctgctgagg ccggggagag gggaccgcac cacagacctg 125280
gagcgagggt ggggcttgct tcctctgggg gatggctgaa tgagatgtgt cttgggggtt 125340
gggggtaccg gggtgcatgt ccatctggga gttggagtgg ggactccatg ctgcctgcac 125400
aggctacaca gggaaggatg gcaggagagc ggccgcctgc agccgctccc tccagggaac 125460
ccctctccaa gtctgccttt cagtaccccc ttcacataga caggtgctta gaccctcagg 125520
gtgacaggac ctattaccta cccacccccct ctactgcact ccatcctctc gcctcctccc 125580
tccttgattg tccaaagcct gagacccccct gactcagctc ggccgtggag cacacagaga 125640
tggggatgcc tctgcccttg aaagcctgca gccccagagt ggcggtgtca gtggggtggt 125700
gggtgtggag gagggtggcc ccagactgca ttgagggagg ggggtgcagg cacatgttgg 125760
agcccagtgg tagggggcag gtgggacccc aaggtgccat gactggaagc aagaacaggc 125820
ccctccccat cttcagactg ttcccacgtg cctggctctc ccaggggaca gaaaagtggt 125880
gcaaaccttc accttcccca ggcctcctcg gagtcctcct cggagtcctc ggagagccag 125940
aattgcccct ctctccttcc agcctcctcc actgccctct cctgatcgcc tcctcccagt 126000
cttcattctt tgttcgcgca cttggctatg cctgctcctg gtgctgggga gccagggctt 126060

-continued cagaagaagg aattcctggg ccaaggggac ctggtggtgt gagcggggtg aggcaaaggc 126120
acctggaggt ctggggctga gaaagaccat gcagacaggg gtgctcctcc cgcggggtcg 126180
gacaggagcg tgggcattgg caggacgtgg gtgggaaggg cgttctaggc acagggaacc 126240
gcatgtgcag gcacaggtgt gcacacatgg agggagatgg ctgcagctca aagggcctcg 126300
gtgctgagcc aagaagctga acttgacctt cagtgagctc tgggaggcgg ggaggggctt 126360
ttaaggggag agtgagccac tctagccatc aattctggag agatggtcta agtgtgggaa 126420
ctcctggagc ctgagagggt ttggaggtgc actagcgggt ggggtgggtg gggtggaagg 126480
ggtggtgctg ggccgggcgc agggaggcac cccagctggg aggagctcgg tgtggcccag 126540
cagcatcgca cgcatgcacg gatggggtca tttccaccct gcccccagcc ccaccaaatg 126600
cagaccctgg ctcctcagct ggggggagta tggggagcag ggagctcctc ctgcctcagg 126660
ccctgggggc aacccaggtc tgcccactct caggctggct ggctcccccg cctggctggg 126720
agcatcactt cgggaaggtc tggccgagta cctctgcttc ccttcccctg ccttgtcgtc 126780
cctggcctcc cgtctatcag gaacagatgt gcctctgagc aggaatccta gctatttggt 126840
ttagccagcc actctcggga atttctgata aggcaaattg gttctctgca gagtcggtgg 126900
aggtagtggg ggagaagaca agcagtgccc acccccacct ttctcctgcc gaggacgggg 126960
cctaggatac gccccagcct ggtccctggc cccagctcag cagcactgtg gggaggaaga 127020
ctttcgaggc ctctcctgat gctccgtggc gctgcagtgg ctgagggctg gccggcccca 127080
gcaggtggga gcgggctgag accacagggg tttcccccac ccctggacct gggctcagag 127140
ctttgtggga gggaaagaaa tctacactgg agccctctgt ggtgttgaag caagcagccg 127200
caaccctccc cagcacccag ccctcagcgg ccacatgtcc catgttccgg gctctgtgcg 127260
ggaccttcca cgacactctg gtccttcctg ccttcatcat ctgttcaata cacatatgcc 127320
aggccctgta caaagcccta gaatcatgaa gatggataaa gttccattcc tgccctcaaa 127380
acaactctag gaagtggcac atcaacataa atgtaacaaa cagcagggct gaggaggggc 127440
ccggctagca ccttgtaaat tattcactca gatcttccct ggatcccaga acatcgtctt 127500
atcttgttct attctgtcca tggttttagc ctgtggaggc catttaaagt atcagtttgg 127560
tcttccagcc acttagctta tatttctcag ccttggacct tcaatgtggg ctccatgaat 127620
ggatgggtgg gttggtggat ggataagcag atgggcagat gggtagatgt atggataggt 127680
agatgatgga gtgggtgggt gatggatggg tgaatagatg tgtgtgtggg tgaatggatg 127740
tatggatgga taaatggatg tgtggatagg tgcaagtcag ctgtaggtca acaagtgtct 127800
acctggattc tcttctgaca tgatccttgt gagggaagag agcaaagaga ctgtaatcca 127860
ttgtatgtct gtgcttatag agattctatg tgttgattca ggttgaatat atcctgtttt 127920
taggatccaa cacatcatag agattaaaag atatttgtcg attaaatgaa atttattggg 127980
aatgatatta aaaggaattt taaaaatgaa atgtaaaggt cttgtttaag tgaacatata 128040
cctggaaatt gtctcaagag gacctagaaa aatctgaaca tatcggccgg gctcagtggc 128100
tcacgcctgt aatcccagca ctttgggagg tcaaggcagg cggatcatga ggtcaggagt 128160
tcgagaccaa cctgatcaac ttggtgaaac cctgtctcta ctaaaaatat aaaaattagc 128220
cggatgtggt ggcgcacgcc tgtaatccca gctactcagg aagctgaggc aggaggatcg 128280
cttgaacccg ggaggcggag gttgcagtga gctgagatca taccactgca ctccagcctg 128340
ggtgacagag cgagactctg tctcaaaaaa aaaaaaaaaa agaaaaagaa aaatctgaaa 128400
atctgaacat accaattacc aggttgtcaa ctgagggtta caagatgcta ccccagaaaa 128460
aggcacaggg cccagagtgt tccacgggaa agttttttaa acactcaaga tcatgcctgt 128520
actatacaaa atgtttcaag tgtagaagat ggacacggtt tctattcatt tttggtgtta 128580
gcataaccct gattaacaaa actcaaacac aatggcacaa aaaaggaaaa accacagtcc 128640
aaggtcacat gtaaagaaag atgcaaaaat tgtcaataag agaattagca aattaaatcc 128700
agcagtgtat taaattaaag taataacaca ccatgaccaa gtagagtttg tttccaggaa 128760
cgcaaggatg actcaacatg aagaaatcca ttaatatcat gatgctaata agccaaagga 128820
agaaaaacca tatgataata ttgagaagtg ccaaaaacgt atgtaataaa atctaaaatg 128880
cactaccagt tataaaccgt gttgagcagg ctaggactaa aaagaaactt cctcaacata 128940
agagaagata cctagtcctc agtttcctgc tatctcctca cccactgaga ggacttttca 129000
cgacaaccac caaccttctt gtagccaaat tcagggcacc cttttttttt tattagactt 129060
gaccactcag cagccttttc ctgctcaccc gcttgctctc actccccact cggaaacttc 129120
tcttggttct ccttctagta tggagtagca aactttaaca aaccagcact cctgcacata 129180
acaactgtaa accccgaatc acaaacaaac agaaactacc aaggactcta gaaagttagc 129240
aaaagcaggt agattttgat ggggtagtca gggtatggtg tgggtatcta taattccaat 129300
agaatgcctg ccatgttcaa cacctgtgaa aaaaagaggg gattaaaaga agtcctgcca 129360
ttattatggc cagaggaagc aggaaaggag ctggaggcaa tcaaagtcgc tggagagtga 129420
gatgagactc tcaaaaaagg ctagagaagg gccttttatg tgtcaaatct gccctggttt 129480
ctggtatggg gcagaaagca atctgaactg agactgggac tcctgtcacc tcaggtgaga 129540
ctctttgcaa ctggcagcta atcaagttaa ttgcctgcta aaacaaatgc atcagtgctc 129600
tccagacaaa tacaggacat ttcagagtct ccaacaacat aatattcaca aagtccagga 129660
ggccatccca aactgtatga catatgtcag ggccagaaac cggtattttc ttctcaaggg 129720
aagacaattg actgaggcca gccatgatgt tggaatcatc aaacaaggcc tctattataa 129780
ctatgcccat gaagataaag aaaaatacac tttcagtgaa tgaaatgaca ggaaatttca 129840
gcagaccagt agaaaatatt taaaaatatc taaattgatg ttttgaactg aaaaatacac 129900
tctctgaaat tagtaaaaaa caaaatactg gatgaaagga tcagtagtgt agagaggaca 129960
gaagaaagtc tgtgaacttg aagacagagc aatagaagtt attcaactca atacgaaaat 130020
gagagagaga gaaaaggctt taaaaacatg aaaagagact caagtacatg tgaatagtgt 130080
taaaaactta acagatggcc aggtgcagtg gctcacacct gtattcccag cacttcgggt 130140
ggctgaggca ggcagatcac ttgaggtcag gagttcaaga gcagcctggc caacatggtg 130200
aaaccccatc tctaccaaaa ctacaaaaat tagccaggca tggtggcacg tgcctgtaat 130260
cccagctact cgggaggctg aggcaggaga agcacttgaa cccaggaggt ggaggttgca 130320
gggagccaag atcacactac tgcactccag cctgggtgac agagtgagac tccatctcaa 130380
aagaaaaaaa aaccccaaaa attaatatat aggaaattgg agttccagaa ggggaggaga 130440
gagcaaatgg agcagaaaaa aaaatattaa agaaataatg atgaaaaagt tctcaaattg 130500
attttaaaaa cataaactta tggattcaag aagttcatca aaatctgaat aggatcaatt 130560
tgaagaaaca aaatctgaat aggatcagtt tgaagaaaat catgcctagg ctcatcaaag 130620
tcaaatggat aaaaatgaaa attaaaaaag aaaatcttga aagaagagaa caaggcacca 130680
catagcaggg aatggtgaat tgaattgcca cagacttctg gtcagaaacc atgggggctg 130740
gaagacaatg gaataacatt ccttaaaccc tgaaatgtgc tatccctttg gctcctgtgg 130800

```
ccacttggtc cagttttact gtcccgtcat tttgttttcc ttgttgctct cccttccatt 130860
aagcactggc ctcatcctgg cctgggcttc ctctatcctt cccttcctcc aacttcaccc 130920
cctggatgaa ctcttccaca ccacagcttt gatgatggca tatgtcctga agactcccaa 130980
acgtggaact cttgtttcgc cctcttgaga ttgggcacgt agatccaatg cctgctcagt 131040
ttatccacta gcatgtgaag ctcttcctcc catctcaagg aataaccatc ccagcccctc 131100
agttgttgac accagaattc tgggtgttag cagtccccat ctctcttacc ttccatcaca 131160
tctaatgaac ctgctatctg gcaagtctta gtccttacaa gccagccttc actccagaag 131220
tttccacaga cagggtgtca ccctgtgcta cctgctgtac atctgttcta tcacttcatc 131280
ctcaaaagta gagctattct ccgcatttta attgatggcc aactgagaaa gacagggacc 131340
tgttgatggt cgttccattg ttcttgagtg ccccaggtta gccactgtgc tgggcattgg 131400
ccacgtagca gacgggcaac tgcagactca cagctggagg cacagacagc caacaaggag 131460
tccattgccc tgatggcatg atgtcaggct gcggagaata gcagggccgt ggggttgctc 131520
accccagtgc ccccaagtcc tcctgtggtc aggcagtacc cacgccatct tgcctcccaa 131580
ggctgaggcc agagatgttt gtgggcctgt gtcttccagg cagttcccgg cctcagcaca 131640
gtcatctctt ccttcctcta ccaggtacag ctctgggtgc aggtgaaatg gaagcagcct 131700
caccctcctc ctgcccaacc ctggccagct cagaaagcca ctcagagagg cagccctagg 131760
gtttgcctcc actcctcact gctgacctga ggccaagggc aagctgttct gaggcttagg 131820
accctctggc accagctcta gaccccacct ggggtctccc tactgcccca ggtcaggcct 131880
gagggcttgc ttgagggtac agttttgaac tacgcaggtg gaggacccag cctgctgccc 131940
agctctcctg cctccccaga ctctgggtgt gaaggtaggg ctttcgcatc acatttctcc 132000
cgctcatggg gctgggcgta ccgagagccc tctgtgtgtg tctccctaaa tgctccccat 132060
gtgtcagggg caggctctgt gcttaccagc cccacccgcc aggtaagaag actgagaccg 132120
cagccggcga gtgaggggca ggccggggtt actcagggtg cgaccaggag gctgccctgt 132180
gtgtgtcccc tctgggccat tgctctggcc ctggtgcccc tcccttcccc tctacgcctc 132240
ctccaccagg catctccccc actcaggccc aggaaacacc acctggagct tggaagatcc 132300
ctcaaggaag gagggcggct tggaggaggg aggccagtat cctgtgtgcg gcctcccttc 132360
tctgtctccc agaacaggcc agtctccgcc gctgaaccca ccactgggca gtggcgagga 132420
agggcttctg tggtgcccca gcaggacccc atcaggtgtg gctggctcag ggctgagtcg 132480
tctcttcttt cagctgggca agatcctccc actagggccc agttcctgtc tgaacgctgg 132540
gtccaggcca gggcccgtgt gcccaggggt gtctgggtca ggccctccat gcatccctgt 132600
cctgggaatg ccggggcatg agtcggggaa tcagctggca ctgtctcaga gcacgagcac 132660
ttccaggcgc tcagggcaga cggcaagccc agcttgggcg aggccttccc ctgagcgcct 132720
ctgggcctgg ggggctccct tgtggaaaac atgggagagg aagcctgagg gggtcggctc 132780
cttactcctg gtctttcccg ctcacccagc gctccccgga aactccttcc tgcagcactg 132840
ggatctgaca tcccggcacg ttctggaaag ttcctcactg aacgttgtgc atgagaagaa 132900
acttggggca gggcccgtcc agctaggagg cgtgcacccg ccactctctg cttgtgatta 132960
gcaaggaggc gagggctgtg ctctctgcgg ttcaccaggg ggtcaagaga attcccagat 133020
ccagaggaat cccactgctg ccaggcctga gacagagggc cctacgggat ggctgcaagc 133080
tcgtgggatg gactgcagga ggccgtcctg gcctgggcga gtaggagata aaccactgcc 133140
agataggaga ccgtgctggg tcgggggatc tgcctctgcc aagttcgcag cctggtgggg 133200
```

-continued gaagccaagg aacatacggg atagtaagga atgggcagag ggagccccag gaagtgaatt 133260
tctctagtct gggctggtcg gtgagggctc cctggaacct tgaggagaag ctccaggaga 133320
atctaatggg gagggtgagg tggtggaggg tggagggggc aggggagagg gcaggtctat 133380
gaacggggct gggaaccatc ccaccaaagc ctcctgacag ggtggtgtgg ctgagtttgg 133440
ggcaggaggt gggactgagc ccaggtctcc cagcccatgg gacgtgggcc agctgccagt 133500
ctcacttaag aatgtccttg atgaagcatt aaactttatt aattctatta aatcttgacc 133560
ctggagtgtg tctttttaat attcgcggag gcacgctcaa agcactccca ctgtagccgg 133620
aagcatgcca gcgtccccag gaaaagctcc tgcacagtgg tttgagttgc aggctcaatg 133680
ggctgcgtgc accgctttta ctgaaccggc gaccggctgg atgtttcctc agagaagaac 133740
aaaaagatcc acttagagaa aaacaactcc tggattttgc tgttggtgac caccttggag 133800
ctttcatgca aacagcagaa ttttgagaaa cttacaactg ccccccttgaa ccagacggtt 133860
ttccaatcct taaagacctt cctgaggagc ctggtgggga cagtcacaaa tgtagttttc 133920
cataacaata aagaatggca tccactcctg gaagagctgc ctgattgtga gattgatatt 133980
ttccaaacga tcaatgcgga acgttacaga ggcacacaca ggaaaagatc cttgaggccg 134040
aggcgggcgg atcgcttgag cccaggagtt caagaccagc ctgagcaaca tggtgaaacc 134100
ctgtctctac aaaaaatgtt aaaattagct gggtgtggtg gtgcatgcct atggtcccag 134160
ctactgggga ggctgatgtg ggaggatccc ctgagcctgg ggaggctgag gctgcagtga 134220
gccatgatca tgcaactgta atccagcctg gatgacagag caagaccctg tctcaaaaat 134280
aaaaataaaa acaaaaaaga ggaaaagatc cttggaaagt gcaagataca ccagttgact 134340
cgttccataa tacacctttt attttggaac aatttcaaga tgacagacga gttgcaagga 134400
ttgtacacac agccccccctc gcccaatccc cctttgttaa ggtcacacct gactgtggta 134460
tggttgtgac aattaagagt gtgacattgc ttctcgactt attaatgtaa cccaggcttc 134520
atctggagtt caccaatgtt tctgttcaca tcctctttct gttccaggat cccattgagg 134580
gtccacggtg catttgttta ttttgttttt tttttgttt tgttttgaga cggagtttct 134640
tttttctttt ttttttttt gaggcggagt ctcactctgt cacccaggct ggagtacagt 134700
ggcacgatcc cggctcactg caagctccgc ctcctgggtt catgccattc tcctgcctca 134760
gcctcccgag tagctgggac tacaggcgcc caccaccacg cccggctaat tttctgtatt 134820
tttagtagag acgggatttc accatgttag ccaggatggt ctcaatctcc tgacctcgtg 134880
atccacccac cttggcctcc caaagtgctg agattacagg cgtgagccac cgtgcctggc 134940
cacattgaga tggagtttca ctcttgtcgc ccaggctgga gtatagtggt gcaatcttgg 135000
ctgactgcaa cctccacctc ccaggttcaa gtgattctcc tgcctcagcc tccttagtaa 135060
ctgggattac aggtgcctgc ctccatgtcc agctaatttt catattttta gtagagacag 135120
ggtttcacta tgttggccag gctggtctcg aactcctgac ctcaggtgat ctgcctgcct 135180
cggcctccca aagtgctggg attccaggcg tgcactacca cgcccagccc cggtgcattt 135240
ggttatgatg cctctgtcgt ttcctaaact gagggactgt aacatcacgg agtctctaaa 135300
ggtcatgggt ttcagattct gcattgcagc taagcttgaa gaaatgacac ttgtcaagtt 135360
ttggtgtagt agcaaaaaga aaatctacaa gcgcataagg ccattaaagt accagcgccc 135420
cccacccccc actcccaacc acgtatgttc gtagatgtcc tcatctacat tcttcccatg 135480
cgctggccaa agcctgcaga ggcgtgatgg gaatccgctg ccttccagca agccacagag 135540

-continued attcgcaaag tgcaaagaca tctcactctt ctcacggaac ttgctttgtt ttgaaaagcc 135600
tagttgtctt ttgtaaacaa atattttatg ttaatgtgta gtagtgagtt tattattgct 135660
gttgtgattt tactgttttg tgttcatttg tttcatatgg ttttgagtca gggtcttgct 135720
ctgtggccca ggccggagtg cagtggcaca atccaggctc actgcagcct cgaccttcca 135780
ggcccaagtg atccttctgc ctcagcctcc cgagtagctg gtgtgtgcca ctatacctgg 135840
cttttttttt taattaagga tattttaatg gccttatgtg cttgtagatt ttctttttga 135900
ttactcctcc ttgtaattcc agcactttgg gaggccaagg tgggaggatc acttgagccc 135960
atgagttcaa gaccagcctg ggtaacatag caacatagcc caggctggtc ttgaactcct 136020
gggctcaagt gatcctcccg ccttggcctc ccaaagtgct ggaattacag gcatgagcca 136080
ccatgcccag cctctgttgt gacttttaaa ttaattcatt taacctattt ttaaaatttc 136140
taatatttta aatattgaaa tatttcaatg tcttagttgt aacttctaag acagtaaata 136200
tcagcagggg tgaccccgta tcaacccact ctctttaagg acttgttcat aactttgggg 136260
aatgcaagag gccctgaggc cggaacattt gagaaccgag gtcgaagagc ccaggcttag 136320
gggccagtag ctgtgcttat aattagcaga ggggcaagtg ttttgactgt ttcaaatcct 136380
ggagtgttgc ctcgcttttc tgttcctcag tgtccccctg tgcaaaagcg agcacctgag 136440
cacggggctc ccaccggatg cgcgtgtaaa cagcctggct cgggtttgtt ctccacaaag 136500
ggagctgctg agagtggcat taaaaagtga tggacagacg gtccttggac aagagtaaaa 136560
ctgggttagg actacagaaa aatcacatgg aaagcacagt gagttcccat ggacctcctg 136620
cctcatgcgt ccaccacagt ttcccctgtt attcacatgt tgcaatatgt gggccttctc 136680
ttagaattga ccagccagca ccagcacaca ctgaggtcca ggctcactct aggggttgtg 136740
cattctatga gtttggacgc aagttatcat gccctatatc caccatcaga ctatcagaca 136800
gagtagtttc actgccccca cagtcatggt tctgcacctc ttcctccctc tcttcctgca 136860
aacgctggca gccaccggtc ttttcactgt ctccatagct ttgccttttc gaggacgtca 136920
tagaggtgga atcctacggg cgtagccttt gcagagtggc ttctctcact tagtatcatg 136980
catttggtgc tcctccatgt cttcttgcgg ctcacagcta acttcttttt agcaccgaat 137040
aacattcctc ggcatagagg taccgctgtg tgtttaccca ctcacgcact gaaagatctc 137100
agttgcttcc aagtttttgg tgattatgaa taaaactgct ataaatactt gtgagcaggt 137160
ttttatgtgg atgtaagtgt tctctttgat tgaattttat tacaaattac taacacatta 137220
tctcaagaca atgcctgagg cagctcctct gtgctcctct gctggaaggg cttctgagat 137280
cctacgctgt ggttttaaat tgtagcgttc tttttttctg gagttttaat gttctttgtg 137340
taggttgctg gttccacttc cagacttcca cttctcctcc ccagcctata tctccatctt 137400
tgcatcagta ccgtgaggtt ttaattattg ttactctaga acatgttcta acttctggca 137460
ggctaaactt ttctgcttta agccccttct attttaaaac atttctttaa aacttgcctc 137520
acatcttcct ttctgaacct ggctcacaga gaccccttcc ccaactcaat gccaccagag 137580
tgagcttctg caggcctcag cgccccagct gggctgtggc agccctttga aggcccttga 137640
cctgcccagc atggctgcca gctcctgccc actcccattg taccccatga gaagcccagc 137700
tagtttgtgt gctctgggct gggtcttggc agcctgggtg gagcagctga gcccaccgtg 137760
gcagagaagg gtgtgtgctg ggagcccacc ctcctctgac ctgcacggct ccactggtca 137820
agcgcgaagc ccaggggttc ctggcggggg agttgcagcc tggccgtttc ctggagggct 137880
gggactgccc agcccagccg agggcctggc tgcagcgcca ccttctaggc agcccgcatg 137940
ctgaggcccc agccctcccc tcatgttcag ggaagaccag ctgcttcctg tttgtgtgaa 138000
gaattcggct gttttcccga gtggtgggtg agggtccaag cacccagtgg gacggtcgct 138060
cctcgtttct gtggggcctg ctgttctgag gagaaactta atcactttgt tttcttggtt 138120
taggttttgc tttttaataa taaaaaaaaa aaaagaccca gcttgtctgc agccccaggg 138180
ccctgtgacg ttcctggcat aacaggcgtt acttttacac gggctgctgc agtgggcggc 138240
tggccgggag ctcccgggga gggcagtggg tctcatggac tcggccctgc ccagctgggc 138300
gtgggcaccg ctgcccgaaa gtgggggggt ctgaaggagc cgacccctgc gtcccgtgct 138360
ggctcagccg ggctccctga gggccctgac cctctcccag ccatgggtca gtgctgggga 138420
gaaggttctc agatgccggg gaggcctggg aaggagaaga gcctgcaggc tccctcagca 138480
agggctggca ggtctgggaa ccgccaggcc acctgacttc cagggcagcc cctccgggag 138540
tcaacacccg cccccctctcc cagaaaccca agccaggaaa gatgggggac agagccctgg 138600
cacccccact ctttctggca ctctcccctc agaggcctca gctgctggac aaggtcctgg 138660
gctccctggg ttgccctctt ggcccaggct ggggatggag aacaacgtac agtcggtgcc 138720
ctggtgtccc ccagggcctc aggatgcctc ccccaccctc caccagctgt tctgcctccc 138780
agccgggccc ttccctatcc cacccaaaac gctggctcta cccttcctgc cctgtggctg 138840
gggaatctgc agagtcatgg ggccagggaa ggggacagta aggagggacc cctcgtctat 138900
ctcagcactg gaggggttca gggtccaggg ctaccccaga aacagtcact gtctcactga 138960
agagctccag gcacaccttg cccctggcgc tcagggtggc ctgagctgag cctattgtgg 139020
ggaaggagga gggggctgga ggtgttggct gggccaggtc accaggtgtc ggcaatggaa 139080
ccacaagaag atggtcagtc tggggctacc ttgcccactg cttctctcac ttcatgtcat 139140
ttgtggaaga aagaagagca tgtcagctgc aggtcatggt agccatgggc ctagatctgc 139200
acttccagga attcggccac tgtgcggccc ccctcacatt aacaggatgg atttgtgtaa 139260
ccaacagtgg gaatgacggc gggtgacttc tgaggccagg tcataattga cactgcagca 139320
tccttcttct tcccccacct ctctcccttc actccctctg ggaaaagctg gctgccatgt 139380
tgtgaggatg cgcaaacctc agaggtttgt gtggaaggac tgagcatccc tccgacagcc 139440
acactaggtt gccaggcatg aaggggacac ttcagtccag caggaccttc agatggctgg 139500
ggcccagggc tggtggcttg gcttggggtg tcagggggtg gcagccaagc caagccacaa 139560
ccaccaggct aagctgctcc tgtactcctg acccacagaa actgagatga taaatatcca 139620
tcactttaag tctttattgt tttaagtttt ggactaattt attctgcagc cataggcaac 139680
gaacaccgtc ttctggcagg ggtgaaatag atgcaactag accagagggg acaaggctgg 139740
tgcaaggaag gcttgtaagg acggagagtt ggaggggagc tcaggagtcc tggccttggg 139800
tctggcctgg ctctgaggct cagcagctgt gagcgctgga caagtctgcc tcccacccag 139860
attagcctgg gtgatgagtg tggtgtgtgg cagaggcgaa tagcctatga tcacacaggg 139920
aggaccagtg tgagtcacac aagggacagc aatcaagggt gacattggag gaacttggct 139980
tgtggtatgg gtacagggga caccagggaa gcctgcagat ggctcagagt ggccaagtcc 140040
ccagagcagg cacagaggaa caaatcagag catggctcaa aacaacgggc agccagcacc 140100
tgcacagtcc agctgggtac atctcttttt gccctttcaa cacctggggc ccagcagttg 140160
ttctcaggtc agtgtgagtg gtctgggaag acagctgccc acctgggcct ttccacttgg 140220
ctacgttcct ggctggcatt cagagaaagg gcatccaccc atccattcat ccatccatgc 140280

-continued atctatccat ccatttatcc aggcatctat ccattcattc atccacccac catccaccca 140340
tccatttata cacccagtca ttatccatgt attcatctat ccatccatcc tttcttccat 140400
ccatccatcc aagcatctat tcactcactc ctacatgtat ccatttatcc atccatctat 140460
ccatccatcc atgcatgcat ccacccattc atacacccac tcattcatcc atgtatttat 140520
ctatctatcc acccatccat gtatccaccc ctctatgcat ctattcatcc atccattcac 140580
ccactcattc atacatccac tcattcaccc atgtatctat ctatctatcc atccatccat 140640
ccatgcatcc acccatctat gcatctattc atccgtccat tcacccacct attcatacac 140700
ccacttattt atccatatat ctatcttcca tccatccatg catccaccca tccatgcatc 140760
cacccaccca ttcatccatc catccatcca cccactcatt tgttcatgta tccatccacc 140820
catccatcct tccttccatc catgcatgca tccatccatc catccatgca cccatccatg 140880
catccatcca tcttcctttc cttccttcct tccttccttc cttccttcct tacttccatg 140940
aatccatgca tccacttatc catccatcca tctgttcatc catccatctg ttcatccacc 141000
catccatgca cccatccatg cacccatcca tgcacccatc tgtgcaccca ttcatcctcc 141060
ctccctccct tcttctcttc cttccttctt tccttccttc cttccttctt tcctcttgcc 141120
ctccctccct ctcttccttc cttccttcct tccttccatg gatccatgca tccacccacg 141180
catccagcca tctacccagc caaccattta cccatctaca tacctttcta gcccccacca 141240
catactcaca tggacatctg gggagagca tctcatggca ggagcagcgg gtacaaggct 141300
tgtagagagg tgatgtggcg tctctgagga gtggtggata gggaggaagc atgggttgtt 141360
gagaaacaca cctgagaaac caaggggagc ttgcccagga aggcatcagg aagccctgaa 141420
ggggatgcag ctttttcttg gagagaagtg gggctagtgg aggtctctgc ttaggagtga 141480
agggatcctg tggctgctga gtgaccagag tgcaagagga gaagtggagg cacctgctgg 141540
gatacacaca gaagggagtg actgggaggg actggtggag gagtgagggt ggttgcaccc 141600
tggtgtgtgc tgagggcaga gtgagagcct ttgctgaggg cctagaggag tgaagagccc 141660
agaaggcccc tgggaaggat ggcatcacct gacagagaag aggagaggca gaaaggtaca 141720
tttggagttt cagggctagg cggtcatgtc cacagaggcc ggggacatcc gtgagagggg 141780
aataatggac agacagcacc tgccaggtca tgttgccaag aggcccctgg ccaggagctc 141840
agaccagcct gggcaagtgg tcaggtcctg gctgctggct gtggccttcg tcctgctggc 141900
ctctcagatg tcacagggag ctctcggagc ctcttgagct gtcccccaat gggctgctac 141960
ctggctccga ggcctggtcc cagccccaca gccccaactt ggtgttcctt cagggcagag 142020
acagatggga caggggtcag tgaggggagg agagttctca ggaggcggtg cttgggctgg 142080
gcctggggag ggaagctcca gggtgctcct ggggcagcag ggtgaaccag ctctgacgtt 142140
ttctgtatta aggagcatct gagaagggag agaacaaacg cttcgctttt ccacatcagg 142200
cacaacatga tcggtcatcc gttttcattc cgggatctgg aaaacagctg attctggaaa 142260
gctacaactt ccctaggtgc agagctctgt ggagaagggc tcccgcaggg ctgggggtgg 142320
gagctcaggc cccaggcact ccagagctgg ctcaggaaag ggtaaggctc agactgggcc 142380
tggagggaag agcccaccaa ggaggaacca gtctccaccc cctgcctctg gccaggtttc 142440
tatagcactg gtgaccagga cactcgagcc tctgggacct cagtgggcta atccgggact 142500
aatcctagca acaggctggg cctgcagcca catgatggcc gagggttgct gagcatgcac 142560
ccatgaccct tcccaggggc ctggccacag tgcctggttt ccctctgtgc cctggcattg 142620
agtggagttg gctccaggag caaggccccc tgggcctttg gtccctttcc tgggcccagc 142680

-continued tctgggccac tggggtcccc atggctgccc tcacctgggg gttggcagga tcagcggaaa 142740
ttaacaggtg agggaggcct catgcatgaa gcacggcttc ctgctgggag cggtggaaac 142800
ctggggattt cggggcgggc tcagggatcc tgatacactc acttggggcc ctgggctggg 142860
gcaaggcaac atggtgagtc ttctgggcca ctggaaccgt gaggaaggac aaagctctgg 142920
aggccttgac caaggaggcc tgctgcgcgt gtgtgtatat gaatgtgtgt ttgcatgtgt 142980
gggcgtgcgt gtgtatatga atgtgtgttt gcatgtgtgg gcatgtgtgt atatgaatgt 143040
gtgtttgtgt gtgtgggcgt gtgtgtatat gaatgtgtgt ttgcatgtgt gggcatgtgt 143100
gtgtatgcat gtgtgtctgt gcgtgcatgt gtgtacccct gtgtgtgtgt gtgcgcactc 143160
cggcacggga gggggttgtg cccctgcctc cgcgccccag aagctctggt tccatctgtg 143220
ttcttgcttt tcatcagtca gccatcattt gttaattcat tcattcaccc atcattcatt 143280
cagcaatggt caggaggagc caggaagcac ccttgtccgt gctgacccag gctgtgggtc 143340
tgttgtgttg gcctcagcag tgtctgggca tcagcaggtg aaagggtgcc tgagtgtcag 143400
tgtgggagcg gcctccactg agaaccacag ctccccggga gtaccctgag cggcagcgct 143460
ctgttccctg ctctgccatc tcctggaccc atgcccttcc tagctgctgg atcagcctct 143520
gcccaggttg ggctgcaggt gctgggtcca ggcctccccg gggtgcccct cgtcaggggt 143580
tgcaggcagc ccctgcgacc atggctggag ctgggctgac ccgggctcaa actcctgact 143640
cttgtgccac ttactgtgtg tctgcgggaa agccacttaa tggagactca tcctcagtct 143700
ccttgtctgg aacagcgaca gtcctgactc cttcagggtt tcgaaggtga tgcttgtgga 143760
acacgctact ggcacctggc catggagggc gtgagggacg gccactgtca ctacccagat 143820
tttccctggg ccagcagtgt gggagcagat gggatttgga gtggagcacg cacaggacgg 143880
ccctcgttca ttttgagtcc acacaggcct gtgtccccag ttcccggccc tgcccctgct 143940
ctgtactgca gcacccctac cctcagaaga gacccccttat ttccatgtgg aaagcgctct 144000
ttgggctcta agtggcttcc caggagggca gagcccctgg agccatctct gggtttccag 144060
gaagcccact gggagggtgg tggatggtgt ctccagggcc gtggaacact ctggctaccc 144120
ttagcacgag agggggagat tctctggttt tcagcttgtc cttctgttcc agggacagct 144180
ctgtgggaga ggctctctcc tgccaatgca ggagacagag ctggagcaga ggagagcccc 144240
tgcttaggcc taagagcccc agcttggtca ctgaaactgg gagccacggt tgggttggaa 144300
agtctggtcc tccgtgccct ggcaagggca gacttggttt tccttcctac tctactcttc 144360
cagtctcctc ctctgccaga ctggccatgg tgggtcagag agaggggcaa ggaaagggaa 144420
gtggggggac agagcaggat gaccataagg aagaggacac aggagagaga aggggatgca 144480
gggccttcca actatggact tgaagaagaa agacgaaaac aagaaaccaa agtcatgtct 144540
tggccaacaa acccccagct cctatctccc tacagaaaga agcttggggg aaactggctc 144600
caggagcctt ggctgcaggg aaggcagcat ttccacgact gagccttttg caaactatgt 144660
gggtcctgct ctttttggcc ctcctgctcc agcccccagc tccctgcatc cagctctgag 144720
ggccccagag ccccatcaga tgtggaggga gcttgggtgg agcagggtgg aggtgcggca 144780
aagatcaggc caggcctcat tgtttagaaa agaaggaact gacttcagct ccgggagcag 144840
ggcctcccac cccacccgga cttcctgctc cctgggcctg ccagtgcgga ctttgtccac 144900
cttatttggg gattgagaag ccacactgct ctatggccct gggggtcatg gcagagaacc 144960
agagactcac agagtggagg gtgcctggca atcattctcc atgattcaag gttacaacac 145020
cttagccaaa gaaagtgcta tttgaggatc cattcattcc tccatccaac tgttcatcca 145080
cccttccatc tacccacctg ctcttcattc atccacctac ttattcatac gtctacattc 145140
atcctcatgt ctccacatcc cccactcacc catccattca tcctttcctc tacccactca 145200
tcctttcatc cgtccatcca tccatccatc ctaatcatcc atccatctca accatccatt 145260
catccattca cacaccacct tcccatccac tcatccaccc atccatccca cacatccttc 145320
cactcaccta catattcact catccatcca tccatccatt ccaacctcca tccattcacc 145380
cacctaccca tccatcgatc atccatccat ccatccattt atccatccat ccatccatcc 145440
atccatccgc tcacccatcc atccatcaat tcacccaccc atctatccac ccacctatct 145500
accacccttt ccaccacaat tctatatcat ccaggtttga taattggaag cccattgcta 145560
agaaaacttc ttgaacaagt tctttggcta agaaacaaga ggctgcctca atttacccac 145620
tgcatctgtg tcttatggat ttgaagtcat cataagtcac atctaagacc aggaccagga 145680
cctgagactg tcctttcagg accttttatt ttccacaatg acagtgacag acacacacag 145740
ggagcactaa ggctggggtc ccagtggacg tcagtgtggg gaagagtctc tcctggctct 145800
gtgtggcctt tgaaagacac ctcattcctt tggtctaggc ttctctgtaa aatgggctgc 145860
caagatggtt gtgcgggtcg atggagagaa gtaatctgcc tgtctttgaa tcattgcctc 145920
caggtgaagg tctcccctct ttctaactct aatctaaaaa cccatgaggt tgaaatcctc 145980
aagccccaag cgacacctgt gaaacggccc aagagaagcg tgccatgagg cagcaggaag 146040
ggcattccag gaggagggaa cagaggtgag agagacgccc tgacatttgg ggacccagca 146100
gggagtttgg cctggctgtc actggaatgg cagcacaggt ggctggagag gaaagagggg 146160
ccaggctgaa ggatcagatg cccctgggaa cacacaggag ctgtggggtg ggccaggtgg 146220
ggttcctgag ggaggggcac aggtgggcca gctggccgag aagaagcttc ctctgcaggg 146280
tggcgagtag aaaggggagt gagccccacc tgcatggctg ccgaggggtc cagtgaggga 146340
aggtggtgag tccagggacc cagcttcaag tgccacacgg gtcccgcttg gccatgctgg 146400
atgggaaggg ttctcctctg gtacactgtg tctggaggcc ccgggtcttc ctcccttggc 146460
ctggcagggt ggtccctccc gctgctcggc tctgtactag gcttgatccc ctgtcttggg 146520
tacagtcctg ccccaacctc cccaggcatc cagtccctcc tgtcctgccc catggagtct 146580
gcaaacccaa tgcccttggc ttctccctgc ctccagcttc cgtccttcag cccgtgccag 146640
gggcctgccc gggaggtctc ttgtcaccag tccccagtgc cagtctccca ctcagcaact 146700
gtggggcacc tggaaggacc tgtgaaataa accccctgaac cctggcccaa agccactgcc 146760
ccccaaaacc tggactcagg gagctcagca gagcatgcag gactgcaacc ggcctgggct 146820
gtccacttgt cctgcgggct ttgggctggg gaagggcaga cggaggggca gggccaggcc 146880
agcctaggag gccccggggt gcagagtggg gcctggttgc atcagggaac ccaggggctc 146940
tggtcccctg ggcccagcaa gcttgagatg ggcctgggca cctccctctc tgcactgggc 147000
gggcttcctg cctggccccg ggaagtggcc cccctgcacc tcccgcagac aggtgacgtc 147060
agcgtctgag ataacaaggc ggccctgccg gcgtctgccc cagcgtatgc ccactgtaat 147120
ctgggctgtc tgggcacagg ggccaccttg gctcggtgaa aagctaccct cgcagtgagc 147180
tccggtgggg ctgaggaaaa cacgtctgca ggcctaggcg gggcaggccc caggggcggc 147240
tctgccttgc gccccctaag atctgtgcca gaactgagct gttcttactg gggcacacag 147300
gacctgaagc ccagcagggt gtgcagtcag taggtgccca ataaatgtgt ggatgagcca 147360
aggaaccctg cacgaattag tgaggctgaa aagcagatga tttagaggca agagaggccg 147420
gaggagcctg ggcttctcca aagaggagga caggatgcag ggcccctggc acacacagcc 147480
cagcccccac tctgccccgc ccccacccag gccagcctca ggcagcctgt cctccaggcc 147540
ctgctaccac tgtggcctgt cctgtggtct gacttggcct ggcaagggca ctcgggcgca 147600
gggccaagag tgtggggcct gccttccttg tagcccactc cagtctcctc cgctggccgg 147660
ggagggcagg ggagcagctg ctggagctgc ggctgagagc gggtgacggg tactgttgtc 147720
aggcaaggcg ggggtgcggc tcccgcttgg catcctccac cagggctgca gtgagaggcg 147780
tggccagcag gtgagcaggc agaggagtgt gtgggtgcac ccagcccagc agcctggcca 147840
cgagggcccc ctggcaccca ggcgctgctc ttcatcagag tctgccctgt gccagctggc 147900
agggccagca tagggatgtt tcacttacgt acacttcaca agggaagcgg caggctgagg 147960
agctgtctgc tgagggccaa gacctgggga cacgccacaa gtggggacag cagttcctga 148020
ggatcccaat gagccctggt gggagggggc catggggagg gtcccaggga gcaggtgctg 148080
ggcactgtag cgtgtctggg ccagctttga ccctcaggag ggtgggctgg ggtcagccaa 148140
gccgcttctt agaacctggg gatatcaaaa agagcagagc tggcctgctg tgcccagcac 148200
cagccaggac aggagacagc aggggagggg caccggcata tcacctactc agggctgcag 148260
gagctgggtg ggggcaggca gcaggcacca ggaaagaagg gggagtgata agggatgtgg 148320
gctgagactg gtgggagttc tgggttcagg ataagcttgg ccacagcctc gaggagagag 148380
gaggaagtcc ccaccccagc tggacccgca tttctggcca tgttcagacg ccctgcggtc 148440
cggtctccac tccaggtgct ctgtccgggc aggaggctgt gacgcaccct ctttgtcaag 148500
gggcattcag ggataaggct cctacctgca aggagctcac tctagaaggg gagcgactct 148560
gaagcagaca ggatggggcc aaccgcgtgg ggtgaggagg aggcatccca accgggagga 148620
tggggaggtc cctgcagggg gtccgaccca atgtgaatgc tcgtctgtca tgatggccgt 148680
ggaggggcag gatccaggag gggtgctggt ggcgccaagg ggcatgagga ctgggcagga 148740
cgctcctgag cttggtgctg gacctggaag ccttgctccc aggaggcctg atgcccctgc 148800
ctcctgcccc agtccttggc aagatgcccg tggtcctggg ttgcccctgc ccaccgtcca 148860
ccagggaccc ccagtgtgtg cctgccacaa gaggtacagg gtcacccacc cccgcgtggc 148920
agttagtcca cctctgtgaa ggtgaatttt cagctttcag gttccccagg tgccctgact 148980
tcatcagaaa ggccctgtcc tgcacccagc ccagaagggc cttcctgcct ctcaaatctg 149040
ggcctgtatc ccagggccct gctggagccg gggggacgct ctgcgacttc cggcagcaca 149100
tgtggggttc tgtgcccagg caggtgattg gtttgcatcc ttggtttggg gtatgcgtgg 149160
gagggcaaag gggcctccag tgctggccct tggaggcccc ttcttggtca gcatttccct 149220
ttctccaggg gacctttctg gactagacac tcctttggtt tcagaaatga aggaaaattt 149280
tggaagacac tggcacaggg ggctggagta ggagtggtca ccagggaaca gcatttccga 149340
aggctggaac agcatgcatg caaggacgag gggggagggc aggcgcccag agggcccatg 149400
tgtgaggtcg gcaggtgtca ggactacagg ggagagacga gagtgagggc ctcccctaag 149460
atcccctggc agcctttctg gagagcgaga tgatcccatg ttgcagacca gcacctgact 149520
cctggacctt ccttgcccga ggccacagag ctcaggcaag aagctgtgct gcctgacccc 149580
gcagcagtct ctgtggacga agggaggcag agatgctgga ggcatgtcct gggtttgtgc 149640
tgctctctca actcacgtcc cctcttccag ggcctcctct gtccccatca ccagctcccg 149700
gtgcagagct cacccagaga ggcattgcac aagttgacct ccttctgccc tggcctggac 149760
cagcacgggc cagagtgggg agggccgggg gagcagtcca ggccaggacc tccagccccg 149820
gccggtgcag cttgcccggc ccttcagcgg ctgcatcctc tgctctgtaa aggcacattc 149880
ctgaggctgc gggttagcgg ccccccttgg tgaggcatta atgaagaaat ggaggctggc 149940
cttgtgtaac cgtgacagcc agatcagagc agccagggcg ggcgggcagg cgcccggacc 150000
tgggtgggga gggctgggac gtggccctgc ccttggcccc cgcccgcctg acccccaagc 150060
tcatggtctg tggctgcggc atgcctgaac cctcccagcc tcccccgcag cgggaagccc 150120
ggggctgggc ctgcactcaa tgtgtcctga gtgagtgtgt gtgtttattc ttcatcactg 150180
agcccgcgcg tagtgcgttc gtttcctgat gtagtaaaca ttttagaagg ccaagatcct 150240
ctccttcctg tctctgtgcc agcgaaattc cccaagacca gcttgtcctt cgtggagtgc 150300
cagagctcat cttcccgagg ggagatcggg gggctcttag accctcccat tggcgccccc 150360
aaggcctccc cagctctctg ggcctccgca tcagtgctgt tctcctctgg gccaagcagc 150420
gcctcccgat gcctcttggg gccgggtggg gcgttcaccg tgggcgggag ggccgtggtg 150480
tgcgggtgcc ccagactggg agcctcagag cctcagagcg ggccctcggg ccagcagttg 150540
gagcaggaag tccctgcatt cggatcccaa cttggtttct taaagctgcg tattctgggc 150600
caaggaatct gcctctccag gggagaaccc caggcagtga agactgtcag tgcccgtgag 150660
cagggcagct tcctgtggag tgggcagttc acggaggggt atggaagggg tctagggagg 150720
agctggggat gctgtggggc agacagcctg ggggcacaga cttgaggggc atgctgcctt 150780
gggggttcag cctctggtac agccttgggt ggcacaactt tgggggtgca gccttggggt 150840
tgtagccttg gggttgcagg ggtaggtcta aggcaggcca gggcagggtt gctatggcca 150900
aaggggaccc actgtgccct ggagcaggcc ctgggtcccc agctgcaagg gcctctgcgg 150960
gacacgggct ggggtcccac atcacgtggc tgtgtgtgct gacatacagg gcctgtcacc 151020
cccccatctc acggattctc caaaggactt tgggaggtgt gaggggcaga gaaagggaaa 151080
ctgaggcaaa gagaaaccaa atgactgcta ggcaggacgg tgggggcctg gacccagcag 151140
cccgcccccc accctgagct cctttcgcaa tatcacagcc gggactgggg aaaaggttac 151200
cctgaggccc tgtgtgtgat gtgcatgctg gcgtgcgtac gtatgtgcaa gcatgtatgt 151260
gcatgtgtgc aggtgcgtgt gtacatgggt gcacgtgcgt ggtccctgtg tgcacgctgc 151320
agcccaggca tggggcctgt gctcctcacc cagctctatc ctcacggctt ctattttctt 151380
atacatgtct ggcatttttt gctgctgagt tggggggccg tggtttgggg ggaggctggg 151440
cagtggggga ggggttgttt atgccaattg ttcaccctgg ctacacattc ttgtggttgt 151500
ctctttaact tggtaaaaat ttgggaaatt tctaaataaa acaaaacaaa ggaaaaacat 151560
tttcaaaagg atttcaaaat cggtgctgcc acttccccca gtaaccggac ctgtggggcc 151620
tgggagatgc ttttgtgagg aggggtctgg aaggtggaac tttctaacca ccagcacctt 151680
tgaaaagtgt tgtgctgtgg agggatgagc ttgctgtcag gagaaacatg gaagccttgg 151740
ggagccgctg ggctgttggc tgagacctgg ccttctctag aaggaatcca agacatcagg 151800
ttcgttagag ggaagtcttg acatctttgg gttctggtgg ccaggactct gagacccgtc 151860
gggacaagag gggtgggcag ggcgagggcc tgcagggagc tggggcaggg ctggtgagat 151920
gagaaatggg ggtgaggaga ggaaggagct cttggccagt gaggacccac ggataggtgt 151980
gcacttggtg agggcaggtc ctattgaccg ctgcattctt ggtgtctggc ctgggctggc 152040
cagagaaggc tctggaaggt ctttgttgag ctgggaggtg taagagcgtg ttggggtggt 152100
tctatgggga tgaccatcag tcatggtcat ctcctaccta cctaaggggt aggtgcctta 152160
gacctacccc tccaccccca acgctacaac cccaaggctg ctcccccaaa gttgtgccat 152220
atcccactgg ggatgaccag tcgggcctgg gcgaggggtc cttgtgggat gagaaagcat 152280
gggctgctgg ggacagaggc tggagaggga ggttgaggtg ggccttggcc tcccacaggg 152340
tgacgtggtg tccacacggg gcacagtggg gtccaagcgg ccctttggcc cccaggcttt 152400
ttcctgtccc aacctggctg cacctctgaa actctgggaa caaggaaggg ggacccagta 152460
tgtgcccagg tggcctggac agacggccct actggaaacc tgtccctggg tgcacggagt 152520
atccctgtgt gcctgggccc tggggagggg ctgggcatgg agccctggga agctgctccc 152580
gggcttcagt tttccactct gtacagtgtc cagtgggact ccagctccat tctggcctgt 152640
ctttaggcca ccaggccctg ggtcgagcc tggggaggga cagcggcagg aatagagagg 152700
ctccgcctcc acctgatggg ggtcccctac ttagtgacat gctctggtct ggtccctggg 152760
gtcccaggat gagctgacca ggcaggatta gggaccacgt ccttctgggg atgtccatcc 152820
acccaggggc cccagggcac aggtgggcct ggagtatccc agcctgtgca gatggcatgt 152880
tcgcagggac cgtgcctgtg accaagccct ggggcgtgca catacccctc tagtccttgc 152940
ctcctgctcc cgggatctta caccctcggc caaacccaaa gccccaagcc agtctcagaa 153000
gagcccagga accccgggaa gtgttacacg ggctcctttg cggtttcacc tttccattgc 153060
acaaccaaac cctccgtttt gtttgccagc agtttttagc tagcgatggc acccagcttt 153120
cccccgggac cctcacgcaa atgttggcat ggagccagta gctgctgggg tctcctgggc 153180
agagctggcc ttagcctccc gggccatcca gctcagggct gtgccgccca gcatccaggc 153240
tggcctgggg caccactgcc accctcctcc atgcctggca gctcggggac taggctttga 153300
gaggccacag acacttacca taatcccagg agagtgccct gggctgtgcg tgggaagctt 153360
tctgggccag gtgccacaag gactccacga gtctacagcc agcggcgtgt caggccatga 153420
tgacgattcc tgacattcag gccctggcca agtcaggctt ctggtccggg ggttcctcct 153480
tgtcctgggc actcgtcctg catgttcctg tctctgcctt ttgcccatac cctgccttcc 153540
cctctctgcc acatgacctc cctgagagcc cccatctctc ttgtgaagcc acatgccagt 153600
ccatggggca ctgccagctt ttggagacag agtctcatcg ctgtggccgg cagggccctc 153660
ttcttgggtg agtgcaattc ttgtcactgt ggccagcagg aagctcctct tgggtgagtg 153720
catggggggt cctgctgatt gtttggtcat ggccaggctg gcgagtgggg cgctgctctg 153780
ttccaaaccc cccagggttc cccagcacct ttggtcccag tccaagctct gtggcctggt 153840
tctctgggtc ctcgccatcc tgcctgctcc cgtggccctc tcctctgaca tccacacacc 153900
caggctcctg ccatgctgga aagtgtagcg cctggccaca ccttgcctta gctgggctgg 153960
cttctcggtg aggagcgcca cctcctttcc tccctgctgc atttccgtac ccagctcaaa 154020
tgtcagttct tccacacaac ttccagacct tcccaggggc tcattttttt ccctcctccg 154080
tggtttcagt ccatctcggg gcatctgatt cagtaggcac catgctaggc ccctcccaca 154140
cagcacctcc ttagccccca cccgaggtgg gtctgtcatc agcaggtcag gggactgggc 154200
tggggttcag ccccctttcc tcatcaccca gccggtaaag gcaggagctg gtgcagggcc 154260
cagccccagg aggggccagg tgggacgtgc tgcaatcaca gcctcaccac ccactgggca 154320
ggaagccagc ctgggagcca gaaagcctca aaccacaggc ggcggctctc acagggaggc 154380
tggcagccac cacctggcga ggccccaagc tgctgcctgg ctgagccagg ggctgctcca 154440
ggcacactct ggcctcggct cccatccagc ctgccaggca gcctcctccc cggggacctg 154500

-continued

```
gttgggagtt ccactggccc gggcctcctc agaagactta ccgggtgagt cagttactac 154560
ccgcacctgg cagcctcctg ctgaccagga gcctccccag cctccccaga agcttccctt 154620
gtttgttcct tcacccagga ccttgtccag tcatggctgg gagctcttgc ttgcttaggg 154680
ccagggtggc tgcagagggg atggatagct ttgcactggc cccaggagct ccctgggcag 154740
ctggcgaggg ctcagggtgt gcagtcagca tggagctgga aggcaggacc ccaggcaatg 154800
gttggggtgt aggaaagagg gttgatggag cgggggcttg caggagggac tagatggggc 154860
tgatgtgggc agcaagcggg gatgagccag tcctaggctg agaagcccca aggcaggggc 154920
tgggaccggc tggggctgct ggaaggagac agtgggggct tgtcaaagcc agcctggcct 154980
cccacctccc ctggagccca cggggaagcc tcagcctctg ccatcaggct ggtcttccag 155040
gggccccaag gcttggcatg ggccagactc tgggcgcttg ctgcttctgc tgccctccgg 155100
gaactgtctc cccactgccc caggcaggcc taccgcttgc acagtggtgc tggaaggcgt 155160
tcctcaatac tccaacatga gcctcagttt ccccttctaa atgatgagca tctcatagtt 155220
gctaggaggg tgaagggcct catgtgtgga cccctggcag catacccagc acacggtgga 155280
gccctggcag ctctcagtaa ccatcccacg tatcacctgg gtgcttggca ggcacagacc 155340
ccggaccctg ggcctgagag catccactag tcagtccaca gcaaagccag ttgcgccaga 155400
ttctcatgct ccaccaggcc ggaggaccag ggacgctttt cccctctgtg cctcagtttc 155460
caatctgtta gtgcaaggca ctcccactgt gcactgttct gcccatccac aaaggacata 155520
gtcccccgta gagggctctg cctgcccttc ccgagccacc ggccccaaag gcgcacaccg 155580
cactacctcc tccgtctgct gtcttgggct ctgcagccat gctggtggct ggggtgcagc 155640
agggagagga cagagatccc ggctctcctg tcttgaggtc cacattcccg tgggctgaca 155700
ggaatgaaca aagtaagggt gtggagtgcc agctgtgatg gcagagacag gcgagtgatg 155760
tacccgcagg cccaggagct ccagcagccc ctggaagcgg gaagaggcag gagggaccct 155820
cccgtagctc ctggaggaag cccagccctg ctgacacctg catttctaaa ttctggcccc 155880
ccagaattgg gacagaaccc atttctgttg ctttaaacca ccgagtttgt ggtcctgtgt 155940
tgcacccaca ggggacgcag atgcagagga ctcctgggtg agatgagagt gtggggtggg 156000
agcagagggg gctccagccc ttgctcatcc tttgccaggg cccctctggc tgctgtcaga 156060
gcatggacac aagagtgggc agggctggcc tggctgcagg gcttccctgg agcccacctg 156120
ctggttctgg ggtggccagg ctcagcagag gcgaagccag ctgggaaaag ggcttgggag 156180
ccggacagga gcaggccctg ttttcctgcc cgcactgtac catgcagctg tgctctgtaa 156240
tttggggctg aggccaccac accccacttc aggtggaggt gagcctggta attacagcct 156300
gggggccagc tccccagccc ccagccccac aggcctccga ccggggctgt gcagccagga 156360
cccagaatcc aagccccttc ttccacctcc acccacatgt gaggcctgca ggttagcctg 156420
tggccccctc cagagtgtca ctccgttcac ccttcccaag cccctcaggg tgtcagagat 156480
aaaaagataa taaataagca aaatttcaag taagtcatta cagtaaaaat ataaataaac 156540
caagcccctc aggaggttgt gctgtgggct gtactggggc ccaaaactcc ccagaagata 156600
tgacaagtca tgggcttcca agagtgtggg ggccgcctga gagttttggg gtctggagga 156660
tgggaggggc ttttcctggt gtgggaagac caggtgcaag gtggtaaggc gtgggacaag 156720
gtttgagtga gggtcctgga ggcgctggct gacccctgca ggccctccag gcctcctacg 156780
tccagtgtca gcaggaaatt ccaggctgca gtggtcttgg tgggaccctg caaggtggcg 156840
gccactctga gcccagcccc agaatccgat gtcttcaaag ctgctgtggc tcttgtcctg 156900
```

ccctcagccc tggacagcca agccctggac atacaagtgt gcgcatagac acggcccgct 156960
tgcctctgtg cgcacttgcc tgtggggatg gcagtggcgg tggcttttca tcagtccaga 157020
tgttggaggc tgcatagcca gatgagcagg cctgtggagg gggccggggg gccgggaagc 157080
aggctggggt cagagagccg ataacgtcac aaggctgaat gggagttttg tggcccagtg 157140
tcttttggaa atgatgtgca aagcccagtt aatccagtgg gtagggcgtg gtggctcctg 157200
ggtgagccga gaggggccag gggtcaggag gctaccaggt ggccagcagg acagggggta 157260
cctgctgagc agaccccatg cccgccctcc ccatggcctt tatgaggact ggagcccccct 157320 ttaaactcag gcagctgctg gccacaggtc tgcctggccc tgccatgcgg gggtagggag 157380
tccaggacca ggcatcctta cgacagggtc tgttggccca gcatcaacaa ggggcagagg 157440
gcagtgaggc ttgtgctgct tgtggctgtg ccctatttag aacttagccc ctcaccttcc 157500
tcccctagct gaattatttt tggcatgctt ggtggcctcg gggtcttcat gctgacttta 157560
ggagccagat ggggctcagc ttccaggtgg ccctgagcag cagcatcggg ggtgttggag 157620
ggtggggcat gagggtggca ggcccagctg gccaggccta ggggggctcc agatgagtca 157680
ctgcccagct tccaggaccc aacccacctc tgcccttaca ctcgcccctc atcgggtggt 157740
agcattcctc gggaccctgg actcagaaca ctctttaatt tgattcccag atctgagggc 157800
ctgaactgtc agctggggac atgaggatcc tatacaccca tctattcact ctagcagtga 157860
atctgctggc acagaggcca cagcctctct agaggccaca ccctctctaa ggccacaccc 157920
tcactagaaa ccacaccctc tctaaggcca caccctcact agaggccaca cccccctctaa 157980 gaccacaccc tctcttaaga cctcaccgtg tctaaggcca gctctctctg aggctctagg 158040
cggaaccctt cctgcatctc tcagctcctg gggggctcccg cggttccatg ctatgtggtc 158100
ccgttcctct catctctgcc tctgtcttca cactgcctcc tccgcccctc tgtcatcaaa 158160
tctccagctg cctccctctt ataaccacct tgtgttggcg tttatggtgt tcagatggtc 158220
caggaccgga ttgccatctc aaagccgttc acctcctcac acctgcacag acccttcttc 158280
ctcattaggt cacattcaga gatgaggatc agacaccttt gcggccatta attccacctg 158340
ctggctccga agacgagcgc ttctgctctg ggctgtgctc ctctcctacc tcctctgaac 158400
cacatccacg ggactgtccc acctccccaa agcagctctc ttcaaggcct ctggtggcct 158460
ctaggtggcc aaacccacga gtcctttctt ggctctgttt ttccccagac agggcagtgc 158520
ctgatgcagg caaacacccg ttacccaaac cacactgctc cctgggcccc tggctctgac 158580
tgcccggctg ctggctcatg cccctttctt ccctttctgt cccaccccat tttcagagct 158640
ggcctccaca ccttccatgt ctgggtggtc cctgccctgc cctccgggcc gactgcccag 158700
ctccccacat ctcctgaggc ctcctgggac tccagaaacc gctcagccct agcccaccag 158760
ccctgccctc acctccacag cccctccttg cgcggccagg ctttctgctc aaaggcccac 158820
atcctggggc cacatttttt tttagatcaa gcatttggat tttcaaaatt aattttatcg 158880
tgttttatta caattggttt tagtcgtggg atcgaggaaa aatgtacaca gctccaagca 158940
gatatttggc aatagggtgt tccacatgcg gatctgacgt ggtattttag ggtttgtggt 159000
ctccaggtct ctgttgtaat gactcagttc caccattgga agcaacctta ggccatacat 159060
aaaaatgatg gggcagagt gtcaataaaa ctttattaac agaagcagat gacggcccgg 159120
tgcccagtgc cggtctggtg tgcacgaagc agcagaatca aatgcccggc actgggtgga 159180
gcctgaagga ggcgtgtggg aggggggcgc tcccgaagag tttcaaagac gctaggggat 159240

-continued tttctcacag ctaggcagga taaacggctt tcctatttgc ttaaacagtg acgaactttt 159300
ctaactgcac caaatcgagt aacctgatca ctgccaaatc cccacatgat agtctaaaaa 159360
tagataggaa aatatggatt cctttattta ttgtggcaaa atagacacac tgtgaattcg 159420
atcatcttca ccgtgtttaa gtgcactgtt ctgtggcact atgtacattc acgacgtcgt 159480
gcagatgtca ccggcatcca tctccagaac tttctcacct tcccacactg aacccccacc 159540
cccatcgaac accgactccg cattccctcc cctagcccct ggtacccctg gcgctttctg 159600
tctctatgac tttgaccact ctagaaagct cgtgtgagtg gaatcatggc gtttgtcctt 159660
tggtgactgg tttctttctt ttttatttgt atttatttat tttgagacag agtctctctc 159720
tgaagcccag gctggagtgc agaggcgcaa tcttggctca ctgcaacctc cgcctcctgg 159780
attcaagcaa ttctcctgcc tcagcctccc aagtagctgg gactacaggc gcccaccacc 159840
acgcccagct aatttttgta cttttagtag agacaaggtt tcaccatgtt ggccaggatg 159900
gtcttgaact cctgacctca gatgatccac tcacctcagc ctcccaaagt gctgggatga 159960
caggcatgag ccgccgcgcc tggccgggga ctggcttctt tcactgagcg tagtgtcttc 160020
aaggctcctc cacattgtcg catgtgccag aatttccctc tgtgttactc cattctcgca 160080
ctgctataaa gaaatacctg agactgggta atttagaaaa agggggttta attggctcat 160140
agttccgcag gctgtatggg aacatggcgc caggcatcca ctcggcttcc gtggaggcct 160200
caggaaggtg agaaggtgat ggggaagctg gtgtctcaca tggcggaatc agagagacac 160260
agcaggggag gtgccacaca cttttaaaca accggatctg ggagaactc actcagtatt 160320 gcaaagacag caccaagagg atggtgctaa gccattcatg agaaatccac ccccgtgatc 160380
aaatcacctc ccaccagacc ccacctccaa cactgggggt tacaattcaa catgagattt 160440
gggtggggac acagatccaa accatatccc cttccttttc atggctgagt catgttccat 160500
tgtatggatg gaccccattt gcttaatcct gtcatcagat ggtagacatt tgggctgttg 160560 gcccttttttg gccaaaggag atggagtgct atgagtgttc atgcacgcat ttgcgtgtgg 160620
acttagggtt tcatttcctg taggcacatt cccaggagcg ggcttgatgg gtggaatggc 160680
aaccgtaggt ttacatgtgt gaggagccca cggccccata gcgttggcac cacggcccat 160740
ccccagcagc acaggcagct ccgactcccc cacgcccagc gcttgccgtg gtctggcttt 160800
gggatggcag ctgtcctact ggttctgacg tgcattcctc ggtaagtagc cagccccgtg 160860
gctcttgtat gtgcactggc cgcttgtccc tgttcgaggg gaacacagaa cctccggaaa 160920
ggtactgcag ggcttgtcct tacctccttt tgtccatgct caggtgtcac cttctctgtg 160980
aggcctttcc tgaccctacc cctcgcctgc caccccgccc ctggcattcc tcatctgcca 161040
ctgcctgcca gtgcagtccc agtgggcctt ggagtggaag tggaggagga gaggccgcct 161100
gtgccggaga cgccacgcag gtctgttcaa tgagtaaatg aggctaaggg ccttcccgtc 161160
cacctgctga gtcccctggc atgaggactg tcccacagaa aggctcagga tgcctggctt 161220
gggaggcaca cctggacccc tggcttgtgg gctcccggag ctggtgcaga gtctggctct 161280
ccccatcaca cacagggccc tgctgagccc tgatccgtgc actgcatggg tggctgggcc 161340
cagtcaggag gaggctggac cttgccacag ctgtgtctct cattacagtc cctggagacc 161400
caaagtctct gggtagcttc caccagtccc tcaaatcctg gcttctttgt ggtgagcaca 161460
gggtgtgggg tgtcctgctc cgaggccata ggaactcaag aagcaactgg agcctgggtc 161520
agtgtgggtg aggggctgcc aggtcccccc cgatagtggc ttctgccccc cagccccttgg 161580 aaatcacccc agatggtcac tcctaagtct cggccacgat acgtgtttgg ttacccttca 161640

-continued ggtgccccaa acccaggcgt cgtctctccc atgccctgga ttcctggtct caggatggat 161700
cagcgtccac cctggcttca aaacgccctc caggcgacca gcctcgagcc cttctgtcac 161760
ccagcagcca cacaccctgc cctgccacac tgaccacgcc cgggggctgg atctcatcat 161820
ccttgggtct ctgggcctcc ccaccccact gccacccccg atcccctctg gccatcctgt 161880
cattgtctga acccttcatg agatttctag agcccctgga tgaaattaca tggactgccc 161940
cggaccagag gcacagaggc cggcacagct gcccgctcca cccactgcct ggtctaggcc 162000
aggcccctcc tggtgtcgtg acagggcctt cccactccca gttacttctt gcccatggcc 162060
cacagaagct tccatcacaa tgcatctggg gtgcaggctg ctcagcttcc cctgccaggc 162120
cttgaagacg cggcccactc attcagctgt gtcctcgaga ccctgacgcc ctcctggagc 162180
gttcactgaa tggaaaggtt ccaggtggtc acggtgggag cacctctgac tggcagacca 162240
tgtgtcagtc ctccccaagg ccaaggcagg cttgcctcct cccgggctcc tgatcaacat 162300
ggttccaagg tctgttcttt ctcccctggg tgtgagtgtg tgatttgagt ctgcgtgtgt 162360
gtgtgtgtgg gtgtgatctg tgtgagtgtg tgtgtgcatg ggtgtgatgt gtgtgagtat 162420
atgtgtgtgt gatgtgagcg tgtgtgatgt gtgtgtggtg gtgtgatatg tgtgtgtgtg 162480
tgtgcatggg tgtgttggat ggtatggtac aggctcattc agtctctgca ctccgcctcc 162540
tgctcagtct ggtggacgct ttcctaccac tgcgtgcgct ttctgagcag tgccgactga 162600
ggaggcagcg gcccctgctc tgtgttctcc tggggttgcc cacctctcca gcctcccctc 162660
ctcaggtcag gcctctcctg ggctacaggc tcacttgtgc attttcttgg tgcaccctgg 162720
agtggactca ctctcgccgt gagtgtcgct gaaacactgg cctcctccca gttcccaccc 162780
cggtgtatgt tgggatggga tgcccctccc aggaaggtgc agcaggctgc tgcgcagagt 162840
gtgttcaacc gtctccattc tctcaccgtc cctgagtgtg cctgcctggg gtcatcaaac 162900
aaatcataaa gtaaagcctg aaagaatcaa cctgcttcca agtaactgaa ctgcatgcag 162960
cccaggacaa agtccaaaca aaatgtataa gagtacaaaa tgctgaacac ccaaaaaggt 163020
acaattcaca atgcacaaca accaatcaaa gatgactaag cacacgaaaa ggcaggaaaa 163080
tatgccccac aatgaggaag atcagccaac tgaaactgat gcagacggac acaaaattat 163140
cagaaaaaga cattgaaaca gcttcctaac tgtgttccac agctgcaaga agttaaagac 163200
atgaagtata gtttaaaaga ctcaaataca acttctaaag taaaaactac catgcctgag 163260
atgaaaaaat acactggatg agattaacag caaaagaaaa gaatactgaa tttgaagaca 163320
tagaaatgga aaccattcaa aataaaatac agagagacaa aagaaatgtt tttaactgca 163380
tcgatgagtt ctggtgtaac tccaggtggc ccaatatatg gataattggc ttccttgaag 163440
gagagatgtg tgtatgtttg gggcaggagg gagaaagaaa aatgtttgaa gaaataatga 163500
ctgaaacatt tccaaactta atgaaaacta taaaccaaga aactcaatga ctccctaggg 163560
caggaaacag gactaaaacc aagccaaggt acatcataat caaattgttt aaactagtga 163620
taaaatgaga atcttaaaag caactagagg caaaaggaac acggtacgtg cagaggaacg 163680
gatggccgca gatttcccac aagacgcaat gcaagaagac gggaaagcaa gacctttaaa 163740
ttgctgaaac aaaaagaacc catcagcatc agaatgctat gcctgggtaa aacatccttc 163800
acaaacgaaa tttaaataag aacattttgg agatataaaa gctgaagctc catcgccggc 163860
agaaccgtgc cgtgaatgac gttcaagaaa ttcactcagg ctgaagcggc gtgaaatcag 163920
acagaaatct acattctact ggaaatggta actacatggg caaacacgtg agattttaaa 163980
atcatttaaa tttctttgga gatgcaaatc aaaaccacaa ggaggccagg cgcggtggct 164040
ctcgcctgta atcccagcac tttgggaggc cgaggtgggc ggatcacttg aggtcaggag 164100
tttgagagcg gcctaaccaa cgtggtgaaa ccctgtctct gctaaaaata caaaaattag 164160
ccaggtgtcg tggcgcatgc ctgtaatctc agctactcag gaggctgagg caggagaatt 164220
gcttgaaccc gggagtcgga gcttgcagtg agccaagatc gcaccactgc actccagcct 164280
gggcaacaga gcgagactct gtctcaaaaa acaaaacaaa acaaaacaac ccacaaggat 164340
ataccatctc acaccagtca gaatgcctat tactaaaaag tcaaaaaaca gatgctgggg 164400
aggttgtgga aaagaaagaa cgcttttctc ttgttggtgg aagtgtaaat tagttcagcc 164460
atcgtggaag acgatatggt aactcctcag acacctagag acagaactac cattcaaccc 164520
agcaatcctt ttactgggta tatacctaga ggaatataag tcattctatc ataaagacac 164580
atgcacgcca ttgcagcact atacaatagc aaggacatgg aatcaaccta aatgcccatc 164640
aatgatagac tggataggct gggcgcggtg gctcatgcct gtaatcgcag cagtttggga 164700
ggccgaggtg ggtggatcat gtgaagccag gacttcgaga ccagcctgac cagcatagcg 164760
aaaccccgtc tctactaaaa atacaaaatt agccaggtgt ggtggtgtgc acctgtggtc 164820
ctagctactt gggaggctga ggcaggagaa tcgcttgaac ccgggaggca gaagttgcag 164880
tgagccagat tgcaccattg cactctagcc taggcaacaa gaagtaaact ccatctcaaa 164940
aaaaaaaaaa aaaaaaaaga cagactagat aaagaaaatg tggtatatat acaccatgga 165000
atactctgca gccataaaaa ggaatgaggt ctggactatt tagaagtgac ttcttaattt 165060
tcaacctttc aagagttcaa taatattttt gtttcagatc tccatcttag caacaaagtg 165120
atcagaaaac atactttttg tgctataaat cccttaaact gtgtggagat tttcttaatg 165180
gctccgtctc tgatcaagtt gtacaaatat actgtgtgtg cttgaataat gcatgtattg 165240
ttgctgctgt gagtgtaggg ttttgtcttc tgtttaagtc catttgttaa tgacgttgtg 165300
tagattttct atatcctcac tgactttttt cgtctgttta atttactcat taatgaaaaa 165360
gatatgttaa aaaaaaaaaa aaggaatggg gtcatgtcct ttgcagagac atgaatggaa 165420
ctggaggcca taatccttcc caaactaaag caggaacaga aaaccaaata ccgcatgttc 165480
tcacttataa gtggaaacta catgatgaga acacgtggag atatggggaa caatgcacac 165540
tggggcttat tgaagggtgg agggtgggag aagggagagg atccggaaaa ataactaatg 165600
gatactaggc ttagtacctg ggtgatgaaa taatctgtac aacaaacccc catgacacac 165660
acttaggtat gtaacaaacc tgcacatcgt gcacatgttc ccctgaactt aaaagttaaa 165720
aaaaaaaaaa aaaaaactct ttggccgggc gcggtggctc acgcctgtaa tcccagcact 165780
ttggaggccg aggcaggcgg atcacgaggt caggagatag agaccatcct ggctagcacg 165840
gtgaaaccca tctctactaa aagtacaaaa aattagccgt gcgtggtggc gggtgcccat 165900
agtcacagct actcgggagg ctgaggcagg agaatggcgt gaacccggga ggcggagctt 165960
gcagtgagcc gagatcgcgc cactgcactc cagtctgggt gacagagcaa gactccgtct 166020
caaaaaaaaa aaagagaaag aaagaaagaa agaaaggaaa actctttaaa agcggggttg 166080
ggagaaggtg gggatggtgg ttaatgagta ctaaaaatag agagaatgac taagacctac 166140
tatttgatag cacaacaggg tgactatagt caataatagc ttaattacat attttaaaat 166200
aaagaatgta attggattat ttgcaactca aaggataaat gcctgaggga atggataccc 166260
cattctccat gttgtgctta tttcacattg catgcctgta tcaaaacatc tcatgtactt 166320
tataaatata gatacctact gtgtacccac aaaaattttt ttaaacaata aaaataattt 166380
aaatcacttt aaaaggtaat agactagaaa aaataataac ggtgtgttat gagattttta 166440
acatacgtaa aagtaaaatg cttgacaaga actgcgtaac gactgagggg aagtggaagg 166500
gtccgagtgc aaggtgcttc cctataagta acgtggtgag acattgtaga gagtgatgct 166560
taaaatgtat actaaaggga ctaacaaaat aaacaagaag ttatagctac aaagtcaaca 166620
aaagagataa aatgaaatca tgacaaatat tcaggctggg tgcagcggct cacacctgta 166680
atcccagaac tttgggaggc tgaggggggg gtgtatccct tgaactcaga agtttgagac 166740
tagccagggc aacgtggtga aactctgttt ctaccaaaaa tacaaaaaat tagccatggc 166800
atagtggcgt gtgtctgtag ttcccgctac tcaggaggct gaggttgaag gatcacttga 166860
gcctgggagg ttgaggctgc agtgagctga gatcgcactg ctgcgctcca gcctgggtga 166920
cagagtgaga ctctgtctca aaagagaaaa aaaatcaatc aattcagaag aagacagaga 166980
agaaaaataa taaagaataa gtgtggcaaa tagaaaacaa ataggaagat gatagaagat 167040
tcaagcctaa tgacatcaat aatcacatga aatacaaatg gtctaaacct cattacaagt 167100
agaaaatgtc aaattgggtt taaaaagcaa ggcctgactg tgtgctgcct acattaaata 167160
tacagacaca aataggccaa aagaaaaaga atgaaaaaag ttacaacatg ctaatgcttg 167220
tctaaagaaa gctggagtga ctatcctgat ttcagataaa ggaggttttg gaggaaagaa 167280
tattataagg ataatgaagg ctattttata atgataaaga ggtcaattct tcaagaggaa 167340
ataagcatcc taaacattta ggcacctaat catatagctt ccaaatgcat gatgagattg 167400
caagaagtaa gcaaaaccat aattacagtc agagatttca ataccccctc tccataacta 167460
tgagaacgag caggcagaaa aactcagtaa ggattgagta gacgtagaca gcgctgtgaa 167520
gaaatttgat ccaattgaca tttataggcc attccaccca acgacggcag actacactct 167580
cctctcaagt gcaggtgggg catttataaa gatagatcat attctgggcc ataaaataag 167640
tcttactaaa ttcagcagaa ttcaagtgat gccaaatgta ttacctggcc ataacagaat 167700
agaattagga atcaataaca aaaatatctc tggaaaattc ccaaatatta agaactaaat 167760
aataggccaa ataacagact tctaaataac tcatggatca aagacaaaat caaaaggcaa 167820
attagaaaat ttgttgaact gaataaaagt aacaacacag cacatgcaaa tttgtgggat 167880
gctgataaac tggtcattaa agaaaaaagt atagcactag ctgctatatt gtaaaagaag 167940
aagtgtctca aagcaacggc ttcaagtttt accttaagaa actgaggaaa gaagagcaaa 168000
ttaaacccaa gtaaaagaga aagaatgaag atcaaaacag aaatcaatga aataggaaac 168060
agaaaaaaag agaaaaccaa tgaaagtaaa aattagtttt ttgggaggct cagtcaaatt 168120
gataagcttc tagccagagt gatcgggcag gagggaggga ggaagagaag gagagaggga 168180
aaaaagagac ctaagttcca aatatcagaa gcaagtgacc caaccacaca ttccacagat 168240
attaaaggga taatagggga atattataaa tgactttatg ccaatgggtt caacaactta 168300
gatgaaatgg aaaaatatta gcaatcaacg ctcagaaatt gaaataacaa catttacaat 168360
ggcatacaaa atatgaagaa cttaggaata aatttgacag aaatgcaaaa ggtatattca 168420
ctgaaaactg caaaatatta cctagaggag ttaaaaaaat ttaaataaat gaaagatata 168480
cctttctcat agaccaggag attcattaat gttaagacgt caattctcct taaactgatc 168540
tacagatgaa atgcaatctc aatccaaatt acaaaagtct tcactgtgga aactgacaag 168600
ctctaagatt catatgaaaa tgcaaaggcc aagcaactcc gaaaaagaag aaaaaggttg 168660
gaggggtctc acaatctggt atcaacagct gttatagtgc ggcatcagca taaagacaga 168720

```
tcaatagtgc cacaataaac atacgtgtgc atgtgtcttt atagcagcat gatttatatt 168780

cctttgggta tatacccagt aatgggatag ctgggtcaaa tggtatttct agttctagat 168840

ccctgaggaa tcaccacact gtcttccaca atggttgaac tagtttactt tgaacaatga 168900

gaacacctgg acacaggaag gggaacatca cacacccggg cctgttgtgg ggtggggggg 168960

agggggaagg gagagcatta ggagatatac ctaatgtaaa tgacgagtta atgggtgcag 169020

cataccaaca tggcacatgt atacatatgt aacaagccta cacattgtga acatgtaccc 169080

tagaacttaa agtataataa aaatatatat atatgtaaaa aataaaaaaa aagtgaaaaa 169140

aaaagacaga ctaatagaac aatggaactg agcagtgggt ccagaaatga gtccacacat 169200

atgtgtccac acaaatgagt ccacacatat gtgtccacac aaatgagtcc acacatatgt 169260

gtccacacaa atgagtccac acatatgtgt ccacacaaat gagtccacac atatgtgtcc 169320

acacaaatga gtccacacat atgtgtccac acaaatgagt ccacacatat gtgtccacac 169380

aaatgagtcc acacatatgt gtacaactat tttgacaaag atacaaagtc aatgctgtta 169440

aaaaaaaaaa agagagagag acaagctttt caaccagtgg tgctggaaca atgaccatac 169500

acaagccccc acccacacac cctcaagcca tgtctcacat atataaaaat tcacccaaaa 169560

tggatgatag acctaaatgt aaaacctaaa aacaccaaat ttctaggaga aaacatcaaa 169620

gaacattttt gtgaccttgg gttaggcaaa gatttcttag ttataccaaa actataattc 169680

ataaaagaac taatggataa catggccttc agccaaatta aaaactgctt cacaaaagag 169740

gctgttaaga gaatgaaaaa acaagccaca gacagggaga aaatctttgc aaatcattaa 169800

tctgatgaag gatatagagt taacaaaact caacaataag aaaacaaaca attcaattaa 169860

acatggtaaa agatttgaac agacactcca tcaaataaga taaacagcta gcaaatgagt 169920

acatggaaag attctcagcc tgatttgtca tcgggtaaac agaacggcta aacttgaaat 169980

gactgattat aaccagcgtt gctgaggatg tggtggaact ggaattc              170027
```

```
<210> SEQ ID NO 14
<211> LENGTH: 51
<212> TYPE: DNA
<213> ORGANISM: Homo sapiens
<220> FEATURE:
<221> NAME/KEY: allele
<222> LOCATION: 26
<223> OTHER INFORMATION: Y is C or T

<400> SEQUENCE: 14

gtggtgtctg tggggagggg gttcayttcc ccaggaagca cagccacgcc g            51


<210> SEQ ID NO 15
<211> LENGTH: 20
<212> TYPE: DNA
<213> ORGANISM: Artificial Sequence
<220> FEATURE:
<223> OTHER INFORMATION: HB-332 forward primer

<400> SEQUENCE: 15

cgaggttagt gagggacggc                                               20


<210> SEQ ID NO 16
<211> LENGTH: 29
<212> TYPE: DNA
<213> ORGANISM: Artificial Sequence
<220> FEATURE:
<223> OTHER INFORMATION: HB-332 reverse primer

<400> SEQUENCE: 16
```

cctcgatcca cccaaaataa tatctataa 29

<210> SEQ ID NO 17
<211> LENGTH: 21
<212> TYPE: DNA
<213> ORGANISM: Artificial Sequence
<220> FEATURE:
<223> OTHER INFORMATION: HB-332 probe oligo

<400> SEQUENCE: 17
aaaaattcat ttccccaaaa a 21

<210> SEQ ID NO 18
<211> LENGTH: 20
<212> TYPE: DNA
<213> ORGANISM: Artificial Sequence
<220> FEATURE:
<223> OTHER INFORMATION: HB-333 forward primer

<400> SEQUENCE: 18
cgaggttagt gagggacggc 20

<210> SEQ ID NO 19
<211> LENGTH: 29
<212> TYPE: DNA
<213> ORGANISM: Artificial Sequence
<220> FEATURE:
<223> OTHER INFORMATION: HB-333 reverse primer

<400> SEQUENCE: 19
cctcgatcca cccaaaataa tatctataa 29

<210> SEQ ID NO 20
<211> LENGTH: 21
<212> TYPE: DNA
<213> ORGANISM: Artificial Sequence
<220> FEATURE:
<223> OTHER INFORMATION: HB-333 probe oligo

<400> SEQUENCE: 20
aaaaattcac ttccccaaaa a 21

<210> SEQ ID NO 21
<211> LENGTH: 22
<212> TYPE: DNA
<213> ORGANISM: Artificial Sequence
<220> FEATURE:
<223> OTHER INFORMATION: HB-351 forward primer

<400> SEQUENCE: 21
gacgaggtta gtgagggacg gc 22

<210> SEQ ID NO 22
<211> LENGTH: 33
<212> TYPE: DNA
<213> ORGANISM: Artificial Sequence
<220> FEATURE:
<223> OTHER INFORMATION: HB-351 reverse primer

<400> SEQUENCE: 22
aactcctcga tccacccaaa ataatatcta taa 33

<210> SEQ ID NO 23
<211> LENGTH: 21
<212> TYPE: DNA

<213> ORGANISM: Artificial Sequence
<220> FEATURE:
<223> OTHER INFORMATION: HB-351 probe oligo

<400> SEQUENCE: 23
aaaaattcay ttccccaaaa a 21

<210> SEQ ID NO 24
<211> LENGTH: 23
<212> TYPE: DNA
<213> ORGANISM: Artificial Sequence
<220> FEATURE:
<223> OTHER INFORMATION: HB-345 forward primer

<400> SEQUENCE: 24
tgacgaggtt agtgagggac ggc 23

<210> SEQ ID NO 25
<211> LENGTH: 35
<212> TYPE: DNA
<213> ORGANISM: Artificial Sequence
<220> FEATURE:
<223> OTHER INFORMATION: HB-345 reverse primer

<400> SEQUENCE: 25
caaactcctc gatccaccca aaataatatc tataa 35

<210> SEQ ID NO 26
<211> LENGTH: 21
<212> TYPE: DNA
<213> ORGANISM: Artificial Sequence
<220> FEATURE:
<223> OTHER INFORMATION: HB-345 probe oligo

<400> SEQUENCE: 26
aaaaattcay ttccccaaaa a 21

<210> SEQ ID NO 27
<211> LENGTH: 25
<212> TYPE: DNA
<213> ORGANISM: Artificial Sequence
<220> FEATURE:
<223> OTHER INFORMATION: HB-346 forward primer

<400> SEQUENCE: 27
cttgacgagg ttagtgaggg acggc 25

<210> SEQ ID NO 28
<211> LENGTH: 36
<212> TYPE: DNA
<213> ORGANISM: Artificial Sequence
<220> FEATURE:
<223> OTHER INFORMATION: HB-346 reverse primer

<400> SEQUENCE: 28
ccaaactcct cgatccaccc aaaataatat ctataa 36

<210> SEQ ID NO 29
<211> LENGTH: 21
<212> TYPE: DNA
<213> ORGANISM: Artificial Sequence
<220> FEATURE:
<223> OTHER INFORMATION: HB-346 probe oligo

<400> SEQUENCE: 29
aaaaattcay ttccccaaaa a 21

-continued

```
<210> SEQ ID NO 30
<211> LENGTH: 23
<212> TYPE: DNA
<213> ORGANISM: Artificial Sequence
<220> FEATURE:
<223> OTHER INFORMATION: HB-347 forward primer

<400> SEQUENCE: 30

tgaggttagt gagggatggt gtg                                23


<210> SEQ ID NO 31
<211> LENGTH: 29
<212> TYPE: DNA
<213> ORGANISM: Artificial Sequence
<220> FEATURE:
<223> OTHER INFORMATION: HB-347 reverse primer

<400> SEQUENCE: 31

ccttgatcca cccaaaataa tatctataa                          29


<210> SEQ ID NO 32
<211> LENGTH: 21
<212> TYPE: DNA
<213> ORGANISM: Artificial Sequence
<220> FEATURE:
<223> OTHER INFORMATION: HB-347 probe oligo

<400> SEQUENCE: 32

aaaaattcay ttccccaaaa a                                  21
```